(12) United States Patent
Johnson et al.

(10) Patent No.: US 12,054,570 B2
(45) Date of Patent: Aug. 6, 2024

(54) FUNCTIONAL OLIGOMERS AND FUNCTIONAL POLYMERS INCLUDING HYDROXYLATED POLYMERS AND CONJUGATES THEREOF AND USES THEREOF

(71) Applicant: Massachusetts Institute of Technology, Cambridge, MA (US)

(72) Inventors: Jeremiah A. Johnson, Boston, MA (US); Wenxu Zhang, Belmont, MA (US); Peyton Shieh, Cambridge, MA (US); Keith Husted, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 660 days.

(21) Appl. No.: 17/022,021

(22) Filed: Sep. 15, 2020

(65) Prior Publication Data
US 2021/0147598 A1 May 20, 2021

Related U.S. Application Data

(60) Provisional application No. 62/935,799, filed on Nov. 15, 2019.

(51) Int. Cl.
*C08F 232/08* (2006.01)
*C07D 321/12* (2006.01)
*C08F 8/12* (2006.01)
*C08F 234/02* (2006.01)

(52) U.S. Cl.
CPC .......... *C08F 232/08* (2013.01); *C07D 321/12* (2013.01); *C08F 8/12* (2013.01); *C08F 234/02* (2013.01)

(58) Field of Classification Search
CPC ........ C08F 232/08; C08F 234/02; C08F 8/12; C07D 321/12
See application file for complete search history.

(56) References Cited

U.S. PATENT DOCUMENTS

| | | | |
|---|---|---|---|
| 3,256,308 A * | 6/1966 | Sterling | C08F 236/06 556/464 |
| 3,337,598 A | 8/1967 | Sterling et al. | |
| 4,510,136 A | 4/1985 | Moberg | |
| 5,811,515 A | 9/1998 | Grubbs et al. | |
| 8,829,206 B2 | 9/2014 | Terrill et al. | |
| 8,829,207 B2 | 9/2014 | Billodeaux et al. | |
| 8,969,598 B2 | 3/2015 | Terrill et al. | |
| 9,944,730 B2 | 4/2018 | Rhodes et al. | |
| 10,591,818 B2 * | 3/2020 | Knapp | C09D 145/00 |
| 10,988,491 B2 | 4/2021 | Johnson et al. | |
| 2001/0006988 A1 | 7/2001 | Kuhnle et al. | |
| 2008/0063937 A1 * | 3/2008 | Lee | H01M 10/0567 429/188 |
| 2018/0312634 A1 | 11/2018 | Chung | |
| 2019/0039617 A1 | 2/2019 | Miura et al. | |
| 2020/0055879 A1 | 2/2020 | Johnson et al. | |
| 2021/0284664 A1 | 9/2021 | Johnson et al. | |
| 2022/0251288 A1 | 8/2022 | Johnson et al. | |

FOREIGN PATENT DOCUMENTS

| | | |
|---|---|---|
| WO | WO 2017/208209 A1 | 12/2017 |
| WO | WO 2020/037236 A1 | 2/2020 |
| WO | WO 2022/099210 A1 | 5/2022 |
| WO | WO 2022/212752 A1 | 10/2022 |

OTHER PUBLICATIONS

International Preliminary Report on Patentability for PCT/US2019/046872, mailed on Mar. 4, 2021.
International Search Report and Written Opinion for Application No. PCT/US2020/050927 mailed Jan. 21, 2021.
International Preliminary Report on Patentability for PCT/US2020/050927, mailed on May 27, 2022.
International Search Report and Written Opinion for Application No. PCT/US2021/061135 mailed Apr. 28, 2022.
Invitation to Pay Additional Fees for Application No. PCT/US2021/058668 mailed Jan. 10, 2022.
International Search Report and Written Opinion for Application No. PCT/US2021/058668 mailed Mar. 10, 2022.
Invitation to Pay Additional Fees for Application No. PCT/US2022/031759 mailed Aug. 16, 2022.
International Search Report and Written Opinion for Application No. PCT/US2022/031759 mailed Aug. 8, 2022.
[No Author Listed], Dimethyl-[(1R)-1-naphthalen-1-yl-2-[(2-naphthalen-2-yloxyacetyl)amino]ethyl]azanium. PubChem CID No. 8701426. Feb. 12, 2015. Retrieved from <https://pubchem.ncbi.nlm.nih.gov/compound/8701426> on Nov. 4, 2022. 7 pages.
Asaro et al., Recycling of rubber wastes by devulcanization. Res Conserv Rec. Jun. 2018; 133:250-62. doi: 10.1016/j.resconrec.2018.02.016.
Autenrieth et al., Stereospecific Ring-Opening Metathesis Polymerization (ROMP) of endo-Dicyclopentadiene by Molybdenum and Tungsten Catalysts. Macromolecules. Apr. 2015;48(8):2480-92. doi: 10.1021/acs.macromol.5b00123.
Bang et al., Polydicyclopentadiene aerogels from first- versus second-generation Grubbs' catalysts: a molecular versus a nanoscopic perspective. J Sol-Gel Sci Technol. 2015;75(2):460-74. doi: 10.1007/s10971-015-3718-0.

(Continued)

*Primary Examiner* — Robert D Harlan
(74) *Attorney, Agent, or Firm* — Wolf, Greenfield & Sacks, P.C.

(57) ABSTRACT

The present disclosure describes functional oligomers or functional polymers. The functional oligomers or functional polymers may contain functional groups, e.g., —OH and/or —CHO. The functional oligomers or functional polymers may be obtained from hydrolyzing certain copolymers and may be soluble in commercially available solvents. The copolymers may be thermosetting polymers. The functional oligomers and functional polymers may be useful for recycling thermosetting polymers and may be useful as starting materials for preparing additional oligomers or polymers.

39 Claims, 58 Drawing Sheets

(56) References Cited

OTHER PUBLICATIONS

Blackmore, P.M., Synthesis and properties of stereoregular fluoropolymers. Doctoral thesis at Durham University. 1986. pp. i-iii, 46, 62. Accessed from <http://etheses.dur.ac.uk/6795/>.

Boadi et al., Alternating Ring-Opening Metathesis Polymerization Provides Easy Access to Functional and Fully Degradable Polymers. Macromolecules. Jul. 28, 2020;53(14):5857-5868. doi: 10.1021/acs.macromol.0c01051. Epub Jul. 16, 2020.

Capelot et al., Catalytic Control of the Vitrimer Glass Transition. ACS Macro Lett. Jul. 17, 2012;1(7):789-792. doi: 10.1021/mz300239f. Epub Jun. 11, 2012.

Chen et al., Thermally Crosslinked Functionalized Polydicyclopentadiene with a High Tg and Tunable Surface Energy. ACS Omega. Oct. 6, 2016;1(4):532-540. doi: 10.1021/acsomega.6b00193. Erratum in: ACS Omega. Jun. 9, 2017;2(6):2593.

Christensen et al., Closed-loop recycling of plastics enabled by dynamic covalent diketoenamine bonds. Nat Chem. May 2019;11(5):442-448. doi: 10.1038/s41557-019-0249-2. Epub Apr. 22, 2019.

Cole et al., Microplastics as contaminants in the marine environment: A review. Mar Pol Bull. Dec. 2011;62(12):2588-97. doi: 10.1016/j.marpolbul.2011.09.025.

Corma et al., Formation and Hydrolysis of Acetals Catalysed by Acid Faujasites. Appl Catal. 1990;59:333-40.

Cuthbert et al., Structure of the Thermally Induced Cross-Link in C-Linked Methyl Ester-Functionalized Polydicyclopentadiene (fPDCPD). Macromolecules. Feb. 28, 2018;51(5):2038-47. doi: 10.1021/acs.macromol.7b02750.

Davidson et al., Polymerization of Dicyclopentadiene: A Tale of Two Mechanisms. Macromolecules. 1996;29:786-8.

Davies et al., Protection of hydroxy groups by silylation: use in peptide synthesis and as lipophilicity modifiers for peptides. J Chem Soc Perkin Trans. 1;1992:3043-8. doi: 10.1039/P19920003043.

Defauchy et al., Kinetic analysis of polydicyclopentadiene oxidation. Polym Degrad Stab. Aug. 2017;142:169-77. doi: 10.1016/j.polymdegradstab.2017.06.005.

Delancey et al., Controlling crosslinking in thermosets via chain transfer with monoterpenes. Polym Chem. Jun. 20, 2011;49(17):3719-27. doi: 10.1002/pola.24808.

Dong et al., A Simple and Versatile Method for the Formation of Acetals/Ketals Using Trace Conventional Acids. ACS Omega. May 7, 2018;3(5):4974-4985. doi: 10.1021/acsomega.8b00159.

Elder et al., Nanovoid formation and mechanics: a comparison of poly(dicyclopentadiene) and epoxy networks from molecular dynamics simulations. Soft Matter. 2016;12:4418-34. doi: 10.1039/C6SM00691D.

Fedorenko et al., Facial selectivity in the reaction of dihalocarbenes with 2-substituted 4,7-dihydro-1,3-dioxepines. Mendeleev Comm. May 29, 2007;17:170-1. doi: 10.1016/J.MENCOM.2007.05.013.

Feist et al., Enol Ethers Are Effective Monomers for Ring-Opening Metathesis Polymerization: Synthesis of Degradable and Depolymerizable Poly(2,3-dihydrofuran). J Am Chem Soc. Dec. 27, 2019;142(3):1186-9. doi: 10.1021/jacs.9b11834.

Flory, P.J., Molecular Size Distribution in Three Dimensional Polymers. I. Gelation. J Am Chem Soc. Nov. 1, 1941;63(11):3083-90. doi: 10.1021/ja01856a061.

Fortman et al., Approaches to Sustainable and Continually Recyclable Cross-Linked Polymers. ACS Sus Chem Eng. Aug. 26, 2018;6(9):11145-59. doi: 10.1021/acssuschemeng.8b02355.

Fortman et al., Mechanically activated, catalyst-free polyhydroxyurethane vitrimers. J Am Chem Soc. Nov. 11, 2015;137(44):14019-22. doi: 10.1021/jacs.5b08084. Epub Nov. 2, 2015.

Fraser et al., Degradable Cyclooctadiene/Acetal Copolymers: versatile Precursors to 1,4-Hydroxytelechelic Polybutadiene and Hydroytelechelic Polyethylene. Macromolecules. Oct. 9, 1995;28(21):7256-61. doi: 10.1021/ma00125a031.

Frauenrath et al., Synthesis of 2,3-substituted tetrahydropyrans by rearrangement of 5,6-dihydro-4H-1,3-dioxocins. Tetrahedron Lett. Jan. 1, 1990;31(5):649-50. doi: 10.1016/S0040-4039(00)94591-X.

Furstner et al., Alkyne metathesis: development of a novel molybdenum-based catalyst system and its application to the total synthesis of epothilone A and C. Chemistry. Dec. 17, 2001;7(24):5299-317. doi: 10.1002/1521-3765(20011217)7:24<5299::aid-chem5299>3.0.co;2-x.

Furstner et al., Mo[N(t-Bu)(Ar)]3 Complexes As Catalyst Precursors:? In Situ Activation and Application to Metathesis Reactions of Alkynes and Diynes. J Am Chem Soc. Sep. 23, 1999;121(40):9453-4. doi: 10.1021/ja991340r.

Gallivan et al., A neutral, water-soluble olefin metathesis catalyst based on an N-heterocyclic carbene ligand. Tetrahedron Lett. Apr. 11, 2005;46(15):2577-80. doi: 10.1016/j.tetlet.2005.02.096.

Grubbs et al., Ring-Closing Metathesis and Related Processes in Organic Synthesis. Acc Chem Res. Nov. 1, 1995;28(11):446-52. doi: 10.1021/ar00059a002.

Gu et al., A (Macro)Molecular-Level Understanding of Polymer Network Topology. Trends Chem. Jun. 2019;1(3):318-34. doi: 10.1016/j.trechm.2019.02.017.

Gu et al., A unifying review of polymer networks: from rubbers and gels to porous frameworks. Angew Chemie Int Ed. Jul. 2019;59(13):5022-49. doi: 0.1002/anie.201902900. Author Manuscript, 66 pages.

Gu et al., Polymer Networks: From Plastics and Gels to Porous Frameworks. Angew Chem Int Ed Engl. Mar. 23, 2020;59(13):5022-5049. doi: 10.1002/anie.201902900. Epub Jan. 15, 2020.

Hann et al., The impact of the use of "oxo-degradable" plastic on the environment. European Commission, Directorate-General for Environment. Sep. 20, 2016. doi: 10.2779/992559. 150 pages.

Hartley et al., Photochemistry of Ketone Polymers. II. Studies of Model Compounds. Macromolecules. Sep. 1, 1968;1(5):413-7. doi: 10.1021/ma60005a009.

Herges et al., Synthesis and Fragmentation of 2,2-Diazido-1,3,2-dioxasila-5-cycloheptenes. The Chemical Vapor Deposition of SiO2. J Am Chem Soc. Dec. 18, 1996;18(50):12752-7. doi: 10.1021/ja9615886.

Hilf et al., End Capping Ring-Opening Olefin Metathesis Polymerization Polymers with Vinyl Lactones. J Am Chem Soc. Jul. 23, 2008;130(33):11040-8. doi: 10.1021/ja8022863.

Hilf et al., Heterotelechelic Ring-Opening Metathesis Polymers. Macromolecules. Nov. 16, 2009;43(1):208-12. doi: 10.1021/ma902074y.

Hilf et al., Monofunctional metathesis polymers via sacrificial diblock copolymers. Angew Chem Int Ed Engl. Dec. 4, 2006;45(47):8045-8. doi: 10.1002/anie.200602323.

Hilf et al., Sacrificial Synthesis of Hydroxy-Telechelic Metathesis Polymers via Multiblock-Copolymers. Macromolecules. Feb. 24, 2009;42(4):1099-106. doi: 10.1021/ma802440k.

Hu et al., Thermal oxidation aging of polydicyclopentadiene and composites. Polym Comp. Jun. 21, 2016;39(5):1742-51. doi: 10.1002/pc.24125.

Huang et al., Thermal oxidation of Poly(dicyclopentadiene)—kinetic modeling of double bond consumption. Polym Degrad Stab. Aug. 2019;166:258-71. doi: 10.1016/j.polymdegradstab.2019.06.003.

Kaburagi et al., Operationally simple and efficient workup procedure for TBAF-mediated desilylation: application to halichondrin synthesis. Org Lett. Feb. 15, 2007;9(4):723-6. doi: 10.1021/ol063113h.

Kawamoto et al., Loops versus Branch Functionality in Model Click Hydrogels. Macromolecules. Dec. 1, 2015;48(24):8980-88. doi: 10.1021/acs.macromol.5b02243.

Kessler et al., Cure kinetics of the ring-opening metathesis polymerization of dicyclopentadiene. J Polym Sci Part A: Polym Chem. May 30, 2002;40:2373-83. doi: 10.1002/pola.10317.

Klimovitskii et al., Conformational isomerism in 3,5,8-trioxabicyclo[5.1.0]octane and its diastereomeric 4-methyl derivatives. A combined IR, X-ray and ab initio study. J Mol Struc. Feb. 28, 2007;828(1-3):147-53. doi: 10.1016/j.molstruc.2006.05.045.

Kloxin et al., Covalent Adaptable Networks (CANs): A Unique Paradigm in Crosslinked Polymers. Macromolecules. Mar. 23, 2010;43(6):2643-2653. doi: 10.1021/ma902596s.

(56) References Cited

OTHER PUBLICATIONS

Kovacic et al., Ring-opening Metathesis Polymerisation derived poly(dicyclopentadiene) based materials. Mater Chem Front. Jun. 4, 2020;4:2235-55. doi: 10.1039/D0QM00296H.

Lexer et al., Acrylates as termination reagent for the preparation of semi-telechelic polymers made by ring opening metathesis polymerization. J Polym Sci Part A: Polym Chem. Jan. 1, 2009;47(1):299-305. doi: 10.1002/pola.23137.

Li et al., Reprocessable Polymer Networks via Thiourethane Dynamic Chemistry: Recovery of Cross-link Density after Recycling and Proof-of-Principle Solvolysis Leading to Monomer Recovery. Macromolecules. Oct. 22, 2019;52(21):8207-16. doi: 10.1021/acs.macromol.9b01359.

Li et al., Vitrimers Designed Both To Strongly Suppress Creep and To Recover Original Cross-Link Density after Reprocessing: Quantitative Theory and Experiments. Macromolecules. Jul. 17, 2018;51(15):5537-46. doi: 10.1021/acs.macromol.8b00922.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

Liu et al., Particles without a box: brush-first synthesis of photodegradable PEG star polymers under ambient conditions. J Vis Exp. Oct. 10, 2013;(80):50874. doi: 10.3791/50874.

Long et al., Ballistic Response of Polydicyclopentadiene vs. Epoxy Resins and Effects of Crosslinking. In: Dynamic Behavior of Materials, vol. 1. Conference Proceedings of the Society for Experimental Mechanics. Chapter 37. 2017:285-90. Springer New York LLC. doi: 10.1007/978-3-319-41132-3_37.

Ma et al., Degradable thermosets based on labile bonds or linkages: A review. Prog Polym Sci. Jan. 2018;76:65-110. doi: 10.1016/j.progpolymsci.2017.07.008.

Machida et al., (2018). Efficient approach to medium-sized cyclic molecules containing (E)-Alkene via z to e photochemical isomerization in the presence of AgNO3-impregnated silica gel. Chemistry Letters, 47(2), 186-188. https://doi.org/10.1246/cl.170937.

Macosko et al., A new derivation of average molecular weights of nonlinear polymers. Macromolecules. Mar.-Apr. 1976;9(2):199-206. doi: 10.1021/ma60050a003.

Mathers et al., Functional Hyperbranched Polymers Using Ring-Opening Metathesis Polymerization of Dicyclopentadiene with Monoterpenes. Macromolecules. Feb. 10, 2009;42(5):1512-8. doi: 10.1021/ma802441t.

Moatsou et al., Degradable precision polynorbornenes via ring-opening metathesis polymerization. J Polym Sci Part A: Polym Chem. May 1, 2016;54(9):1236-42. doi: 10.1002/pola.27964.

Mohite et al., Polydicyclopentadiene aerogels grafted with PMMA: I. Molecular and interparticle crosslinking. Soft Matter. Dec. 6, 2012;9:1516-30. doi: 10.1039/C2SM26931G.

Montarnal et al., Silica-like malleable materials from permanent organic networks. Science. Nov. 18, 2011;334(6058):965-8. doi: 10.1126/science.1212648.

Nagarkar et al., End functional ROMP polymers via degradation of a ruthenium Fischer type carbene. Chem Sci. Sep. 2, 2014;5(12):4687-92. doi: 10.1039/C4SC02242D.

Ogata et al., Scissionable polymer resists for extreme ultraviolet lithography. Proceedings of the SPIE, Extreme Ultraviolet (EUV) Lithography. Mar. 22, 2010;7636:763634/1. doi: 10.1117/12.847320.

Parker et al., Halogen radicals contribute to photooxidation in coastal and estuarine waters. Proc Natl Acad Sci U S A. May 24, 2016;113(21):5868-73. doi: 10.1073/pnas.1602595113. Epub May 9, 2016.

Parrott et al., Tunable bifunctional silyl ether cross-linkers for the design of acid-sensitive biomaterials. J Am Chem Soc. Dec. 22, 2010;132(50):17928-32. doi: 10.1021/ja108568g. Epub Nov. 24, 2010.

Perring et al., Epoxidation of the surface of polydicyclopentadiene for the self-assembly of organic monolayers. J Mater Chem. Sep. 8, 2010;20:8679-85. doi: 10.1039/C0JM01999B.

Post et al., A Review on the Potential and Limitations of Recyclable Thermosets for Structural Applications. Polym Rev. Oct. 8, 2019;60(2):359-88. doi: 10.1080/15583724.2019.1673406.

Reddy et al., Mechanism of cyclic acetal formation. Tetrahedron. 1982;38(12):1825-6. doi: 10.1016/0040-4020(82)80257-3.

Robertson et al., Alkyl Phosphite Inhibitors for Frontal Ring-Opening Metathesis Polymerization Greatly Increase Pot Life. ACS Macro Lett. Jun. 20, 2017;6(6):609-612. doi: 10.1021/acsmacrolett.7b00270. Epub May 24, 2017.

Robertson et al., Frontal Ring-Opening Metathesis Polymerization of Exo-Dicyclopentadiene for Low Catalyst Loadings. ACS Macro Lett. May 17, 2016;5(5):593-596. doi: 10.1021/acsmacrolett.6b00227. Epub Apr. 25, 2016.

Robertson et al., Rapid energy-efficient manufacturing of polymers and composites. Nature. May 9, 2018;557:223-7. doi: 10.1038/s41586-018-0054-x.

Rohde et al., Thermoset Blends of an Epoxy Resin and Polydicyclopentadiene. Macromolecules. Nov. 30, 2016;49(23):8960-70. doi: 10.1021/acs.macromol.6b01649.

Rule et al., ROMP Reactivity of endo- and exo-Dicyclopentadiene. Macromolecule. Sep. 6, 2002;35:7878-82. doi: 10.1021/MA0209489.

Röttger et al., High-performance vitrimers from commodity thermoplastics through dioxaborolane metathesis. Science. Apr. 7, 2017;356(6333):62-65. doi: 10.1126/science.aah5281.

Saha et al., Cross-linked ROMP polymers based on odourless dicyclopentadiene derivative. Polym Chem. Apr. 14, 2016;7:3071-5. doi: 10.1039/C6PY00378H.

Sanda et al., Vinylcyclopropanone Cyclic Acetal-Synthesis, Polymerization, Structure of the Polymer and Mechanism of the Polymerization. Macromolecules. Feb. 1994;27(5):1099-111. doi: 10.1021/ma00083a006.

Schrock et al., Tungsten(VI) neopentylidyne complexes. Organometallics. Dec. 1, 1982;1(12):1645-51. doi: 10.1021/om00072a018.

Sheng et al., The influence of cross-linking agents on ring-opening metathesis polymerized thermosets. J Thermal Analys Calorimet. Jul. 19, 2007;89(2):459-64. doi: 10.1007/s10973-006-8468-3.

Shieh et al., Cleavable comonomers enable degradable, recyclable thermoset plastics. Nature. Jul. 2020;583(7817):542-547. doi: 10.1038/s41586-020-2495-2. Epub Jul. 22, 2020. Erratum in: Nature. Sep. 2020;585(7823):E4. Supplementary Information, 55 pages.

Shieh et al., A Comonomer Strategy for Triggered Degradation and Re/Upcycling of High-Performance Thermoset Plastics. Dec. 13, 2019. 18 pages. Accessed Dec. 27, 2022 from <https://chemrxiv.org/engage/chemrxiv/article-details/60c7467bee301c7f63c79516>.

Shieh et al., Tailored silyl ether monomers enable backbone-degradable polynorbornene-based linear, bottlebrush and star copolymers through ROMP. Nat Chem. Dec. 2019;11(12):1124-1132. doi: 10.1038/s41557-019-0352-4. Epub Oct. 28, 2019.

Snyder et al., Reprocessable Acid-Degradable Polycarbonate Vitrimers. Macromolecules. Jan. 4, 2018;51(2):389-97. doi: 10.1021/acs.macromol.7b02299.

Sommazzi et al., Olefin-carbon monoxide copolymers. Prog Polym Sci. 1997;22(8):1547-605. doi: 10.1016/S0079-6700(97)00009-9.

Stockmayer et al., Theory of Molecular Size Distribution and Gel Formation in Branched Polymers II. General Cross Linking. J Chem Phys. Apr. 1944;12(4):125-31. doi: 10.1063/1.1723922.

Takahashi et al., Degradable epoxy resins prepared from diepoxide monomer with dynamic covalent disulfide linkage. Polymer. Jan. 15, 2016;82:319-26. doi: 10.1016/J.POLYMER.2015.11.057.

Takayama et al., Topographical Micropatterning of Poly(dimethylsiloxane) Using Laminar Flows of Liquids in Capillaries. Adv Mater. Apr. 18, 2001;13(8):570-4. doi: 10.1002/1521-4095(200104)13:8<570::AID-ADMA570>3.0.CO;2-B.

Tanino et al., Control of Stereochemistry by sigma—Participation of a Silyl Group. A Novel Method for Diastereoselective Polyol Synthesis. J Org Chem. Jun. 27, 1997;62(13):4206-4207. doi: 10.1021/jo9703515. PMID: 11671736.

Tong et al., Copolymers of Functionalized and Nonfunctionalized Polydicyclopentadiene. ACS Applied Polymer Materials. Jan. 8, 2021;3(1):110-115.

(56) References Cited

OTHER PUBLICATIONS

Tournier et al., An engineered PET depolymerase to break down and recycle plastic bottles. Nature. Apr. 2020;580(7802):216-219. doi: 10.1038/s41586-020-2149-4. Epub Apr. 8, 2020.

Veysset et al., Dynamics of supersonic microparticle impact on elastomers revealed by real-time multi-frame imaging. Sci Rep. May 9, 2016;6:25577. doi: 10.1038/srep25577. Erratum in: Sci Rep. Feb. 16, 2018;8:46944.

Wang et al., Counting loops in sidechain-crosslinked polymers from elastic solids to single-chain nanoparticles. Chem Sci. May 1, 2019;10(20):5332-5337. doi: 10.1039/c9sc01297d.

Wang et al., Counting Secondary Loops Is Required for Accurate Prediction of End-Linked Polymer Network Elasticity. ACS Macro Lett. Feb. 6, 2018;7(2):244-9. doi: 10.1021/acsmacrolett.8b00008.

Wang et al., Readily recyclable carbon fiber reinforced composites based on degradable thermosets: a review. Green Chem. Sep. 19, 2019;21(21):5781-96. doi: 10.1039/C9GC01760G.

Wiles et al., Polyolefins with controlled environmental degradability. Polym Degrad Stab. Jul. 2006;91(7):1581-92. doi: 10.1016/j.polymdegradstab.2005.09.010.

Winne et al., Dynamic covalent chemistry in polymer networks: a mechanistic perspective. Polym Chem. Oct. 16, 2019;10:6091-108. doi: 10.1039/C9PY01260E.

Yang et al., Curing Kinetics and Mechanical Properties of endo-Dicyclopentadiene Synthesized Using Different Grubbs' Catalysts. Ind Eng Chem Res. Jan. 28, 2014;53(8):3001-11. doi: 10.1021/ie403285q.

Yang et al., Curing study of dicyclopentadiene resin and effect of elastomer on its polymer network. Polymer. Mar. 1997;38(5):1121-30. doi: 10.1016/S0032-3861(96)00599-X.

Yang et al., Reworkable Epoxies: Thermosets with Thermally Cleavable Groups for Controlled Network Breakdown. Chem Mater. Jun. 1998;10(6):1475-82.

Zhang et al., Loading dependent swelling and release properties of novel biodegradable, elastic and environmental stimuli-sensitive polyurethanes. J Control Release. Oct. 21, 2008;131(2):128-36. doi: 10.1016/j.jconrel.2008.07.026. Epub Jul. 24, 2008.

Zhong et al., Quantifying the impact of molecular defects on polymer network elasticity. Science. Sep. 16, 2016;353(6305):1264-8. doi: 10.1126/science.aag0184.

Zhou et al., Counting primary loops in polymer gels. Proc Natl Acad Sci U S A. Nov. 20, 2012;109(47):19119-24. doi: 10.1073/pnas.1213169109. Epub Nov. 6, 2012.

PCT/US2019/046872, Oct. 29, 2019, International Search Report and Written Opinion.

International Search Report and Written Opinion for PCT/US2019/046872, mailed on Oct. 29, 2019.

Corey et al., Diisopropylsilyl ditriflate and di-tert-butylsilyl ditriflate: new reagents for the protection of diols. Tetra Lett. 1982;23(47):4871-4874.

Gu et al., Mechanism of the reactions of dimethylsilylene with oxetanes. J. Am. Chem. Soc. 1980;102(5):1641-1644.

Hoye et al., Silicon tethered ring-closing metathesis reactions for self- and cross-coupling of alkenols. Tetrahedron Letters. 1999;40(8):1429-1432. https://doi.org/10.1016/S0040-4039(98)02697-5.

Prevost et al., Strained organosilacyclic compounds: synthesis of anti-Bredt olefins and trans-dioxasilacyclooctenes. Dalton Trans. 2010;39:9275-9281.

Tomooka et al., Planar chiral dialkoxysilane: introduction of inherent chirality and high reactivity in conventional achiral alkene. Chemistry. Jun. 16, 2014;20(25):7598-602. doi: 10.1002/chem.201402434. Epub May 6, 2014. PMID: 24802258.

\* cited by examiner

Image of Soluble Fragments after THF Removal

FUNCTIONAL OLIGOMERS AND FUNCTIONAL POLYMERS INCLUDING HYDROXYLATED POLYMERS AND CONJUGATES THEREOF AND USES THEREOF

RELATED APPLICATION

The present application claims priority under 35 U.S.C. § 119(e) to U.S. Provisional Application, U.S. Ser. No. 62/935,799, filed Nov. 15, 2019, which is incorporated herein by reference in its entirety.

GOVERNMENT SUPPORT

This invention was made with Government support under Grant No. CHE1629358 awarded by the National Science Foundation. The Government has certain rights in the invention.

BACKGROUND OF THE INVENTION

Thermosets play a key role in the modern plastics and rubber industries, representing approximately 18% of current polymer material production with a worldwide annual production of 65 million tons. However, the high density of chemical crosslinks that give thermosets their useful properties (e.g., chemical/thermal resistance, and tensile strength) comes at the cost of limited opportunities for degradation and reprocessing (1, 2). As a consequence, the vast majority of currently produced thermoset materials is incinerated or stored in landfills following use; a negligible fraction is repurposed or reused. Thus, novel thermoset reprocessing and upcycling strategies that can seamlessly integrate with existing manufacturing workflows could offer tremendous opportunities to minimize plastic and rubber waste.

To date, perhaps the most widely studied strategies for enabling reprocessing of thermosets involve the use of dynamic covalent bond exchange reactions (3). For example, "vitrimers," which are polymer networks that undergo associative covalent bond exchange (e.g., transesterification) upon heating and/or in the presence of a catalyst (4, 5), display many of the desirable properties of thermosets with additional features such as moldability and dissolvability into smaller cyclic fragments for re/upcycling. Nevertheless, commercially important high-performance thermosets often lack appropriate bonding motifs for facile conversion into vitrimers.

SUMMARY OF THE INVENTION

The present disclosure describes functional oligomers and functional polymers comprising:
 i) one or more instances of linear units, wherein each instance of the linear units is of the formula:

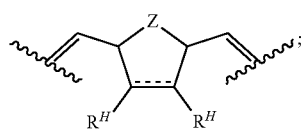

ii) one or more instances of functional units, wherein each instance of the functional units is independently of the formula:

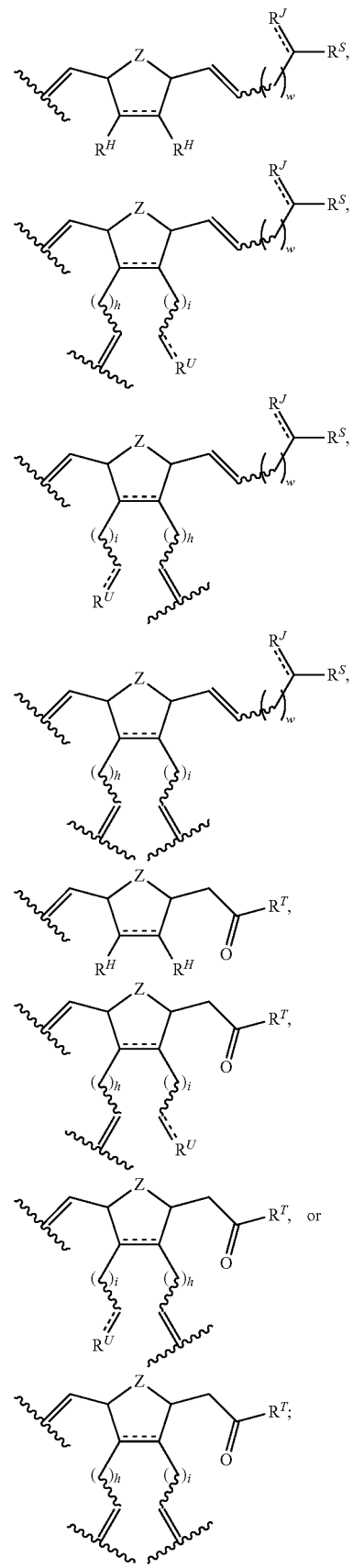

iii) optionally one or more instances of crosslinking units, wherein each instance of the crosslinking units is of the formula:

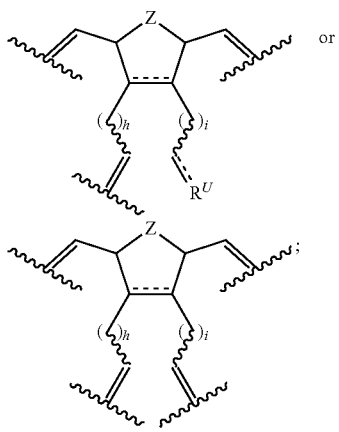

and
iv) optionally one or more additional linear units, one or more additional terminal units, and/or one or more additional crosslinking units.

The present disclosure describes hydroxylated polymers prepared by hydrolyzing a copolymer prepared by a method comprising polymerizing in the presence of a metathesis catalyst:
i) one or more instances of a first monomer of the formula:

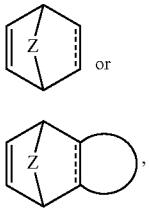

(A′)

(A″)

and
ii) one or more instances of a second monomer of Formula (B):

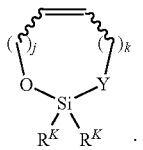

(B)

The present disclosure also describes conjugates prepared by reacting a hydroxy-reacting substance with a hydroxylated polymer. The present disclosure further describes methods of preparation, compositions, and kits.

The hydroxylated polymers may represent a new class of low-cost, densely hydroxylated, alkene-functionalized hydrocarbon frameworks with numerous potential opportunities for repurposing and/or upcyling (FIGS. 3c, 3d). The size of the hydroxylated polymers may be readily tuned by modifying the molar ratio of the first monomer to the second monomer. The hydroxylated polymers may be soluble (e.g., soluble in water at 1 atm and 20° C.). The hydroxylated polymers may be crosslinked.

The hydroxylated polymers may form conjugates by reacting with a hydroxy-reacting substance (e.g., hydroxy-reacting small molecule, hydroxy-reacting polymer). The mechanical properties of the conjugates may be better than those of the hydroxylated polymers and/or those of the hydroxy-reacting substance. The stability (e.g., physical stability, chemical stability) of the conjugates may be better than those of the hydroxylated polymers and/or those of the hydroxy-reacting substance.

In certain embodiments, the functional oligomer or functional is prepared by a method comprising hydrolyzing a copolymer prepared by a method comprising polymerizing in the presence of a metathesis catalyst:
i) one or more instances of a first monomer, wherein each instance of the first monomer is of the formula:

(A)

or salt thereof;
ii) one or more instances of a second monomer, wherein each instance of the second monomer is of the formula:

(B1)

or a salt thereof; and
iii) optionally one or more instances of a third monomer;

In certain embodiments, the functional oligomer or functional polymer is prepared by a method comprising polymerizing in the presence of a metathesis catalyst:
i) one or more instances of a first monomer, wherein each instance of the first monomer is of the formula:

(A)

or salt thereof;
ii) one or more instances of a second monomer, wherein each instance of the second monomer is of the formula:

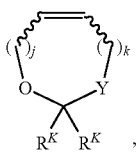

or a salt thereof; and
  iii) optionally one or more instances of a third monomer;
  wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other; and
  wherein the step of hydrolyzing the copolymer comprises hydrolyzing one or more instances of the —O—Si bonds of the copolymer to form —OH.

In certain embodiments, the functional oligomer or functional polymer is prepared by a method comprising hydrolyzing a copolymer prepared by a method comprising polymerizing in the presence of a metathesis catalyst:
  i) one or more instances of a first monomer, wherein each instance of the first monomer is of the formula:

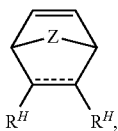
(A)

or salt thereof;
  ii) one or more instances of a second monomer, wherein each instance of the second monomer is of the formula:

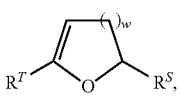
(B2)

or a salt thereof; and
  iii) optionally one or more instances of a third monomer;
  The present disclosure also describes compounds of Formula (B1):

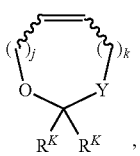
(B1)

and salts thereof.
The present disclosure also describes copolymers prepared by a method comprising polymerizing:
  one or more instances of a first monomer;
  one or more instances of a second monomer, wherein the second monomer is a compound of Formula (B1), or a salt thereof; and
  optionally one or more instances of a third monomer;
  wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other;
  in the presence of a metathesis catalyst.

The present disclosure also describes method of preparing copolymers comprising polymerizing:
  one or more instances of a first monomer;
  one or more instances of a second monomer, wherein the second monomer is a compound of Formula (B1), or a salt thereof; and
  optionally one or more instances of a third monomer;
  wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other;
  in the presence of a metathesis catalyst.

In certain embodiments, at least one instance of the first monomer is of Formula:

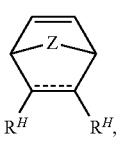
(A)

or salt thereof.

Thermosetting polymers are typically difficult to be recycled. The functional oligomers and functional polymers may be degradation (e.g., hydrolysis) products of thermosetting polymers. The functional oligomers or functional polymers may contain functional groups, e.g., —OH and/or —CHO. The functional oligomers and functional polymers may be soluble in, e.g., commercially available solvents (e.g., THF). The functional oligomers and functional polymers may be useful for recycling thermosetting polymers. The functional oligomers and functional polymers may be useful as starting materials for preparing additional oligomers or polymers.

The details of certain embodiments of the invention are set forth in the Detailed Description of Certain Embodiments, as described below. Other features, objects, and advantages of the invention will be apparent from the Definitions, Figures, Examples, Clauses, and Claims. The aspects described herein are not limited to specific embodiments, methods, apparati, or configurations, and as such can, of course, vary. The terminology used herein is for the purpose of describing particular aspects only and, unless specifically defined herein, is not intended to be limiting.

BRIEF DESCRIPTION OF THE DRAWINGS

(FIG. 1A) The incorporation of silyl ethers within polynorbornene strands (with iPrSi) or between polynorbornene strands (with SiXL) are expected to yield dramatically different results. (FIG. 1B) pDCPD doped with 20% v/v SiXL remains intact after 12 hour TBAF treatment. (FIG. 1C) Shear rheology on THF-swollen samples shows a more dramatic TBAF-dependent loss in storage modulus for samples containing small amounts (2.5 vol % and 5 vol %) of iPrSi compared to 20 vol % of SiXL, highlighting the greater contribution of cleavable strands to network integrity. Samples were exposed to TBAF for 12 h at room temperature. Centre values denote average. Error bars denote s.e.m.; n=3 for mass quantification, n=2-4 for rheology.

(FIG. 2A) Doped pDCPD shows no statistically significant difference in modulus at low iPrSi loadings by dynamic mechanical analysis. (FIG. 2B) iPrSi doping results in increased carbon release in synthetic seawater. n.s.—P>0.1, *—P<0.05, **—P<0.01.

(FIG. 3A) Comparison of $^{13}$C NMR spectra of pDCPD derived from CP-MAS or from analysis of soluble fragments after TBAF treatment. (FIG. 3B) High-resolution $^{13}$C NMR enables assignment and characterization of pDCPD. (FIG. 3C) pDCPD fragments are poised for further modification and reprocessed into new materials. (FIG. 3D) TEM images of fragments before PDMS modification. TEM images of fragments (stained with RuO4) derived from 10 vol % iPrSi-pDCPD, showing an average particle size of ~4 nm (FIG. 3E) Images of PDMS composites containing different weight percents of pDCPD fragments. (FIG. 3F) Mechanical characterization of composites with or without 0.5 wt % pDCPD fragments. *—P<0.05, **—P<0.01.

(FIG. 7A) Image of weathering setup. Samples were kept inside clear glass vials over the course of weathering. (FIG. 7B) Measured irradiance for samples during weathering experiments and comparison to solar reference spectra. (FIG. 7C) Images of samples before and after weathering, showing some bleaching of the material.

(FIG. 14A) $^1$H NMR and (FIG. 14B) DOSY spectra of pDCPD fragments after PLA growth.

(FIG. 16A) $^1$H NMR and (FIG. 16B) DOSY spectra of pDCPD fragments after PEG conjugation.

(FIG. 17A) Schematic showing thermosets are often synthesized from the crosslinking of linear prepolymers with f crosslink functionalities. The resulting materials can have outstanding properties, but they often have unknown numbers of crosslinks (c) and they are typically non-degradable/non-reprocessable. (FIG. 17B) Theoretical model describing the amount of cleavable monomer (x) relative to non-cleavable crosslinks (c) that will result in degradation of materials composed of strands of functionality f=3,000 into soluble products. (FIG. 17C) The silyl ether-based monomer iPrSi copolymerizes efficiently with norbornenes through ROMP, which introduces cleavable silyl ether sites within the polynorbornene strands of pDCPD. The introduction of x cleavable bonds within the strands of pDCPD with c crosslinks provides degradation fragments with (c/(x+1)) crosslinks per strand. (FIG. 17D) The silyl ether crosslinker SiXL copolymerizes with norbornenes through ROMP, but introduces cleavable silyl ether sites between polynorbornene strands (that is, in crosslinks). The introduction of y cleavable crosslinks produces pDCPD with c+y crosslinks. Thus, soluble products can only be generated when y>>c, suggesting that complete material degradation at low cleavable crosslinker loadings will be difficult. stat, statistical copolymer.

(FIG. 18A) iPrSi-doped pDCPD samples show iPrSi volume-fraction-dependent dissolution in a THF solution of TBAF. Samples containing 10% or 15% iPrSi are almost entirely dissolved. (FIG. 18B) Quantification of residual mass of pDCPD samples after TBAF treatment at room temperature for 12 h or 17 d for iPrSi- or SiXL-doped samples, respectively. The 7.5% and 10% iPrSi-doped samples show nearly complete mass loss, whereas samples prepared with up to 80% of SiXL remain intact.

(FIG. 19A) iPrSi-doped pDCPD shows no significant difference in Young's modulus (measured at room temperature) between 0% and 10% iPrSi. The 33% and 50% iPrSi-doped samples are closer to or above their Tg value at room temperature (46±7° C. and 14±2° C., respectively), which explains their different tensile behaviours compared to that of native pDCPD. (FIG. 19B) iPrSi-doped pDCPD shows no significant difference in strain at break at low iPrSi loadings. (FIG. 19C) Stress-strain curves obtained at room temperature for iPrSi-doped pDCPD samples and native pDCPD, highlighting the similarity between the 10% iPrSi-doped sample and native pDCPD, as well as the ability to control stress-strain behaviour with comonomer loading. (FIG. 19D) iPrSi-doped pDCPD samples show comparable reduced moduli to native pDCPD, as assessed by nanoindentation. (FIG. 19E) iPrSi-doped pDCPD shows similar decomposition temperatures as native pDCPD. (FIG. 19F).

Representative image sequences of impact and rebound for 0% and 10% iPrSi-doped pDCPD impacted by steel microparticles. (FIG. 19G) Coefficient of restitution plots for 0% and 10% iPrSi-doped pDCPD. Positive, zero and negative coefficients of restitution correspond to particle rebound, embedment and film perforation, respectively. These results suggest that the comonomer approach could enable optimization of degradation for applications of interest. NS, not significant, P>0.1; *P<0.05; **P<0.01. Statistical significance determined through a Student's t-test. Centre values denote average. Error bars denote s.e.m. n=3 for the 0% and 10% samples, n=4 for the 20% sample, n=2 for the 33% sample and n=1 for the 50% sample used for tensile testing, n=46-49 for the nanoindentation measurements, n=3 for DMA and n=3 for weathering experiments.

(FIG. 20A) GPC traces of fragments derived from the dissolution of iPrSi-doped pDCPD. As expected, increased iPrSi loading leads to smaller degradation products, as evidenced by increases in retention time. (FIG. 20B) Images of representative recycled and new pDCPD samples. Discolouration of the recycled sample is attributed to residual Ru from the first crosslinking and degradation process. Samples prepared using fragments from the TBAF dissolution method (right). Samples prepared using fragments from the HF-pyridine dissolution method (left). (FIG. 20C) Stress-strain curves from dogbone-shaped samples of new and recycled pDCPD, showing comparable stress-strain curves with increased strain at break for the recycled samples. (FIG. 20D) Elastic moduli of native and recycled pDCPD, as assessed by DMA and tensile testing. (FIG. 20E) Carbon fibre recovery from 10% iPrSi-doped pDCPD composites. Costly carbon fibre filler is often unrecoverable from thermoset composites. The degradable comonomer approach allows its recovery under mild conditions. (FIG. 20F) Raman spectra of pristine and recovered carbon fibres, suggesting no chemical damage to the carbon fibre material. Centre values denote average. Error bars denote s.e.m; n=3 for all conditions. a.u., arbitrary units.

(FIG. 22A) Images of pDCPD with various amounts of iPrSi and without iPrSi. (FIG. 22B) Images of pDCPD with and without 20 vol % SiXL. (FIG. 22C) pDCPD doped with up to 80 vol % SiXL remains intact after 12 h of TBAF treatment.

(FIG. 23A) Samples containing different amounts of iPrSi (0, 2.5, 5, 7.5 and vol %) were incubated in 0.5 M TBAF in THF overnight, showing iPrSi-dependent degradation. (FIG. 23B) Loss moduli for native pDCPD and 2.5% and 5% iPrSi-doped samples before and after TBAF treatment, as measured by oscillatory rheology. The storage moduli are presented in FIG. 1C. (FIG. 23C) THF swelling ratios (THF swollen mass divided by dry mass) for native pDCPD and 2.5% and 5% iPrSi-doped samples following TBAF treatment. Centre values denote average. Error bars denote s.e.m. n=3 for all samples.

(FIG. 24A) Tan-delta plots of pDCPD samples as a function of iPrSi incorporation. (FIG. 24B) Storage moduli collected at $T_g$—60° C. for all samples. n=3 for all samples, except for 33% where n=S.

(FIG. 25A) Structure of EtSi, which differs from iPrSi in terms of the alkyl substituents on the silyl ether group. The less sterically hindered ethyl groups render this monomer more susceptible to cleavage. (FIG. 25B) Images of 10% EtSi- or iPrSi-doped pDCPD. (FIG. 25C) 10% EtSi dissolves in 0.5 M TBAF in TH after 12 h. (FIG. 25D) Images of 10% EtSi-doped (left) and iPrSi-doped (right) pDCPD exposed to THF containing 15% concentrated aqueous HCl (12.1 N). The EtSi sample shows noticeably more rapid degradation under these conditions as compared to the iPrSi sample. Both samples are largely degraded within 12 h. In this case, acidic hydrolysis is facilitated by the presence of organic solvent to swell the network.

(FIG. 26A) Measured irradiance for samples during the weathering experiments and comparison to solar reference spectra (ASTM G177). (FIG. 26C) Ultraviolet-visiblespectra for the 0%, 10% and 20% iPrSi- and 10% EtSi-doped pDCPD samples. The sample thickness was 1 mm.

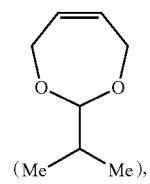

+/−HCl

Figure 30:
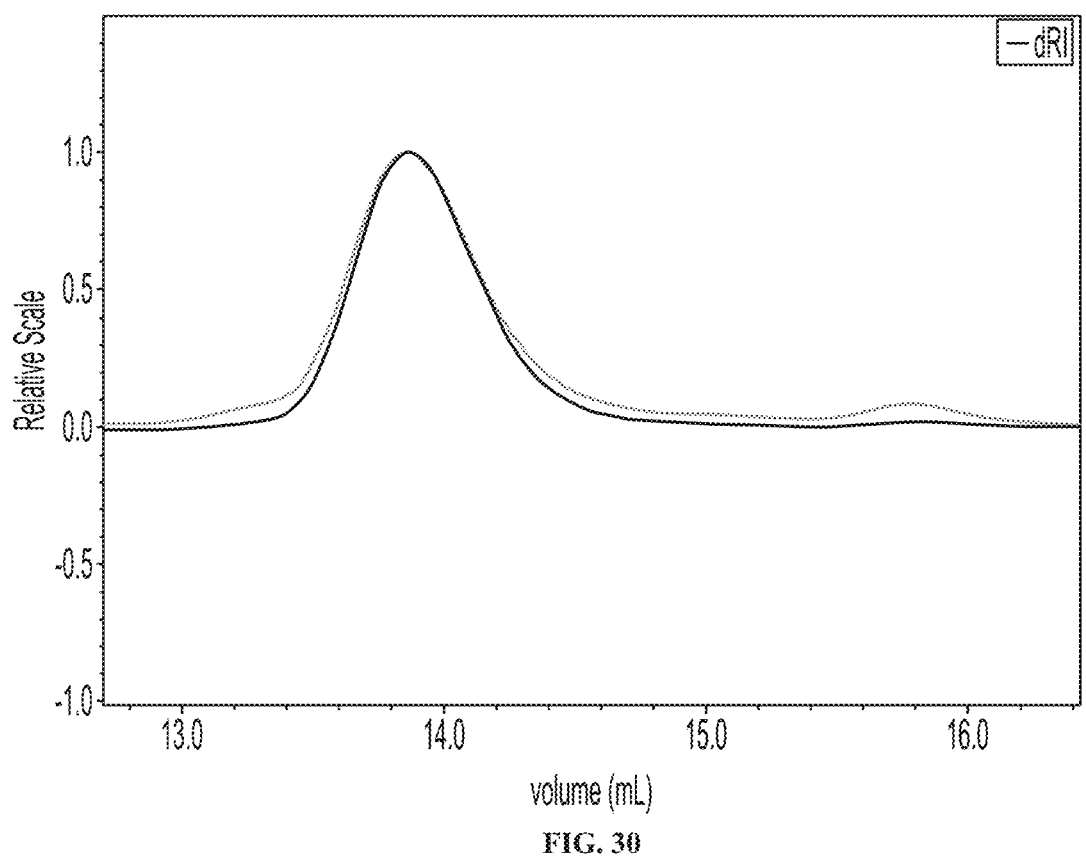

FIG. 30. GPC analysis of PEG Bottlebrush, DP=30, 1:1 PEG/iPrAc

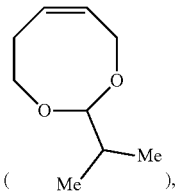 [SMILES: CC(C)C1OC/C=C\CCO1]

+/−HCl

Figure 31:
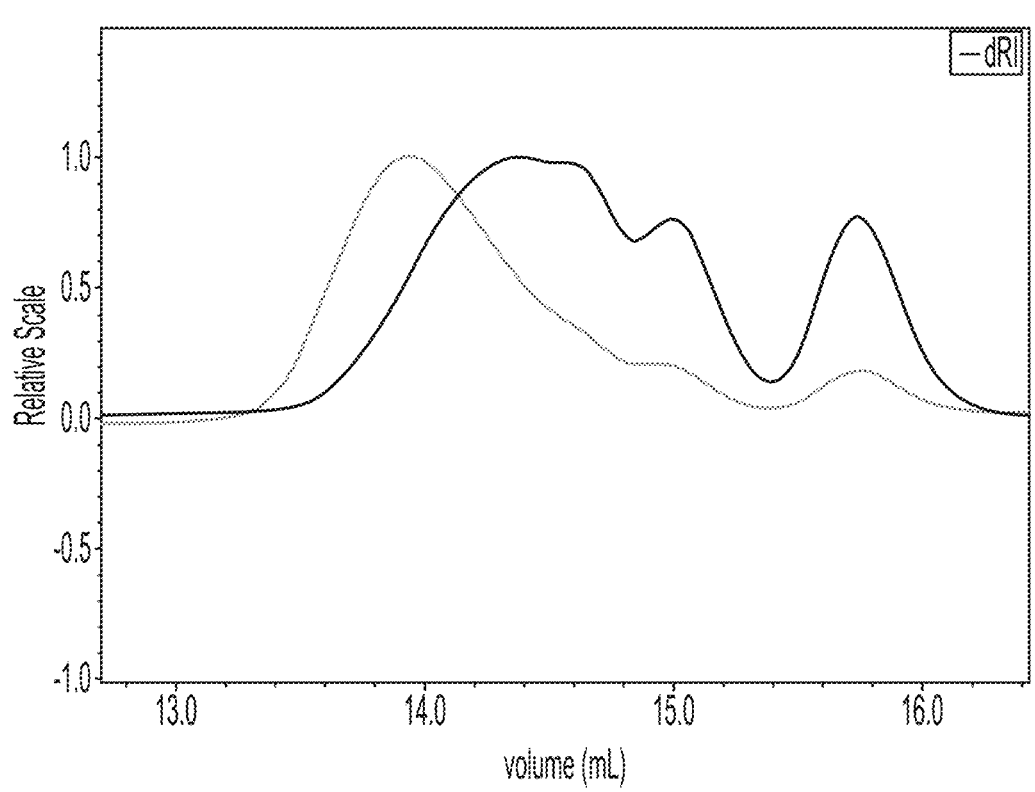

FIG. 31. GPC analysis of PEG Bottlebrush, DP=30, 1:1 PEG/iPrAc (M)+/−HCl

Figure 32:
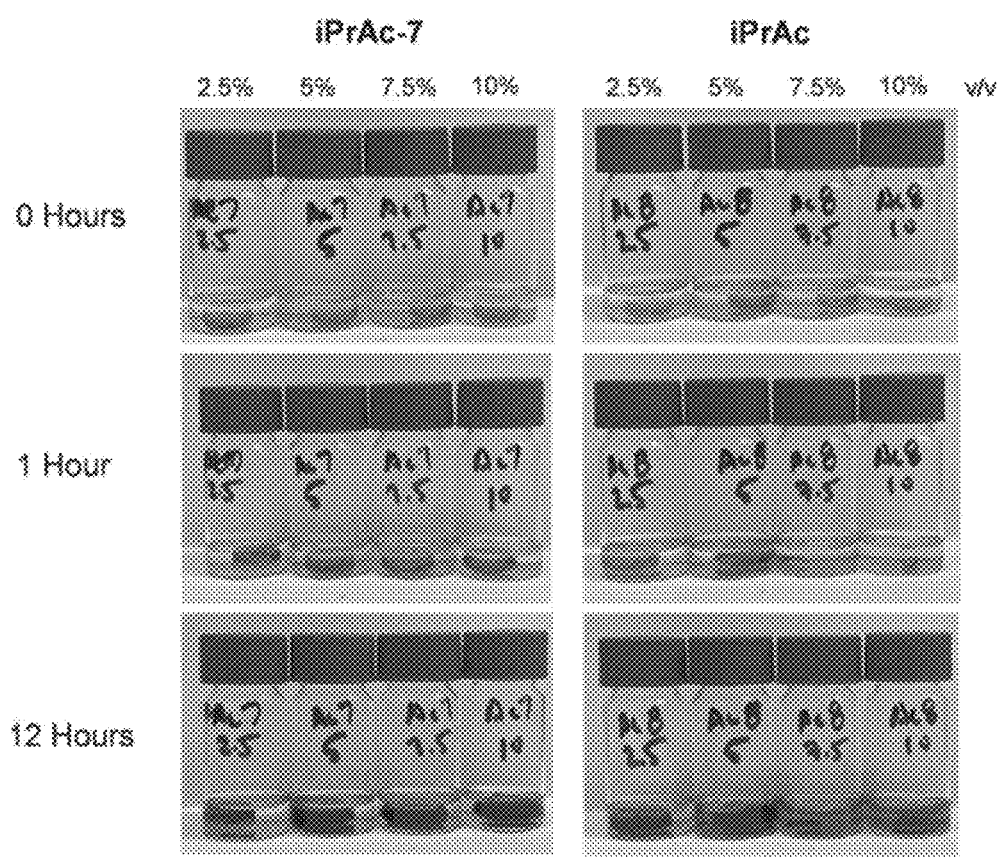

FIG. 32. GPC analysis of Acetal pDCPD: 7 vs. 8 Membered Acetals in pDCPD

Figure 33A:
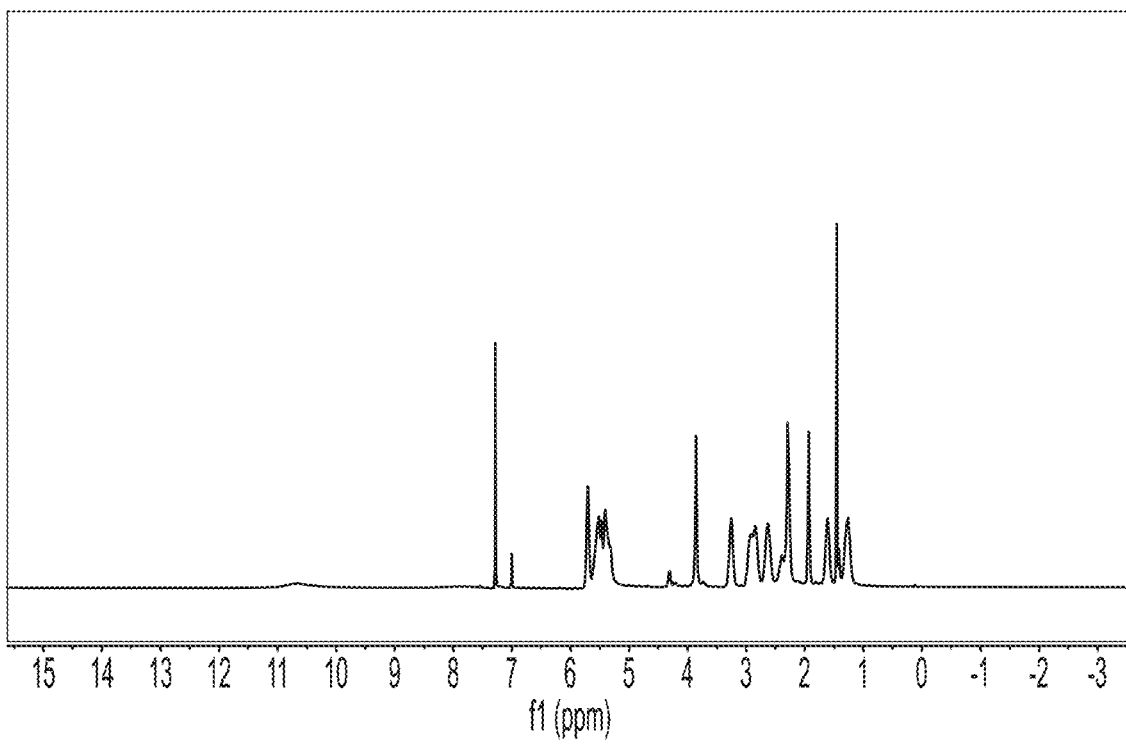
Figure 33B:
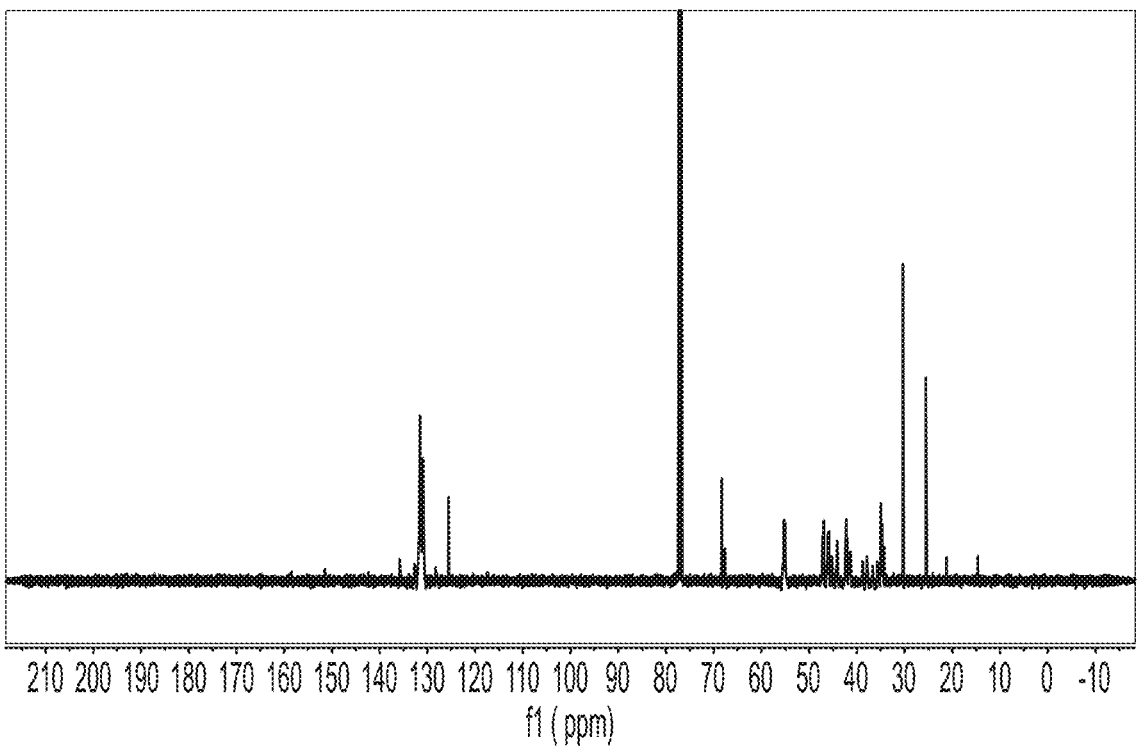

FIGS. 33A-33B. $^1$HNMR (FIG. 33A) and $^{13}$C NMR of fragments (FIG. 33B) from pDCPD with iPrAc.

Figure 34:
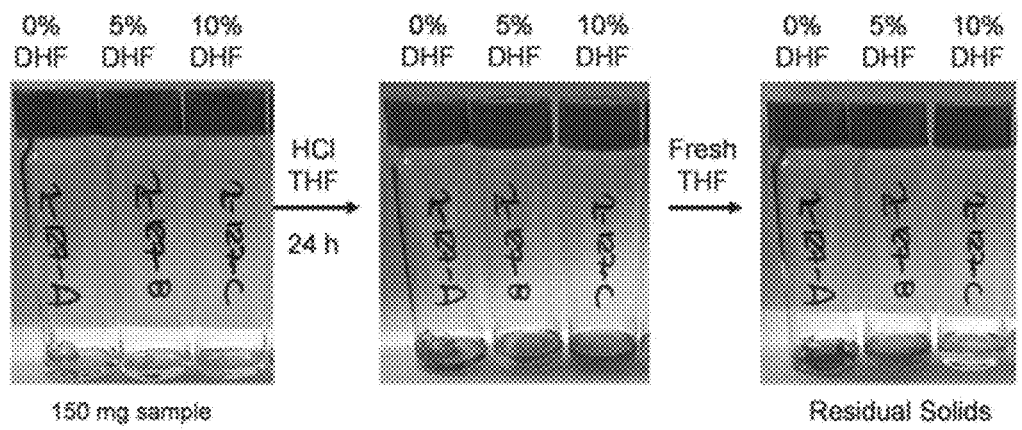

FIG. 34. Dissolution of pDCPD with non silyl-ether comonomers.

Figure 35:
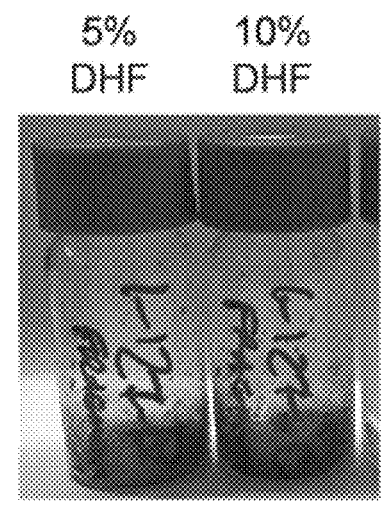

FIG. 35. Images of pDCPD fragments with non silyl-ether comonomers.

Figure 36:
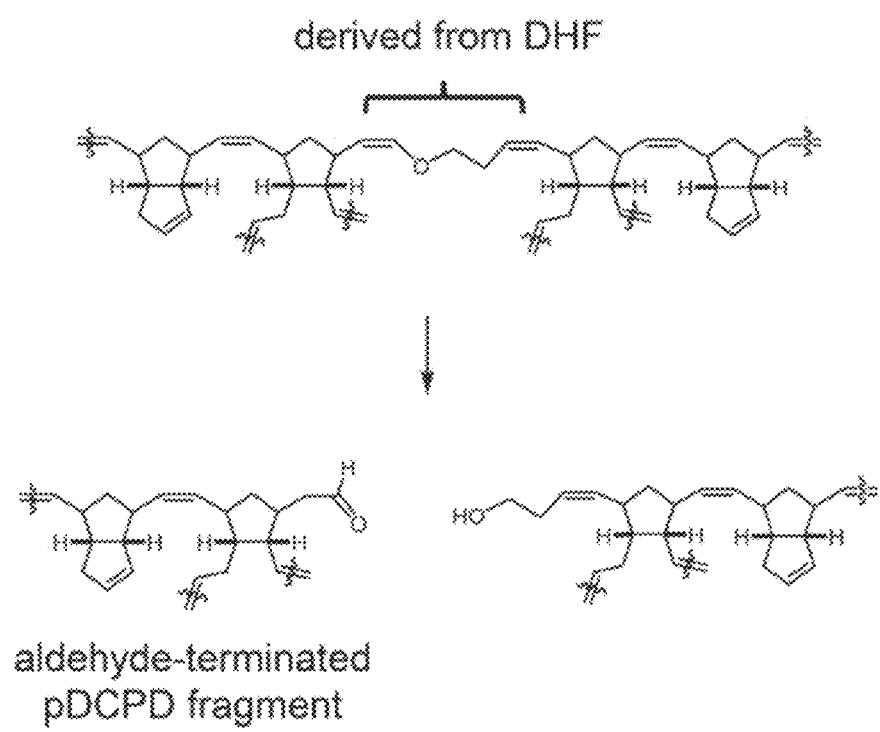
Figure 37A:
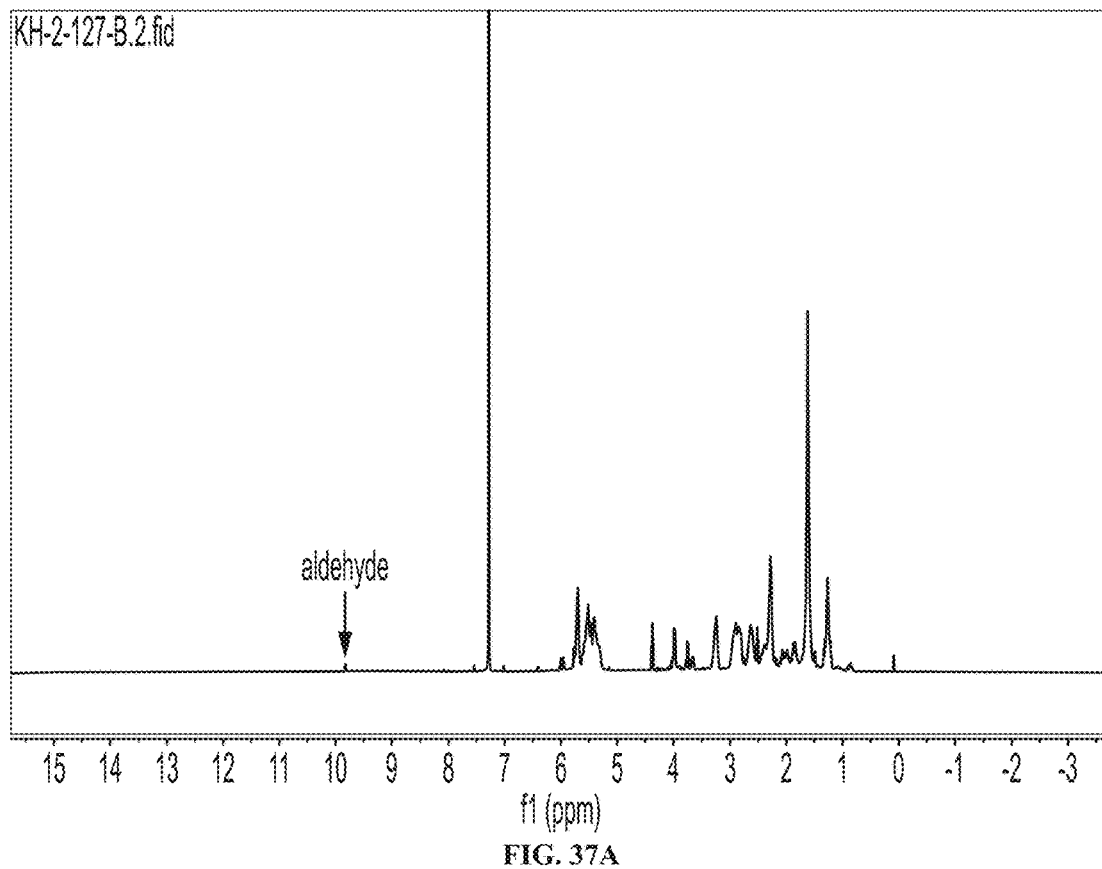
Figure 37B:
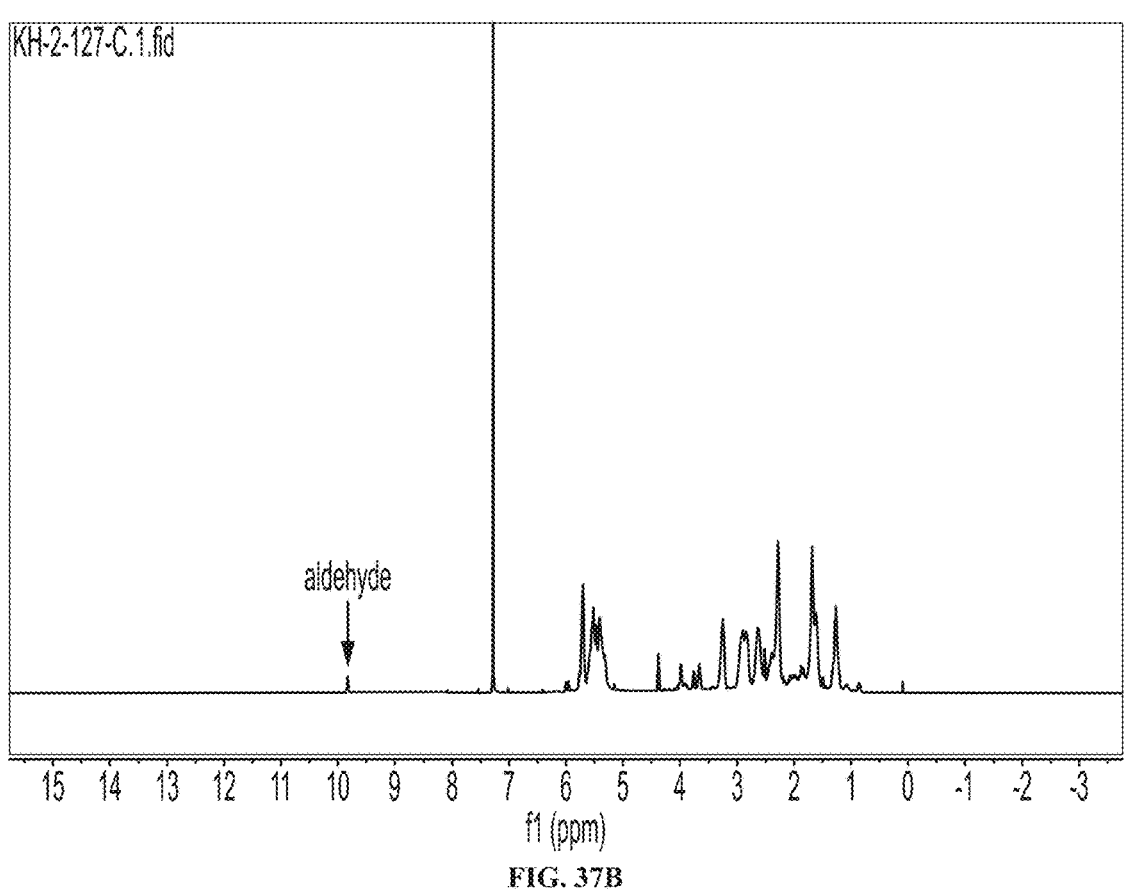

FIG. 36. Schematic on generation of aldehyde-terminated pDCPD fragment FIGS. 37A-37B. $^1$HNMR of pDCPD fragments with aldehyde functional groups. Results of 5% (FIG. 37A) and 10% (FIG. 37B) DHF

in pDCPD are shown.

Figure 38:
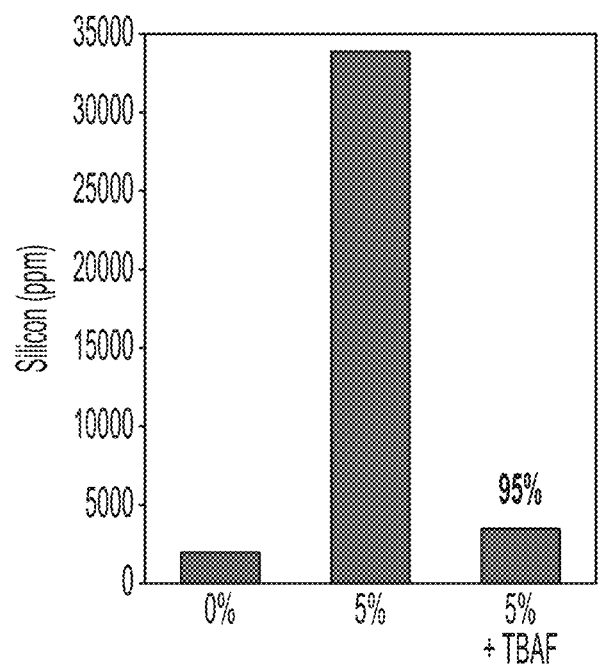

FIG. 38. ICP-OES data on solid 0% and 5% iPrSi doped pDCPD samples before and after TBAF treatment. These results demonstrate that at least 95% of the silyl ether groups in the material are cleaved under our conditions. The residual silicon signal in the 0/sample, which is expected to show no silicon in ICP-OES analysis in theory, is likely derived from environmental sources of silicon such as the glass used to prepare and digest the material.

Figure 39A:
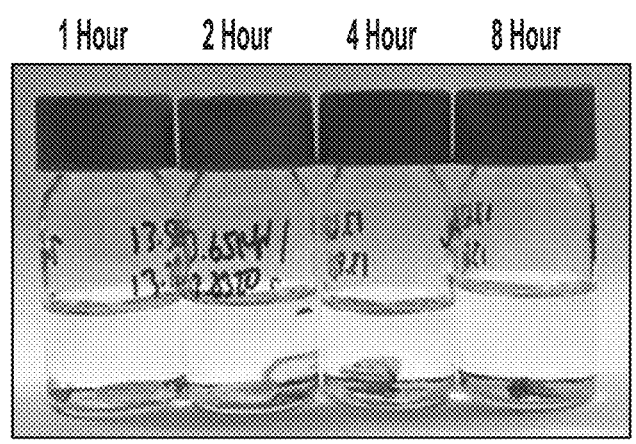
Figure 39B:
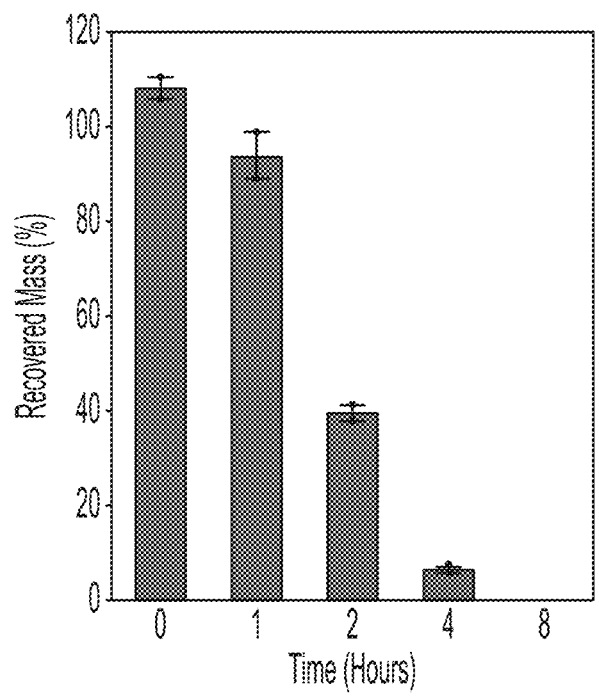

FIGS. 39A-39B. Dissolution of iPrSi doped pDCPD as a function of time. 10% iPrSi doped pDCPD was incubated with TBAF at 1, 2, 4, or 8 hours in the presence of 200 mol % TBAF. (FIG. 39A) Images of samples after treatment with TBAF for various times, followed by washing with THF to remove unreacted TBAF and to stop the reaction. (FIG. 39B) Quantification of residual solid mass as a percentage of initial sample mass. Minimal swelling of the material was visually observed, suggesting that degradation of the material proceeds via surface erosion and that diffusion of TBAF into the material is rate-limiting.

Figure 40:
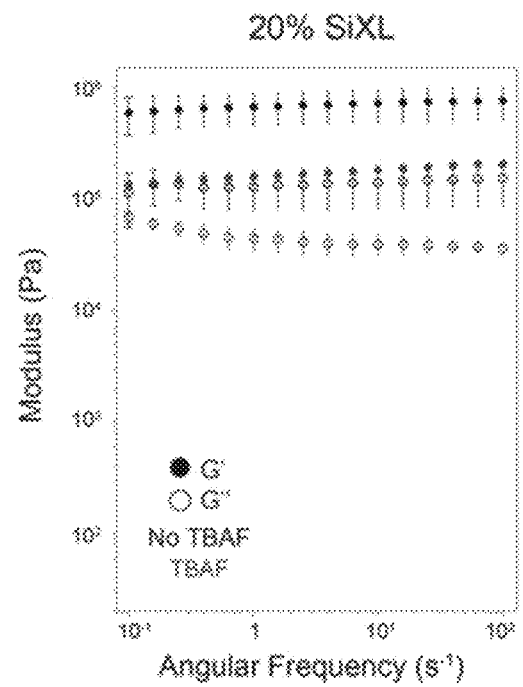

FIG. 40. Frequency sweep rheology of THF swollen samples containing 20% v/v of SiXL FIG. 41. 10% iPrSi doped pDCPD readily dissolves in the presence of hydrogen fluoride-pyridine complex in THF.

Figure 42:
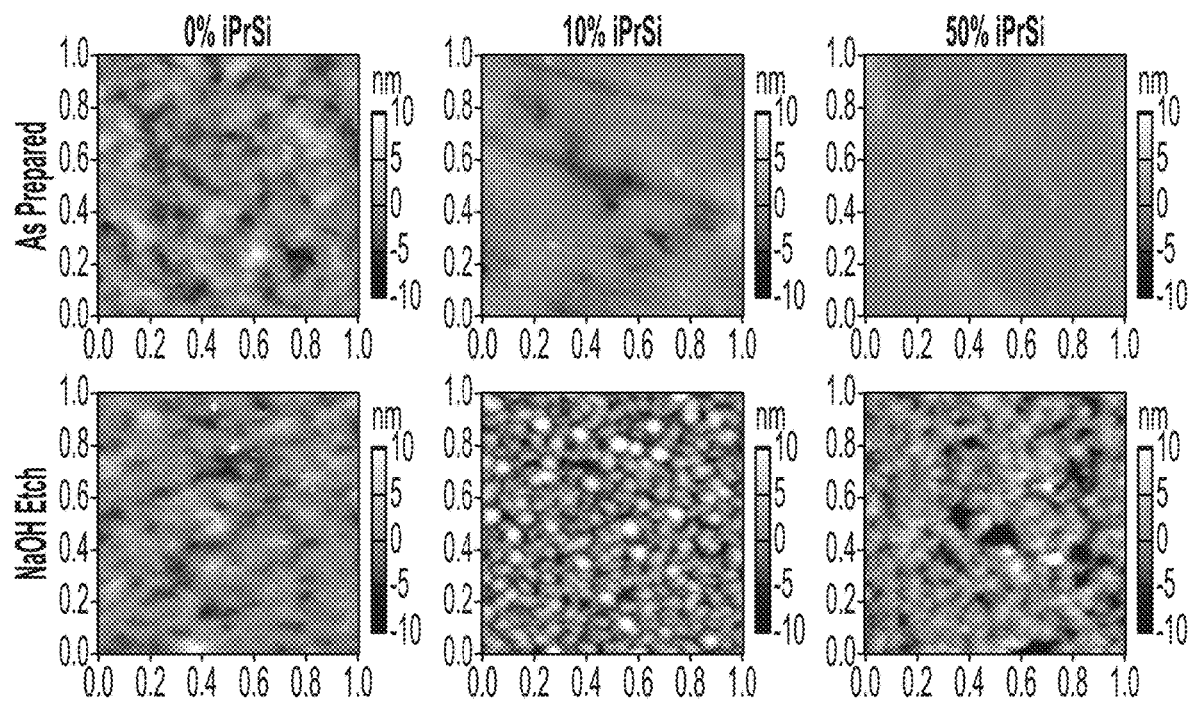

FIG. 42. iPrSi doped samples display distinct surface morphologies following exposure to aqueous NaOH as assessed by atomic force microscopy, suggesting base-mediated etching of silyl ether groups at the surface of the material.

Figure 43:
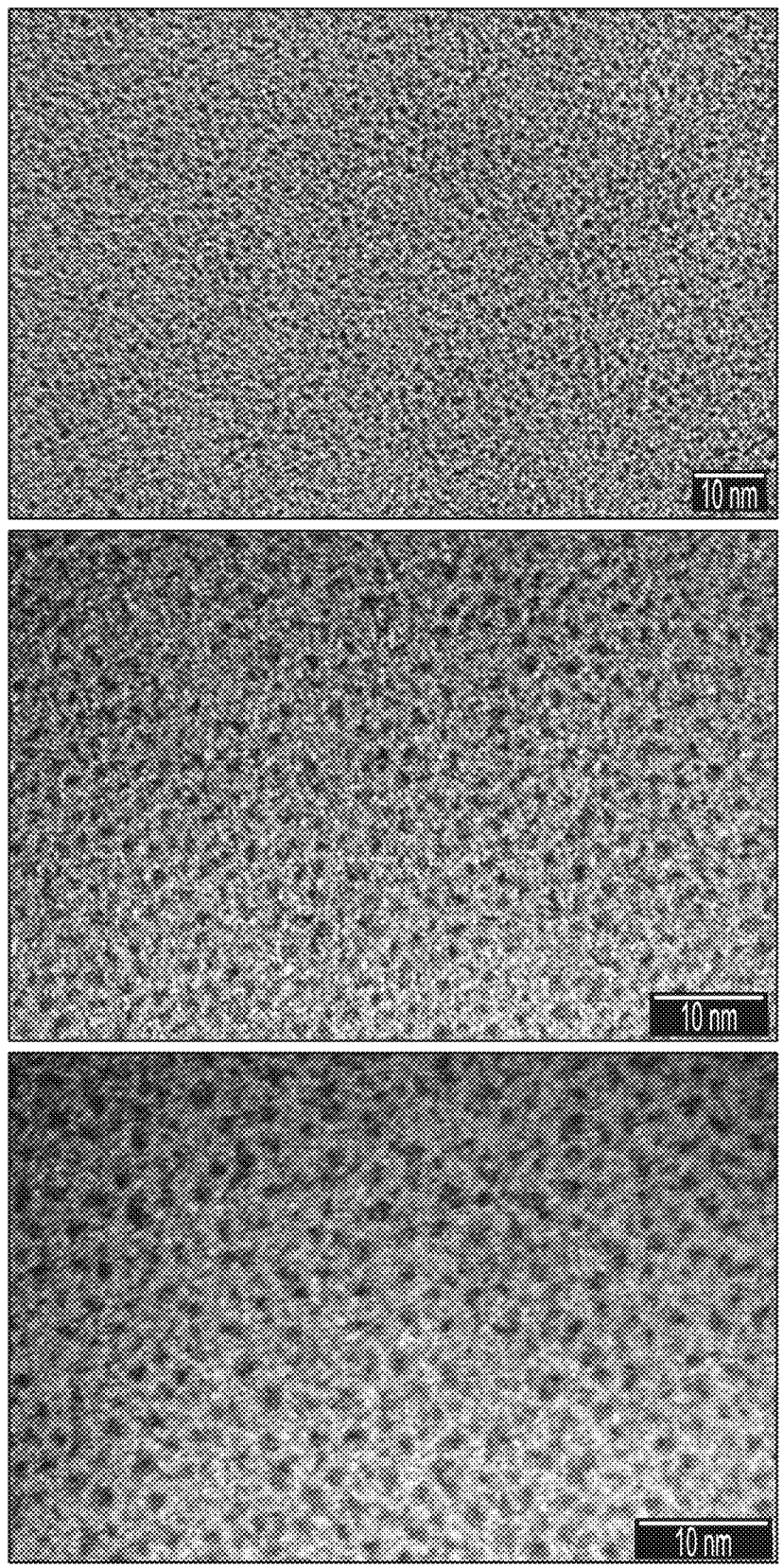

FIG. 43. TEM images of organic extracts from weathering samples, showing the presence of nanoparticles formed over the course of weathering. Scale bars are 10 nm for all images.

Figure 44:
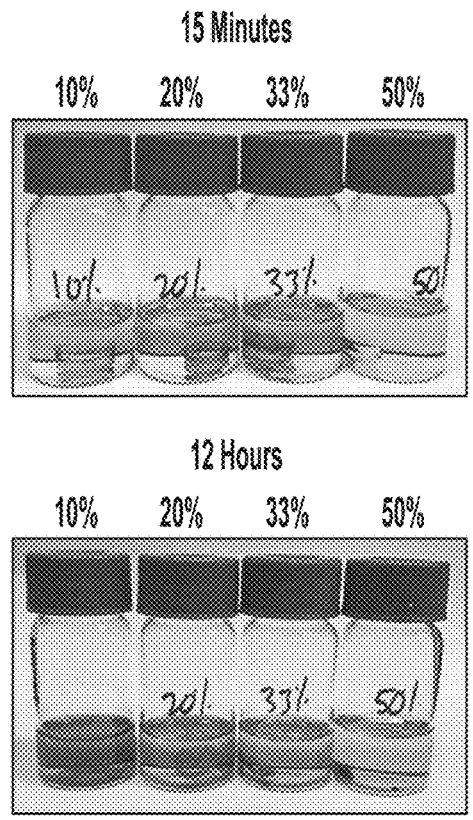

FIG. 44. Samples of pDCPD containing 10, 20, 33, and 50% iPrSi dissolve in the presence of 2 equivalents of TBAF in THF at room temperature.

Figure 45:
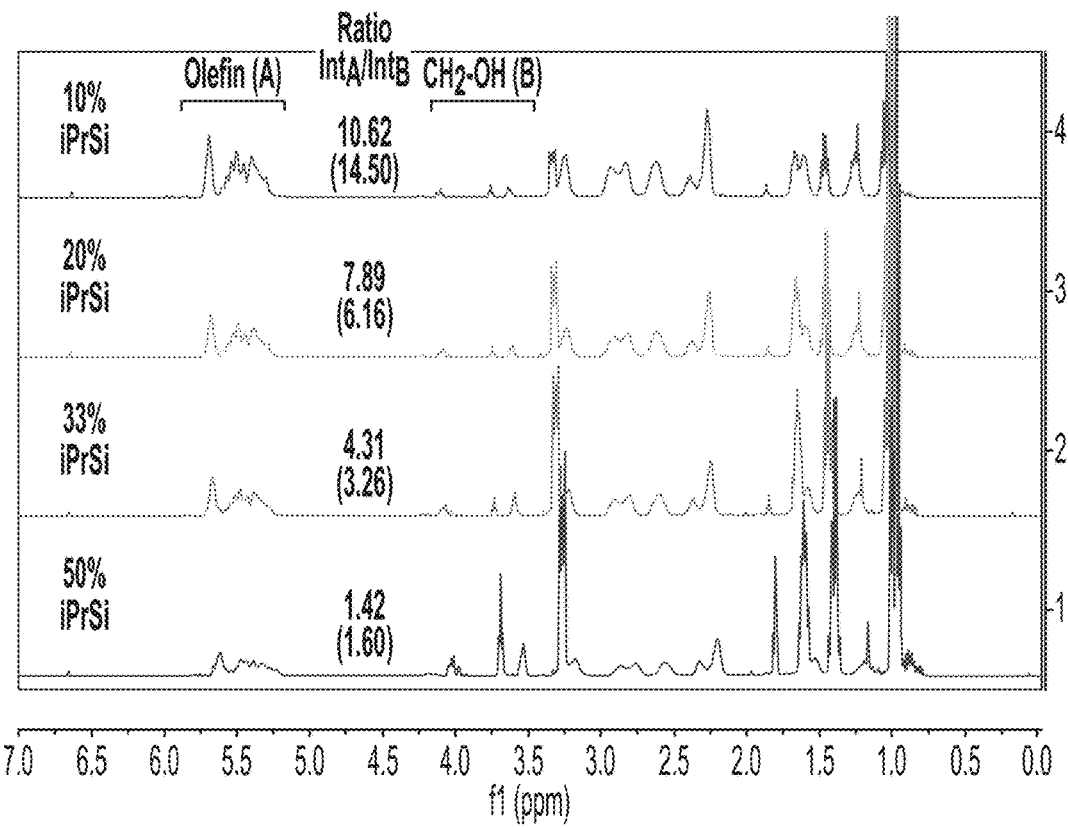

FIG. 45. $^1$H NMR (CDCl$_3$; 500 MHz.) of soluble fragments derived from materials with different amounts of hydroxyl groups, showing increased levels of silyl ether-derived fragments from pDCPD doped with more iPrSi. In parentheses are the theoretical integration values assuming equal addition of equal volumes of the two materials. These results also indicate full consumption of the norbornene component of DCPD in our materials, as the sharp peaks corresponding to unreacted DCPD are absent.

Figure 46:
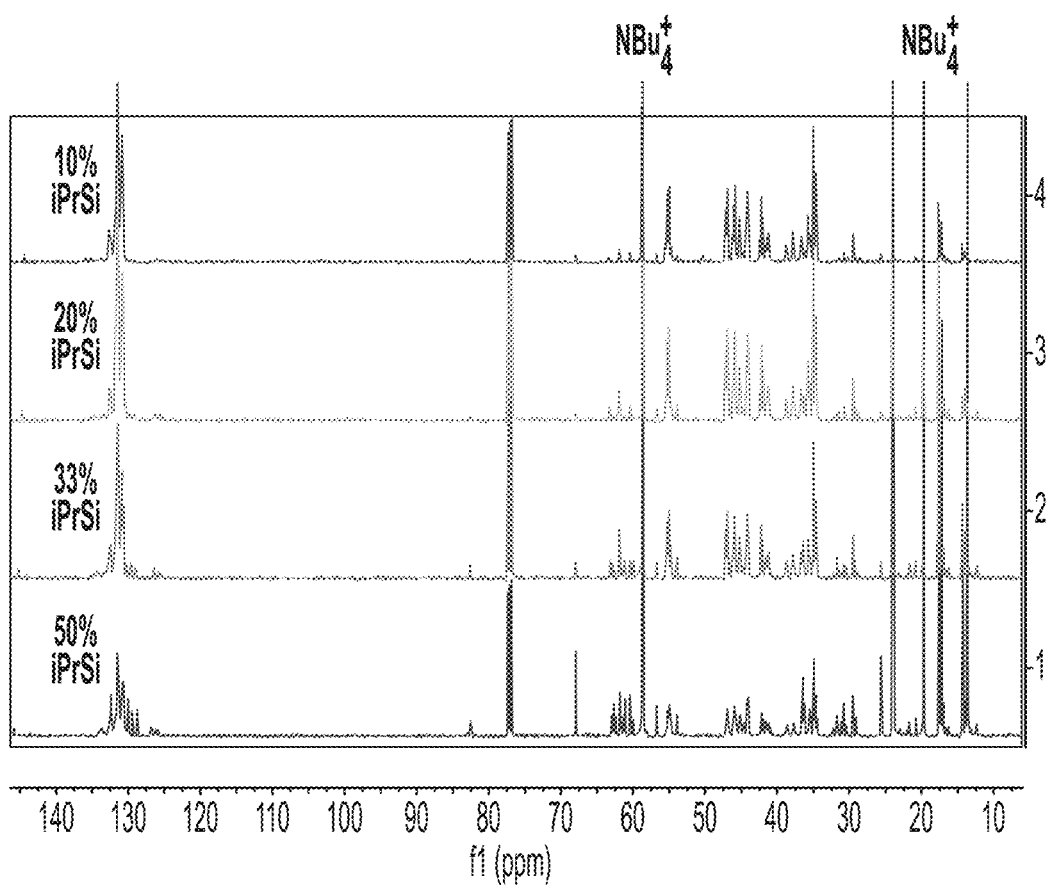

FIG. 46. Full solution-phase $^{13}$C NMR spectra (CDCl$_3$; 500 MHz) of the degradation solution, enabling characterization of crosslink density within the parent pDCPD material.

Figure 47:
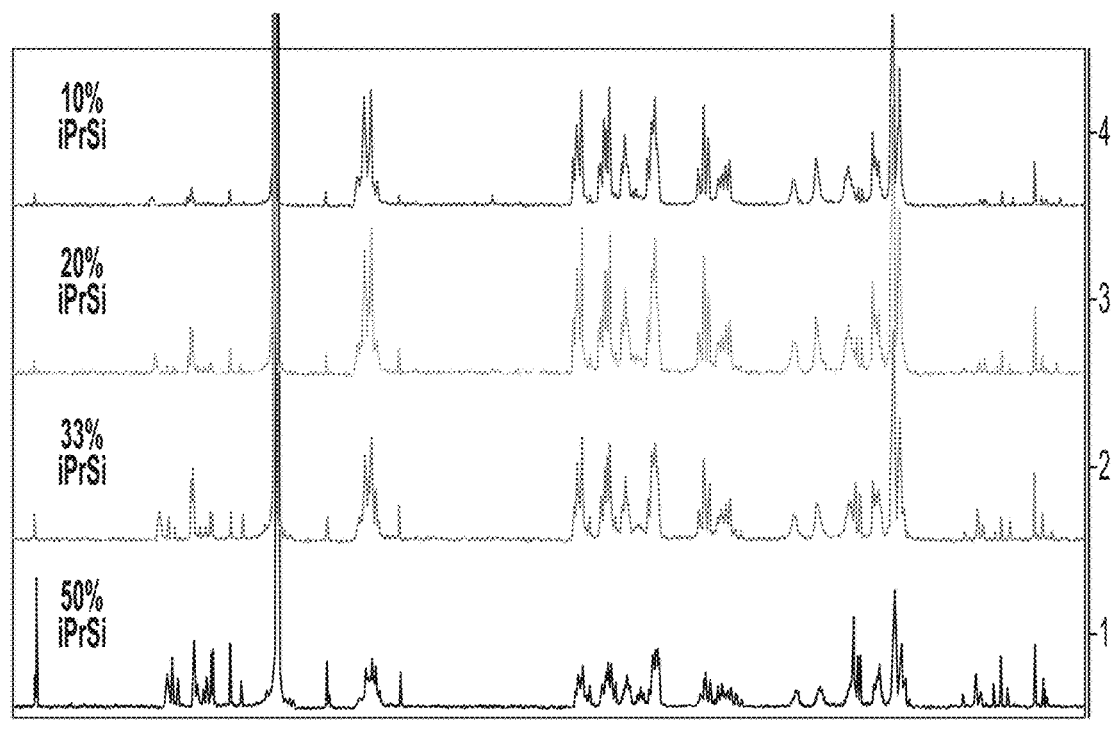
Figure 47:
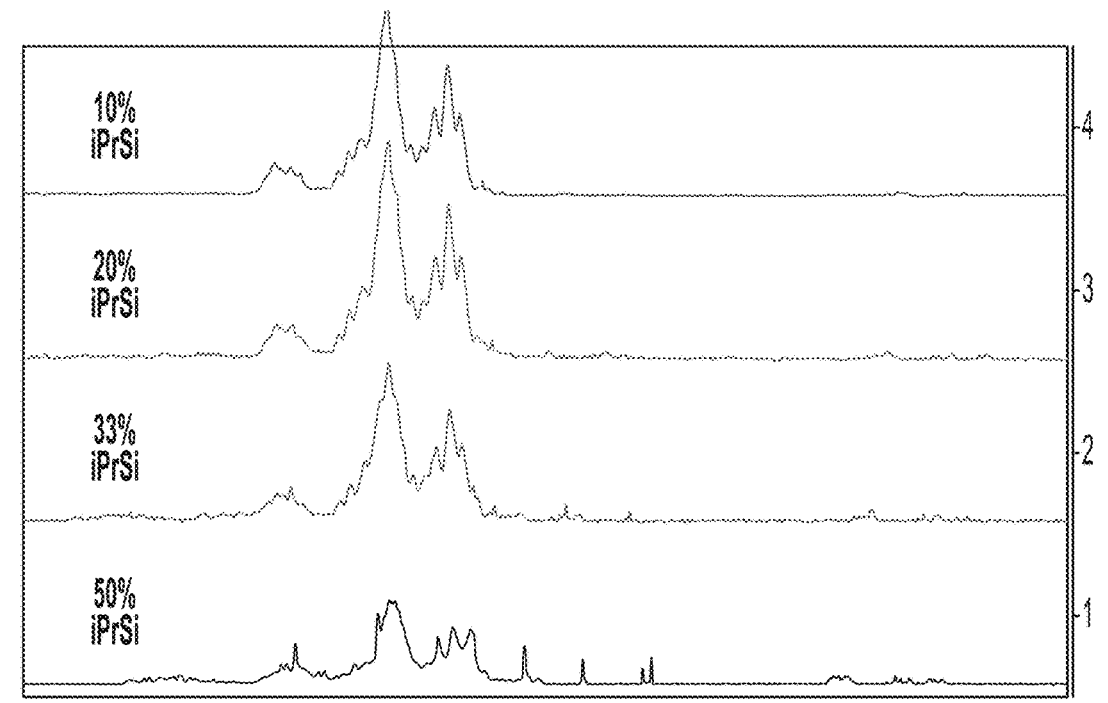

FIG. 47. $^{13}$C NMR spectra (CDCl$_3$; 125 MHz) of pDCPD fragments with different amounts of iPrSi doping.

Figure 48:
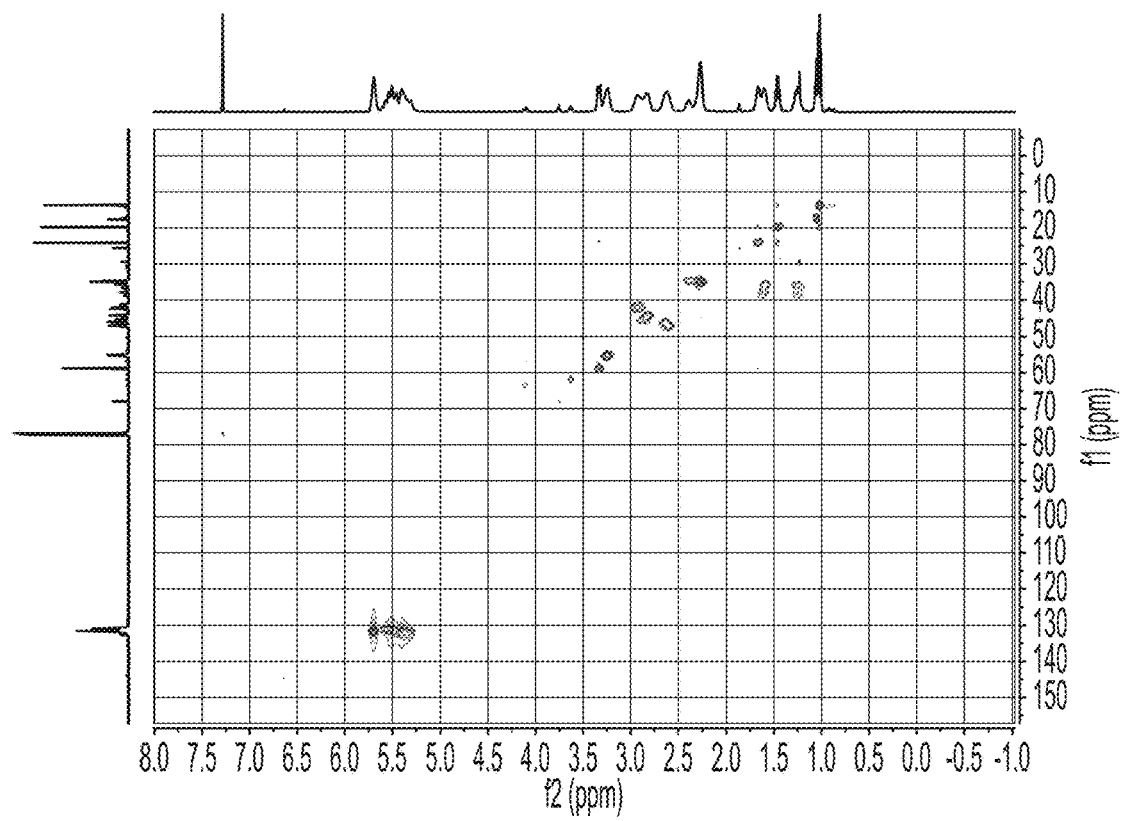

FIG. 48. Solution-phase HSQC spectrum (CDCl$_3$; 500 MHz) of the degradation solution derived from 10% iPrSi doped pDCPD.

Figure 49:
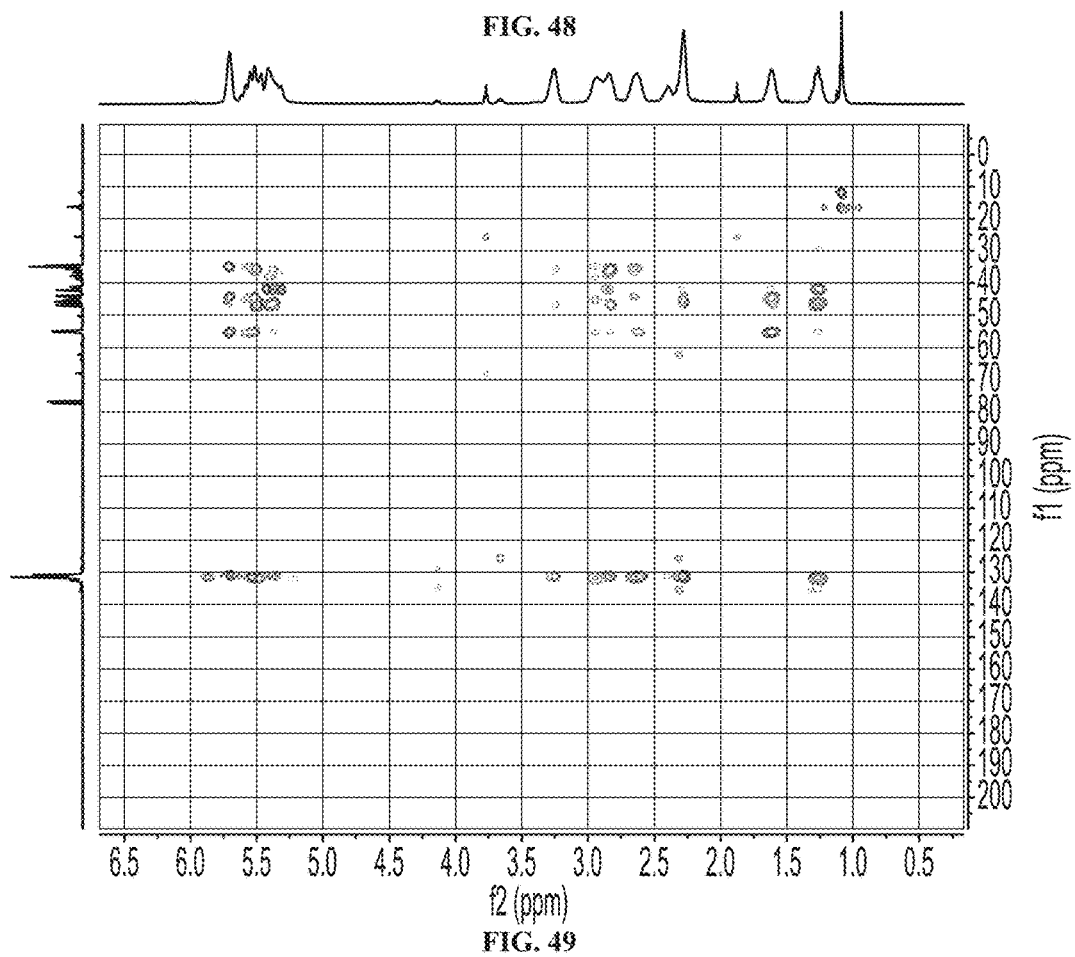

FIG. 49. Solution-phase HMBC spectrum (CDCl$_3$; 500 MHz) of the degradation solution derived from 10% iPrSi doped pDCPD.

Figure 50:
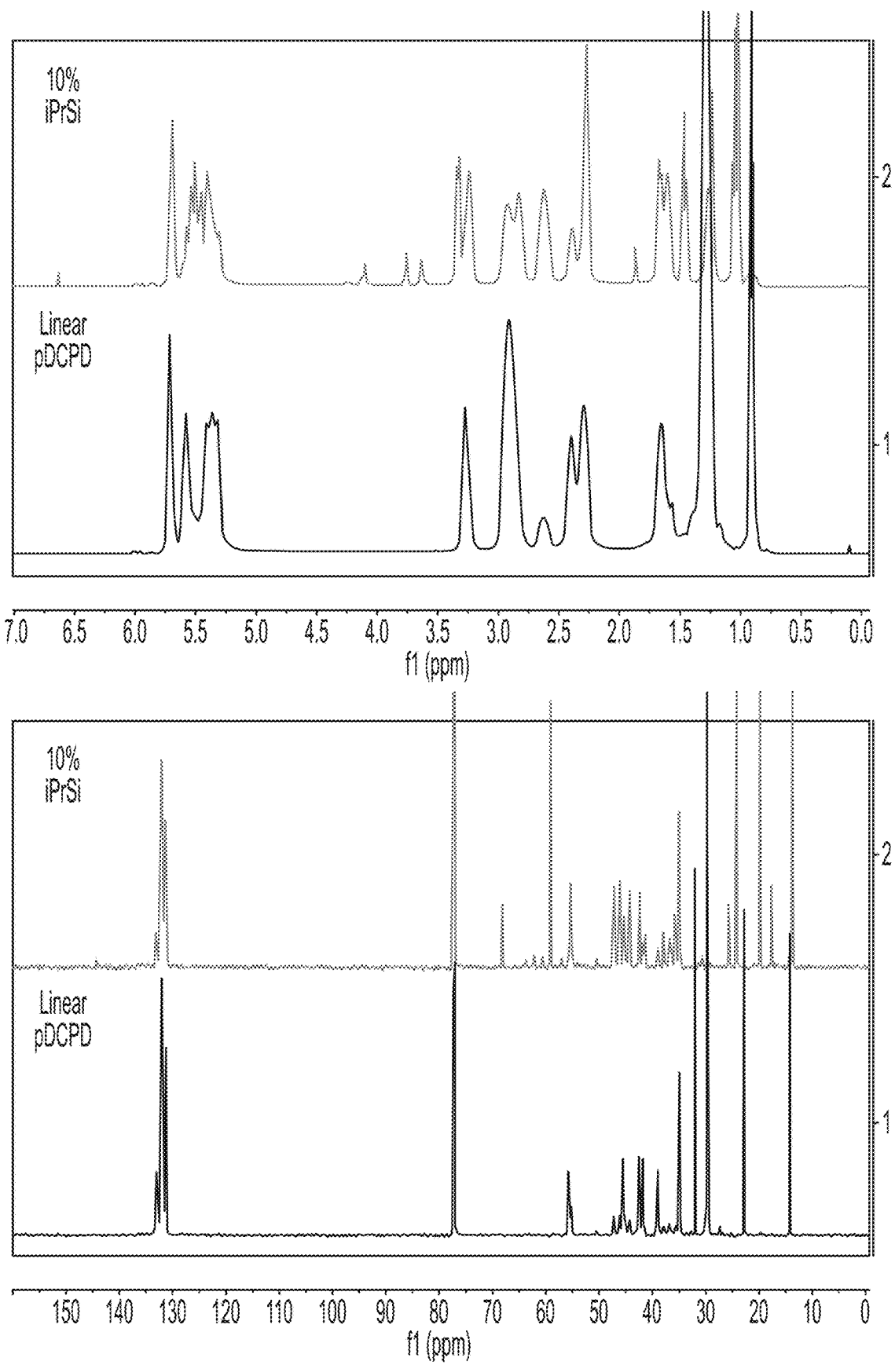

FIG. 50. Comparison of $^1$H NMR spectra (CDCl$_3$; 500 MHz/125 MHz) from our pDCPD fragments and independently synthesized linear pDCPD. Linear pDCPD was synthesized through the polymerization of DCPD with Schrock's Mo-catalyst (XiMo).

Figure 51:
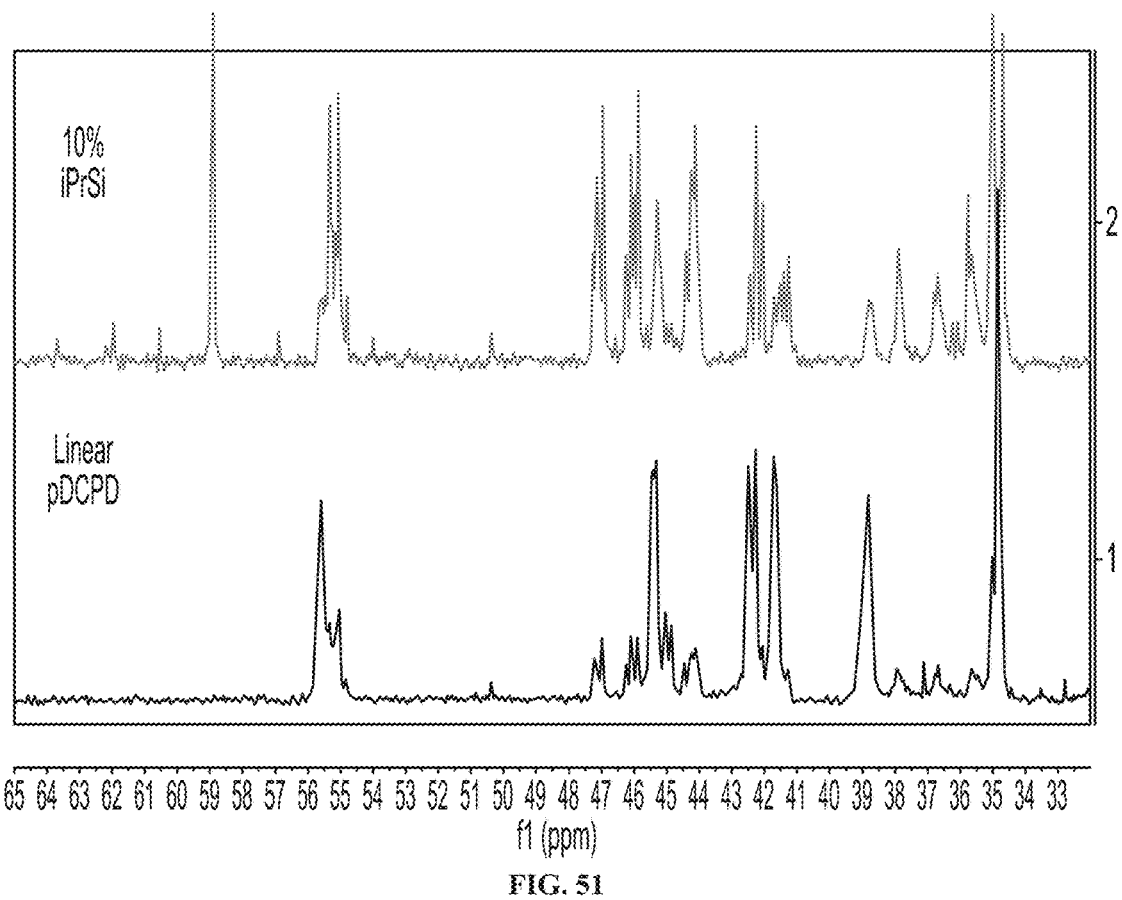

FIG. 51. $^{13}$C spectra comparing pDCPD fragments to linear pDCPD (CDCl$_3$; 125 MHz).

Figure 52:
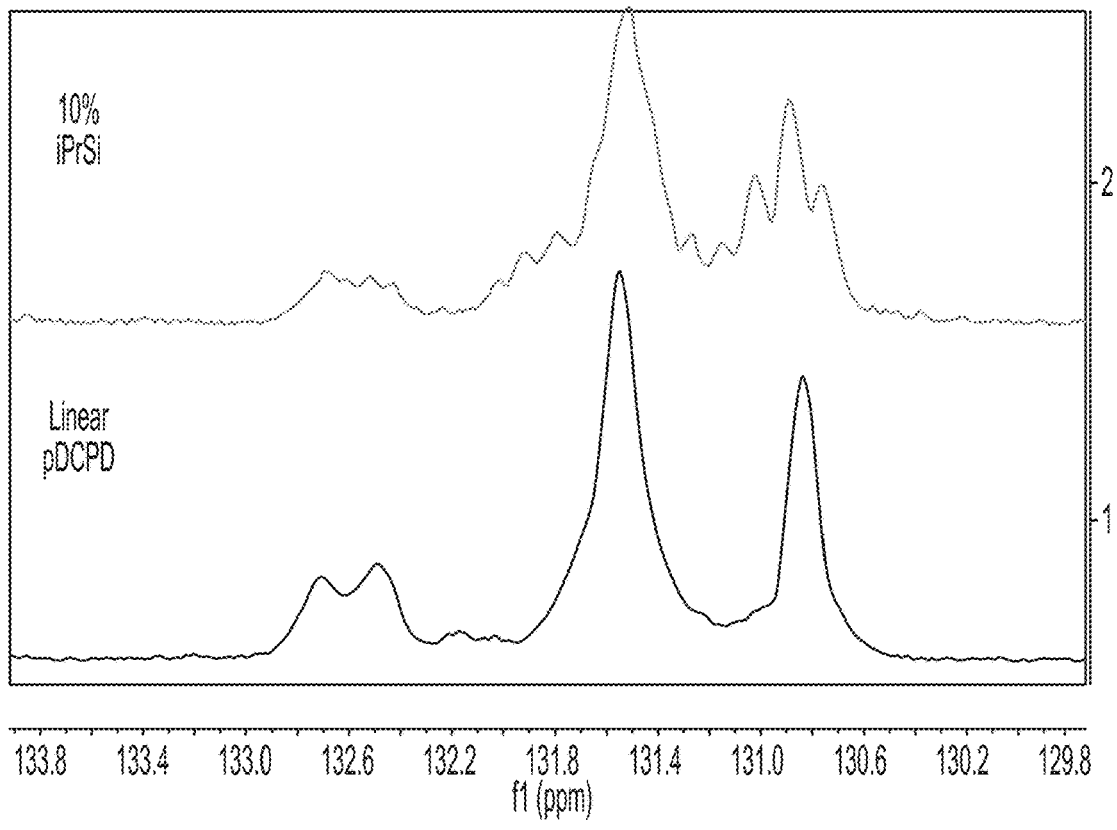

FIG. 52. $^{13}$C spectra comparing pDCPD fragments to linear pDCPD (CDCl$_3$; 125 MHz). $^{13}$C spectra, zoomed into the olefinic region, to highlight differences between pDCPD fragments and linear pDCPD. Some of the differences are assigned in the olefinic region to pDCPD crosslinks.

Figure 53:
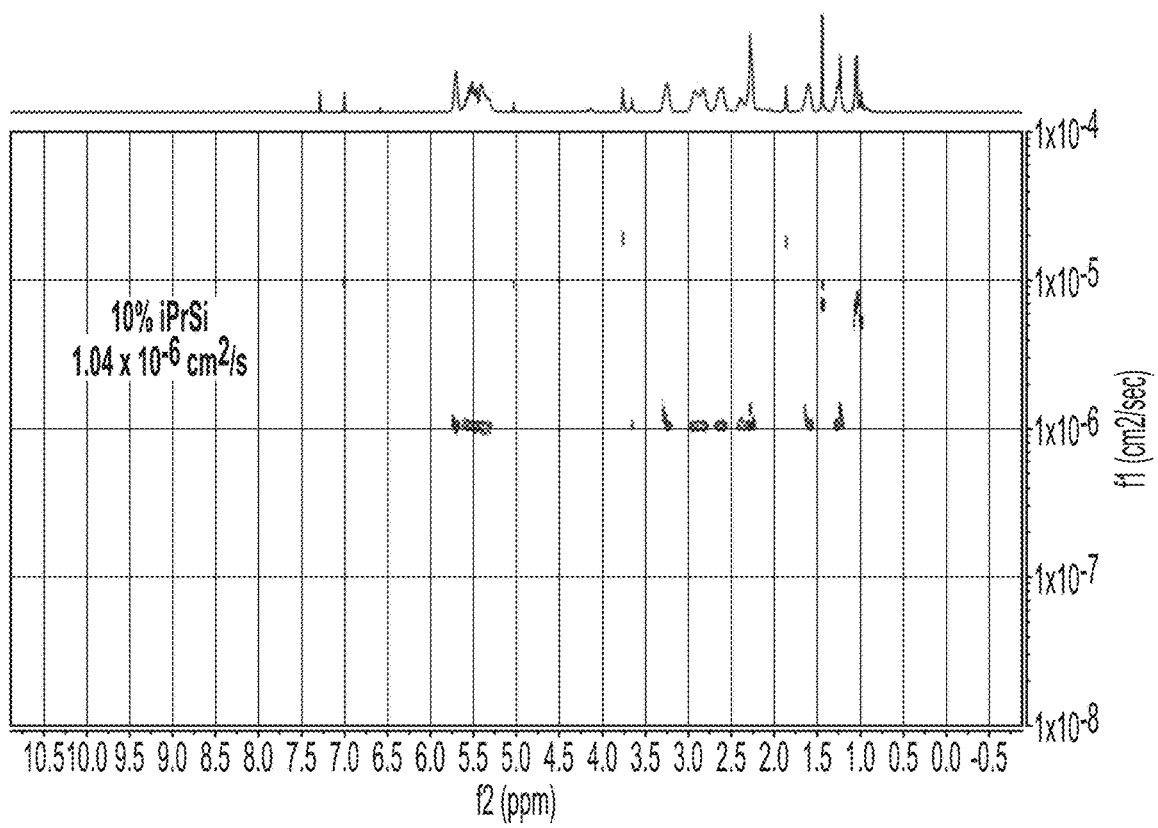

FIG. 53. DOSY spectrum (CDCl$_3$; 500 MHz) of the degradation solution from pDCPD doped with 10% iPrSi.

Figure 54:
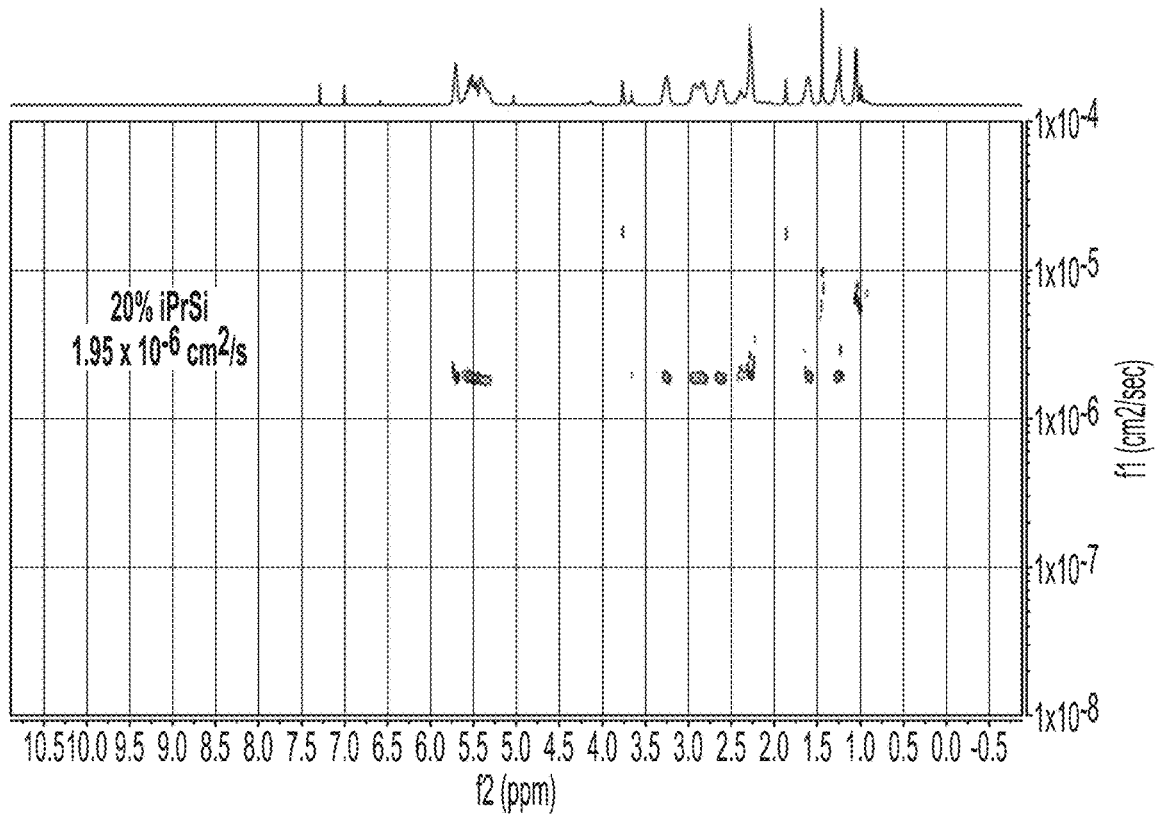

FIG. 54. DOSY spectrum (CDCl$_3$; 500 MHz) of the degradation solution from pDCPD doped with 20% iPrSi.

Figure 55:
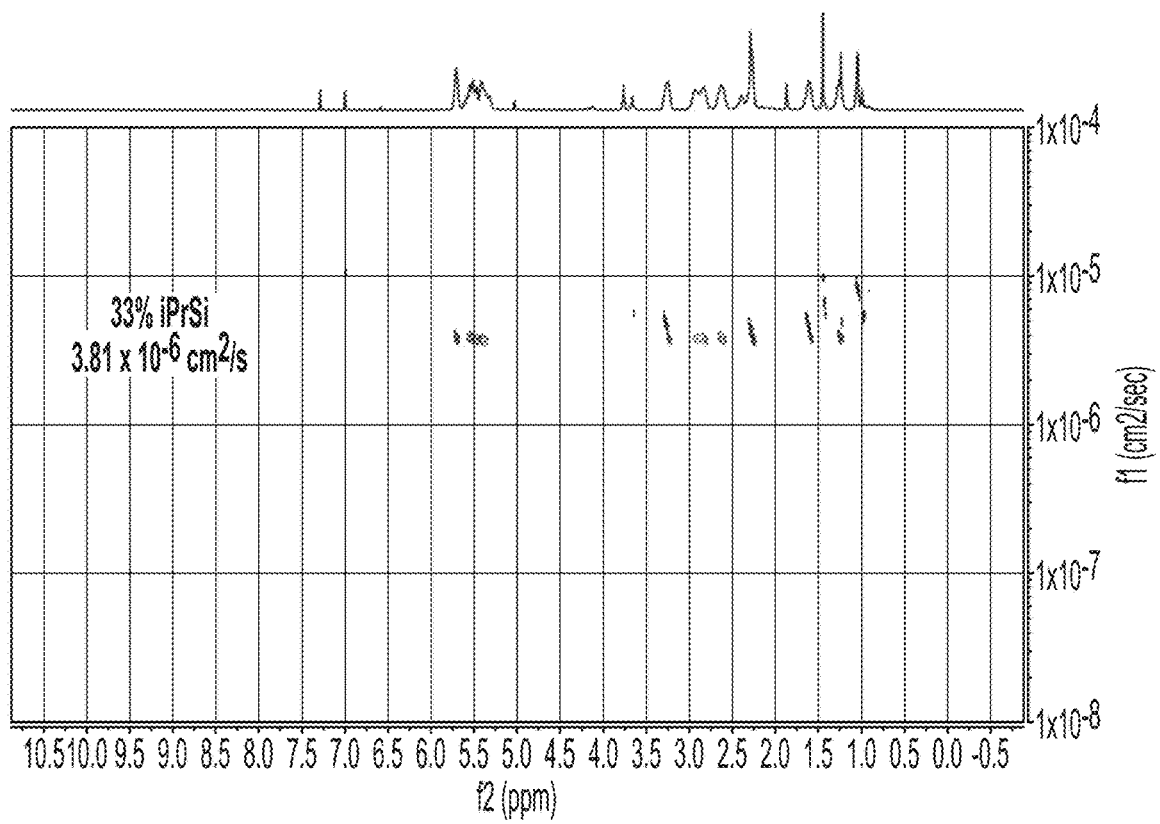

FIG. 55. DOSY spectrum (CDCl$_3$; 500 MHz) of the degradation solution from pDCPD doped with 33% iPrSi.

Figure 56:
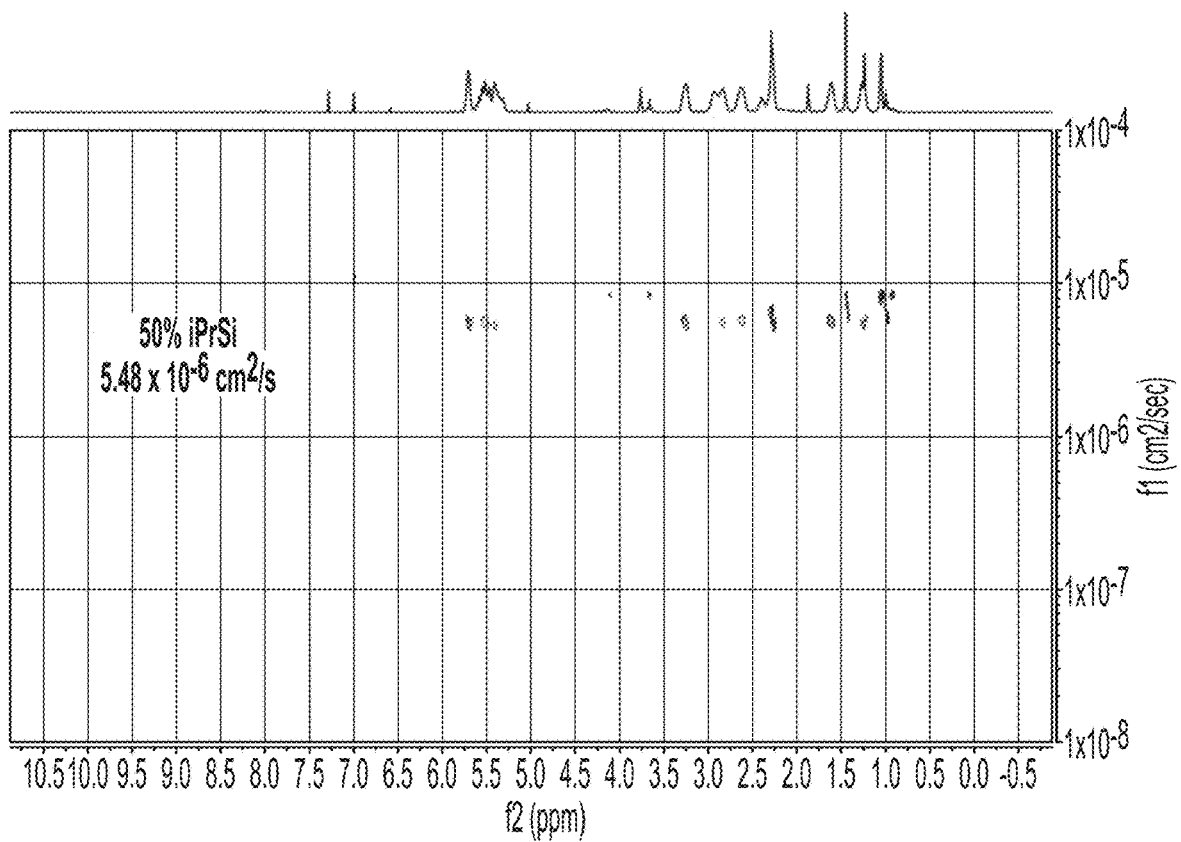

FIG. 56. DOSY spectrum (CDCl$_3$; 500 MHz) of the degradation solution from pDCPD doped with 50% iPrSi.

Figure 57:
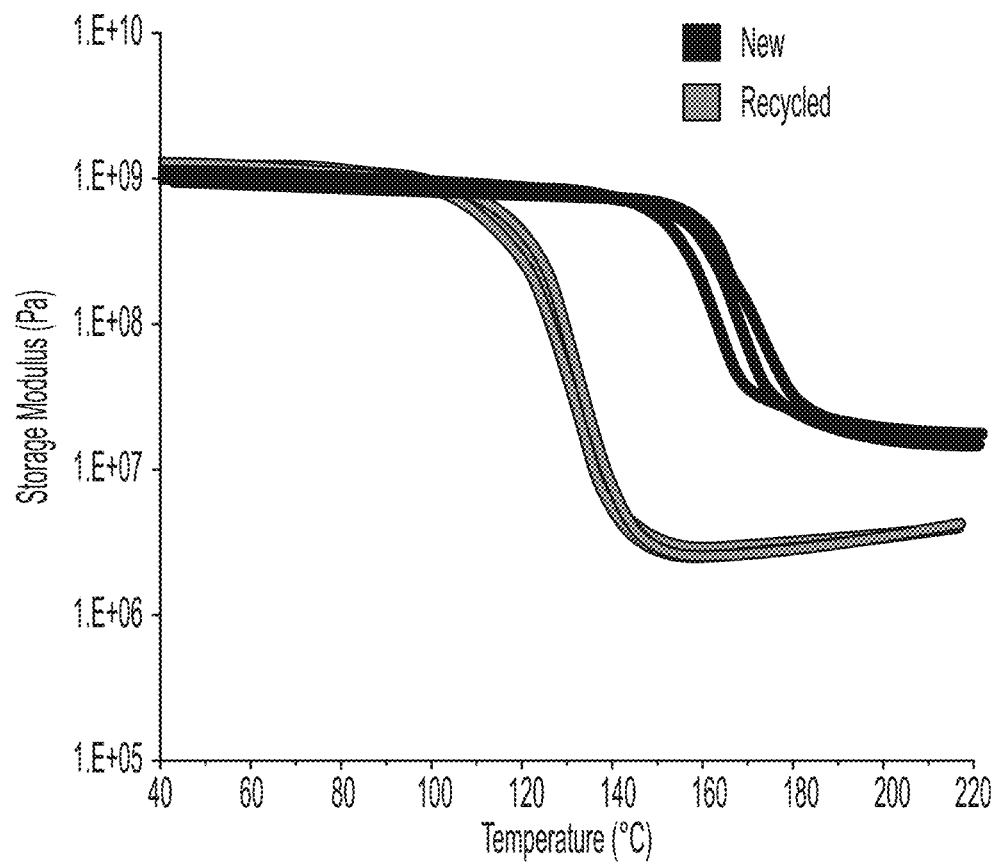

FIG. 57. DMA traces of recycled pDCPD (containing 25% pDCPD fragments).

Figure 58:
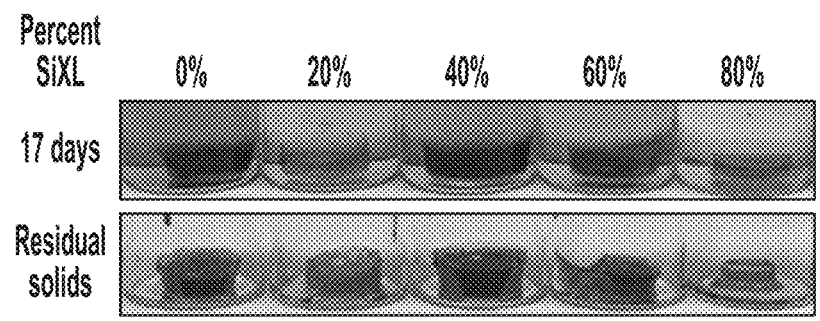

FIG. 58. Images of SiXL-doped samples after treatment with TBAF for 17 days.

Figure 59:
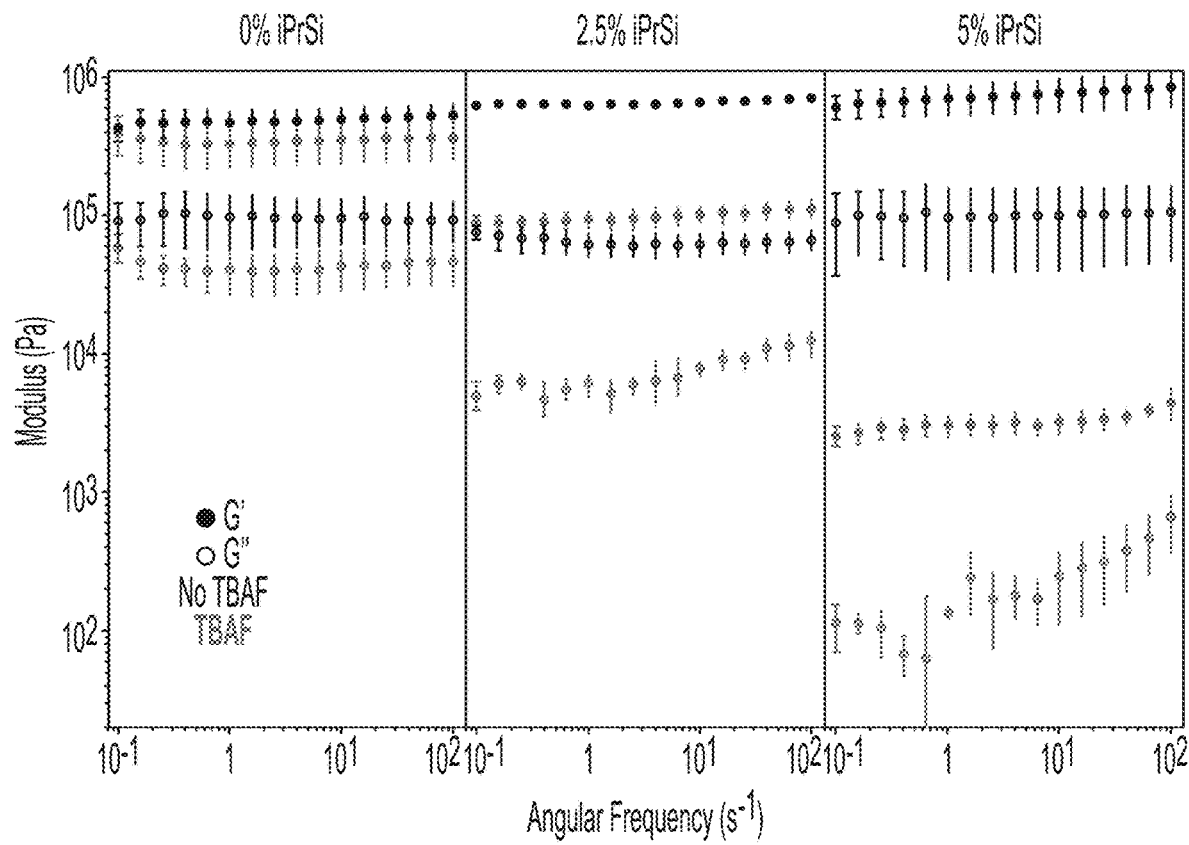

FIG. 59. Frequency sweep rheology of THF swollen samples of degraded pDCPD samples showing decreasing moduli after TBAF treatment with increasing iPrSi. In contrast, all three samples show similar moduli in the absence of TBAF.

Figure 60:
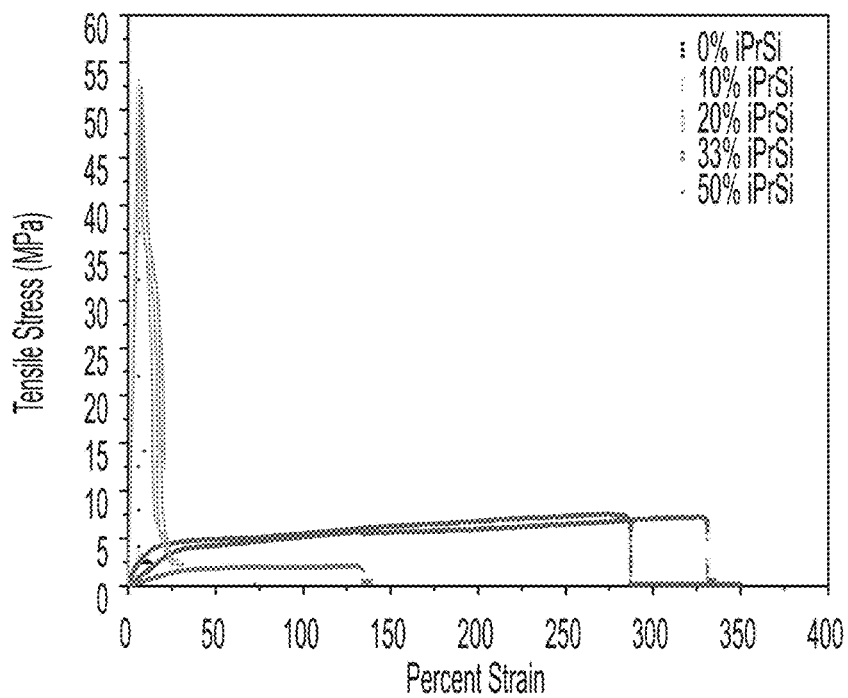

FIG. 60. Full stress-strain curves from pDCPD samples containing different levels of iPrSi.

Figure 61:
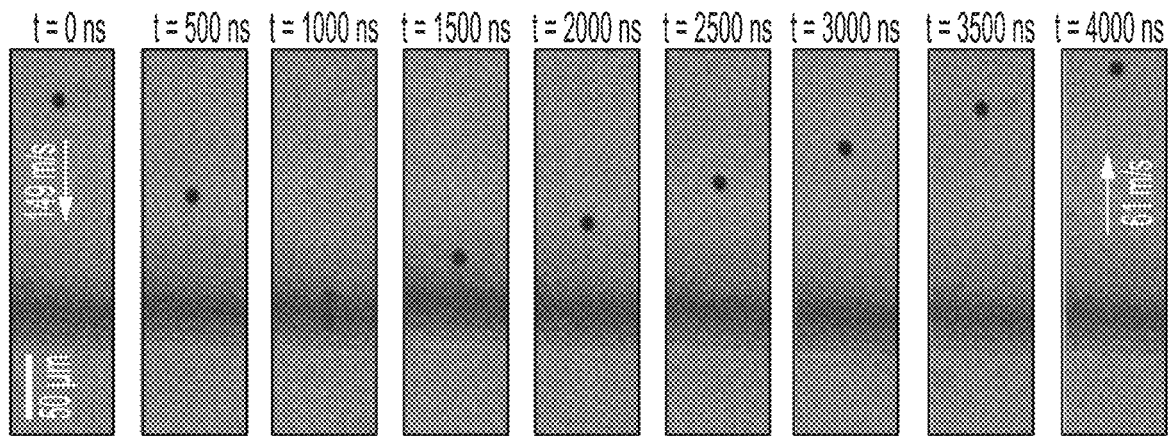

FIG. 61. A representative LIPIT image sequence from a 10% iPrSi-doped pDCPD sample showing particle rebound.

Figure 62:
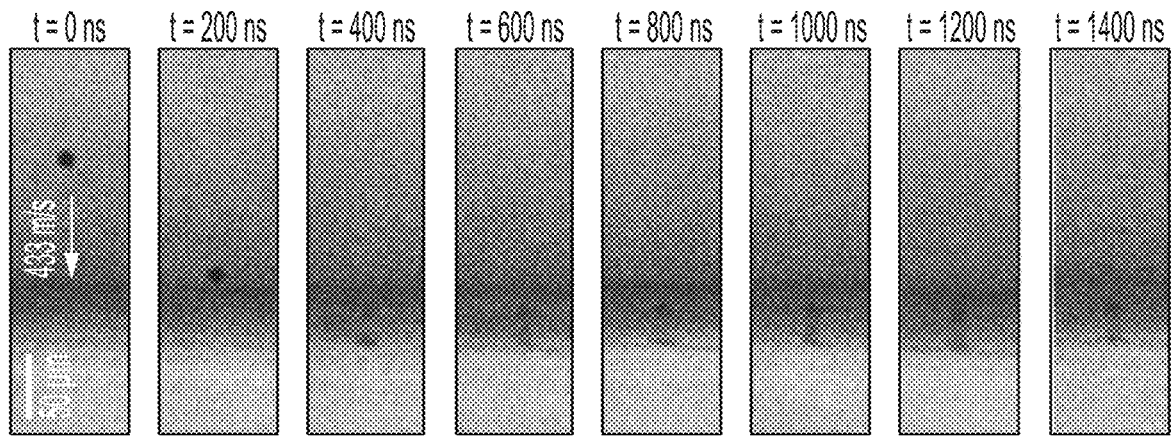

FIG. 62. A representative LIPIT image sequence from a 10% iPrSi-doped pDCPD sample showing particle embedment.

Figure 63:
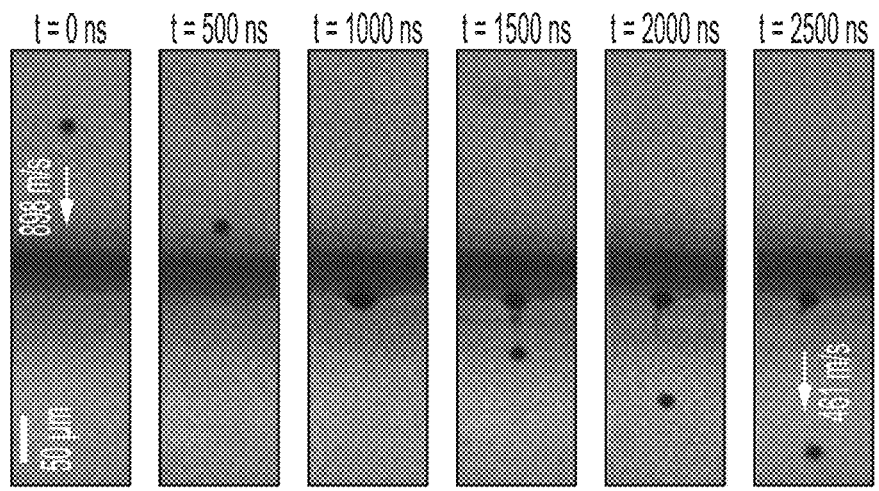

FIG. 63. A representative LIPIT image sequence from a 10% iPrSi-doped pDCPD sample showing particle perforation.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC), supercritical fluid chromatography (SFC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions*p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

In a formula, the bond ~~~ is a single bon, the dashed line - - - is a single bond or absent, and the bond ═══ or ≡≡≡ is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-5}$, $C_4$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-6}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("C-7 alkyl"). In some embodiments, an alkyl group has 1 to 6 carbon atoms ("$C_{1-6}$ alkyl"). In some embodiments, an alkyl group has 1 to carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-12}$ alkyl (e.g., —$CH_3$(Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)). The attachment point of alkyl may be a single bond (e.g., as in —$CH_3$), double bond (e.g., as in =$CH_2$), or triple bond (e.g., as in —CH). The moieties =$CH_2$ and —CH are also alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more (e.g., two, three, or four, as valency permits) carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-5}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be in the (E)- or (Z)-configuration.

"Alkynyl" refers to a radical of a straight-chain or branched hydrocarbon group having from 2 to 20 carbon atoms, one or more (e.g., two, three, or four, as valency permits) carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 13 ring carbon atoms ("$C_{3-13}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged, or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl may include zero, one, or more (e.g., two, three, or four, as valency permits) C=C double bonds in all the rings of the carbocyclic ring system that are not aromatic or heteroaromatic. Carbocyclyl including one or more (e.g., two or three, as valency permits) C=C double bonds in the carbocyclic ring is referred to as "cycloalkenyl." Carbocyclyl including one or more (e.g., two or three, as valency permits) C=C triple bonds in the carbocyclic ring is referred to as "cycloalkynyl." Carbocyclyl includes aryl. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl. In certain embodiments, the carbocyclyl is substituted or unsubstituted, 3- to 7-membered, and monocyclic. In certain embodiments, the carbocyclyl is substituted or unsubstituted, 5- to 13-membered, and bicyclic.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 13-membered non-aromatic ring system having ring carbon atoms and 1 to 4 ring heteroatoms, wherein each heteroatom is independently selected from nitrogen, oxygen, and sulfur ("3-13 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"). A heterocyclyl group can be saturated or can be partially unsaturated. Heterocyclyl may include zero, one, or more (e.g., two, three, or four, as valency permits) double bonds in all the rings of the heterocyclic ring system that are not aromatic or heteroaromatic. Partially unsaturated heterocyclyl groups includes heteroaryl. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, and monocyclic. In certain embodiments, the heterocyclyl is substituted or unsubstituted, 5- to 13-membered, and bicyclic.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include azirdinyl, oxiranyl, or thiiranyl. Exemplary 4-membered heterocyclyl groups containing one heteroatom include azetidinyl, oxetanyl and thietanyl. Exemplary 5-membered heterocyclyl groups containing one heteroatom include tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include dioxolanyl, oxasulfuranyl, disulfuranyl, and oxazolidin-2-one. Exemplary 5-membered heterocyclyl groups containing three heteroatoms include triazolinyl, oxadiazolinyl, and thiadiazolinyl. Exemplary 6-membered heterocyclyl groups containing one heteroatom include piperidinyl, tetrahydropyranyl, dihydropyridinyl, and thianyl. Exemplary 6-membered heterocyclyl groups containing two heteroatoms include piperazinyl, morpholinyl, dithianyl, and dioxanyl. Exemplary 6-membered heterocyclyl groups containing two heteroatoms include triazinanyl. Exemplary 7-membered heterocyclyl groups containing one heteroatom include azepanyl, oxepanyl and thiepanyl. Exemplary 8-membered heterocyclyl groups containing one heteroatom include azocanyl, oxecanyl, and thiocanyl. Exemplary 5-membered heterocyclyl groups fused to a $C_6$ aryl ring (also referred to herein as a 5,6-bicyclic heterocyclic ring) include indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g, having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include pyrrolyl, furanyl and thiophenyl. Exemplary 5-membered heteroaryl groups containing two heteroatoms include imidazolyl, pyrazolyl, oxazolyl, isoxazolyl, thiazolyl, and isothiazolyl. Exemplary 5-membered heteroaryl groups containing three heteroatoms include triazolyl, oxadiazolyl, and thiadiazolyl. Exemplary 5-membered heteroaryl groups containing four heteroatoms include tetrazolyl. Exemplary 6-membered heteroaryl groups containing one heteroatom include pyridinyl. Exemplary 6-membered heteroaryl groups containing two heteroatoms include pyridazinyl, pyrimidinyl, and pyrazinyl. Exemplary 6-membered heteroaryl groups containing three or four heteroatoms include triazinyl and tetrazinyl, respectively. Exemplary 7-membered heteroaryl groups containing one heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include halogen, —CN, —NO$_2$, —N$_3$, —SO$_2$, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O) SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^b$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups:

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-4}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-4}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^9$ groups;

each instance of R$^{ff}$ is, independently, selected from hydrogen, C$_{1-6}$ alkyl, C$_{1-6}$ perhaloalkyl, C$_{2-4}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^9$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-4}$alkyl)(C$_{1-6}$alkyl), —N(OH)(C$_{1-6}$ alkyl), —NH(OH), —SH, —SC$_{1-6}$alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_4$ alkyl), —C(=O)NH$_2$, —C(=O)N(C$_{1-6}$ alkyl)$_2$, —OC(=O)NH(C$_{1-6}$alkyl), —NHC(=O)(C$_{1-4}$ alkyl), —N(C$_{1-6}$ alkyl)C(=O)(C$_{1-6}$ alkyl), —NHCO$_2$(C$_{1-6}$alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$alkyl, —C(=NH)N(C$_{1-6}$alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —S$_2$OC$_{1-6}$ alkyl, —OSO$_2$C$_{1-6}$alkyl, —SOC$_{1-6}$ alkyl, —Si(C$_{1-6}$ alkyl)$_3$, —OSi(C$_{1-4}$ alkyl)$_3$-C(=S)N(C$_4$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ to aryl, 3-10 membered heterocyclyl, 5-10 membered heteroaryl; or two geminal $R^{gg}$ substituents can be joined to form =O or =S; wherein X is a counterion.

In certain embodiments, the carbon atom substituents are independently halogen, substituted (e.g., substituted with one or more halogen) or unsubstituted $C_{1-6}$ alkyl, —$OR^{aa}$, —$SR^{aa}$, —$N(R^{bb})_2$, —CN, —SCN, —$NO_2$, —$C(=O)R^{aa}$, —$CO_2R^{aa}$, —$C(=O)N(R^{bb})_2$, —$OC(=O)R^{aa}$, —$OCO_2R^{aa}$, —$OC(=O)N(R^{bb})_2$, —$NR^{bb}C(=O)R^{aa}$, —$NR^{bb}CO_2R^{aa}$, or —$NR^{bb}C(=O)N(R^{bb})_2$. In certain embodiments, the carbon atom substituents are independently halogen, substituted (e.g., substituted with one or more halogen) or unsubstituted $C_{1-6}$ alkyl, —$OR^{aa}$, —SR, —$N(R^{aa})_2$, —CN, —SCN, —$NO_2$, —$C(=O)R^{aa}$, —$CO_2R^{aa}$, —$C(=O)N(R^{bb})_2$, —$OC(=O)R^{aa}$, —$OCO_2R^{aa}$, —$OC(=O)N(R^{bb})_2$, —$NR^{bb}C(=O)R^{aa}$, —$NR^{bb}CO_2R^{aa}$, or —$NR^{bb}C(=O)N(R^{bb})_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group. In certain embodiments, the carbon atom substituents are independently halogen, substituted (e.g., substituted with one or more halogen) or unsubstituted $C_{1-6}$ alkyl, —$OR^{aa}$, —SR, —$N(R^{bb})_2$, —CN, —SCN, or —$NO_2$. In certain embodiments, the carbon atom substituents are independently halogen, substituted (e.g., substituted with one or more halogen moieties) or unsubstituted $C_{1-6}$ alkyl, —$OR^{aa}$, —$SR^{aa}$, —$N(R^{bb})_2$, —CN, —SCN, or —$NO_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g, $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(OR^{cc})_2$, —$P(=O)(R^{aa})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^dd$ groups, and wherein $R^{aa}$, $R^{bb}$, $R^{cc}$ and $R^{dd}$ are as defined above.

In certain embodiments, the nitrogen atom substituents are independently substituted (e.g., substituted with one or more halogen) or unsubstituted $C_{1-6}$ alkyl, —$C(=O)R^{aa}$, —$CO_2R^{aa}$, —$C(=O)N(R^{bb})_2$, or a nitrogen protecting group. In certain embodiments, the nitrogen atom substituents are independently substituted (e.g., substituted with one or more halogen) or unsubstituted $C_{1-6}$ alkyl, —$C(=O)R^{aa}$, —$CO_2R^{aa}$, —$C(=O)N(R^{bb})_2$, or a nitrogen protecting group, wherein $R^{aa}$ is hydrogen, substituted (e.g., substituted with one or more halogen) or unsubstituted $C^{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the nitrogen atom substituents are independently substituted (e.g., substituted with one or more halogen) or unsubstituted $C_{1-6}$ alkyl or a nitrogen protecting group.

In certain embodiments, the substituent present on a nitrogen atom is a nitrogen protecting group (also referred to as an amino protecting group). Nitrogen protecting groups include —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$S_2R^{cc}$, —$SO_2OR^{cc}$, —$SOR^{aa}$, —$C(=S)N(R^{cc})_2$, —$C(=O)SR^{cc}$, —$C(=S)SR^{aa}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R_{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —$C(=O)R^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o- nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine, onitrobenzamide, and o-(benzoyloxymethyl)benzamide.

Carbamate nitrogen protecting groups (e.g., —C(=O)OR$^{aa}$) include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-(4-biphenylyl)ethyl carbamate (Bpoc), 1-(3,5-di-1-butylphenyl)-1-methylethyl carbamate (l-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), s-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N p-methoxybenzylideneamine, N-diphenylmethyleneamine, N-[(2-pyridyl)mesityl]methyleneamine, N-(N',N'-dimethylaminomethylene) amine, N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine Noxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or an oxygen protecting group. In certain embodiments, the oxygen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or an oxygen protecting group, wherein R$^{aa}$ is hydrogen, substituted (e.g., substituted with one or more halogen) or unsubstituted $C_{1-6}$ alkyl, or an oxygen protecting group when attached to an oxygen atom; and each R$^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)R^{aa}$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, l-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-<dimethoxybenzyl, o nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, 1-butyldimethylsilyl (TBDMS), i-butyldiphenylsilyl (TBDPS), tribenzylsilyl, tri-p-xylylsilyl, triphenylsilyl, diphenylmethylsilyl (DPMS), 1-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, —$C(=O)R^{aa}$, —$CO_2R^{aa}$, —$C(=O)N(R^{bb})_2$, or a sulfur protecting group. In certain embodiments, the sulfur atom substituents are independently substituted (e.g, substituted with one or more halogen) or unsubstituted $C_{1-6}$ alkyl, —$C(=O)R^{aa}$, —$CO_2R^{aa}$, —$C(=O)N(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

The "molecular weight" of —R, wherein —R is any monovalent moiety, is calculated by subtracting the atomic weight of a hydrogen atom from the molecular weight of the molecule R—H. The "molecular weight" of -L-, wherein -L- is any divalent moiety, is calculated by subtracting the combined atomic weight of two hydrogen atoms from the molecular weight of the molecule H-L-H.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, NO-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS($=$O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other examples of leaving groups are water, ammonia, alcohols, ether moieties, thioether moieties, zinc halides, magnesium moieties, diazonium salts, and copper moieties.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

"Compounds" include, e.g., small molecules and macromolecules. Macromolecules include, e.g., polymers, peptides, proteins, carbohydrates, monosaccharides, oligosaccharides, polysaccharides, nucleoproteins, mucoproteins, lipoproteins, synthetic polypeptides or proteins, glycoproteins, steroids, nucleic acids, DNAs, RNAs, nucleotides, nucleosides, oligonucleotides, antisense oligonucleotides, lipids, hormones, vitamins, and cells.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 2,000 g/mol. In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present disclosure.

The term "oligomer" refers to a compound comprising two to ten, inclusive, covalently connected repeating units. In certain embodiments, an oligomer comprises two to five, inclusive, covalently connected repeating units. In certain embodiments, an oligomer comprises six to ten, inclusive, covalently connected repeating units.

The term "polymer" refers to a compound comprising eleven or more covalently connected repeating units. In certain embodiments, a polymer is naturally occurring. In certain embodiments, a polymer is synthetic (e.g., not naturally occurring). In certain embodiments, the $M_W$ of a polymer is between 1,000 and 2,000, between 2,000 and 10,000, between 10,000 and 30,000, between 30,000 and 100,000, between 100,000 and 300,000, between 300,000 and 1,000,000, g/mol, inclusive. In certain embodiments, the $M_W$ of a polymer is between 2,000 and 1,000,000, g/mol, inclusive.

The term "average molecular weight" may encompass the number average molecular weight ($M_n$), weight average molecular weight ($M_w$), higher average molecular weight ($M_z$ or $M_z+1$), GPC/SEC (gel permeation chromatography/size-exclusion chromatography)-determined average molecular weight ($M_p$), and viscosity average molecular weight ($M_v$). Average molecular weight may also refer to average molecular weight as determined by gel permeation chromatography.

The term "degree of polymerization" (DP) refers to the number of repeating units in a polymer. In certain embodiments, the DP is determined by a chromatographic method, such as gel permeation chromatography. For a homopolymer, the DP refers to the number of repeating units included in the homopolymer. For a copolymer of two types of monomers (e.g., a first monomer and a second monomer) wherein the molar ratio of the two types of monomers is about 1:1, the DP refers to the number of repeating units of either one of the two type of monomers included in the copolymer. For a copolymer of two types of monomers (e.g., a first monomer and a second monomer) wherein the molar ratio of the two types of monomers is not about 1:1, two DPs may be used. A first DP refers to the number of repeating units of the first monomer included in the copolymer, and a second DP refers to the number of repeating units of the second monomer included in the copolymer. Unless provided otherwise, a DP of "xx", wherein xx is an integer, refers to the number of repeating units of either one of the two types of monomers of a copolymer of two types of monomers (e.g., a first monomer and a second monomer) wherein the molar ratio of the two types of monomers is about 1:1. Unless provided otherwise, a DP of "xx-yy", wherein xx and yy are integers, refers to xx being the number of repeating units of the first monomer, and yy being the number of repeating units of the second monomer, of a copolymer of two types of monomers (e.g., a first monomer and a second monomer) wherein the molar ratio of the two types of monomers is not about 1:1.

The term "ring-opening metathesis polymerization (ROMP)" refers to a type of olefin metathesis chain-growth polymerization that is driven by the relief of ring strain in cyclic olefins (e.g. norbornene or cyclopentene). The catalysts used in the ROMP reaction ("metathesis catalyst") include RuCl$_3$/alcohol mixture, bis(cyclopentadienyl)dimethylzirconium(IV), dichloro[1,3-bis(2,6-isopropylphenyl)-2-imidazolidinylidene](benzylidene)(tricyclohexylphosphine)ruthenium(II), dichloro[1,3-Bis(2-methylphenyl)-2-imidazolidinylidene](benzylidene)(tricyclohexylphosphine) ruthenium(II), dichloro[1,3-bis(2,4,6-trimethylphenyl)-2-imidazolidinylidene][3-(2-pyridinyl)propylidene]ruthenium (II), dichloro(3-methyl-2-butenylidene)bis (tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis(tricyclohexylphosphine)ruthenium(II) (Grubbs I), dichloro[1,3-bis(2,4,6-trimethylphenyl)-2-imidazolidinylidene](benzylidene)(tricyclohexylphosphine) ruthenium(II) (Grubbs II), and dichloro[1,3-bis(2,4,6-trimethylphenyl)-2-imidazolidinylidene] (benzylidene)bis(3-bromopyridine)ruthenium(II) (Grubbs III).

The term "v/v" refers to volume per volume and is used herein to express concentrations of monomers. Unless otherwise provided, a percent concentration of a second monomer in a first monomer is expressed in v/v. For example, a mixture of a first monomer and 10% second monomer refers to a mixture of a first monomer and a second monomer, wherein the volume of the second monomer is 10% of the combined volumes of the first and second monomers.

The disclosure is not intended to be limited in any manner by the above exemplary listing of substituents. Additional terms may be defined in other sections of this disclosure.

DETAILED DESCRIPTION OF CERTAIN EMBODIMENTS

There is a need to improve the reprocessability of thermosets. An approach to convert existing thermosets into degradable variants would involve the use of a low-cost co-monomer additive that, when introduced at low levels during standard thermoset formulation conditions, could introduce cleavable bonds at precise locations within the thermoset polymer network enabling material degradation with otherwise little to no impact on properties. The use of such co-monomer strategies to imbue commodity polymers with degradability or reprocessability is exceedingly rare (6, 7). To our knowledge, such an approach has not been demonstrated in the context of existing high-performance thermosets (8-10).

Here, in one aspect, we establish this co-monomer approach in the context of commercially important thermosets, such as poly-dicyclopentadiene (pDCPD). pDCPD may be prepared through ring-opening metathesis polymerization (ROMP) of the abundant hydrocarbon feedstock dicyclopentadiene (DCPD). See, e.g., U.S. patent application Ser. No. 16/542,824, filed Aug. 16, 2019, which is incorporated herein by reference. In this curing process, the norbornene component of DCPD polymerizes rapidly to produce linear polymer strands that are subsequently crosslinked through metathesis reactions of their cyclopentene sidechains. The resulting entirely hydrocarbon thermoset is valued for its high impact resistance and compatibility with reaction injection molding processes (11-18). Moreover, emerging manufacturing concepts, such as frontal polymerization, enable pDCPD curing with energy consumption orders-of-magnitude lower than other thermosets (e.g., epoxies) (15, 16).

We show that by incorporation of a cyclic silyl ether

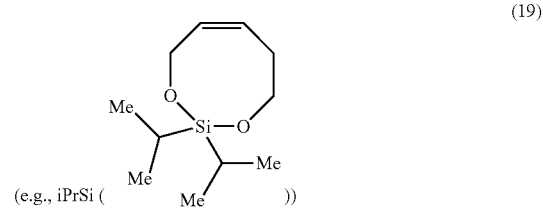 [SMILES: CC(C)[Si]1(C(C)C)OC/C=C\CCO1]

(19)

into the existing pDCPD manufacturing workflow, it is possible to prepare pDCPD derivatives with properties that are nearly indistinguishable from native pDCPD, but with the capability to be readily degraded into soluble, hydroxylated hydrocarbon fragments that are functional scaffolds for upcycling. Moreover, solution-state NMR studies of these soluble products provide unprecedent insight into the structure of pDCPD. Remarkably, when materials prepared using a co-monomer approach, which feature degradable linkages within their polynorbornene strands, were compared to analogous pDCPD derivatives with cleavable crosslinks, we found that only the former materials fully degrade into soluble species at low co-monomer incorporation. This observation is rationalized by natural topological differences between strands and crosslinks in pDCPD that are shared across many types of polymer networks, establishing a key design principle—cleavable bond location—that may augment the development of degradable thermosets.

Functional Oligomers, Functional Polymers, Hydroxylated Polymers, Compounds, Copolymers, and Methods of Preparation, Compositions, and Kits Thereof In one aspect, the present disclosure describes functional oligomer or functional polymer comprising:
  i) one or more instances of linear units, wherein each instance of the linear units is of the formula:

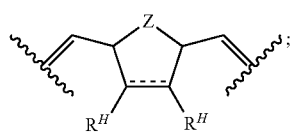

ii) one or more instances of functional units, wherein each instance of the functional units is independently of the formula:

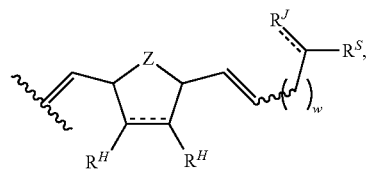

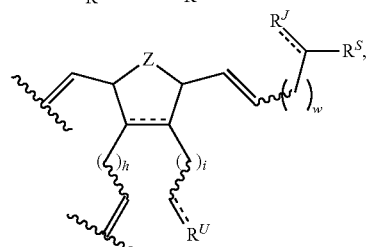

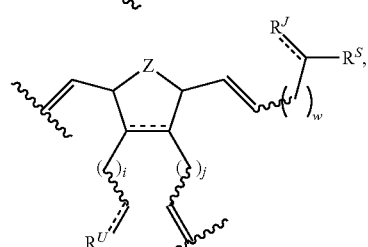

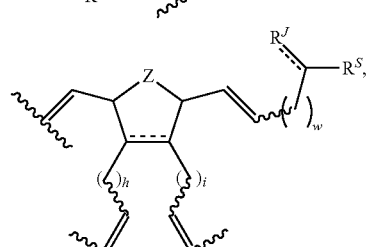

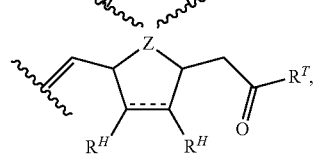

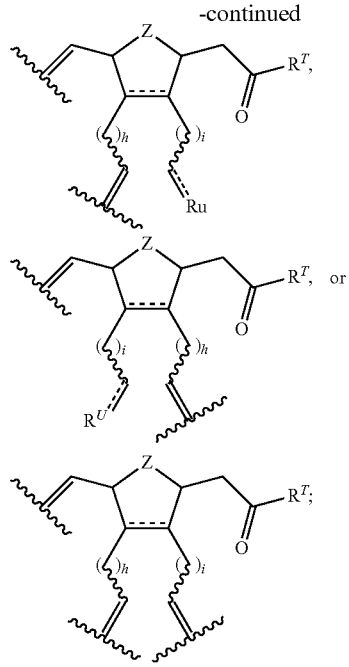

iii) optionally one or more instances of crosslinking units, wherein each instance of the crosslinking units is of the formula:

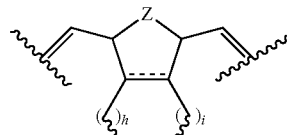

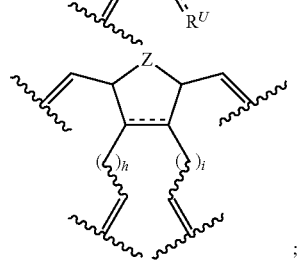

and
  iv) optionally one or more additional linear units, one or more additional terminal units, and/or one or more additional crosslinking units;
  wherein:
  each instance of Z is independently a single bond, $C(R^P)_2$, or O;
  each instance of $R^P$ is independently hydrogen, halogen, or substituted or unsubstituted, $C_{1-6}$ alkyl;
  each instance of ══ is independently a single or double bond;
  each instance of $R^H$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —OCN, —OC(═O)R$^a$, —OC(═S)R$^a$, —OC(═O)OR$^a$, —OC(═O)N(R$^a$)$_2$, —OS(═O)R$^a$, —OS(═O)OR$^a$, —OS(═O)N(R$^a$)$_2$, —OS(═O)$_2$R$^a$, —OS(═O)$_2$OR$^a$, —OS(═O)$_2$N(R$^a$)$_2$, —OSi(R$^a$)$_3$, —OSi(R$^a$)$_2$(OR$^a$), OSi(R$^a$)(OR$^a$)$_2$, —OSi(OR$^a$)$_3$, oxo, —N(R$^a$)$_2$, —N═C(R$^a$)$_2$, ═NR$^a$, —NC, —NCO, —N$_3$, —NO$_2$, —NR$^a$C(═O)R$^a$, —NR$^a$C(═O)OR$^a$, —NR$^a$C(═O)N(R$^a$)$_2$, —NR$^a$S(═O)R$^a$, —NR$^a$S(═O)OR$^a$, —NR$^a$S(═O)N(R$^a$)$_2$, —NR$^a$S(═O)$_2$R$^a$, —NR$^a$S(═O)$_2$OR$^a$, —NR$^a$S(═O)$_2$N(R$^a$)$_2$, —SR, —SCN, —S(═O)R$^a$, —S(═O)OR, —S(═O)N(R$^a$)$_2$, —S(═O)$_2$R$^a$, —S(═O)$_2$OR$^a$, —S(═O)$_2$N(R$^a$)$_2$, —SeR$^a$, halogen, —CN, —C(═NR$^a$)R$^a$, —C(═NR$^a$)OR$^a$, —C(═NR$^a$)N(R$^a$), —C(═O)R$^a$, —C(═O)OR$^a$, —C(═O)SR$^a$, —C(═S)OR, or —C(═O)N(R$^a$)$_2$;

or the two instances of R$^H$ of one or more instances of

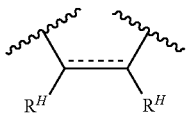

are joined with the intervening carbon atoms to independently form a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of R$^a$ is independently hydrogen, substituted or unsubstituted alkyl, substituted or unsubstituted alkenyl, substituted or unsubstituted alkynyl, substituted or unsubstituted, monocyclic carbocyclyl, substituted or unsubstituted, monocyclic heterocyclyl, substituted or unsubstituted, monocyclic aryl, substituted or unsubstituted, monocyclic heteroaryl, a nitrogen protecting group when attached to a nitrogen atom, an oxygen protecting group when attached to an oxygen atom, or a sulfur protecting group when attached to a sulfur atom, or two instances of R$^a$ are joined to form substituted or unsubstituted heterocyclyl or substituted or unsubstituted heteroaryl;

each instance of R$^J$ is independently —OR, —OCN, —OC(═O)R$^a$, —OC(═S)R$^a$, —OC(═O)OR$^a$, —OC(═O)N(R$^a$)$_2$, —OS(═O)R$^a$, —OS(═O)OR$^a$, —OS(═O)N(R$^a$)$_2$, —OS(═O)$_2$R$^a$, —OS(═O)$_2$OR$^a$, —OS(═O)$_2$N(R$^a$)$_2$, —OSi(R$^a$)$_3$, —OSi(R$^a$)$_2$(OR$^a$), —OSi(R$^a$)(OR$^a$)$_2$, —OSi(OR$^a$)$_3$, oxo, —N(R$^a$)$_2$, —N═C(R$^a$)$_2$, ═NR, —NC, —NCO, —N$_3$, —NO$_2$, —NR$^a$C(═O)R$^a$, —NR$^a$C(═O)OR$^a$, —NR$^a$C(═O)N(R$^a$)$_2$, —NR$^a$S(═O)R$^a$, —NR$^a$S(═O)OR, —NR$^a$S(═O)N(R$^a$)$_2$, —NR$^a$S(═O)$_2$R$^a$, —NR$^a$S(═O)$_2$OR$^a$, —NR$^a$S(═O)$_2$N(R$^a$)$_2$, —SR, —SCN, —S(═O)R$^a$, —S(═O)OR$^a$, —S(═O)N(R$^a$)$_2$, —S(═O)$_2$R$^a$, —S(═O)$_2$OR$^a$, —S(═O)$_2$N(R$^a$)$_2$, —SeR$^a$, halogen, —CN, —C(═NR$^a$)R$^a$, —C(═Na)OR$^a$, —C(═NR$^a$)N(R$^a$)$_2$, —C(═O)R$^a$, —C(═O)OR$^a$, —C(═O)SR$^a$, —C(═S)OR, or —C(═O)N(R$^a$)$_2$;

each instance of R$^S$ is independently hydrogen or —OR$^a$;
each instance of w is independently 0, 1, 2, 3, or 4;
each instance of h is independently 0, 1, 2, or 3;
each instance of i is independently 0, 1, 2, or 3;
each instance of R$^U$ is independently hydrogen, substituted or unsubstituted alkyl, substituted or unsubstituted alkenyl, substituted or unsubstituted alkynyl, substituted or unsubstitutedcarbocyclyl, substituted or unsubstitutedheterocyclyl, substituted or unsubstituted aryl, substituted or unsubstituted heteroaryl, —OR$^a$, —OCN, —OC(═O)R$^a$, —OC(═S)R$^a$, —OC(═O)OR$^a$, —OC(═O)N(R$^a$)$_2$,OS(═O)R$^a$, —OS(═O)OR$^a$, —OS(═O)N(R$^a$)$_2$, —OS(═O)$_2$R$^a$, —OS(═O)$_2$OR$^a$, —OS(═O)$_2$N(R$^a$)$_2$, —OSi(R$^a$)$_3$, —OSi(R$^a$)$_2$(OR$^a$), —OSi(R$^a$)(OR$^a$)$_2$, —OSi(OR$^a$)$_3$, oxo, —N(R$^a$)$_2$, —N═C(R$^a$)$_2$, ═NR, —NC, —NCO, —N, —NO$_2$, —NR$^a$C(═O)R$^a$, —NR$^a$C(═O)OR, —NR$^a$C(═O)N(R$^a$)$_2$, —NRS(═O)R$^a$, —NR$^a$S(═O)OR, —NR$^a$S(═O)N(R$^a$)$_2$, —NR$^a$S(═O)$_2$R$^a$, —NR$^a$S(═O)$_2$OR$^a$, —NR$^a$S(═O)$_2$N(R$^a$)$_2$, —SR, —SCN, —S(═O)R$^a$, —S(═O)OR$^a$, —S(═O)N(R$^a$)$_2$, —S(═O)$_2$R$^a$, —S(═O)$_2$OR$^a$, —S(═O)$_2$N(R$^a$)$_2$, —SeR$^a$, halogen, —CN, —C(═NR$^3$)R$^a$, —C(═NR$^a$)OR$^a$, —C(═NR$^a$)N(R$^a$)$_2$, —C(═O)R$^a$, —C(═O)OR, —C(═O)SR$^a$, —C(═S)OR$^a$, or —C(═O)N(R$^a$)$_2$; and each instance of R$^T$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, the functional polymer is a hydroxylated polymer. In one aspect, the present disclosure describes hydroxylated polymers prepared by hydrolyzing a copolymer prepared by a method comprising polymerizing in the presence of a metathesis catalyst:

i) one or more instances of a first monomer, wherein each instance of the first monomer is independently of the formula:

or salt thereof, wherein:
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of Z is independently C(R$^P$)$_2$ or O;

each instance of R$^P$ is independently hydrogen, halogen, or substituted or unsubstituted, C$_{1-6}$alkyl; and each instance of ═══ is independently a single bond or double bond; and ii) one or more instances of a second monomer, wherein each instance of the second monomer is of Formula (B):

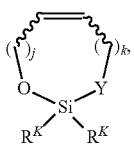
(B)

or a salt thereof; wherein:
  each instance of Y is independently O or C(R$^Q$)$_2$;
  each instance of R$^Q$ is independently hydrogen, halogen, or substituted or unsubstituted, C$_{1-6}$alkyl;
  each instance of R$^K$ is independently hydrogen, halogen, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or —OR$^N$;
  each instance of R$^N$ is independently hydrogen, substituted or unsubstituted acyl, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
  each instance of j is independently 1, 2, or 3; and
  each instance of k is independently 0, 1, 2, or 3;
  wherein any two instances of the first monomer are the same as or different from each other, and any two instances of the second monomer are the same as or different from each other; and
  wherein the step of hydrolyzing the copolymer comprises hydrolyzing one or more instances of the —O—Si bonds of the copolymer to form —OH.

In certain embodiments, the functional oligomer or functional is prepared by a method comprising hydrolyzing a copolymer prepared by a method comprising polymerizing in the presence of a metathesis catalyst:
  i) one or more instances of a first monomer, wherein each instance of the first monomer is of the formula:

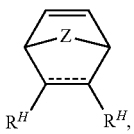
(A)

or salt thereof;
  ii) one or more instances of a second monomer, wherein each instance of the second monomer is of the formula:

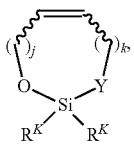
(B1)

or a salt thereof; wherein:
  Y is O or C(R$^Q$)$_2$;
  each instance of R$^Q$ is independently hydrogen, halogen, or substituted or unsubstituted, C$_{1-6}$ alkyl;
  each instance of R$^K$ is independently hydrogen, halogen, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or —OR$^N$;
  each instance of R$^N$ is independently hydrogen, substituted or unsubstituted acyl, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
  j is 1, 2, or 3; and
  k is 0, 1, 2, or 3, and
  iii) optionally one or more instances of a third monomer;
  wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other; and
  wherein the step of hydrolyzing the copolymer comprises hydrolyzing one or more instances of the —O—Si bonds of the copolymer to form —OH.

In certain embodiments, the functional oligomer or functional polymer is prepared by a method comprising hydrolyzing a copolymer prepared by a method comprising polymerizing in the presence of a metathesis catalyst:
  i) one or more instances of a first monomer, wherein each instance of the first monomer is of the formula:

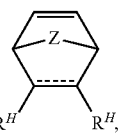
(A)

or salt thereof;
  ii) one or more instances of a second monomer, wherein each instance of the second monomer is of the formula:

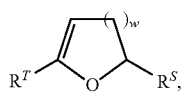
(B2)

or a salt thereof, and
  iii) optionally one or more instances of a third monomer;
  wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other; and
  wherein the step of hydrolyzing the copolymer comprises hydrolyzing one or more instances of

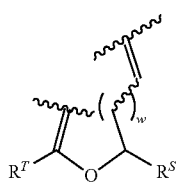

of the copolymer to form

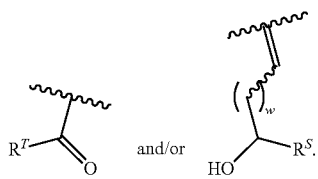

In another aspect, the present disclosure describes methods of preparing a hydroxylated polymer comprising hydrolyzing a copolymer prepared by a method comprising polymerizing in the presence of a metathesis catalyst:

i) one or more instances of a first monomer, wherein each instance of the first monomer is independently of the formula:

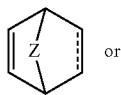   (A')

or

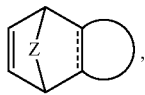   (A''), or salt thereof, wherein:

each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of Z is independently $C(R^P)_2$ or O;

each instance of $R^P$ is independently hydrogen, halogen, or substituted or unsubstituted, $C_{1-6}$ alkyl; and each instance of ═══ is independently a single bond or double bond; and ii) one or more instances of a second monomer, wherein each instance of the second monomer is of Formula (B):

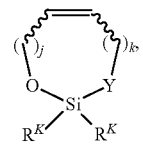   (B1)

or a salt thereof; wherein:

each instance of Y is independently O or $C(R^Q)_2$;

each instance of $R^Q$ is independently hydrogen, halogen, or substituted or unsubstituted, $C_{1-6}$ alkyl;

each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or $-OR^N$.

each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

each instance of j is independently 1, 2, or 3; and each instance of k is independently 0, 1, 2, or 3;

wherein any two instances of the first monomer are the same as or different from each other, and any two instances of the second monomer are the same as or different from each other; and wherein the step of hydrolyzing the copolymer comprises hydrolyzing one or more instances of the —O—Si bonds of the copolymer to form —OH.

In another aspect, the present disclosure describes methods of preparing a functional oligomer or functional polymer comprising hydrolyzing a copolymer prepared by a method comprising polymerizing in the presence of a metathesis catalyst:

i) one or more instances of a first monomer, wherein each instance of the first monomer is of the formula:

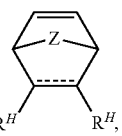   (A)

or salt thereof;

ii) one or more instances of a second monomer, wherein each instance of the second monomer is of the formula:

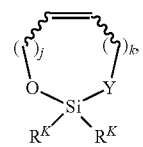   (B1)

or a salt thereof; and iii) optionally one or more instances of a third monomer;

wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other; and wherein the step of hydrolyzing the copolymer comprises hydrolyzing one or more instances of the —O—Si bonds of the copolymer to form —OH.

In another aspect, the present disclosure describes methods of preparing a functional oligomer or functional polymer comprising hydrolyzing a copolymer prepared by a method comprising polymerizing in the presence of a metathesis catalyst:
  i) one or more instances of a first monomer, wherein each instance of the first monomer is of the formula:

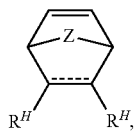

(A)

or salt thereof;
  ii) one or more instances of a second monomer, wherein each instance of the second monomer is of the formula:

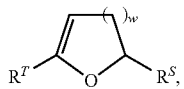

(B2)

or a salt thereof; and
  iii) optionally one or more instances of a third monomer;
  wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other; and wherein the step of hydrolyzing the copolymer comprises hydrolyzing one or more instances of

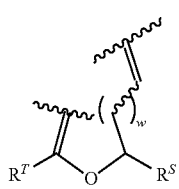

of the copolymer to form

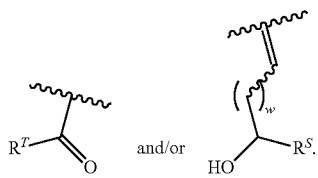

In another aspect, the present disclosure describes compounds of Formula (B1):

(B1)

and salts thereof; wherein:
  Y is O or $C(R^Q)_2$;
  each instance of $R^Q$ is independently hydrogen, halogen, or substituted or unsubstituted, $C_{1-6}$ alkyl;
  each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;
  each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
  j is 1, 2, or 3; and
  k is 0, 1, 2, or 3;
provided that the compound is not of the formula:

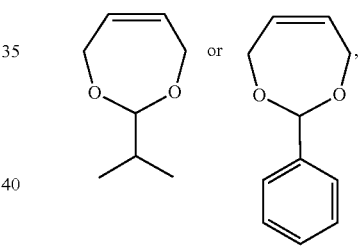

In certain embodiments, the compound is of the formula:

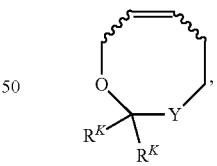

or a salt thereof.

In certain embodiments, the compound is of the formula:

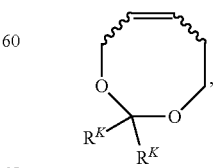

or a salt thereof.

In certain embodiments, the compound is of the formula:

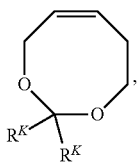

or a salt thereof.

In certain embodiments, the compound is of the formula:

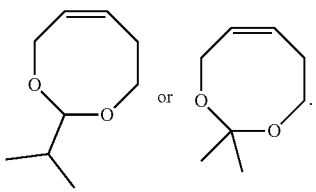

In another aspect, the present disclosure describes copolymers prepared by a method comprising polymerizing:
one or more instances of a first monomer;
one or more instances of a second monomer, wherein the second monomer is a compound of Formula (B1), or a salt thereof; and
optionally one or more instances of a third monomer;
wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other;
in the presence of a metathesis catalyst.

In another aspect, the present disclosure describes methods of preparing a copolymer comprising polymerizing:
one or more instances of a first monomer;
one or more instances of a second monomer, wherein the second monomer is a compound of Formula (B1), or a salt thereof; and
optionally one or more instances of a third monomer;
wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other;
in the presence of a metathesis catalyst.

In certain embodiments, the method of preparing the copolymer further comprises (b) exposing the copolymer to a solvent.

In certain embodiments, the method of preparing the copolymer further comprises (c) solid-liquid phase separation. In certain embodiments, Step (c) is subsequent to Step (b).

In certain embodiments, the method of preparing the copolymer further comprises curing. In some embodiments, curing forms a resin. In certain embodiments, curing is carried out at 70 to 150° C., inclusive. In certain embodiments, curing is carried out at 100 to 150° C., inclusive. In certain embodiments, curing is carried out at 100 to 130° C., inclusive. In certain embodiments, curing is carried out at 110 to 120° C., inclusive. In some embodiments, curing is carried out at about 110° C. In some embodiments, curing is carried out at about 120° C. In some embodiments, curing is carried out for 1 minute to 3 hours, inclusive. In some embodiments, curing is carried out for 15 minutes to 1 hour, inclusive. In some embodiments, curing is carried out for 15 minutes. In certain embodiments, curing is carried out for 30 minutes. In some embodiments, curing is carried out for 1 hour. In certain embodiments, curing is carried out at ambient pressure. In some embodiments, curing is carried out at lower-than-ambient pressure. In some embodiments, curing is carried out at higher-than-ambient pressure.

The preparation of the copolymers may involve a metathesis reaction. In certain embodiments, the metathesis reaction is a ring-opening metathesis copolymerization (ROMP) (see, e.g., Liu el al. *J. Am. Chem. Soc.* 2012, 134, 16337; Liu, J.; Gao, A. X.; Johnson, J. A. *J Vis Exp* 2013, e50874).

In certain embodiments, the metathesis catalyst (e.g., ROMP catalyst) is a tungsten (W), molybdenum (Mo), or ruthenium (Ru), metathesis catalyst. In certain embodiments, the metathesis catalyst is a ruthenium metathesis catalyst. Metathesis catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *Am. Chem. Soc.* (1999) 121:9453; and *Chem. Eur. J.* (2001) 7:5299; the entire contents of each of which are incorporated herein by reference.

In certain embodiments, the metathesis catalyst is a Grubbs catalyst. In certain embodiments, the Grubbs catalyst is selected from the group consisting of:

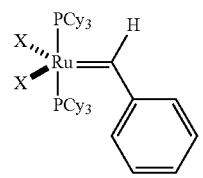

X = Cl; or Br, I
Cy = cyclohexyl

Benzylidenebis-(tricyclohexylphosphine)-dichlororuthenium (X=Cl); Benzylidenebis-(tricyclohexylphosphine)-dibromoruthenium (X=Br); Benzylidenebis-(tricyclohexylphosphine)-diiodoruthenium (X=I);

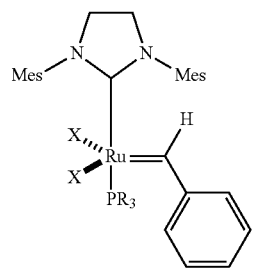

X = Cl; or Br, I
R = cyclohexyl (Cy); phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl); 1,3-(Bis(mesityl)-2-imidazolidinylidene)dibromo-(phenylmethylene) (tricyclohexyl-phosphine)ruthenium (X=Br; R=cyclohexyl); 1,3-(Bis(mesityl)-2-imidazolidinylidene)diiodo-(phenylmethylene) (tricyclohexyl-phosphine)ruthenium (X=I; R=cyclohexyl); 1,3-Bis(mesityl)-2-imidazolidinylidene)dichloro-(phenylmethylene) (triphenylphosphine)ruthenium (X=Cl; R=phenyl); 1,3-(Bis(mesityl)-2-imidazolidinylidene)dichloro-(phenylmethylene) (tribenzylphosphine)ruthenium (X=Cl; R=benzyl);

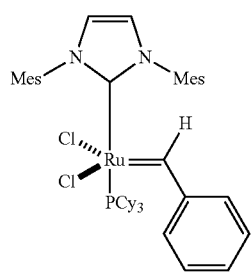

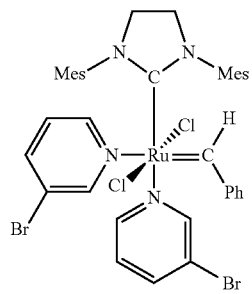

R = cyclohexyl (Cy); phenyl (Ph)
R′ = methyl; phenyl

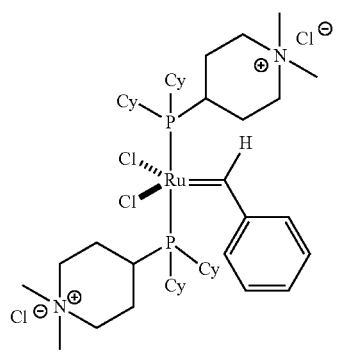

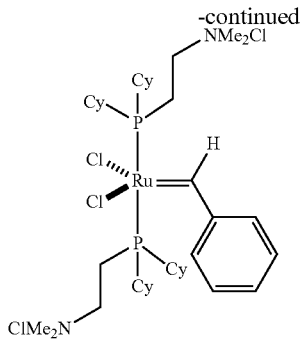

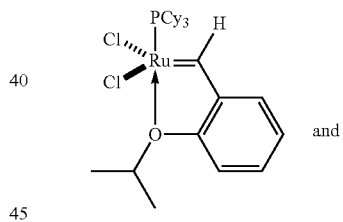

Py = pyridine
Ph = phenyl

In certain embodiments, the metathesis catalyst is a Grubbs-Hoveyda catalyst. In certain embodiments, the Grubbs-Hoveyda catalyst is selected from the group consisting of:

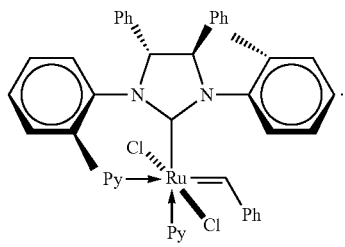 and

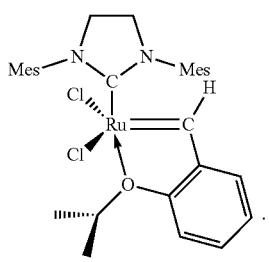

In certain embodiments, the metathesis catalyst is selected from the group consisting of:

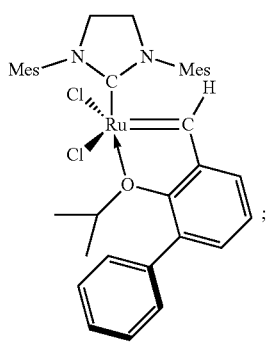

Blechart Catalyst

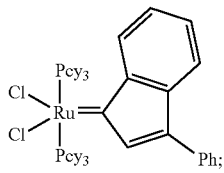

Neolyst™ M1

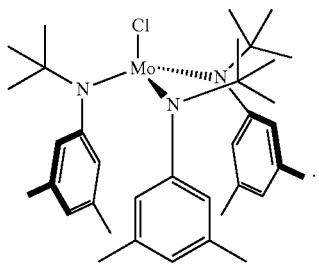

Furstner Catalyst

In certain embodiments, the metathesis catalyst is of the formula.

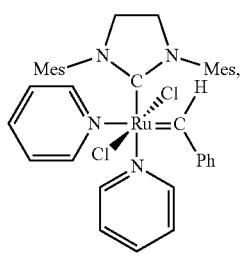

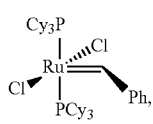

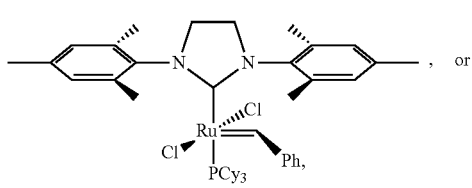, or

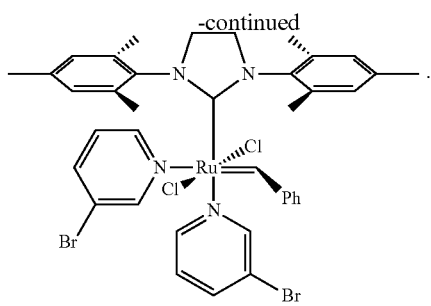

In certain embodiments, the metathesis catalyst is the second-generation Grubbs catalyst.

In certain embodiments, the ratio of the combined molar amounts of the first monomer, second monomer, and third monomer if present to the molar amount of the metathesis catalyst is not less than 2,000. In certain embodiments, the ratio of the combined molar amounts of the first monomer, second monomer, and third monomer if present to the molar amount of the metathesis catalyst is between 1,000 and 1,500, exclusive. In certain embodiments, the ratio of the combined molar amounts of the first monomer, second monomer, and third monomer if present to the molar amount of the metathesis catalyst is between 1,500 and 2,000, inclusive. In certain embodiments, the ratio of the combined molar amounts of the first monomer, second monomer, and third monomer if present to the molar amount of the metathesis catalyst is between 2,000 and 10,000, inclusive. In certain embodiments, the ratio of the combined molar amounts of the first monomer, second monomer, and third monomer if present to the molar amount of the metathesis catalyst is between 10,000 and 30,000, inclusive. In certain embodiments, the ratio of the combined molar amounts of the first monomer, second monomer, and third monomer if present to the molar amount of the metathesis catalyst is between 30,000 and 100,000, inclusive.

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

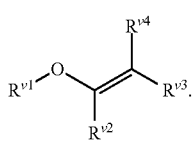

Each of $R^{v1}$, $R^{v2}$, $R^{v3}$, and $R^{v4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{v1}$ is optionally substituted alkyl, and $R^{v2}$, $R^{v3}$, and $R^{v4}$ are hydrogen. In certain embodiments, $R^{v1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$, and $R^{V4}$ are hydrogen. In certain embodiments, $R^{V1}$ is propyl, and $R^{V2}$, $R^{V3}$, and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$, and $R^{V4}$ are hydrogen. In certain embodiments, $R^{V1}$ is vinyl, and $R^{V2}$, $R^{V3}$, and $R^{V4}$ are hydrogen. In certain embodiments, at least one of $R^{V1}$, $R^{V2}$, $R^{V3}$, and $R^{V4}$ is conjugated with a diagnostic agent as defined above. In certain embodiments, the ROMP is quenched by ethyl vinyl ether. Excess ethyl vinyl ether can be removed from the copolymer under reduced pressure.

In certain embodiments, at least two instances of a variable (e.g., a moiety) are different from each other. In certain embodiments, all instances of a variable are different from each other. In certain embodiments, all instances of a variable are the same.

In certain embodiments, at least one instance of the first monomer is of Formula:

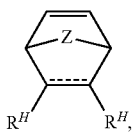

(A)

or salt thereof, wherein
each instance of Z is independently $C(R^P)_2$ or O;
each instance of $R^P$ is independently hydrogen, halogen, or substituted or unsubstituted, $C_{1-6}$ alkyl;
each instance of ==== is independently a single bond or double bond:
each instance of $R^H$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —OCN, —OC(=O)$R^a$, OC(=S)$R^a$, —OC(=O)O$R^a$, —OC(=O)N($R^a$)$_2$, —OS(=O)$R^a$, —OS(=O)O$R^a$, —OS(=O)N($R^a$)$_2$, —OS(=O)$_2R^a$, —OS(=O)$_2$O$R^a$, —OS(=O)$_2$N($R^a$)$_2$, —OSi($R^a$)$_3$, —OSi($R^a$)$_2$(OR), Si($R^a$)(OR$^a$)$_2$, Si(OR$^a$)$_3$, oxo, —N($R^a$)$_2$, —N=C($R^a$)$_2$, =N$R^a$, —NC, —NCO, —N$_3$, —NO$_2$, —NR$^a$C(=O)$R^a$, —NR$^a$C(=O)OR$^a$, —NR$^a$C(=O)N($R^a$)$_2$, —NR$^a$S(=O)$R^a$, —NR$^a$S(=O)OR$^a$, —NR$^a$S(=O)N($R^a$)$_2$, —NR$^a$S(=O)$_2R^a$, —NR$^a$S(=O)$_2$OR$^a$, NR$^a$S(=O)$_2$N($R^a$)$_2$, —SR, —SCN, —S(=O)$R^a$, —S(=O)OR, —S(=O)N($R^a$)$_2$, —S(=O)$_2R^a$, —S(=O)$_2$OR$^a$, —S(=O)$_2$N($R^a$)$_2$, —SeR$^a$, halogen, —CN, —C(=NR$^a$)R$^a$, —C(=NR$^a$)OR$^a$, —C(=NR$^a$)N($R^a$)$_2$, —C(=$^a$)R$^a$, C(=O)OR$^a$, C(=O)SR$^a$, —C(=S)OR, or —C(=O)N($R^a$)$_2$;
or the two instances of $R^H$ of one or more instances of

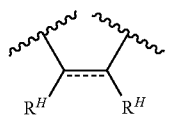

are joined with the intervening carbon atoms to independently form a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring; and
each instance of $R^a$ is independently hydrogen, substituted or unsubstituted alkyl, substituted or unsubstituted alkenyl, substituted or unsubstituted alkynyl, substituted or unsubstituted, monocyclic carbocyclyl, substituted or unsubstituted, monocyclic heterocyclyl, substituted or unsubstituted, monocyclic aryl, substituted or unsubstituted, monocyclic heteroaryl, a nitrogen protecting group when attached to a nitrogen atom, an oxygen protecting group when attached to an oxygen atom, or a sulfur protecting group when attached to a sulfur atom, or two instances of $R^a$ are joined to form substituted or unsubstituted heterocyclyl or substituted or unsubstituted heteroaryl.

In certain embodiments, each instance of the first monomer is independently of Formula (D1) or (D2):

(D1)

(D2)

or a salt thereof, wherein:
each instance of x is independently 0, 1, or 2; and
each instance of y is independently 0, 1, or 2.

In certain embodiments, at least one instance of Z is $C(R^P)_2$. In certain embodiments, each instance of Z is $C(R^P)_2$. In certain embodiments, at least one instance of Z is $CH_2$. In certain embodiments, each instance of Z is $CH_2$.

In certain embodiments, each instance of $R^P$ is hydrogen. In certain embodiments, at least one instance of $R^P$ is hydrogen. In certain embodiments, at least one instance of $R^P$ is halogen. In certain embodiments, at least one instance of $R^P$ is unsubstituted, $C_{1-6}$ alkyl or $C_{1-6}$ alkyl substituted with one or more halogen. In certain embodiments, at least one instance of $R^P$ is unsubstituted methyl.

In certain embodiments, at least one instance of $R^H$ is hydrogen. In certain embodiments, each instance of $R^H$ is hydrogen.

In certain embodiments, at least one instance of $R^H$ is substituted or unsubstituted alkyl (e.g., —CF$_3$). In certain embodiments, at least one instance of $R^H$ is —CN. In certain embodiments, at least one instance of $R^H$ is —C(=O)OR$^a$ (e.g., —C(=O)OCH$_3$). In certain embodiments, at least one instance of $R^H$ is —C(=O)R$^a$. In certain embodiments, at least one instance of $R^H$ is —C(=O)N($R^{aa}$)$_2$.

In certain embodiments, each instance of the linear units is of the formula:

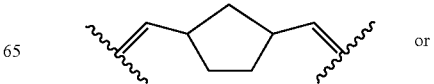 or

-continued

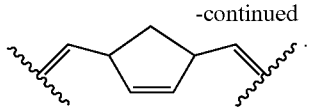

In certain embodiments, each instance of the first monomer is of Formula (D).

In certain embodiments, each instance of the first monomer is of the formula:

In certain embodiments, each instance of the first monomer is of the formula:

In certain embodiments, the two instances of R of one or more instances of

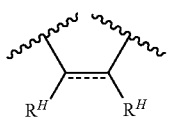

are joined with the intervening carbon atoms to independently form a substituted or unsubstituted, monocyclic carbocyclic ring, or substituted or unsubstituted, monocyclic heterocyclic ring. In certain embodiments, the two instances of $R^H$ of one or more instances of

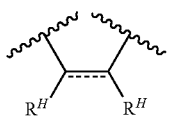

are joined with the intervening carbon atoms to independently form a substituted or unsubstituted, monocyclic cycloalkenyl ring. In certain embodiments, the two instances of $R^H$ of one or more instances of

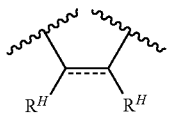

are joined with the intervening carbon atoms to independently form a substituted or unsubstituted, monocyclic, saturated heterocyclic ring. In certain embodiments, at least one instance of the first monomer comprises a substituted or unsubstituted partially unsaturated monocyclic carbocyclic ring or a substituted or unsubstituted partially unsaturated monocyclic heterocyclic ring.

In certain embodiments, each instance of the linear units is of the formula:

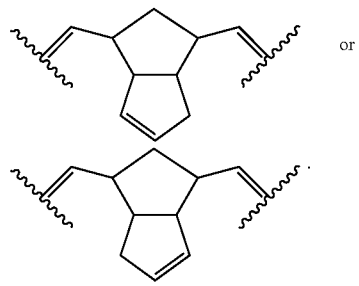 or

In certain embodiments, each instance of the first monomer is of Formula (D2).

In certain embodiments, each instance of x is 0. In certain embodiments, each instance of x is 1. In certain embodiments, each instance of x is 2.

In certain embodiments, each instance of y is 1. In certain embodiments, each instance of y is 0. In certain embodiments, each instance of y is 2.

In certain embodiments, each instance of x is 1, and each instance of y is 1. In certain embodiments, each instance of x is 1, and each instance of y is 0. In certain embodiments, each instance of x is 0, and each instance of y is 1.

In certain embodiments, each instance of the first monomer is of the formula:

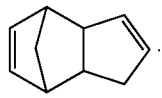

In certain embodiments, each instance of the first monomer is of the formula:

In certain embodiments, each instance of the first monomer is of the formula:

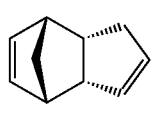

In certain embodiments, at least one instance of $R^J$ is —OH. In certain embodiments, each instance of $R^J$ is —OH. In certain embodiments, at least one instance of $R^J$ is —$OR^a$, provided that $R^a$ is not H. In certain embodiments, at least one instance of $R^J$ is —OCN. In certain embodiments, at least one instance of $R^J$ is —$OSi(R^a)_3$, —$OSi(R^a)_2(OR^a)$, —$OSi(R^a)(OR^a)_2$, or —$OSi(OR)_3$. In certain embodiments, at least one instance of $R^J$ is —$NH_2$. In certain embodiments, at least one instance of $R^J$ is —$NHR^a$, provided that $R^a$ is not H. In certain embodiments, at least one instance of $R^J$ is —$N(R^a)_2$, provided that $R^a$ is not H. In certain embodiments, at least one instance of $R^J$ is —$N_3$. In certain embodiments, at least one instance of $R^J$ is —NC. In certain embodiments, at least one instance of $R^J$ is —NCO. In certain embodiments, at least one instance of $R^J$ is —SH. In certain embodiments, at least one instance of $R^J$ is —SR, provided that $R^a$ is not H. In certain embodiments, at least one instance of $R^J$ is —SCN. In certain embodiments, at least one instance of $R^J$ is —SeH. In certain embodiments, at least one instance of $R^J$ is —SeR$^a$, provided that $R^a$ is not H. In certain embodiments, at least one instance of $R^J$ is halogen (e.g., F, Cl, Br, or I). In certain embodiments, at least one instance of $R^J$ is —CN. In certain embodiments, at least one instance of $R^J$ is —N═C(R$^a$)$_2$ or ═NR. In certain embodiments, at least one instance of $R^J$ is oxo. In certain embodiments, at least one instance of $R^J$ is —C(═O)R$^a$. In certain embodiments, at least one instance of $R^J$ is —C(═O)H. In certain embodiments, each instance of $R^J$ is —C(═O)H. In certain embodiments, at least one instance of $R^J$ is —C(═O)N(R$^a$)$_2$. In certain embodiments, at least one instance of $R^J$ is —OC(═S)R$^a$, —C(═O)SR, or —C(═S)OR$^a$, provided that $R^J$ is not H. In certain embodiments, at least one instance of $R^J$ is —C(═O)OH. In certain embodiments, at least one instance of $R^J$ is —C(═O)OR$^a$, provided that $R^a$ is not H. In certain embodiments, at least one instance of $R^J$ is —OC(═O)OR$^a$. In certain embodiments, at least one instance of $R^J$ is —NR$^a$C(═O)OR$^a$ or —OC(═O)N(R$^a$)$_2$.

In certain embodiments, at least one instance of $R^S$ is hydrogen. In certain embodiments, each instance of $R^S$ is hydrogen. In certain embodiments, at least one instance of $R^S$ is —OH. In certain embodiments, at least one instance of $R^S$ is —OR, provided that $R^a$ is not H. In certain embodiments, at least one instance of $R^S$ is —O(substituted or unsubstituted alkyl) (e.g., —OMe).

In certain embodiments, at least one instance of the functional units is independently of the formula:

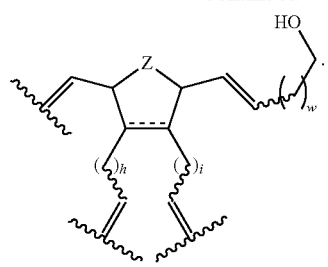

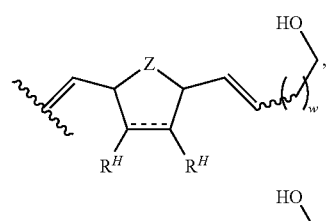

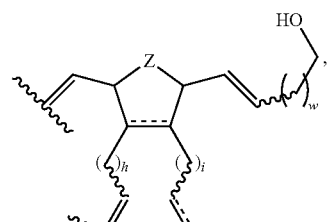

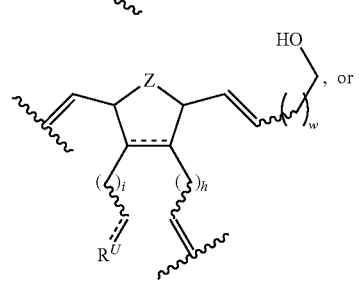

In certain embodiments, at least one instance of the functional units is independently of the formula:

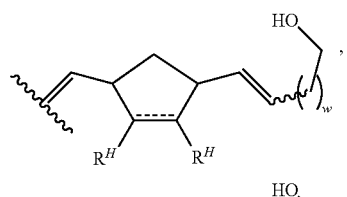

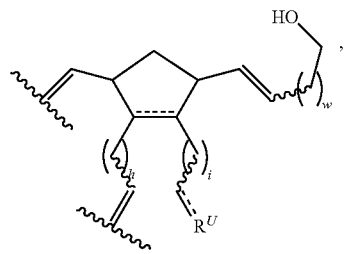

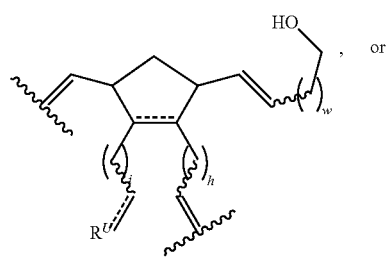

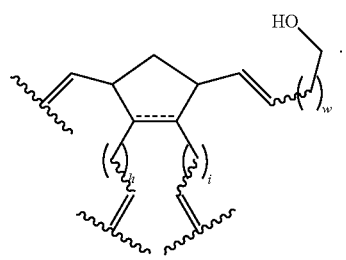

In certain embodiments, at least one instance of the functional units is independently of the formula:

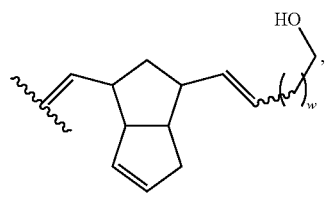

-continued

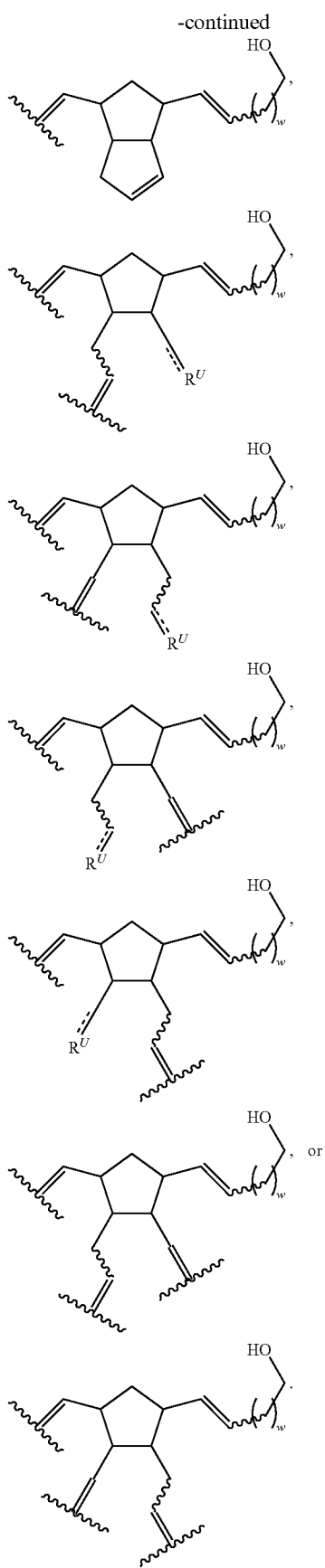

In certain embodiments, at least one instance of w is 0. In certain embodiments, at least one instance of w is 1. In certain embodiments, at least one instance of w is 2. In certain embodiments, at least one instance of w is 2 or 3. In certain embodiments, at least one instance of w is 3. In certain embodiments, at least one instance of w is 4.

In certain embodiments, at least one instance of $R^T$ is hydrogen. In certain embodiments, each instance of $R^T$ is hydrogen. In certain embodiments, at least one instance of $R^T$ is substituted or unsubstituted alkyl.

In certain embodiments, at least one instance of the functional units is independently of the formula:

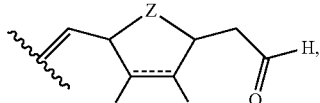

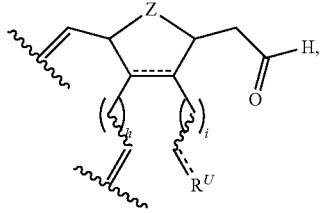

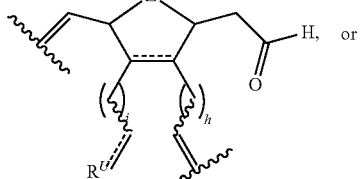

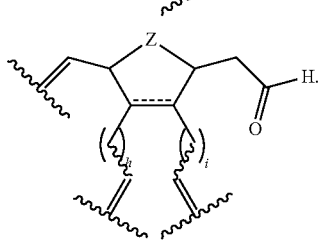

In certain embodiments, at least one instance of the functional units is independently of the formula:

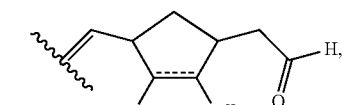

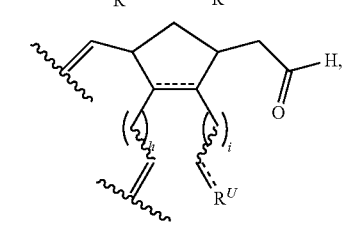

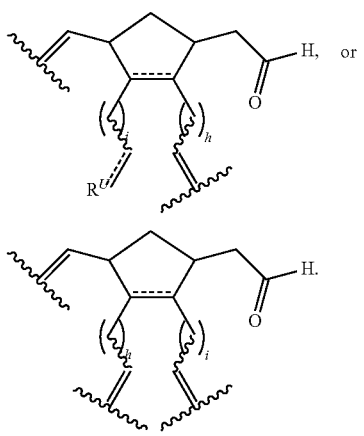

In certain embodiments, at least one instance of h is 0 or 1. In certain embodiments, each instance of h is 0 or 1.

In certain embodiments, at least one instance of i is 0 or 1. In certain embodiments, each instance of i is 0 or 1.

In certain embodiments, in the same repeating unit, the sum of h and i is 1.

In certain embodiments, at least one instance of the functional units is independently of the formula:

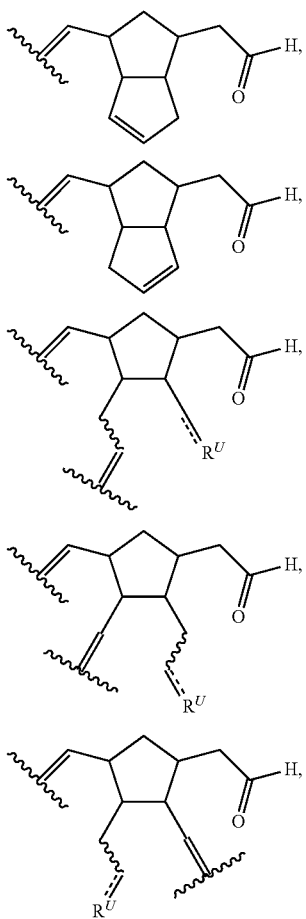

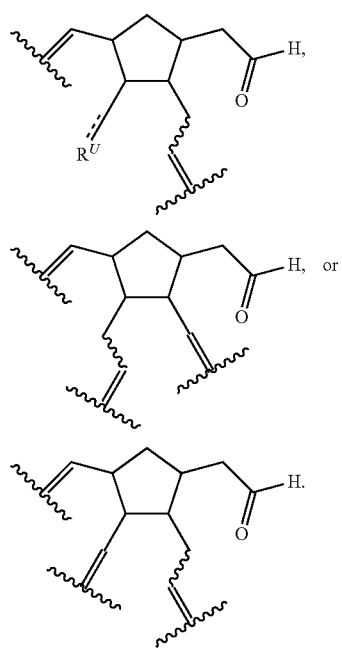

In certain embodiments, the functional oligomer or functional polymer comprises two or more instances of the functional units.

In certain embodiments, at least one instance of the crosslinking units is independently of the formula:

In certain embodiments, at least one instance of the crosslinking units is independently of the formula:

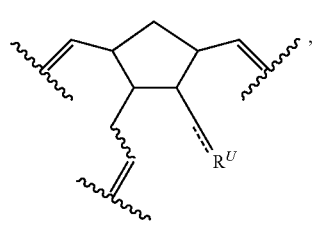

-continued

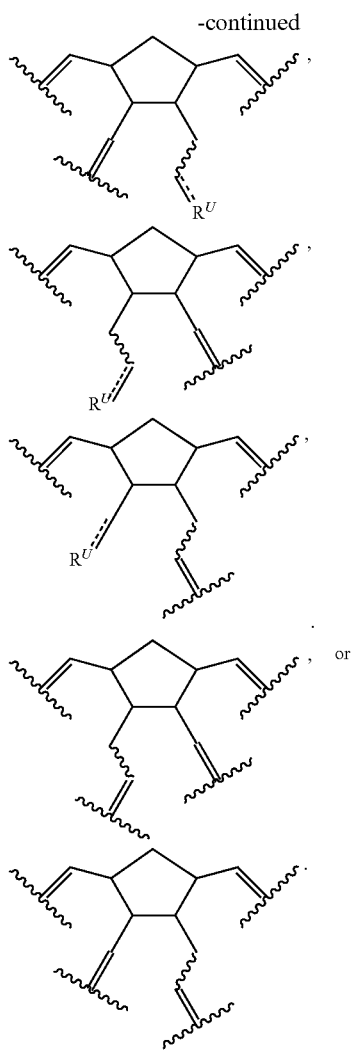

, or

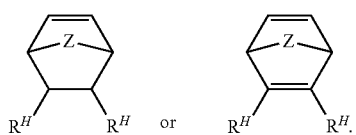

.

In certain embodiments, the functional oligomer or functional polymer does not comprise one or more instances of the functional units. In certain embodiments, the functional oligomer or functional polymer comprises one or more instances of the functional units.

In certain embodiments, at least one instance of $R^U$ is substituted or unsubstituted alkenyl, wherein the attachment point is a double bond. In certain embodiments, at least one instance of $R^U$ is =CH-(substituted or unsubstituted phenyl) or =CH—O-(substituted or unsubstituted alkyl).

In certain embodiments, at least one instance of the first monomer is of the formula:

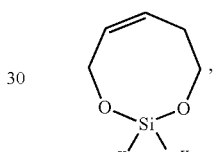

In certain embodiments, each instance of Y is O. In certain embodiments, each instance of Y is $C(R^Q)_2$ (e.g., —CH$_2$— or —C(CH$_3$)$_2$—). In certain embodiments, each instance of Y is —CH$_2$—

In certain embodiments, at least one instance of $R^Q$ is hydrogen. In certain embodiments, each instance of $R^Q$ is hydrogen. In certain embodiments, at least one instance of $R^Q$ is halogen (e.g., F). In certain embodiments, at least one instance of $R^Q$ is substituted or unsubstituted, $C_{1-6}$ alkyl (e.g., —CH$_3$).

In certain embodiments, each instance of j is 1. In certain embodiments, each instance of j is 2. In certain embodiments, each instance of j is 3.

In certain embodiments, each instance of k is 1. In certain embodiments, each instance of k is 2. In certain embodiments, each instance of k is 3. In certain embodiments, each instance of k is 0.

In certain embodiments, each instance of j is 1 and each instance of k is 1, each instance of j is 1 and each instance of k is 2, or each instance of j is 2 and each instance of k is 2. In certain embodiments, each instance of j is 1 and each instance of k is 2. In certain embodiments, the sum of each instance of j and each instance of k is 3.

In certain embodiments, the C=C double bond in Formula (B) is of E configuration. In certain embodiments, the C=C double bond in Formula (B) is of Z configuration.

In certain embodiments, each instance of the second monomer is of the formula:

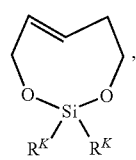

, or a salt thereof.

In certain embodiments, each instance of the second monomer is of the formula:

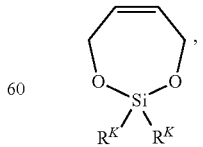

, or a salt thereof.

In certain embodiments, each instance of the second monomer is of the formula:

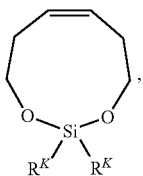

or a salt thereof.

In certain embodiments, each instance of $R^K$ is independently hydrogen, substituted or unsubstituted, $C_{1-6}$ alkyl, or substituted or unsubstituted phenyl. In certain embodiments, at least one instance of $R^K$ is hydrogen. In certain embodiments, at least one instance of $R^K$ is substituted or unsubstituted $C_{1-6}$ alkyl. In certain embodiments, each instance of $R^K$ is independently substituted or unsubstituted $C_{1-6}$ alkyl. In certain embodiments, at least one instance of $R^K$ is unsubstituted $C_{1-4}$ alkyl. In certain embodiments, at least one instance of $R^K$ is unsubstituted $C_{1-3}$ alkyl. In certain embodiments, each instance of $R^K$ is unsubstituted $C_{1-3}$ alkyl. In certain embodiments, each instance of $R^K$ is Me. In certain embodiments, each instance of $R^K$ is Et. In certain embodiments, each instance of $R^K$ is n-Pr. In certain embodiments, each instance of $R^K$ is i-Pr. In certain embodiments, at least one instance of $R^K$ is substituted or unsubstituted carbocyclyl, substituted or unsubstituted heterocyclyl, substituted or unsubstituted aryl, or substituted or unsubstituted heteroaryl. In certain embodiments, each instance of $R^K$ is independently substituted or unsubstituted carbocyclyl, substituted or unsubstituted heterocyclyl, substituted or unsubstituted aryl, or substituted or unsubstituted heteroaryl. In certain embodiments, at least one instance of $R^K$ is substituted or unsubstituted phenyl. In certain embodiments, each instance of $R^K$ is independently substituted or unsubstituted phenyl. In certain embodiments, at least one instance of $R^K$ is unsubstituted phenyl. In certain embodiments, each instance of $R^K$ is unsubstituted phenyl. In certain embodiments, one instance of $R^K$ is substituted or unsubstituted $C_{1-6}$ alkyl, and the other instance of $R^K$ is substituted or unsubstituted phenyl. In certain embodiments, at least one instance of $R^K$ is —$OR^N$ (e.g., —O(unsubstituted $C_{1-6}$ alkyl)). In certain embodiments, each instance of $R^K$ is —$OR^N$ (e.g., —O(unsubstituted $C_{1-6}$ alkyl)).

In certain embodiments, at least one instance of $R^N$ is substituted or unsubstituted, $C_{1-6}$ alkyl, or substituted or unsubstituted phenyl. In certain embodiments, each instance of $R^N$ is independently substituted or unsubstituted, $C_{1-6}$ alkyl, or substituted or unsubstituted phenyl. In certain embodiments, each instance of $R^N$ is unsubstituted $C_{1-3}$ alkyl or unsubstituted phenyl. In certain embodiments, each instance of $R^N$ is unsubstituted methyl. In certain embodiments, each instance of $R^N$ is unsubstituted ethyl. In certain embodiments, each instance of $R^N$ is unsubstituted propyl (e.g., isopropyl). In certain embodiments, each instance of $R^N$ is unsubstituted phenyl. In certain embodiments, at least one instance of $R^N$ is hydrogen. In certain embodiments, at least one instance of $R^N$ is halogen. In certain embodiments, at least one instance of $R^N$ is substituted or unsubstituted, $C_{1-10}$ alkyl. In certain embodiments, at least one instance of $R^N$ is an oxygen protecting group. In certain embodiments, at least one instance of $R^N$ is substituted or unsubstituted carbocyclyl, substituted or unsubstituted heterocyclyl, substituted or unsubstituted aryl, or substituted or unsubstituted heteroaryl.

In some embodiments, each instance of the second monomer has a molecular weight between 110 g/mol and 320 g/mol, inclusive. In some embodiments, each instance of the second monomer has a molecular weight between 110 g/mol and 200 g/mol, inclusive.

In certain embodiments, each instance of the second monomer is of the formula:

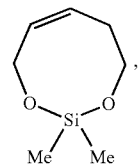

or a salt thereof.

In certain embodiments, each instance of the second monomer is of the formula:

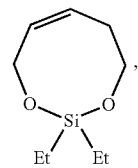

or a salt thereof.

In certain embodiments, each instance of the second monomer is of the formula:

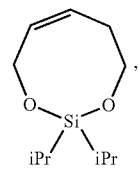

or a salt thereof.

In certain embodiments, each instance of the second monomer is of the formula:

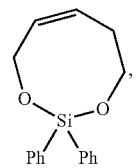

or a salt thereof.

In certain embodiments, each instance of the second monomer is of the formula:

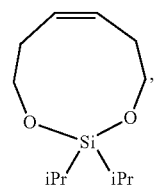 [SMILES: CC(C)[Si]1(C(C)C)OCC/C=C\CCO1]

or a salt thereof.

In certain embodiments, each instance of the second monomer is of the formula:

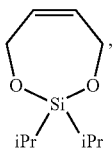

or a salt thereof.

In certain embodiments, the functional oligomer or functional polymer, hydroxylated polymer, or copolymer is crosslinked. In certain embodiments, the functional oligomer or functional polymer is crosslinked because it comprises one or more instances of the crosslinking units. In certain embodiments, the crosslinking degree of the hydroxylated polymer is about 12% mole:mole. In certain embodiments, the crosslinking degree of the hydroxylated polymer is between 10% and 15%, inclusive, mole:mole. In certain embodiments, the crosslinking degree of the hydroxylated polymer is between 5% and 20%, inclusive, mole:mole. In certain embodiments, the crosslinking degree is between 5% and 10%, inclusive, mole:mole. In certain embodiments, the crosslinking degree is between 10% and 15%, inclusive, mole:mole. In certain embodiments, the crosslinking degree is between 15% and 20%, inclusive, mole:mole. In certain embodiments, the crosslinking degree is not greater than the concentration of all the instances of the second monomer in the functional oligomer or functional polymer, hydroxylated polymer, or copolymer, mole:mole.

In certain embodiments, the functional polymer is a thermosetting polymer. In certain embodiments, the hydroxylated polymer is a thermosetting polymer. In certain embodiments, the copolymer is a thermosetting polymer.

In certain embodiments, the aqueous solubility of the functional oligomer or functional polymer is between 0.1 and 0.3, between 0.3 and 1, between 1 and 3, between 3 and 10, between and 30, or between 30 and 100, inclusive, g/L, at 1 atmosphere and 20° C. In certain embodiments, the aqueous solubility of the functional oligomer or functional polymer is between 1 and 10, inclusive, g/L, at 1 atmosphere and 20° C.

In certain embodiments, the aqueous solubility of the hydroxylated polymer is between 0.1 and 0.3, between 0.3 and 1, between 1 and 3, between 3 and 10, between 10 and 30, or between 30 and 100, inclusive, g/L, at 1 atmosphere and 20° C. In certain embodiments, the aqueous solubility of the hydroxylated polymer is between 1 and 10, inclusive, g/L, at 1 atmosphere and 20° C.

In certain embodiments, the molar ratio of the one or more instances of the first monomer to one or more instances of a second monomer is between 1:2 and 2:1, inclusive, 6:1 and 19:1, inclusive, or 5:1 and 35:1, inclusive. In certain embodiments, the molar ratio of the one or more instances of the first monomer to the one or more instances of the second monomer is between 1:2 and 2:1, inclusive. In certain embodiments, the molar ratio of the one or more instances of the first monomer to the one or more instances of the second monomer is between 1:10 and 10:1 (e.g., between 1:5 and 5:1), inclusive. In some embodiments, the molar ratio of the one or more instances of the first monomer to the one or more instances of the second monomer is between 1:35 and 35:1, inclusive. In some embodiments, the molar ratio of the one or more instances of the second monomer to the one or more instances of the first monomer is between 1:33 and 1:27, inclusive. In some embodiments, the molar ratio of the one or more instances of the second monomer to the one or more instances of the first monomer is between 1:17 and 1:11, inclusive. In some embodiments, the molar ratio of the one or more instances of the second monomer to the one or more instances of the first monomer is between 1:11 and 1:6, inclusive. In certain embodiments, the molar ratio of the one or more instances of the first monomer to the one or more instances of the second monomer is about 1:1.

In certain embodiments, the average molecular weight of the functional oligomer or functional polymer is between 300 Da and 1 kDa, between 1 kDa and 3 kDa, between 3 kDa and kDa, between 10 kDa and 100 kDa, or between 100 kDa and 1,000 kDa, inclusive. In certain embodiments, the average molecular weight of the functional oligomer or functional polymer is between 1 kDa and 10 kDa, inclusive. In certain embodiments, the average molecular weight is as determined by gel permeation chromatography. In certain embodiments, the average molecular weight of the functional oligomer or functional polymer as determined by gel permeation chromatography is between 300 Da and 1,000 kDa, inclusive. In certain embodiments, the average molecular weight of the functional oligomer or functional polymer as determined by gel permeation chromatography is between 1 kDa and 8 kDa, inclusive.

In certain embodiments, the average molecular weight of the hydroxylated polymer is between 300 Da and 1 kDa, between 1 kDa and 3 kDa, between 3 kDa and 10 kDa, between 10 kDa and 100 kDa, or between 100 kDa and 1,000 kDa, inclusive. In certain embodiments, the average molecular weight of the hydroxylated polymer is between 1 kDa and 10 kDa, inclusive. In certain embodiments, the average molecular weight is as determined by gel permeation chromatography. In certain embodiments, the average molecular weight of the hydroxylated polymer as determined by gel permeation chromatography is between 300 Da and 1,000 kDa, inclusive. In certain embodiments, the average molecular weight of the hydroxylated polymer as determined by gel permeation chromatography is between 1 kDa and 8 kDa, inclusive.

In certain embodiments, the average molecular weight of the copolymer is between 10 kDa and 10,000 kDa, inclusive. In certain embodiments, the average molecular weight of the copolymer is between 10 kDa and 30 kDa, between 30 kDa and 100 kDa, between 100 kDa and 1,000 kDa, between 1,000 kDa and 10,000 kDa, or between 10,000 kDa and 100,000 kDa, inclusive. In certain embodiments, the average molecular weight of the copolymer is between 10 kDa and 100 kDa, inclusive. In certain embodiments, the average molecular weight is as determined by gel permeation chromatography. In certain embodiments, the average molecular weight of the copolymer as determined by gel permeation chromatography is between 10 kDa and 100,000 kDa, inclusive. In certain embodiments, the number average polymerization degree is between 2 and 1,000, inclusive, with respect to the first monomer: and between 2 and 1,000, inclusive, with respect to the second monomer. In certain embodiments, the number average polymerization degree is between 10 and 200, inclusive, with respect to the first monomer; and between 10 and 200, inclusive, with respect to the second monomer. In certain embodiments, the number average polymerization degree is between 15 and 100, inclusive, with respect to the first monomer; and between 15 and 100, inclusive, with respect to the second monomer. In certain embodiments, the number average polymerization degree is between 2 and 1,000, between 10 and 1,000, between 100 and 1,000, between 2 and 100, between 10 and 100, between 2 and 10, inclusive, with respect to the first monomer. In certain embodiments, the number average polymerization degree is between 2 and 1,000, between 10 and 1,000, between 100 and 1,000, between 2 and 100, between 10 and 100, between 2 and 10, inclusive, with respect to the second monomer.

In certain embodiments, the dispersity (Đ) of the copolymer is between 1 and 2, between 1.1 and 2, between 1.3 and 2, between 1.5 and 2, between 1.1 and 1.5, between 1.1 and 1.3, between 1.3 and 2, between 1.3 and 1.5, between 1.5 and 2, inclusive.

In certain embodiments, the average hydrodynamic diameter of the functional oligomer or functional polymer is between 1 and 100 nm, inclusive. In certain embodiments, the average hydrodynamic diameter of the functional oligomer or functional polymer is between 1 and 10 nm, inclusive. In certain embodiments, the average hydrodynamic diameter of the functional oligomer or functional polymer is between 10 and 30 nm, inclusive. In certain embodiments, the average hydrodynamic diameter of the functional oligomer or functional polymer is between 30 and 100 nm, inclusive. In certain embodiments, the average hydrodynamic diameter of the hydroxylated polymer is between 1 and 100 nm, inclusive. In certain embodiments, the average hydrodynamic diameter of the hydroxylated polymer is between 1 and 10 nm, inclusive. In certain embodiments, the average hydrodynamic diameter of the hydroxylated polymer is between 10 and 30 nm, inclusive. In certain embodiments, the average hydrodynamic diameter of the hydroxylated polymer is between 30 and 100 nm, inclusive. In certain embodiments, the average hydrodynamic diameter is as determined by diffusion ordered spectroscopy (DOSY).

In certain embodiments, the copolymer is a block copolymer, preferably a block polymer comprising at least four consecutive blocks, wherein:
 each of the first consecutive block and the third consecutive block independently comprises one or more repeating units formed from the first monomer or the third monomer if present; and
 each of the second consecutive block and the fourth consecutive block independently comprises one or more repeating units formed from the second monomer.

In certain embodiments, the copolymer is a random copolymer.

In certain embodiments, the step of polymerizing is substantially free (e.g., between 90%/6-99% free) of a chain transfer agent.

In certain embodiments, the step of hydrolyzing the copolymer comprises hydrolyzing at least 50% of the —O—Si bonds of the copolymer to form —OH. In certain embodiments, the step of hydrolyzing the copolymer comprises hydrolyzing between 50% and 70%, inclusive, of the —O—Si bonds of the copolymer to form —OH. In certain embodiments, the step of hydrolyzing the copolymer comprises hydrolyzing between 70% and 90%, inclusive, of the —O—Si bonds of the copolymer to form —OH. In certain embodiments, the step of hydrolyzing the copolymer comprises hydrolyzing between 90% and 99%, inclusive, of the —O—Si bonds of the copolymer to form —OH. In certain embodiments, the step of hydrolyzing the copolymer comprises hydrolyzing at least 95% of the —O—Si bonds of the copolymer to form —OH.

In certain embodiments, the step of hydrolyzing the copolymer comprises hydrolyzing at least 50% of

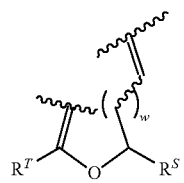

of the copolymer to form

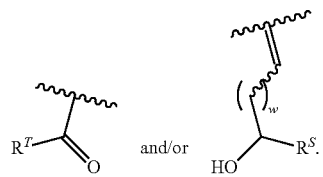

In certain embodiments, the step of hydrolyzing the copolymer comprises hydrolyzing between 50% and 70%, inclusive, of

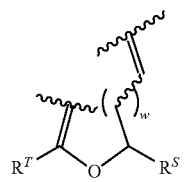

of the copolymer to form

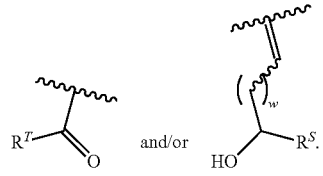

In certain embodiments, the step of hydrolyzing the copolymer comprises hydrolyzing between 70% and 90%, inclusive, of

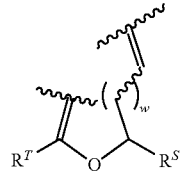

of the copolymer to form

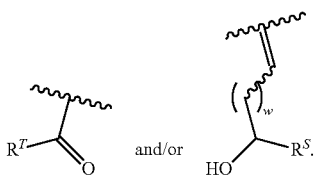

In certain embodiments, the step of hydrolyzing the copolymer comprises hydrolyzing between 90% and 99%, inclusive, of

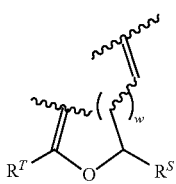

of the copolymer to form

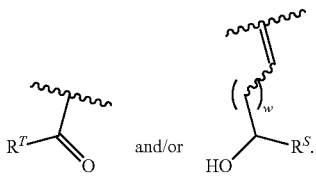

In certain embodiments, the step of hydrolyzing the copolymer comprises hydrolyzing at least 95% of

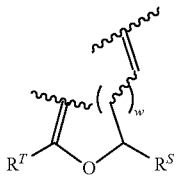

of the copolymer to form

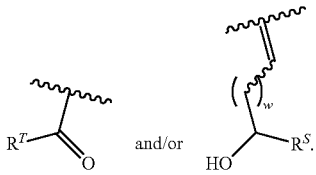

In certain embodiments, the step of hydrolyzing the copolymer comprises ambient temperature, ambient pressure, and a reaction time of between 1 hour and 48 hours (e.g., between 1 hour and 6 hours, between 6 hour and 24 hours, between 24 hour and 48 hours), inclusive.

In certain embodiments, the step of hydrolyzing the copolymer comprises reacting the copolymer with a fluoride source. In certain embodiments, the fluoride source is tetra (unsubstituted alkyl)-ammonium fluoride. In certain embodiments, the fluoride source is tetra(unsubstituted $C_{1-6}$ alkyl)-ammonium fluoride (e.g., TBAF). In certain embodiments, the fluoride source is a metal fluoride (e.g., alkali metal fluoride or alkaline earth metal fluoride). In certain embodiments, a polymer is chemically degradable in the presence of tetra-n-butylammonium fluoride (TBAF).

In some embodiments, the amount of the fluoride source is about 1 equivalent (mole:mole) relative to the amount of the second monomer. In some embodiments, the amount of the fluoride source is in excess (e.g., about 2 equivalents) relative to the amount of the second monomer.

In certain embodiments, the step of hydrolyzing the copolymer comprises reacting the copolymer with an acid.

In certain embodiments, the acid is an aqueous solution of an acid. In certain embodiments, the acid is an inorganic acid. In certain embodiments, the acid is an organic acid. In certain embodiments, the acid has a pKa value of less than 3, less than 2, less than 1, or less than 0, under ambient conditions. In certain embodiments, the acid is HCl, HBr, HI, $HClO_4$, $HNO_3$, $H_2SO_4$, $CH_3SO_3H$, or $CF_3SO_3H$. In certain embodiments, the acid is HCl. In certain embodiments, the acid is $CF_3CO_2H$.

In some embodiments, the amount of the acid is about 1 equivalent (mole:mole) relative to the amount of the second monomer. In some embodiments, the amount of the acid is in excess (e.g., about 2 equivalents) relative to the amount of the second monomer.

In another aspect, the present disclosure describes compositions comprising:
 a hydroxylated polymer; and
 optionally an excipient.

Compositions described herein can be prepared by any method known in the art. In general, such preparatory methods include bringing the hydroxylated polymer into association with an excipient, and/or one or more other accessory ingredients, and then, if necessary and/or desirable, shaping, and/or packaging the product into a desired unit.

In another aspect, the present disclosure describes kits comprising:
 a hydroxylated polymer; and
 instructions for using the hydroxylated polymer.

Kits may be commercial packs or reagent packs. The kits may further comprise a container (e.g., a vial, ampule, bottle, syringe, and/or dispenser package, or other suitable container). In certain embodiments, a kit further comprises instructions for using the hydroxylated polymer (e.g., for preparing a conjugate).

Conjugates, and Methods of Preparation, Compositions, and Kits Thereof

In another aspect, the present disclosure describes conjugates prepared by reacting a hydroxy-reacting substance with a hydroxylated polymer described herein, wherein hydroxy-reacting substance comprises at least one instance of a hydroxy-reacting moiety.

In another aspect, the present disclosure describes methods of preparing a conjugate comprising reacting a hydroxy-reacting substance with a hydroxylated polymer described herein, wherein hydroxy-reacting substance comprises at least one instance of a hydroxy-reacting moiety.

In certain embodiments, the hydroxy-reacting substance is a hydroxy-reacting small molecule. In certain embodiments, the hydroxy-reacting substance is lactide. In certain embodiments, the hydroxy-reacting substance is a hydroxy-reacting polymer. In certain embodiments, the average molecular weight of the hydroxy-reacting polymer is between 1 kDa and 3 kDa, between 3 kDa and 10 kDa, between 10 kDa and 30 kDa, between 30 kDa and 100 kDa, or between 100 kDa and 1,000 kDa, inclusive. In certain embodiments, the average molecular weight of the hydroxy-reacting polymer is between 3 kDa and 30 kDa, inclusive. In certain embodiments, the average molecular weight is as determined by gel permeation chromatography. In certain embodiments, the average molecular weight of the hydroxy-reacting polymer as determined by gel permeation chromatography is between 1 kDa and 1,000 kDa, inclusive.

In certain embodiments, the hydroxy-reacting substance is a polysiloxane, wherein the polysiloxane comprises at least one instance of a hydroxy-reacting moiety. In certain embodiments, the hydroxy-reacting substance is a polydimethylsiloxane (PDMS), wherein the PDMS comprises at least one instance of a hydroxy-reacting moiety (e.g., hydride (e.g., Si(IV)-H)).

In certain embodiments, at least one instance of the hydroxy-reacting moiety is Si(IV)—H, Si(IV)-(a leaving group), C(IV)-(a leaving group), —C(=O)—OH, —C(=O)-(a leaving group), —C(=O)—O—, —C(=O)—O—C(=O)—, —S(=O)—OH, —S(=O)-a leaving group), —S(=O)$_2$—OH, —S(=O)$_2$-(a leaving group), —OH, or —O-(a leaving group). In certain embodiments, at least one instance of the hydroxy-reacting moiety is Si(IV)—H. In certain embodiments, at least one instance of the hydroxy-reacting moiety is —C(=O)-(a leaving group). In certain embodiments, at least one instance of the hydroxy-reacting moiety is —O-(a leaving group).

In certain embodiments, the hydroxy-reacting substance is a polylactic acid (PLA). In certain embodiments, the hydroxy-reacting substance is a polyethylene glycol (PEG).

In another aspect, the present disclosure describes compositions comprising:
 a conjugate; and
 optionally an excipient.

Compositions described herein can be prepared by any method known in the art. In general, such preparatory methods include bringing the conjugate into association with an excipient, and/or one or more other accessory ingredients, and then, if necessary and/or desirable, shaping, and/or packaging the product into a desired unit.

In another aspect, the present disclosure describes kits comprising:
 a conjugate: and
 instructions for using the conjugate.

Kits may be commercial packs or reagent packs. The kits may further comprise a container (e.g., a vial, ampule, bottle, syringe, and/or dispenser package, or other suitable container). In certain embodiments, a kit further comprises instructions for using the conjugate (e.g., for use as a bulk material).

Embodiments

Embodiment 1. A hydroxylated polymer prepared by hydrolyzing a copolymer prepared by a method comprising polymerizing in the presence of a metathesis catalyst:
 i) one or more instances of a first monomer, wherein each instance of the first monomer is independently of the formula:

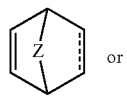

(A')

or

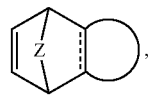

(A'')

or salt thereof, wherein:
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;
 each instance of Z is independently C(R$^P$)$_2$ or O;
 each instance of R$^P$ is independently hydrogen, halogen, or substituted or unsubstituted, C$_{1-6}$ alkyl; and
 each instance of ═══ is independently a single bond or double bond; and
 ii) one or more instances of a second monomer, wherein each instance of the second monomer is of Formula (B):

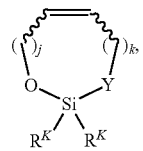

(B)

or a salt thereof; wherein:
 each instance of Y is independently O or C(R$^Q$)$_2$;
 each instance of R$^Q$ is independently hydrogen, halogen, or substituted or unsubstituted, C$_{1-6}$alkyl;
 each instance of R$^K$ is independently hydrogen, halogen, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or —OR$^N$;
 each instance of R$^N$ is independently hydrogen, substituted or unsubstituted acyl, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
 each instance of j is independently 1, 2, or 3; and
 each instance of k is independently 0, 1, 2, or 3;
 wherein any two instances of the first monomer are the same as or different from each other, and any two instances of the second monomer are the same as or different from each other; and
 wherein the step of hydrolyzing the copolymer comprises hydrolyzing one or more instances of the —O—Si bonds of the copolymer to form —OH.

Embodiment 2. A method of preparing a hydroxylated polymer comprising hydrolyzing a copolymer prepared by a method comprising polymerizing in the presence of a metathesis catalyst:

i) one or more instances of a first monomer, wherein each instance of the first monomer is independently of the formula:

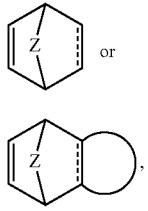

or salt thereof, wherein:
each instance of

is Ring B, wherein each instance of Ring B is independently a substituted or unsubstituted, monocyclic carbocyclic ring, substituted or
  unsubstituted, monocyclic heterocyclic ring, substituted or unsubstituted, monocyclic aryl ring, or substituted or unsubstituted, monocyclic heteroaryl ring;
each instance of Z is independently $C(R^P)_2$ or O;
each instance of $R^P$ is independently hydrogen, halogen, or substituted or unsubstituted, $C_{1-6}$ alkyl; and
each instance of ==== is independently a single bond or double bond; and
ii) one or more instances of a second monomer, wherein each instance of the second monomer is of Formula (B);

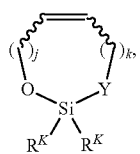

or a salt thereof; wherein:
each instance of Y is independently O or $C(R^C)_2$;
each instance of $R^Q$ is independently hydrogen, halogen, or substituted or unsubstituted, $C_{1-6}$ alkyl;
each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or $-OR^N$.
each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
each instance of j is independently 1, 2, or 3; and
each instance of k is independently 0, 1, 2, or 3;
wherein any two instances of the first monomer are the same as or different from each other, and any two instances of the second monomer are the same as or different from each other; and
wherein the step of hydrolyzing the copolymer comprises hydrolyzing one or more instances of the —O—Si bonds of the copolymer to form —OH.

Embodiment 3. The hydroxylated polymer or method of any one of the preceding embodiments, wherein the metathesis catalyst is a ruthenium metathesis catalyst.

Embodiment 4. The hydroxylated polymer or method of any one of the preceding embodiments, wherein the metathesis catalyst is a Grubbs catalyst.

Embodiment 5. The hydroxylated polymer or method of any one of the preceding embodiments, wherein each instance of the first monomer is independently of Formula (D1) or (D2):

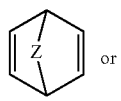

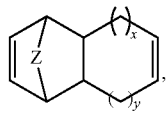

or a salt thereof, wherein:
each instance of x is independently 0, 1, or 2; and
each instance of y is independently 0, 1, or 2.

Embodiment 6. The hydroxylated polymer or method of any one of the preceding embodiments, wherein at least one instance of Z is $C(R^P)_2$.

Embodiment 7. The hydroxylated polymer or method of any one of the preceding embodiments, wherein each instance of $R^P$ is hydrogen.

Embodiment 8. The hydroxylated polymer or method of any one of the preceding embodiments, wherein each instance of the first monomer is of Formula (D1).

Embodiment 9. The hydroxylated polymer or method of any one of the preceding embodiments, wherein each instance of the first monomer is of the formula:

Embodiment 10. The hydroxylated polymer or method of any one of the preceding embodiments, wherein each instance of the first monomer is of Formula (D2).

Embodiment 11. The hydroxylated polymer or method of any one of the preceding embodiments, wherein each instance of x is 0.

Embodiment 12. The hydroxylated polymer or method of any one of the preceding embodiments, wherein each instance of y is 1.

Embodiment 13. The hydroxylated polymer or method of any one of the preceding embodiments, wherein each instance of the first monomer is of the formula:

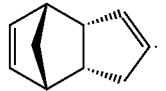

Embodiment 14. The hydroxylated polymer or method of any one of the preceding embodiments, wherein each instance of Y is O.

Embodiment 15. The hydroxylated polymer or method of any one of the preceding embodiments, wherein each instance of j is 1 and each instance of k is 1, each instance of j is 1 and each instance of k is 2, or each instance of j is 2 and each instance of k is 2.

Embodiment 16. The hydroxylated polymer or method of any one of the preceding embodiments, wherein each instance of the second monomer is of the formula:

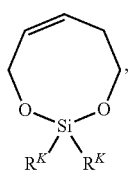

or a salt thereof.

Embodiment 17. The hydroxylated polymer or method of any one of the preceding embodiments, wherein each instance of the second monomer is of the formula:

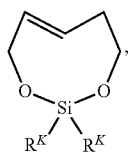

or a salt thereof.

Embodiment 18. The hydroxylated polymer or method of any one of the preceding embodiments, wherein each instance of the second monomer is of the formula:

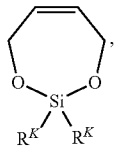

or a salt thereof.

Embodiment 19. The hydroxylated polymer or method of any one of the preceding embodiments, wherein each instance of the second monomer is of the formula:

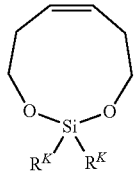

or a salt thereof.

Embodiment 20. The hydroxylated polymer or method of any one of the preceding embodiments, wherein each instance of $R^K$ is independently hydrogen, substituted or unsubstituted, $C_{1-6}$ alkyl, or substituted or unsubstituted phenyl.

Embodiment 21. The hydroxylated polymer or method of any one of the preceding embodiments, wherein each instance of $R^K$ is unsubstituted $C_{1-3}$ alkyl.

Embodiment 22. The hydroxylated polymer or method of any one of the preceding embodiments, wherein each instance of $R^K$ is unsubstituted phenyl.

Embodiment 23. The hydroxylated polymer or method of any one of the preceding embodiments, wherein each instance of the second monomer is of the formula:

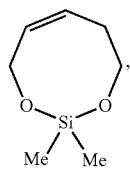

or a salt thereof.

Embodiment 24. The hydroxylated polymer or method of any one of the preceding embodiments, wherein each instance of the second monomer is of the formula:

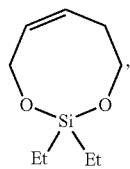

or a salt thereof.

Embodiment 25. The hydroxylated polymer or method of any one of the preceding embodiments, wherein each instance of the second monomer is of the formula:

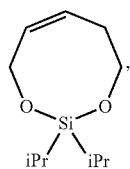

or a salt thereof.

Embodiment 26. The hydroxylated polymer or method of any one of the preceding embodiments, wherein each instance of the second monomer is of the formula:

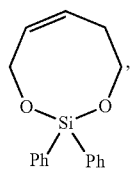

or a salt thereof.

Embodiment 27. The hydroxylated polymer or method of any one of the preceding embodiments, wherein each instance of the second monomer is of the formula:

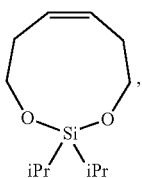

or a salt thereof.

Embodiment 28. The hydroxylated polymer or method of any one of the preceding embodiments, wherein each instance of the second monomer is of the formula:

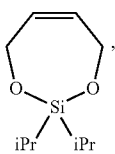

or a salt thereof.

Embodiment 29. The hydroxylated polymer or method of any one of the preceding embodiments, wherein the hydroxylated polymer is crosslinked.

Embodiment 30. The hydroxylated polymer or method of any one of the preceding embodiments, wherein the cross-linking degree of the hydroxylated polymer is between 5% and 20%, inclusive, mole:mole.

Embodiment 31. The hydroxylated polymer or method of any one of the preceding embodiments, wherein the hydroxylated polymer is a thermosetting polymer.

Embodiment 32. The hydroxylated polymer or method of any one of the preceding embodiments, wherein the molar ratio of the one or more instances of the first monomer to one or more instances of a second monomer is between 1:2 and 2:1, inclusive, 6:1 and 19:1, inclusive, or 5:1 and 35:1, inclusive.

Embodiment 33. The hydroxylated polymer or method of any one of the preceding embodiments, wherein the average molecular weight of the hydroxylated polymer as determined by gel permeation chromatography is between 300 Da and 1,000 kDa, inclusive.

Embodiment 34. The hydroxylated polymer or method of any one of the preceding embodiments, wherein the average molecular weight of the copolymer as determined by gel permeation chromatography is between 10 kDa and 100,000 kDa, inclusive.

Embodiment 35. The hydroxylated polymer or method of any one of the preceding embodiments, wherein the average hydrodynamic diameter of the hydroxylated polymer is between 1 and 100 nm, inclusive.

Embodiment 36. The hydroxylated polymer or method of any one of the preceding embodiments, wherein the step of hydrolyzing the copolymer comprises hydrolyzing at least 50% of the —O—Si bonds of the copolymer to form —OH.

Embodiment 37. The hydroxylated polymer or method of any one of the preceding embodiments, wherein the step of hydrolyzing the copolymer comprises ambient temperature, ambient pressure, and a reaction time of between 1 hour and 48 hours, inclusive.

Embodiment 38. The hydroxylated polymer or method of any one of the preceding embodiments, wherein the step of hydrolyzing the copolymer comprises reacting the copolymer with a fluoride source.

Embodiment 39. The hydroxylated polymer or method of any one of the preceding embodiments, wherein the fluoride source is tetra(unsubstituted $C_{1-6}$alkyl)-ammonium.

Embodiment 40. The hydroxylated polymer or method of any one of the preceding embodiments, wherein the step of hydrolyzing the copolymer comprises reacting the copolymer with an acid.

Embodiment 41. The hydroxylated polymer or method of any one of the preceding embodiments, wherein the acid is HCl.

Embodiment 42. A composition comprising:
a hydroxylated polymer of any one of any one of the preceding embodiments; and
optionally an excipient.

Embodiment 43. A kit comprising:
a hydroxylated polymer of any one of any one of the preceding embodiments; and instructions for using the hydroxylated polymer.

Embodiment 44. A conjugate prepared by reacting a hydroxy-reacting substance with a hydroxylated polymer of any one of the preceding embodiments, wherein hydroxy-reacting substance comprises at least one instance of a hydroxy-reacting moiety.

Embodiment 45. A method of preparing a conjugate comprising reacting a hydroxy-reacting substance with a hydroxylated polymer of any one of the preceding embodiments.

Embodiment 46. The conjugate or method of any one of the preceding embodiments, wherein the hydroxy-reacting substance is a hydroxy-reacting small molecule.

Embodiment 47. The conjugate or method of any one of the preceding embodiments, wherein the hydroxy-reacting substance is lactide.

Embodiment 48. The conjugate or method of any one of the preceding embodiments, wherein the hydroxy-reacting substance is a hydroxy-reacting polymer.

Embodiment 49. The conjugate or method of any one of the preceding embodiments, wherein the average molecular weight of the hydroxy-reacting polymer as determined by gel permeation chromatography is between 1 kDa and 1,000 kDa, inclusive.

Embodiment 50. The conjugate or method of any one of the preceding embodiments, wherein the hydroxy-reacting substance is a polysiloxane, wherein the polysiloxane comprises at least one instance of a hydroxy-reacting moiety.

Embodiment 51. The conjugate or method of any one of the preceding embodiments, wherein at least one instance of the hydroxy-reacting moiety is Si(IV)—H, Si(IV)-(a leaving group), C(IV)-(a leaving group), —C(=O)—OH, —C(=O)-(a leaving group), —C(=O)—O—, —C(=O)—O—C(=O)—, —S(=O)—OH, —S(=O)-(a leaving group), —S(=O)$_2$—OH, —S(=O)$_2$-(a leaving group), —OH, or —O-a leaving group).

Embodiment 52. The conjugate or method of any one of the preceding embodiments, wherein the hydroxy-reacting substance is a polyethylene glycol.

Embodiment 53. A composition comprising:
a conjugate of any one of the preceding embodiments; and
optionally an excipient.

Embodiment 54. A kit comprising:
a conjugate of any one of the preceding embodiments; and instructions for using the conjugate.

Examples

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Materials and Methods

All reagents were purchased from commercial suppliers and used without further purification unless otherwise noted. Grubbs $2^{nd}$ Generation catalyst was purchased from Sigma-Aldrich, dissolved in dry dichloromethane, concentrated under vacuum, and finely powdered immediately before use. $^1$H nuclear magnetic resonance ($^1$H-NMR) and $^{13}$C nuclear magnetic resonance ($^{13}$C-NMR) spectra were acquired at the MIT Department of Chemistry Instrumentation Facility on a Varian Mercury 300, Bruker AVANCE III DRX 400, or a Varian Inova 500. Chemical shifts are reported in ppm relative to signals from the NMR solvent: for $CDCl_3$, this corresponds to 7.26 for $^1$H and 77.0 for $^{13}$C spectra. Solid state NMR was performed on a Bruker AVANCE III501. High-resolution mass spectrometry (HRMS) measurements were obtained on a JEOL AccuTOF system at the MIT Department of Chemistry Instrumentation Facility. GPC analysis was performed on a Tosoh EcoSEC HLC-8320 with dual TSKgel SuperH3000 columns and a chloroform mobile phase at a flow rate of 1 mL/min. Molecular weight calculations were performed using linear polystyrene standards.

Preparation of Monomers

The monomers were prepared according to the methods described in U.S. patent application Ser. No. 16/542,824.

Preparation of Copoymers

The copolymers were prepared according to the methods described in U.S. patent application Ser. No. 16/542,824.

Preparation of Hydroxylated Polymers

200 μL pellets of a copolymer where the first monomer is DCPD was placed in 5 mL of THF. Next, sufficient amounts of TBAF were added for 2 equivalents relative to the second monomer. The mixture was allowed to sit for 12 hours, after which the mixture almost completely dissolved. The mixture were carefully transferred to another vial to separate them from any residual solids and then concentrated under reduced pressure. The residue was then analyzed by NMR and GPC. To remove tetrabutylammonium salts, which interfered with DOSY and 2D NMR analysis, a THF solution of the residue was incubated with an excess of H-Dowex resin and calcium carbonate and filtered following literature protocol (36).

Surface Mechanical Measurements by Nanoindentation

Mechanical testing was performed on a TriboIndenter (Hysitron) using a Berkovich diamond tip. Indentations were performed using a sequence of 10 s approach, 10 s static hold, and 10 s departure. Indentation depths of 300 and 1000 nm were performed to explore the influence of indentation depth on material mechanical properties. Experiments were performed at the MIT Department of Materials Science and Engineering NanoMechanical Technology Laboratory.

Weathering Experiments

To assess plastic degradability under marine environment, a major potential application area for degradable pDCPD, we exposed the material to 300 nm UV light in a synthetic seawater matrix (37). We hypothesized that photooxidation of iPrSi-doped pDCPD would further enhance the aqueous solubility by introducing oxygen functional groups, assisting the hydrolysis of silyl ether groups. Around 100 mg of polymer pellet was submerged in the bottom of 60 mL synthetic seawater matrix in a clear vial sealed with PTFE-lined cap. The vial was then exposed to 300 nm UV light, providing a maximum of 0.19 W/m$^2$ between 280-320 nm (measured by OceanInsight FLAME-S-XR-ES spectroradiometer), in a Rayonet reactor for 16 days. Solar irradiance between 280-320 nm was used as a reference (ATSM G173-03 reference spectra) to estimate the longevity of materials under realistic solar condition. We calculated degradation as the mass of carbon released in the seawater solution over the mass of carbon in the original material, with the assumption of a constant degradation rate. Total organic carbon was measured as non-purgable organic carbon by Shimazu TOC-5000. Prior to analysis, the sample was acidified with 50% HC to pH<3 and sparged with $N_2$ for 8 min to remove inorganic carbon in seawater matrix. Total organic carbon in the virgin polymer was inferred from chemical formula and mass fraction of iPrSi or EtSi co-monomers. A paired t-Test was performed to determine whether content of iPrSi or light exposure has an impact on degradability.

TABLE 1

Statistical analysis of weathering experiments.

| Comparative group | Test | n | P value (0.05 significance level) |
|---|---|---|---|
| Light 0% vs 10% iPrSi | Two sample t-Test | 3 | $7.4 \times 10^{-4}$ |
| Light 0% vs 20% iPr-Si | Two sample t-Test | 3 | 0.001 |
| Light 10% vs 20% iPr-Si | Two sample t-Test | 3 | 0.005 |
| Light 10% EtSi vs 10% iPrSi | Two sample t-Test | 3 | 0.001 |
| Dark 0% vs 10% iPrSi | Two sample t-Test | 3 | 0.02 |
| Dark 0% vs 20% iPrSi | Two sample t-Test | 3 | 0.001 |
| Dark 10% vs 20% iPrSi | Two sample t-Test | 3 | 0.06 |
| Dark 10% EtSi vs 10% iPrSi | Two sample t-Test | 3 | 0.26 |
| Light vs Dark | Two sample t-Test | 12 | $2.9 \times 10^{-7}$ |
| 0% iPrSi Light vs Dark | Two sample t-Test | 3 | $2.9 \times 10^{-4}$ |
| 10% iPrSi Light vs Dark | Two sample t-Test | 2 | $1.4 \times 10^{-4}$ |
| 209 iPrSi Light vs Dark | Two sample t-Test | 3 | $4.3 \times 10^{-4}$ |
| 10% EtSi Light vs Dark | Two sample t-Test | 3 | $2.6 \times 10^{-5}$ |

TABLE 2

Mass of carbon released into seawater matrix during 16 days of UV light exposure.

| Doped pDCPD | Light | | Dark | |
|---|---|---|---|---|
| | g C released / g C in polymer | Standard deviation | g C released / g C in polymer | Standard deviation |
| 0% iPrSi | 0.0033 | 0.0003 | 0.0005 | 0.0002 |
| 10% iPrSi | 0.0052 | 0.0001 | 0.0015 | 0.0003 |
| 20% iPrSi | 0.0081 | 0.0007 | 0.0023 | 0.0007 |
| 10% EtSi | 0.0073 | 0.0003 | 0.0019 | 0.0007 |

Seawater matrix blank has an organic carbon content of 0.73+/−0.06 mg/L and was subtracted when presenting the dissolved carbon in sample incubated with pDCPD pellets. All samples were measured in triplicate.

Gel Permeation Chromatography

A hydroxylated polymer where the first monomer is DCPD was dissolved in $CHCl_3$ at a concentration of 2 mg/mL. The solution was then filtered through a 0.2 μm Teflon filter before analysis. GPC analysis was performed on a EcoSEC HLC-8320 (Tosoh) with dual TSKgel SuperH3000 columns and a chloroform mobile phase at a flow rate of 1 mL/min. Molecular weight calculations were performed using linear polystyrene standards.

Transmission Electron Microscopy

A dilute solution of a hydroxylated polymer where the first monomer is DCPD and the second monomer is 10% iPrSi (prepared from TBAF dissolution of the copolymer followed by Dowex/$CaCO_3$ clean-up) in DCM was dropcast onto a copper grid and stained with RuO4 vapors. The samples were then imaged on an FEI Tecnai transmission electron microscope.

Synthesis of PLA-Containing Conjugates 50 mg of a hydroxylated polymer where the first monomer is DCPD and 500 mg of rac-lactide were dissolved in 2 mL of dry THF. Next, 20 µL of 1 M DBU in THF was added and the reaction mixture was allowed to stir at RT for 2 hours. The reaction was then quenched with 1 mg of benzoic acid and precipitated into MeOH to yield 153 mg of the PLA-containing conjugates as a white solid.

Synthesis of PEG-Containing Conjugates 50 mg of a hydroxylated polymer where the first monomer is DCPD were dissolved in 500 µL of dry DCM and cooled to 0° C. Next, 10 mg of para-nitrophenyl chloroformate was added, followed by 50 µL of pyridine. The reaction was allowed to stir at RT for 1 hour. Next, to the reaction was added 130 mg of α-amino-ω-hydroxy-polyethylene glycol (average molecular weight of 3000) and 50 µL of triethylamine. The reaction was allowed to stir at RT for another 30 minutes, then concentrated and rediluted in 1 mL of THF. Another 50 µL of triethylamine was added and the reaction was heated to 50° C. and stirred under nitrogen for 12 hours. The material was then concentrated under vacuum, taken up in 4 mL DCM, washed with 2×2 mL 0.1 M HCl, 2×2 mL sat. $NaHCO_3$, and 2×2 mL 0.1 M NaOH before drying with sodium sulfate and concentrating to yield the PEG-containing conjugates as a pale yellow solid.

Synthesis of PDMS-Containing Conjugates 190.5 mg (0.174 mmol OH) of a hydroxylated polymer where the first monomer is DCPD were added to a 5 mL vial. Next, 1 mL of dry DCM and 35.8 µL (0.261 mmol) triethylamine were added and the mixture stirred under nitrogen. After all reagents had fully dissolved, the mixture was cooled to 0° C. To this mixture was slowly added 49.7 mg (0.157 mmol) of neat 1-chloro-1,1,3,3,5,5,7,7-octamethyltetrasiloxane. The material was then warmed to RT and stirred for 1 hour. The material was then diluted with 20 mL of DCM and washed 2× with 0.0001 M HCl, 3× with water, 2× brine, and dried under vacuum. The fragments were triturated three times with hexanes to remove any unreacted tetrasiloxane and dried under vacuum to yield 201.6 mg (85%) of PDMS-containing conjugates.

Synthesis of PDMS-Containing Conjugates

PDMS starting materials were degassed by removing the product lids and placing under vacuum for 3 days. 5.05 g (5.46 mmol Si—CH=$CH_2$) of degassed 28 kDa 8% vinyl functionalized PDMS was added into a 40 mL vial. Next, 21.5 g (2.53 mmol Si—H) of degassed 17 kDa dihydride PDMS was added to achieve a molar ratio of silyl hydride to vinyl silane of roughly 1:2, leaving excess vinyl groups available for further modification. This master mix was slowly stirred for 2 hours to ensure full mixing of components without the introduction of addition air into the sample. During this time, 24.3 mg of the PDMS-containing conjugates of the above example (~0.017 mmol Si—H) were dissolved in 5 mL of DCM. In a separate vial, 4.00 g of the PDMS master mix was blended with 5 mL DCM. To this solution was added the PDMS-containing conjugates solution and the mixture was immediately vortexed for 1 minute. The mixture was then immediately concentrated under rotary evaporation at 50° C. for 20 minutes, then for 3 minutes on a Schlenk apparatus to fully remove DCM. Finally, 20 µL Karstedt's catalyst solution in xylenes (2 wt % platinum, Sigma Aldrich) was added and the PDMS mixture vortexed for 2 minutes. The material was poured into folded PTFE liners (~1×1×0.25 inch) and cured in a vacuum oven at 70° C. for 12 hours. The low relative Si—H functionality found in pDCPD dopants relative to the network mix suggests that mechanical improvements are due to the physical presence of pDCPD and not increased crosslinking density.

Dynamic Mechanical Analysis of Composites

DMA was performed on a Discovery DMA 850 System (TA). Samples with dimensions ca. 1.5×1.5×8 mm (w×t×1) were tested in tension mode. Measurements were recorded at a frequency of 1 Hz, an amplitude of 10 µm from −90 to 40° C. at a rate of 3° C. min-1 with a data sampling interval of 3 s/pt using a 125% force tracking and 0.01 N preload force. DMA data were obtained using Trios software and exported to Microsoft Excel for analysis. Experiments were performed at the MIT Institute for Soldier Nanotechnologies. The reported modulus at 25° C. was determined by averaging measurements from 20° C. to 30° C., while the modulus at −70° C. is reported as is.

Discussion

Figure 3A:
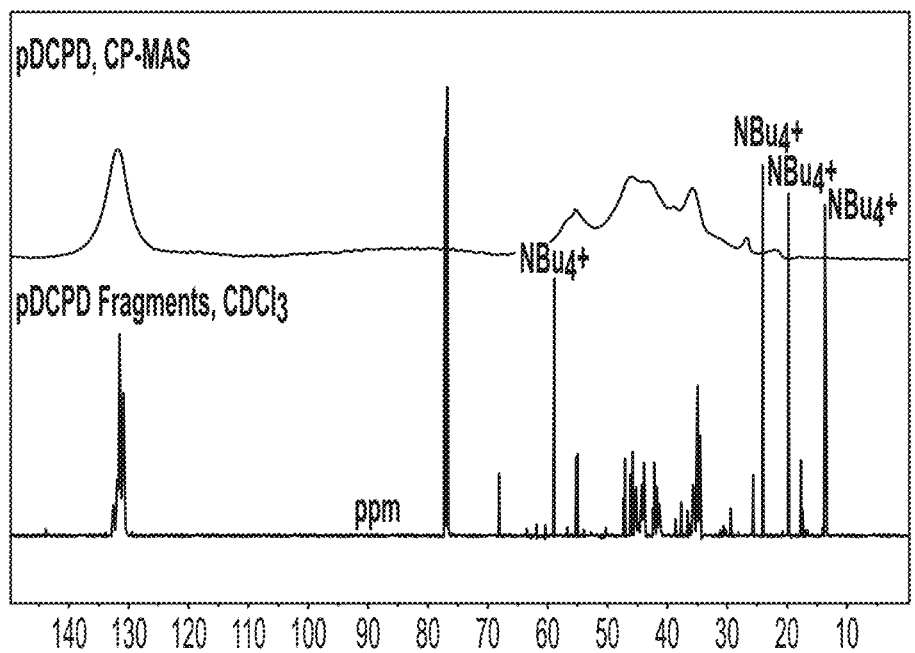
FIGS. 3A-3F. Soluble pDCPD fragments (e.g., a hydroxylated polymer described herein) enable high-resolution characterization of the parent material and can be functionalized and incorporated into new materials.
Figure 3B:
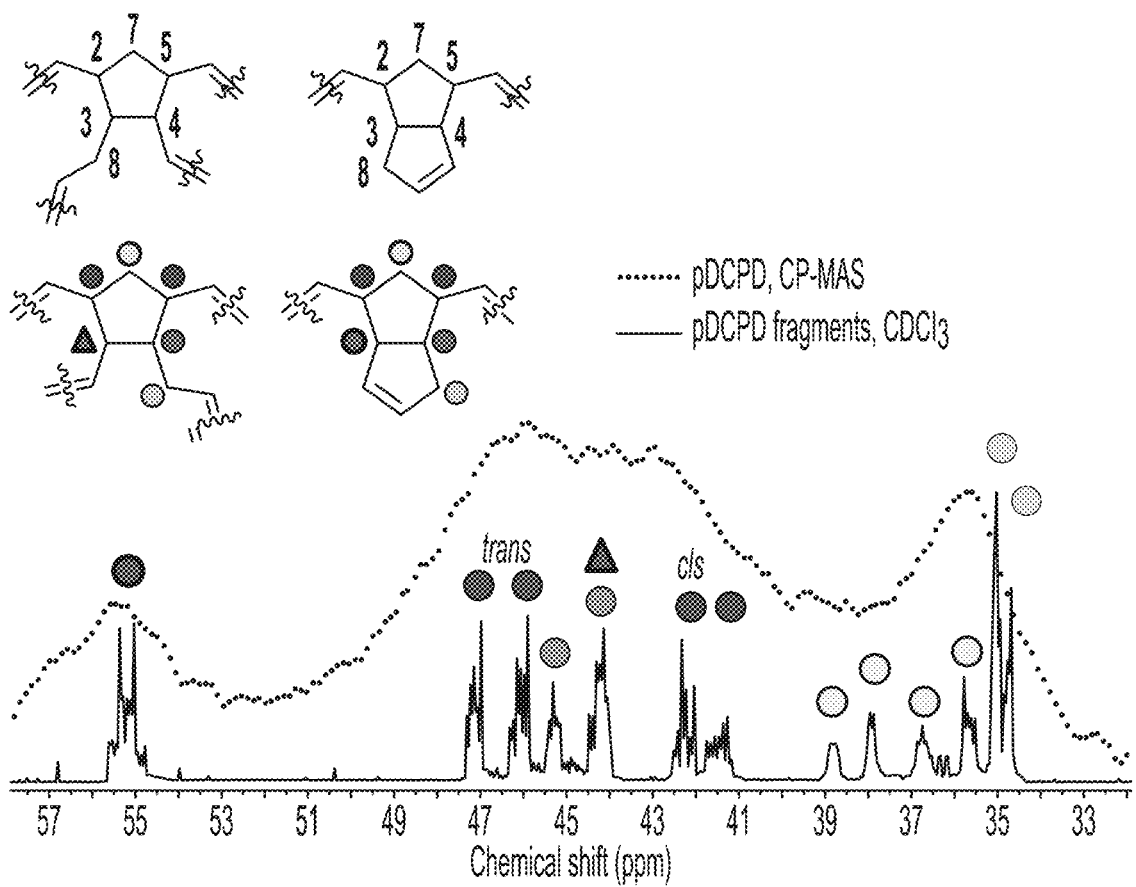
Figure 3C:
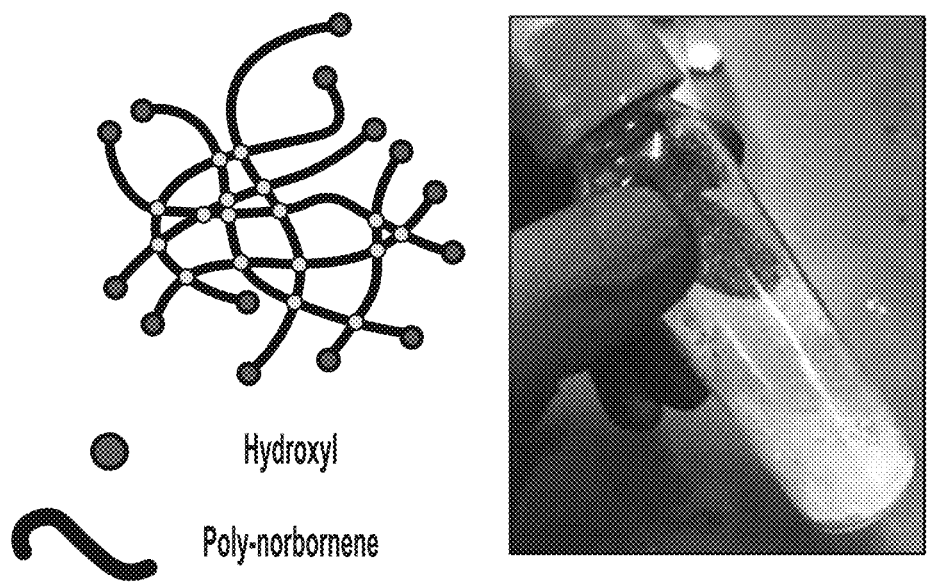
Figure 3D:
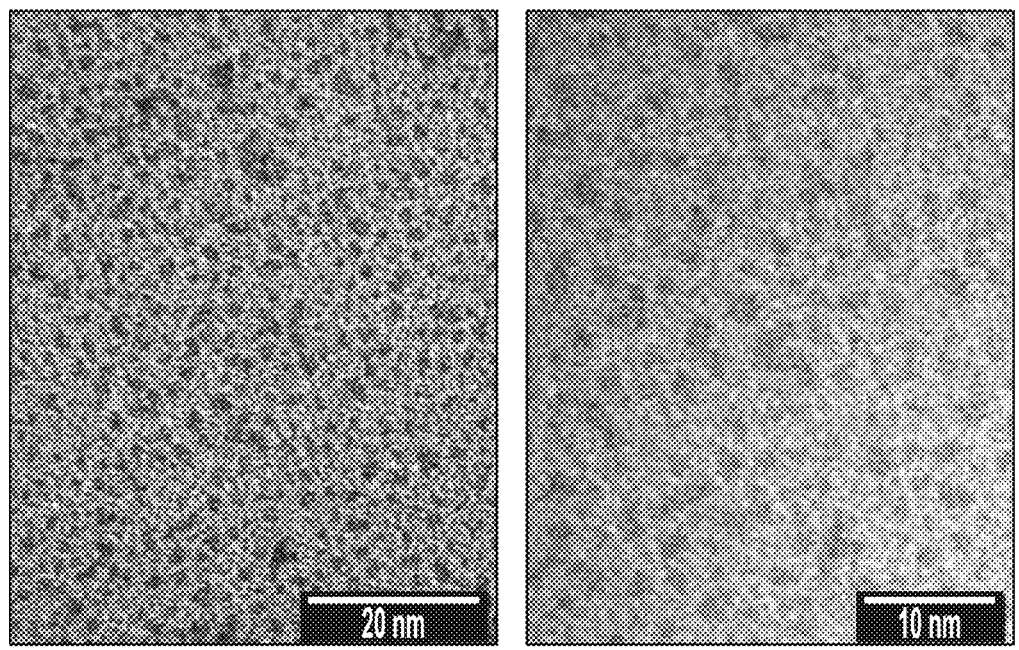
Figure 10:
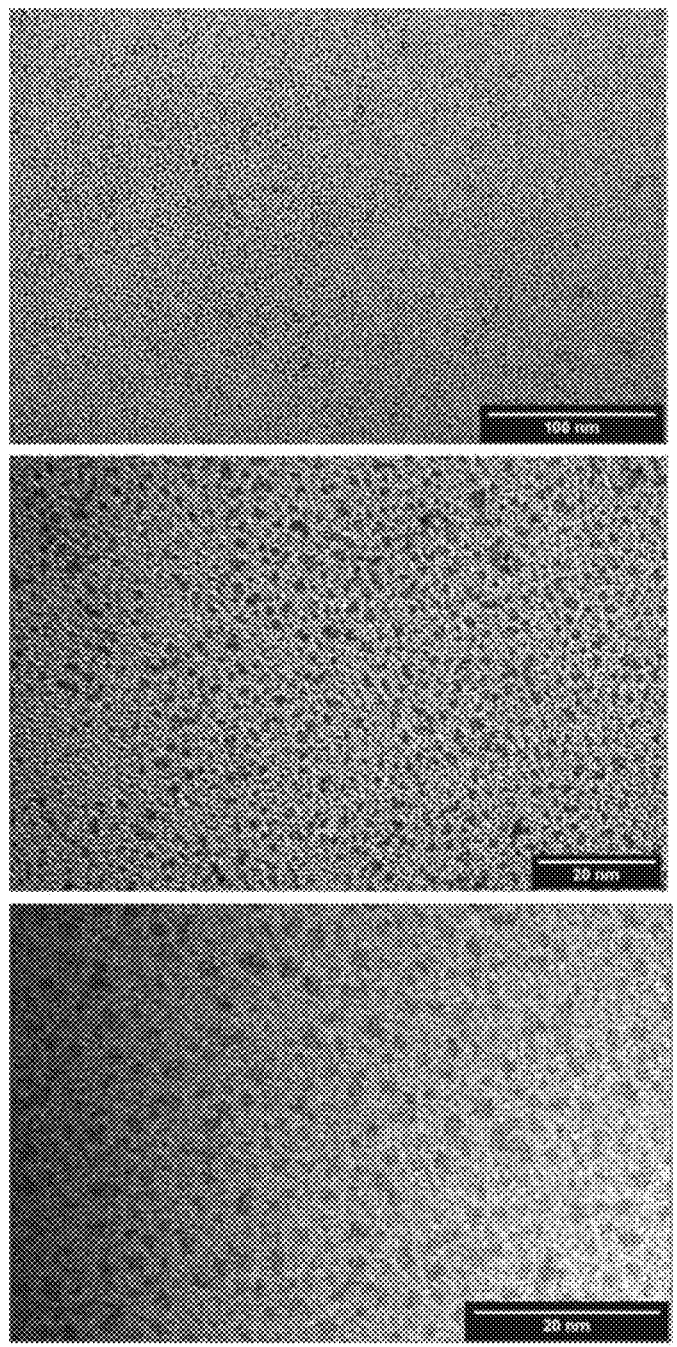
FIG. 10. Additional TEM images of fragments derived from 10% iPrSi-doped pDCPD.

The products of degradation of our iPrSi-doped samples represent a new class of low-cost densely hydroxylated, alkene-functionalized hydrocarbon frameworks with numerous potential opportunities for repurposing and/or upcyling (FIGS. 3c, 3d). The size of these fragments can be readily tuned by modifying the iPrSi loading. Diffusion ordered spectroscopy (DOSY) was used to further study this relationship, showing a clear trend between particle size and the amount of iPrSi used. From DOSY, we estimate that the average hydrodynamic diameter of the fragments obtained from the 10% iPrSi-doped pDCPD sample was ~4 nm, which was further corroborated by TEM imaging (FIG. 3d, FIG. 10).

The excellent mechanical properties of pDCPD suggest that utilizing these degradation fragments as fillers for other materials may yield composites with improved mechanical properties.

Figure 3E:
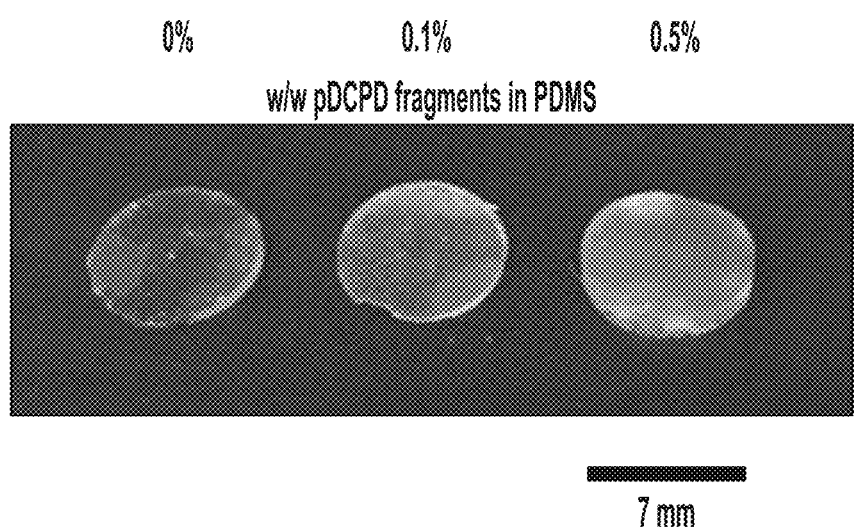
Figure 3F:
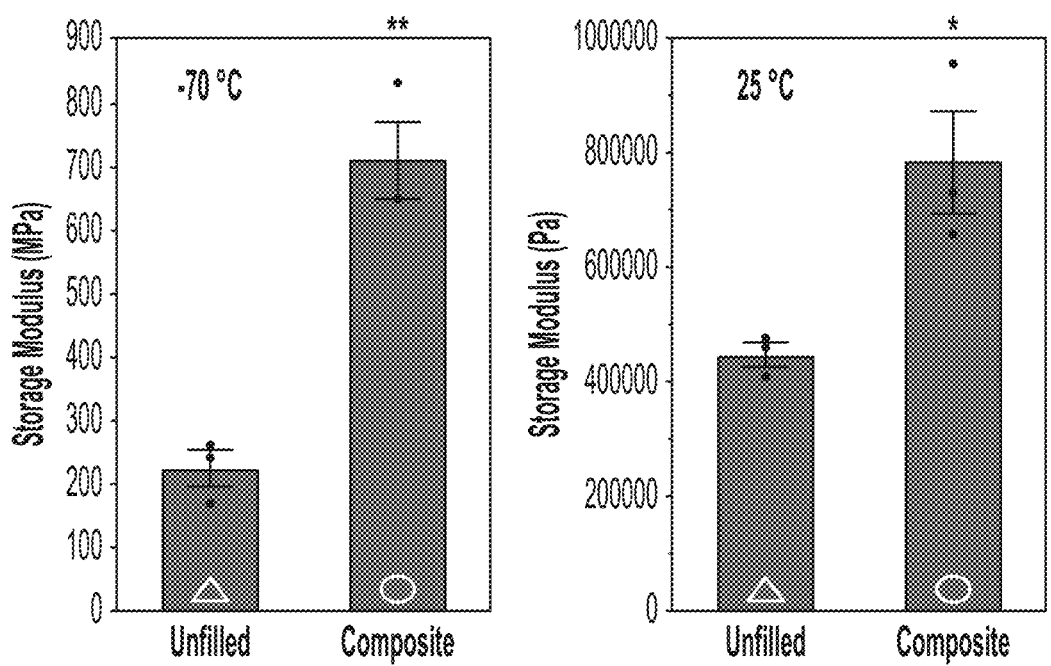
Figure 11A:
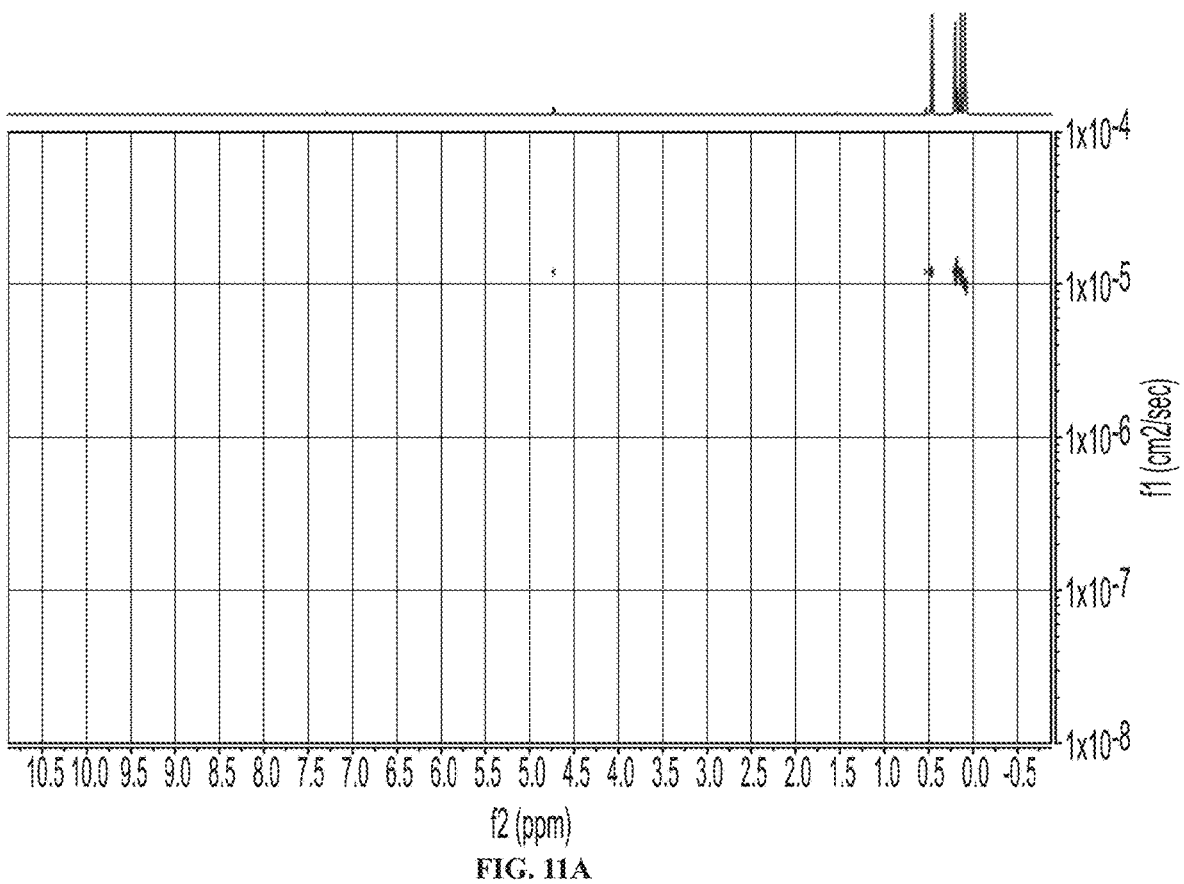
FIGS. 11A-11B. DOSY spectra confirming successful conjugation of PDMS and fragments derived from 10% iPrSi-doped pDCPD. Spectra of the (FIG. 11A) Starting PDMS chloride and (FIG. 11B) fragments after PDMS conjugation show slower rates of diffusion for peaks in the PDMS region.
Figure 11B:
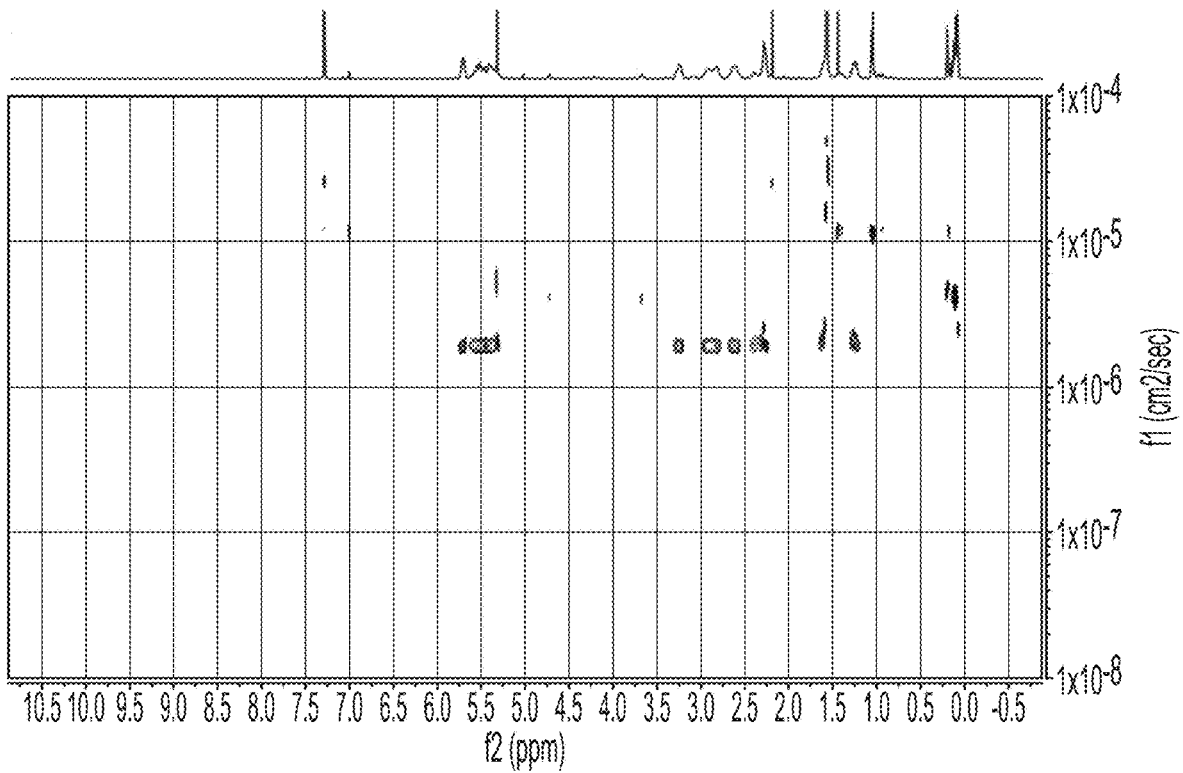
Figure 12:
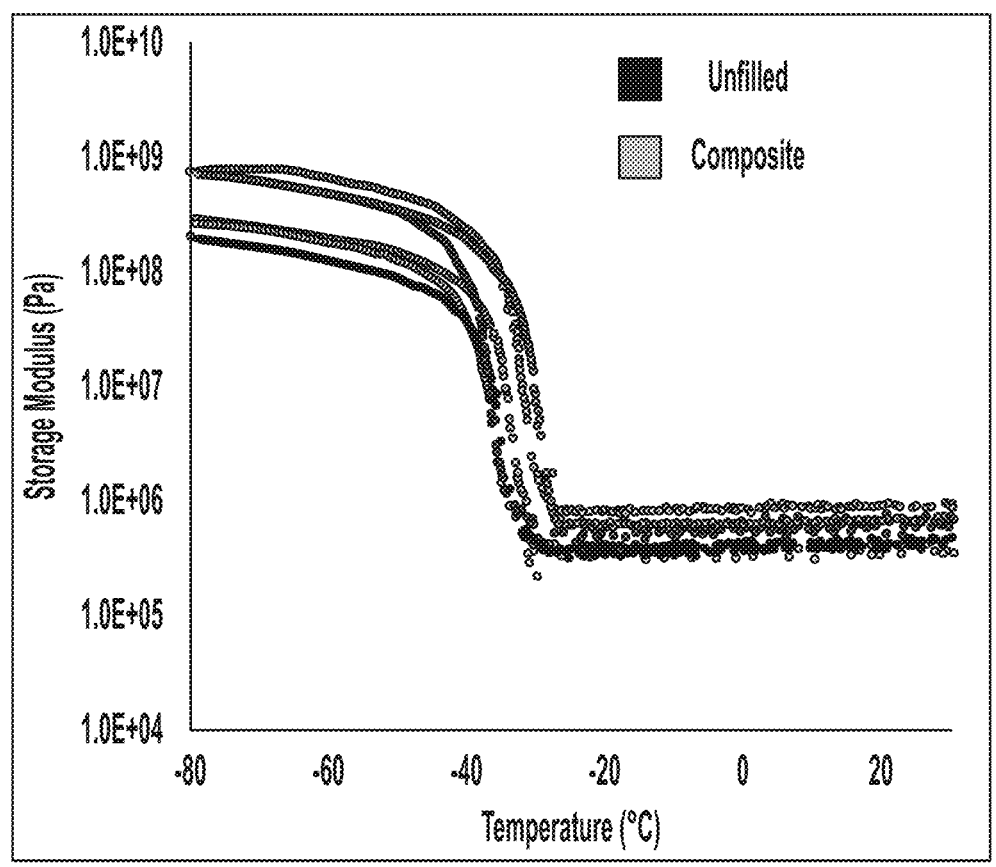
FIG. 12. DMA traces of unfilled PDMS and PDMS composites containing 0.5% w/w pDCPD fragments.

To test this hypothesis, we explored their potential as fillers for another industrially relevant class of thermosets: silicone elastomers. Hydride-terminated 350 Da polydimethylsiloxane (PDMS) was covalently grafted to the surface of the pDCPD fragments through nucleophilic substitution; successful conjugation was confirmed by DOSY NMR (FIGS. 11A-11B). Filled PDMS elastomers were prepared using varying amounts of the PDMS-grafted pDCPD fragments as fillers through platinum-catalyzed hydrosilylation of 17.2 kDa Si—H terminated PDMS and a 28 kDa linear PDMS bearing 8% vinyl functionality. The mechanical properties of the elastomers were characterized through constant frequency temperature sweeps using DMA (FIG. 3e). The PDMS-grafted fragments showed improved miscibility with PDMS, and, notably, the filled materials displayed significantly increased storage moduli at only 0.5 wt % loading (FIG. 3f, FIG. 12).

Figure 13:
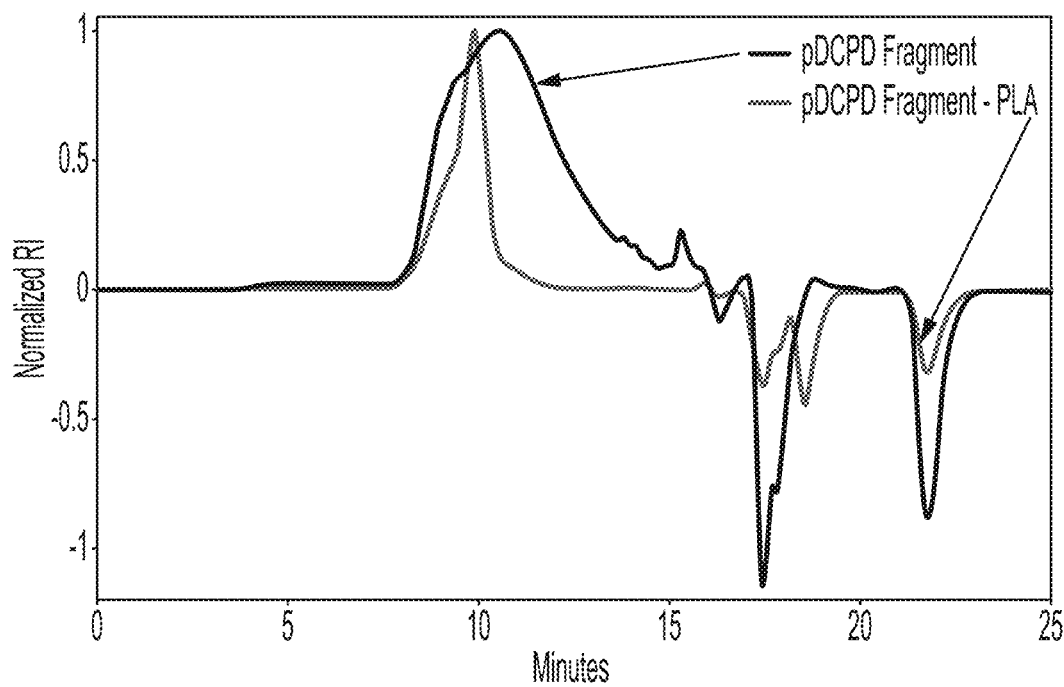
FIG. 13. Normalized GPC traces of pDCPD fragments before and after PLA growth.
Figure 14A:
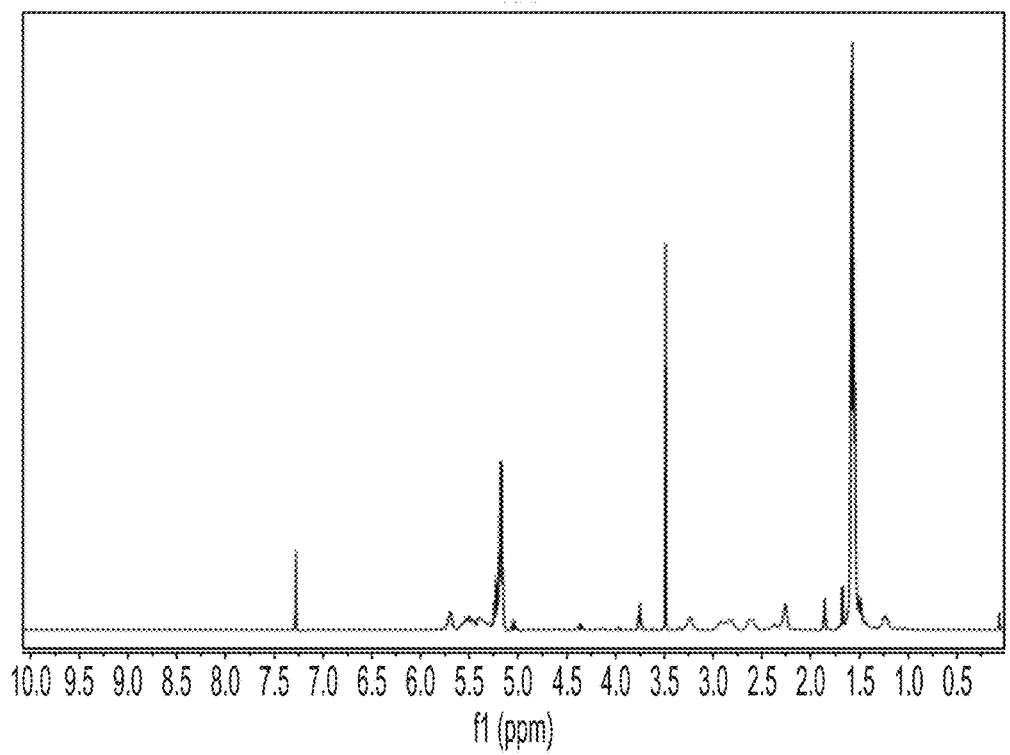
FIGS. 14A-14B.
Figure 14B:
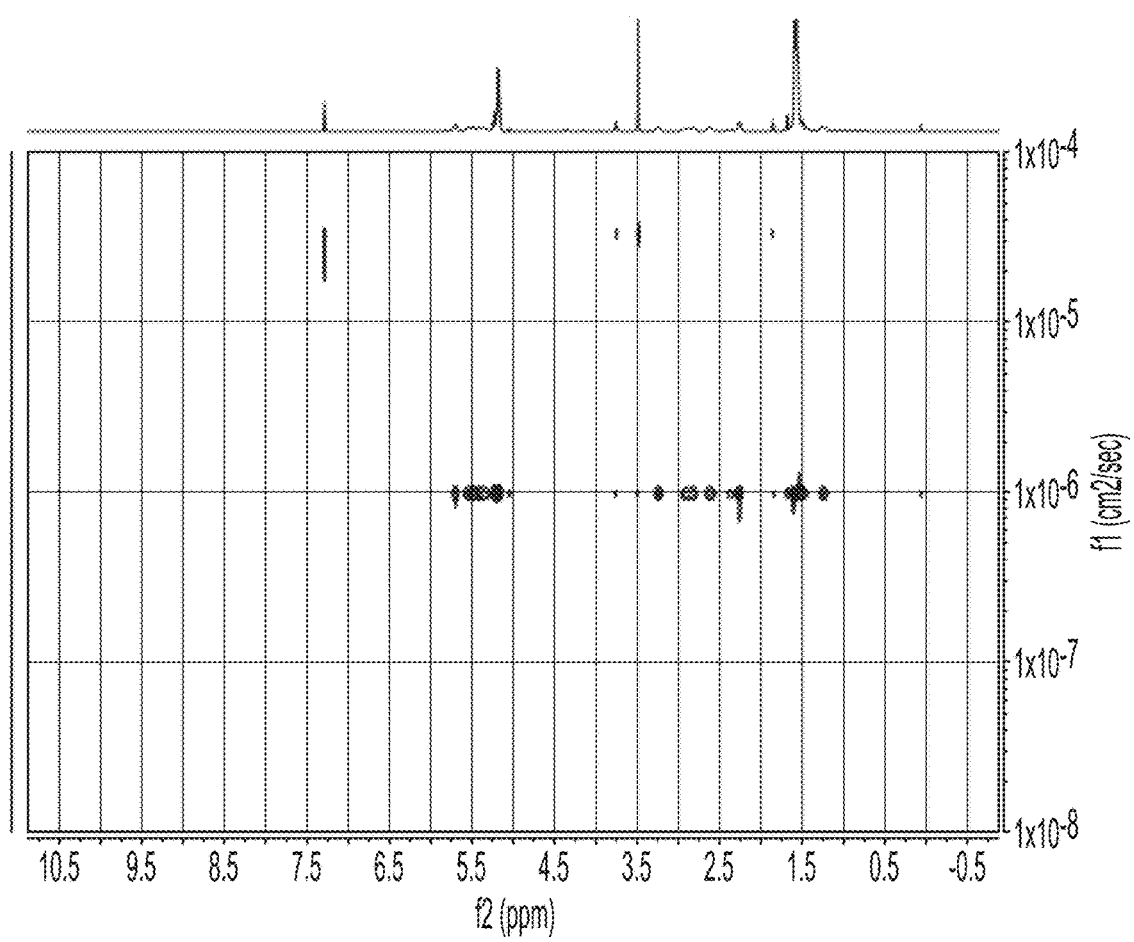
Figure 15:
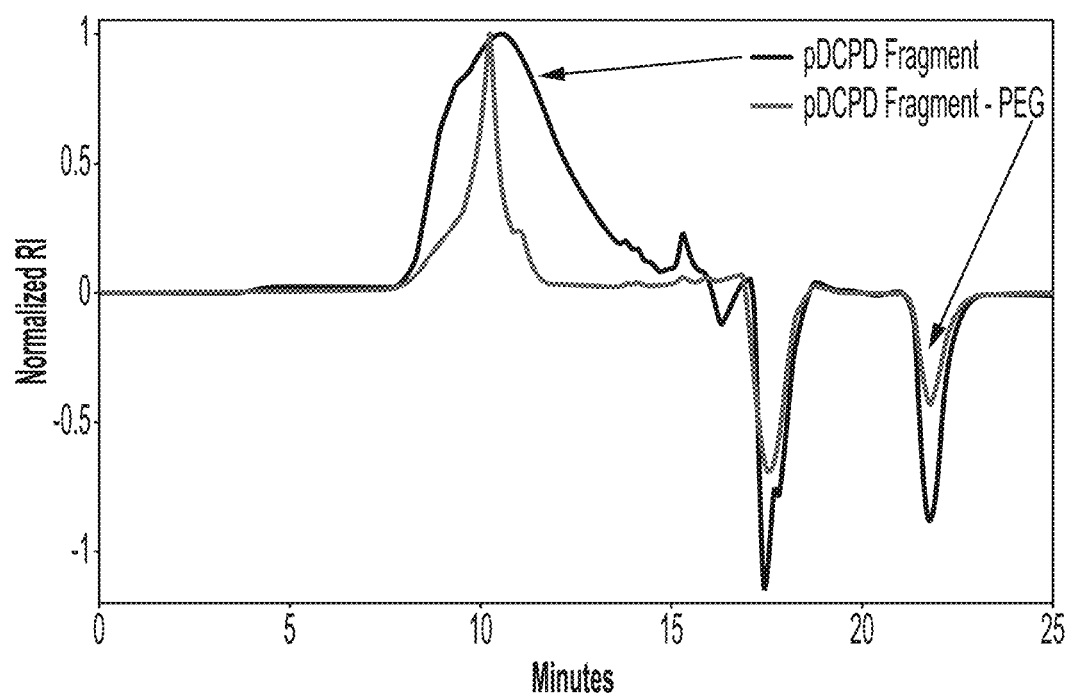
FIG. 15. Normalized GPC traces of pDCPD fragments before and after PEG conjugation.
Figure 16A:
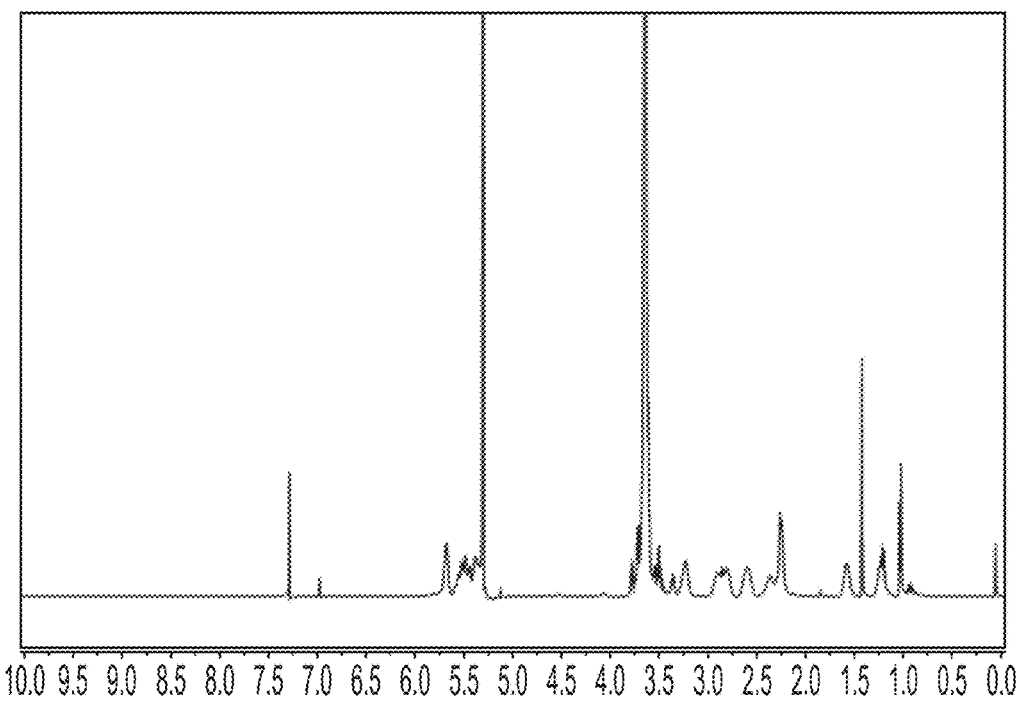
FIGS. 16A-16B.
Figure 16B:
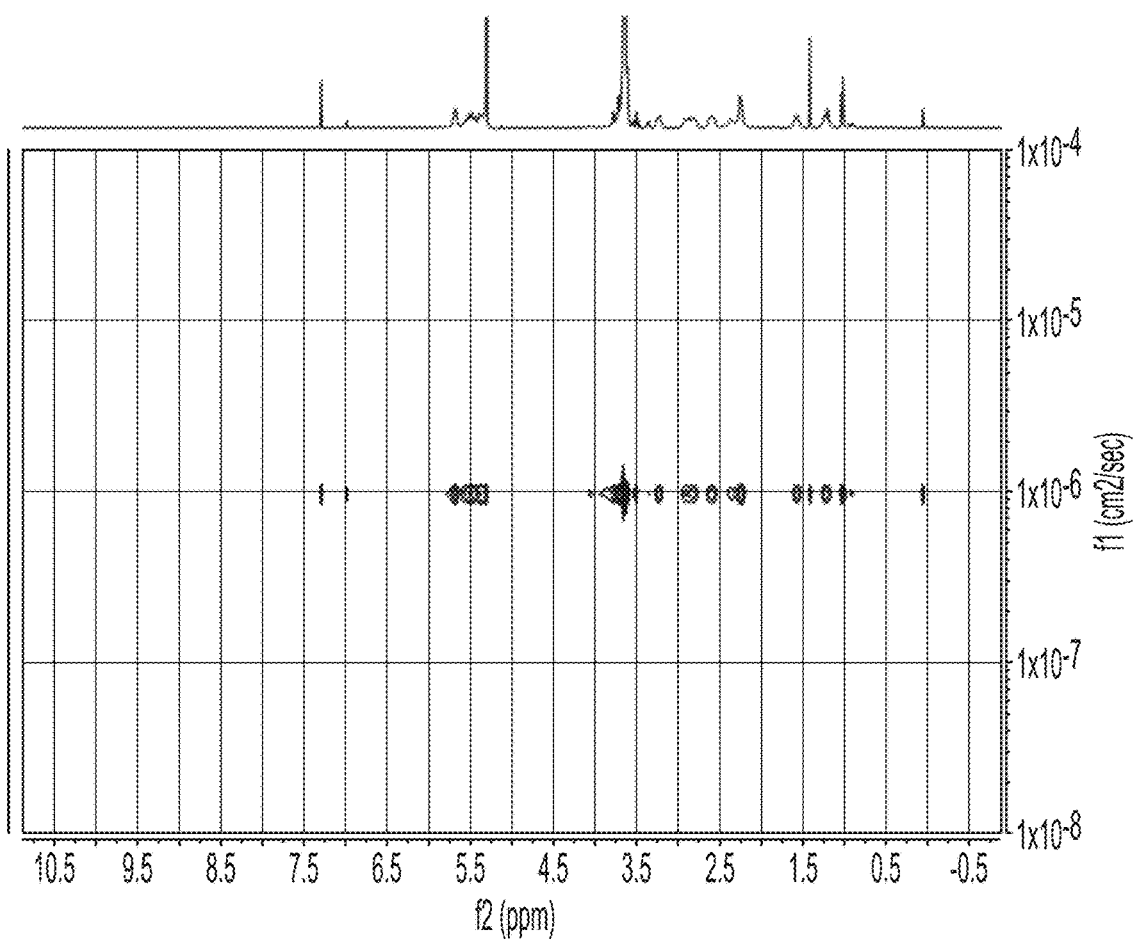

To further illustrate the broad chemical versatility of these pDCPD fragments, we employed them as macroinitiators for the growth of polylactide (FIGS. 13-14), a commodity polyester, and as scaffolds for covalent conjugation of polyethylene glycol, a commonly used biomaterial (FIGS. 15-16). Altogether, these results hint at many new opportunities to repurpose or upcycle pDCPD that are enabled by our simple co-monomer strategy.

In summary, we describe a co-monomer strategy to prepare upcyclable versions of the industrially-relevant thermoset pDCPD. The low potential cost of our co-monomer and the small amount needed to endow pDCPD with upcyclability paves a path toward the broader deployment of this approach to larger scales. Moreover, our finding that the installation of cleavable bonds into strands versus crosslinks provides a design principle that should be applicable to many other thermosetting systems. While thermosets have served as a pillar of the plastics and rubber industries since their first description in the early$_{20}$th century, our approach, which is uniquely enabled by recent innovations in polymer chemistry, may breathe new life into these old materials and address the concerns broadly facing 21' century materials design challenges.

REFERENCES

1. J. S. Chen, C. K. Ober, M. D. Poliks, Characterization of thermally reworkable thermosets: Materials for environmentally friendly processing and reuse. *Polymer* (*Guild*). 43, 131-139 (2001).
2. S. Yang, J.-S. Chen, H. Korner, T. Breiner, C. K. Ober, M. D. Poliks, Reworkable Epoxies: Thermosets with Thermally Cleavable Groups for Controlled Network Breakdown. *Chem. Mater.* 10, 1475-1482 (1998).
3. C. J. Kloxin, T. F. Scott, B. J. Adzima, C. N. Bowman, Covalent adaptable networks (CANs): A unique paradigm in cross-linked polymers. *Macromolecules*. 43 (2010), pp. 2643-2653.
4. D. Montarnal, M. Capelot, F. Tournilhac, L. Leibler, Silica-like malleable materials from permanent organic networks. *Science* (80-.). 334, 965-968 (2011).
5. M. Röttger, T. Domenech, R. Van Der Weegen, A. Breuillac, R. Nicolaÿ, L. Leibler, High-performance vitrimers from commodity thermoplastics through dioxaborolane metathesis. *Science* (80-.). 356, 62-65 (2017).
6. G. H. Hartley, J. E. Guillet, Photochemistry of ketone polymers. II. Studies of model compounds. *Macromolecules*. 1, 413-417 (1968).
7. A. Sommazzi, F. Garbassi, Olefin-carbon monoxide copolymers. *Prog. Poym. Sci.* 22 (1997), pp. 1547-1605.
8. S. Ma, D. C. Webster, Degradable thermosets based on labile bonds or linkages: A review. *Prog. Polym. Sci.* 76, 65-110 (2018).
9. B. Wang, S. Ma, S. Yan, J. Zhu, Readily recyclable carbon fiber reinforced composites based on degradable thermosets: a review. *Green Chem.* (2019), doi:10.1039/c9gc01760g.
10. D. J. Fortman, J. P. Brutman, G. X. De Hoe, R. L. Snyder, W. R. Dichtel, M. A. Hillmyer, Approaches to Sustainable and Continually Recyclable Cross-Linked Polymers. *ACS Sustain. Chem. Eng.* 6, 11145-11159 (2018).
11. J. D. Rule, J. S. Moore, ROMP reactivity of endo- and exo-dicyclopentadiene. *Macromolecules*. 35, 7878-7882 (2002).
12. P. J. Hine, T. Leejarkpai, E. Khosravi, R. A. Duckett, W. J. Feast, Structure property relationships in linear and cross-linked poly(imidonorbornenes) prepared using ring opening metathesis polymerisation (ROMP). *Polymer* (*Guildf*). 42, 9413-9422 (2001).
13. C. Zhang, K. Zhao, T. Hu, X. Cui, N. Brown, T. Boland, Loading dependent swelling and release properties of novel biodegradable, elastic and environmental stimuli-sensitive polyurethanes. *J. Control. Release*. 131, 128-36 (2008).
14. I. D. Robertson, E. L. Pruitt, J. S. Moore, Frontal Ring-Opening Metathesis Polymerization of Exo-Dicyclopentadiene for Low Catalyst Loadings. *ACS Macro Lett.* 5, 593-596(2016).
15. I. D. Robertson, L. M. Dean, G. E. Rudebusch, N. R. Sottos, S. R. White, J. S. Moore, Alkyl Phosphite Inhibitors for Frontal Ring-Opening Metathesis Polymerization Greatly Increase Pot Life. *ACS Macro Lett.* 6, 609-612 (2017).
16. I. D. Robertson, M. Yourdkhani, P. J. Centellas, J. E. Aw, D. G. Ivanoff, E. Goli, E. M. Lloyd, L. M. Dean, N. R. Sottos, P. H. Geubelle, J. S. Moore, S. R. White, Rapid energy-efficient manufacturing of polymers and composites via frontal polymerization. *Nature*. 557, 223-227 (2018).
17. J. Chen, F. P. Burns, M. G. Moffitt, J. E. Wulff, Thermally Crosslinked Functionalized Polydicyclopentadiene with a High T g and Tunable Surface Energy. *ACS Omega*. 1, 532-540(2016).
18. M. R. Kessler, S. R. White, Cure kinetics of the ring-opening metathesis polymerization of dicyclopentadiene. *J. Polym. Sci. Part A Polym. Chem.* 40, 2373-2383 (2002).
19. P. Shieh, H. V.-T. Nguyen, J. A. Johnson, Tailored silyl ether monomers enable backbone-degradable polynorbornene-based linear, bottlebrush and star copolymers through ROMP. *Nat. Chem.* (2019), doi:10.1038/s41557-019-0352-4.
20. X. Sheng, M. R. Kessler, J. K. Lee, The influence of cross-linking agents on ring-opening metathesis polymerized thermosets. *J. Therm. Anal. Calorim.* 89, 459-464 (2007).
21. J. Wang, R. Wang, Y. Gu, A. Sourakov, B. D. Olsen, J. A. Johnson, Counting loops in sidechain-crosslinked polymers from elastic solids to single-chain nanoparticles. *Chem. Sci.* 10, 5332-5337 (2019).
22. Y. Gu, J. Zhao, J. A. Johnson, A unifying review of polymer networks: from rubbers and gels to porous frameworks. *Angew. Chemie Int. Ed.* (2019), doi:10.1002/anie.201902900.
23. Y. Gu, J. Zhao, J. A. Johnson, A (Macro)Molecular-Level Understanding of Polymer Network Topology. *Trends Chem.* 1 (2019), pp. 318-334.
24. M. Zhong, R. Wang, K. Kawamoto, B. D. Olsen, J. A. Johnson, Quantifying the impact of molecular defects on polymer network elasticity. *Science* (80-.). 353, 1264-1268 (2016).
25. H. Zhou, J. Woo, A. M. Cok, M. Wang, B. D. Olsen, J. A. Johnson, Counting primary loops in polymer gels. *Proc. Natl. Acad Sci.* 109, 19119-19124 (2012).
26. K. Kawamoto, M. Zhong, R. Wang, B. D. Olsen, J. A. Johnson, Loops versus Branch Functionality in Model Click Hydrogels. *Macromolecules*. 48, 8980-8988 (2015).
27. J. Wang, T. S. Lin, Y. Gu, R. Wang, B. D. Olsen, J. A. Johnson, Counting Secondary Loops Is Required for Accurate Prediction of End-Linked Polymer Network Elasticity. *ACS Macro Lett.* 7, 244-249 (2018).
28. J. S. Davies, C. L. Higginbotham, E. J. Tremeer, C. Brown, R. C. Treadgold, Protection of hydroxy groups by silylation; use in peptide synthesis and as lipophilicity modifiers for peptides. *J. Chem. Soc. Perkin Trans.* 1, 3043 (1992).
29. M. C. Parrott, J. C. Luft, J. D. Byrne, J. H. Fain, M. E. Napier, J. M. DeSimone, Tunable Bifunctional Silyl Ether Cross-Linkers for the Design of Acid-Sensitive Biomaterials. *J. Am. Chem. Soc.* 132, 17928-17932 (2010).
30. T. J. Cuthbert, T. Li, A. W. H. Speed, J. E. Wulff, Structure of the Thermally Induced Cross-Link in C-Linked Methyl Ester-Functionalized Polydicyclopentadiene (f PDCPD). *Macromolecules*. 51, 2038-2047 (2018).
31. B. Autenrieth, H. Jeong, W. P. Forrest, J. C. Axtell, A. Ota, T. Lehr, M. R. Buchmeiser, R. R. Schrock, Stereospecific ring-opening metathesis polymerization (ROMP) of endo-dicyclopentadiene by molybdenum and tungsten catalysts. *Macromolecules.* 48, 2480-2492 (2015).
32. A. Bang, D. Mohite, A. M. Saeed, N. Leventis, C. Sotiriou-Leventis, Polydicyclopentadiene aerogels from first- versus second-generation Grubbs' catalysts: a molecular versus a nanoscopic perspective. *J. Sol-Gel Sci. Technol.* 75, 460-474 (2015).
33. B. J. Rohde, K. M. Le, R. Krishnamoorti, M. L. Robertson, Thermoset Blends of an Epoxy Resin and Polydicyclopentadiene. *Macromolecules.* 49, 8960-8970 (2016).
34. R. M. Elder, D. B. Knorr, J. W. Andzelm, J. L. Lenhart, T. W. Sirk, Nanovoid formation and mechanics. A comparison of poly(dicyclopentadiene) and epoxy networks from molecular dynamics simulations. *Soft Matter.* 12, 4418-4434 (2016).
35. G. Yang, J. K. Lee, Curing kinetics and mechanical properties of endo-dicyclopentadiene synthesized using different grubbs' catalysts. *Ind. Eng. Chem. Res.* 53, 3001-3011 (2014).
36. Y. Kaburagi, Y. Kishi, Operationally simple and efficient workup procedure for TBAF-mediated desilylation: Application to halichondrin synthesis. *Org Lett.* 9, 723-726 (2007).
37. K. M. Parker, W. A. Mitch, Halogen radicals contribute to photooxidation in coastal and estuarine waters. *Proc. Natl. Acad. Sci. U.S.A* 113, 5868-5873 (2016).
38. G. Yang, J. K. Lee, Curing kinetics and mechanical properties of endo-dicyclopentadiene synthesized using different grubbs' catalysts. *Ind. Eng. Chem. Res.* 53, 3001-3011 (2014).

Cleavable Comonomers Enable Degradable, Recyclable Thermoset Plastics

Theoretical Framework for Degradable Thermosets Via Copolymerization

To estimate the amount of cleavable comonomer x required to degrade networks of strands with f crosslinkable functional groups and c crosslinks into soluble products, we derived a reverse gel-point model based on Miller-Macosko[23] and Flory-Stockmayer[24,25] theories (FIG. 17B, FIGS. 21A-21B; see Methods, below):

$$x > \frac{c(2f-1)-f}{c+f}$$

From this equation, it is observed that when f>>c, degradation into soluble products is expected when x>~2c. If it was instead assumed that that f≈c, then degradation to soluble products is expected when:

$$x > c-1$$

Thus, the model predicts what is also intuitive: degradation of thermosets to soluble products can be achieved when the number of cleavable bonds in strands is similar in magnitude to the number of crosslinks. This model assumes that the cleavable bonds are randomly distributed along strands, that equivalent functional groups have equal and independent reactivity, and that there are no intramolecular reactions; thus, it provides an estimate of x—the presence of loops that consume functionality yet do not contribute to gelation will further lower the number of degradable bonds needed to achieve degradation (vide infra).[26]

Cleavable Bond Location Determines Degradability in pDCPD

Figure 17A:
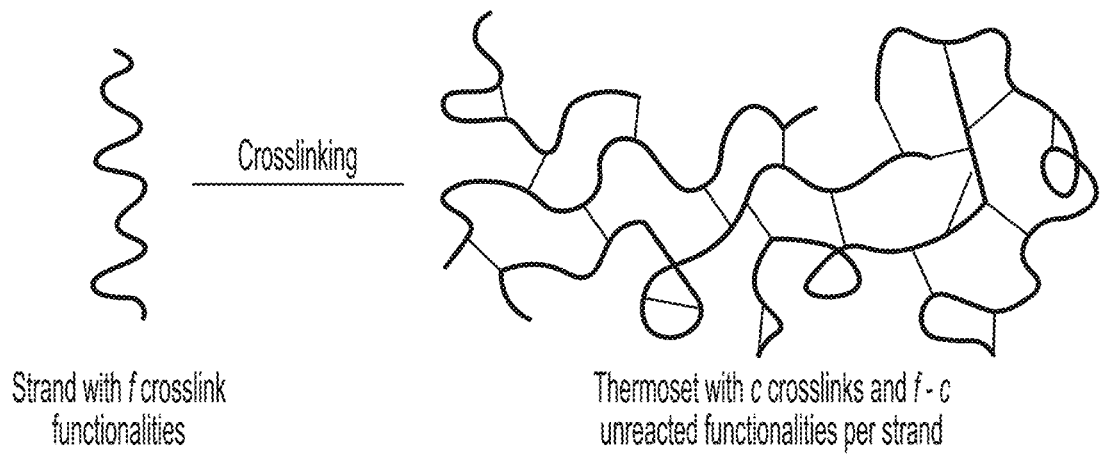
FIGS. 17A-17D.
Figure 17B:
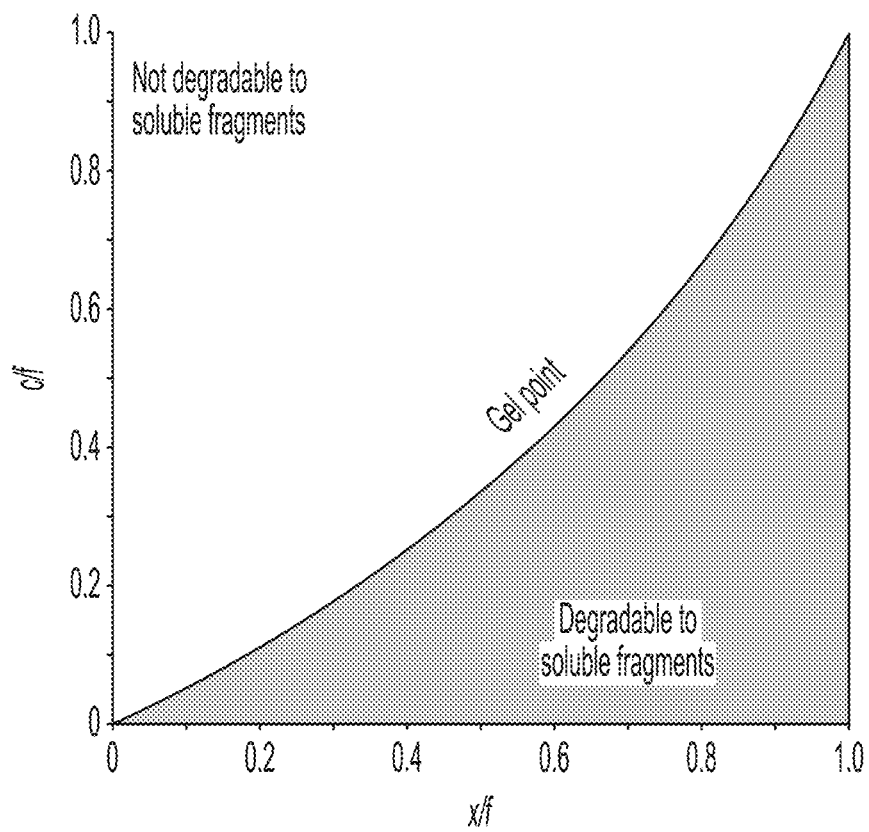
Figure 17C:
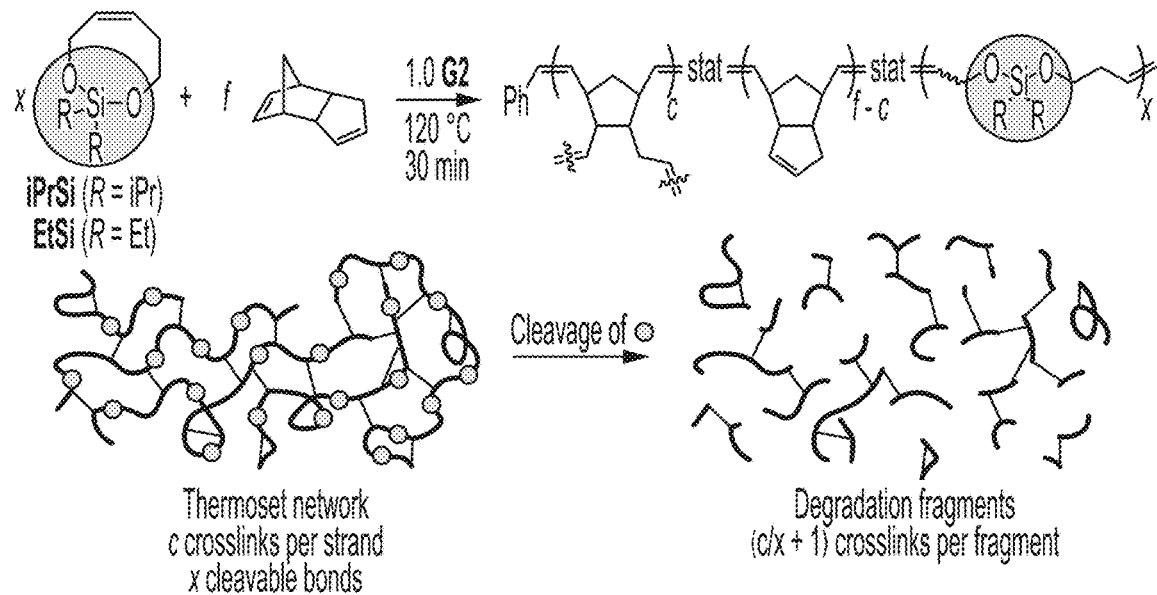

To test the validity of this model, recently reported silyl ether monomers that copolymerize with norbornene derivatives by ROMP were leveraged to produce degradable statistical copolymers.[17] Here, DCPD was mixed with different amounts of the silyl ether monomer iPrSi (0, 5, 10, or 15% v/v or one equivalent of iPrSi per 30.8, 14.6, and 9.2 equivalents of DCPD, respectively, FIG. 17C); the mixtures were cured in the presence of Grubbs $2^{nd}$-generation ROMP initiator. While this curing protocol was not further optimized, the resulting materials displayed Young's moduli in the GPa range (vide infra) as expected for pDCPD thermosets. In the initial stage of pDCPD curing, the norbornene component of DCPD copolymerizes with iPrSi to form linear polymer strands with f cyclopentene sidechains as potential crosslinking sites and x cleavable silyl ether linkages (FIG. 17C). Cyclopentene sidechain metathesis leads to iPrSi-doped pDCPD with c crosslinks. Silyl ether cleavage is expected to generate fragments with <c/x+1> crosslinks per strand, thus, as x approaches c, smaller soluble products should be produced. This approach stands in contrast to the indiscriminate degradation of thermosets, which produces products of uncontrolled size and chemical composition that typically have much lower value: the comonomer strategy provides a way to trigger thermoset degradation at low comonomer loadings and control degradation product size and composition (vide infra). Lastly, a preliminary technoeconomic analysis suggested that iPrSi can be manufactured inexpensively, making it potentially feasible for large-scale use especially if added as an additive to existing pDCPD workflows.

Figure 17D:
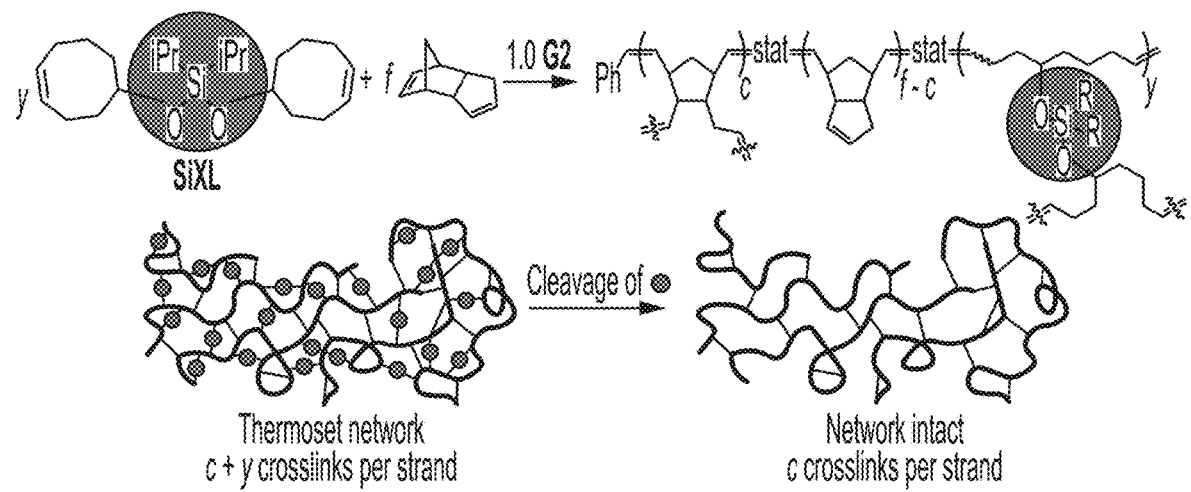

To compare iPrSi-doped pDCPD to analogs with cleavable crosslinks, pDCPD samples were prepared in the presence of up to 80% v/v of a bis-cyclooctene crosslinker featuring a silyl ether linkage (SiXL, FIG. 17D). In this case, the addition of y cleavable crosslinks (from SiXL) was expected to yield thermosets with c+y crosslinks; cleavage of the y linkages leaves a network with c crosslinks, precluding the formation of soluble products for all y values other than those much greater than c (FIG. 17D). In thermosetting materials with mostly cleavable crosslinks, theoretically it is possible, though often difficult in practice, to achieve material degradation once nearly all of the crosslinks are cleaved.[9] For thermosets that lack naturally cleavable crosslinks, however, the addition of a small number of cleavable crosslinks is not expected to produce degradable materials.

Figure 18A:
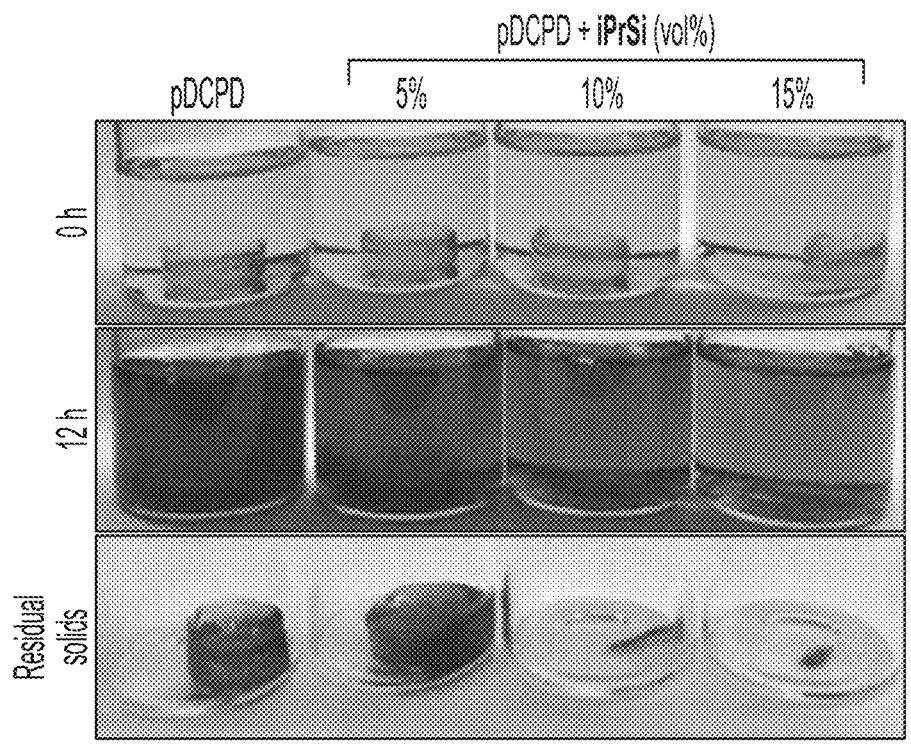
FIGS. 18A-18B. Precise placement of a small number of degradable bonds within the strands of pDCPD thermosets enables degradation into soluble products.
Figure 18B:
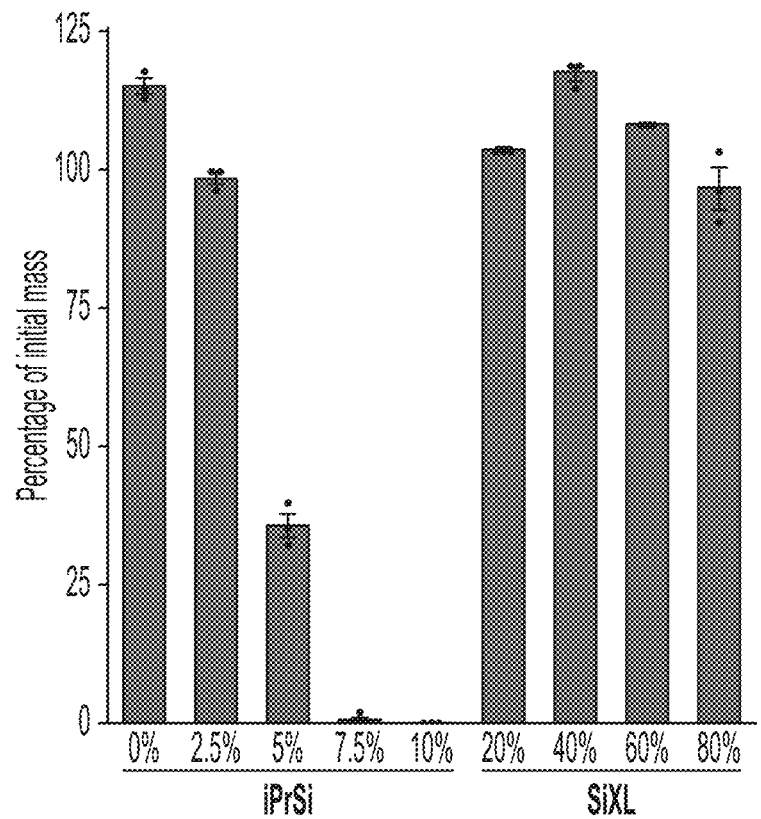

To test this hypothesis, samples of iPrSi-doped, SiXL-doped, and native pDCPD (FIG. 18A, FIGS. 22A-22C) were exposed to an excess of tetrabutylammonium fluoride (TBAF), a fluoride reagent that selectively cleaves silyl ethers and is often used to etch silicone elastomers,[27] at room temperature. After 12 h, the native pDCPD remained fully intact (FIG. 18B). In contrast, samples with only 10 or 15% v/v iPrSi dissolved (FIGS. 18A-18B). While the 5% iPrSi-doped sample remained intact, it was noticeably swollen, suggesting a decrease in crosslink density that was further confirmed by analysis of Si content using ICP-OES (FIG. 38. In each case, degradation of the iPrSi-doped samples occurred over the course of ~4 h, presumably limited by fluoride diffusion into the materials (FIGS. 39A-39B). Meanwhile, SiXL-doped materials did not degrade into soluble products even at 80% SiXL loading (FIG. 18B, FIGS. 22A-22C, FIG. 58). The rate of SiXL cleavage by fluoride was observed to be similar to that of iPrSi, suggesting that this difference in extent of degradation is due to network topology.

To further compare the roles of cleavable strands versus crosslinks in these materials, samples of 5% v/v and 10% v/v iPrSi and 20% v/v SiXL doped pDCPD were swollen to equilibrium in tetrahydrofuran (THF) and characterized by oscillatory rheology (FIG. 1C, FIGS. 23A-23C, FIG. 59). Strikingly, treatment of the iPrSi-doped samples with TBAF led to large decreases in storage modulus (~100-fold for 5% iPrSi doped pDCPD) while the modulus of the 20% v/v SiXL-doped sample decreased by only ~5-fold.

Functional Evaluation of pDCPD Samples with Degradable Strands

Figure 1A:
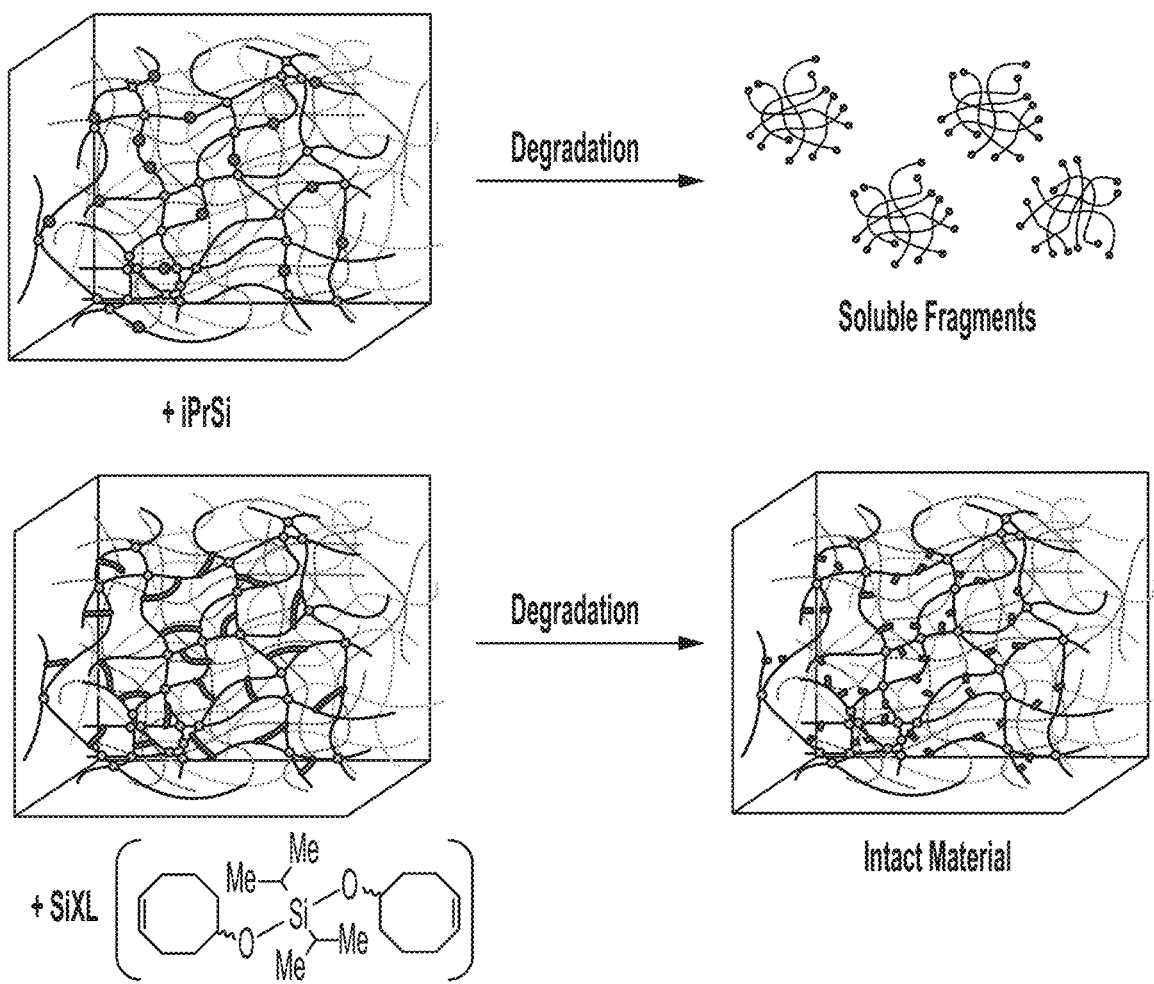
FIGS. 1A-1C. Precise placement of degradable bonds within polynorbornene strands is crucial for degradation into soluble fragments at low monomer loadings.
Figure 1B:
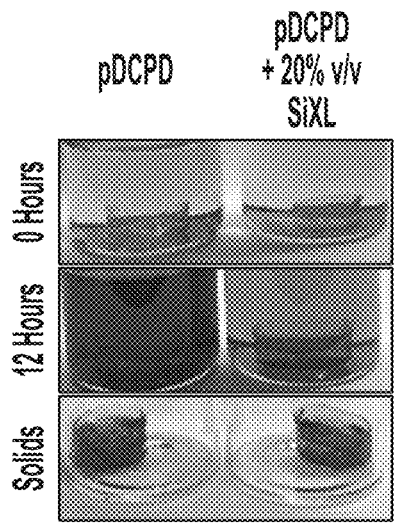
Figure 1C:
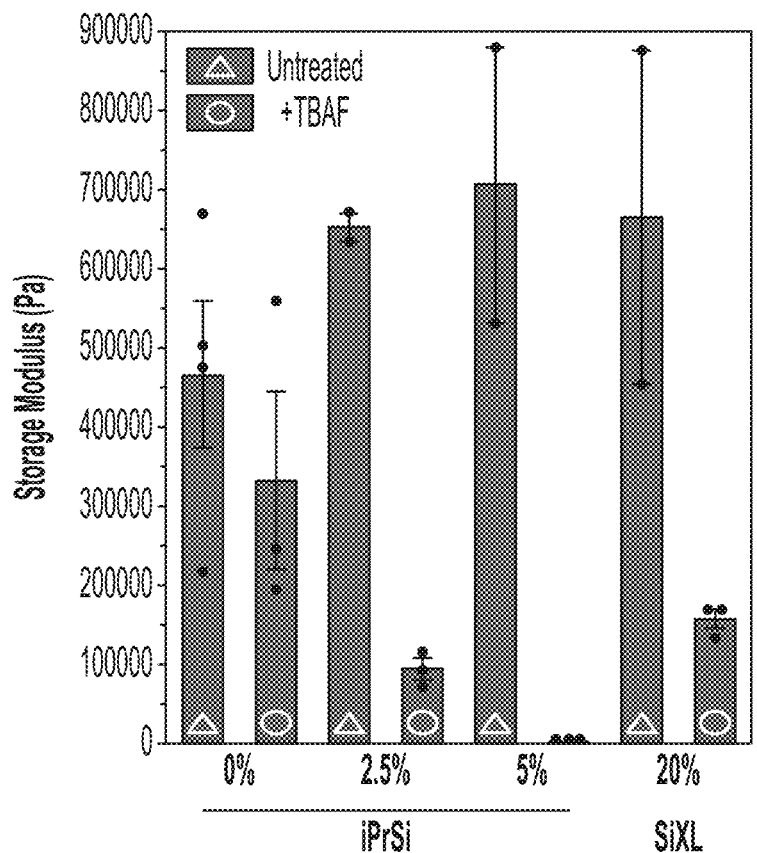
Figure 2A:
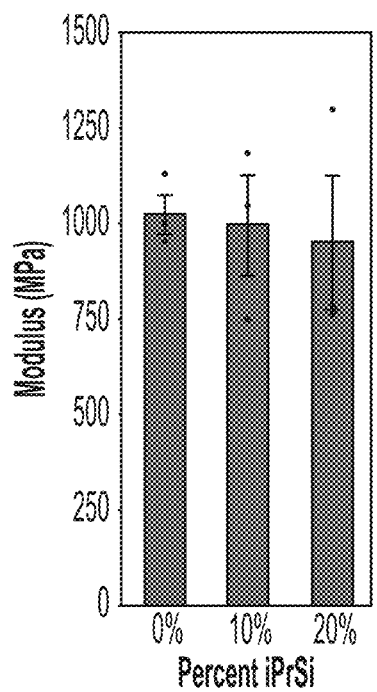
FIGS. 2A-2B. Functional evaluation of doped pDCPD (e.g., a copolymer described herein).
Figure 2B:
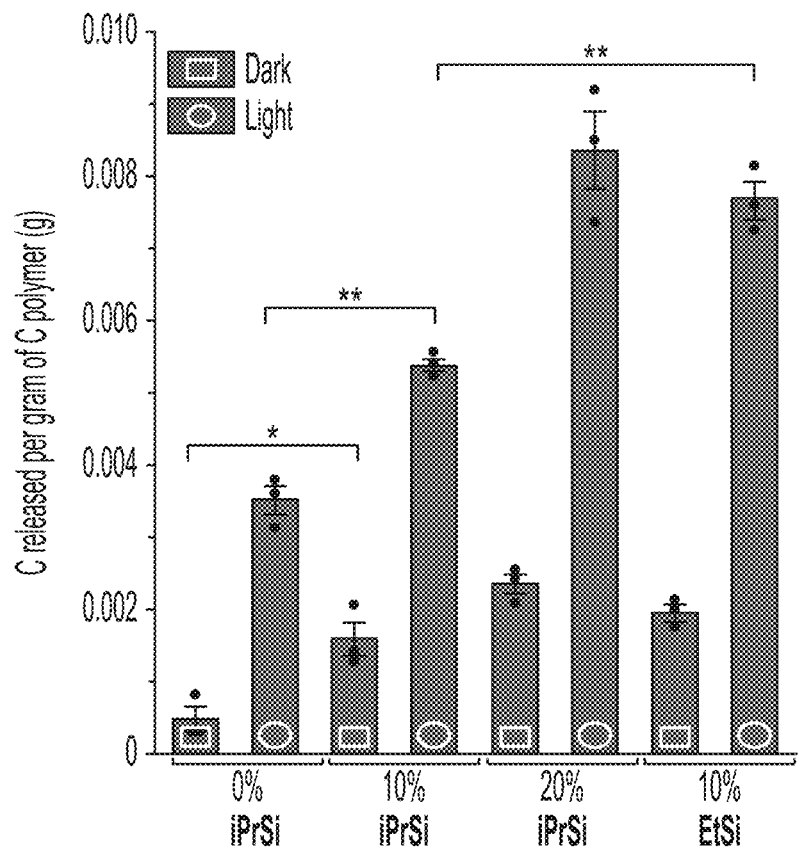
Figure 19A:
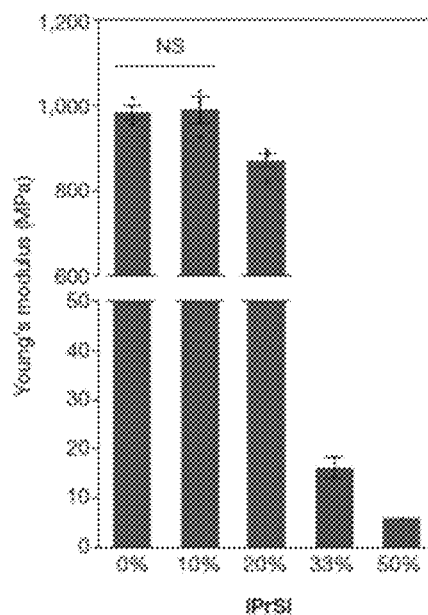
FIGS. 19A-19G. Functional evaluation of doped pDCPD.
Figure 19B:
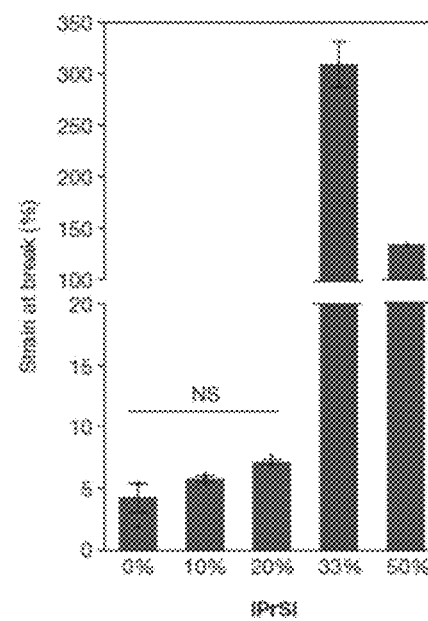
Figure 19C:
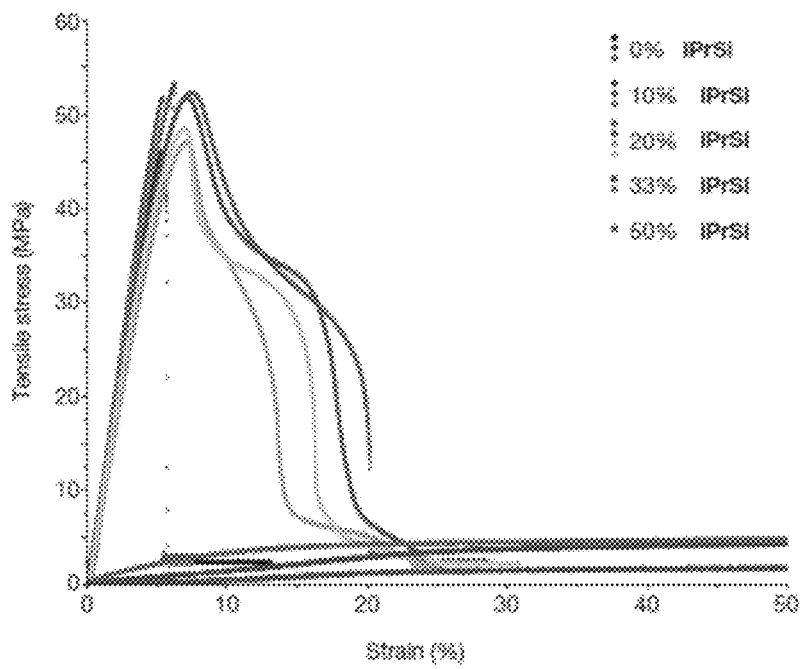
Figure 19D:
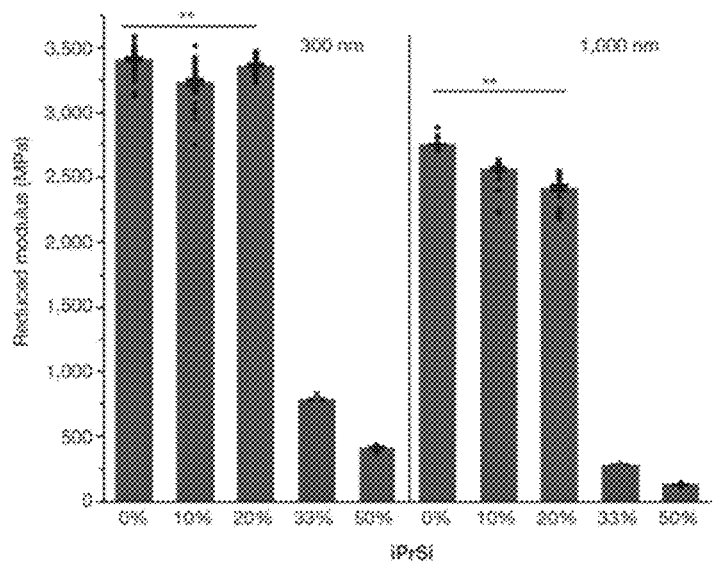

Next, the functional performance of iPrSi-doped pDCPD was studied for comparison to the native material. In tensile tests, the 10% and 20% iPrSi-doped samples showed nearly identical Young's moduli and elongations at break compared to pDCPD (FIGS. 19A-19C, FIG. 60) while 33% and 50% iPrSi-doped samples showed much lower moduli. These results were corroborated by dynamic mechanical analyses (DMA) and nanoindentation studies (FIG. 19D, FIG. 2A,).

Figure 4:
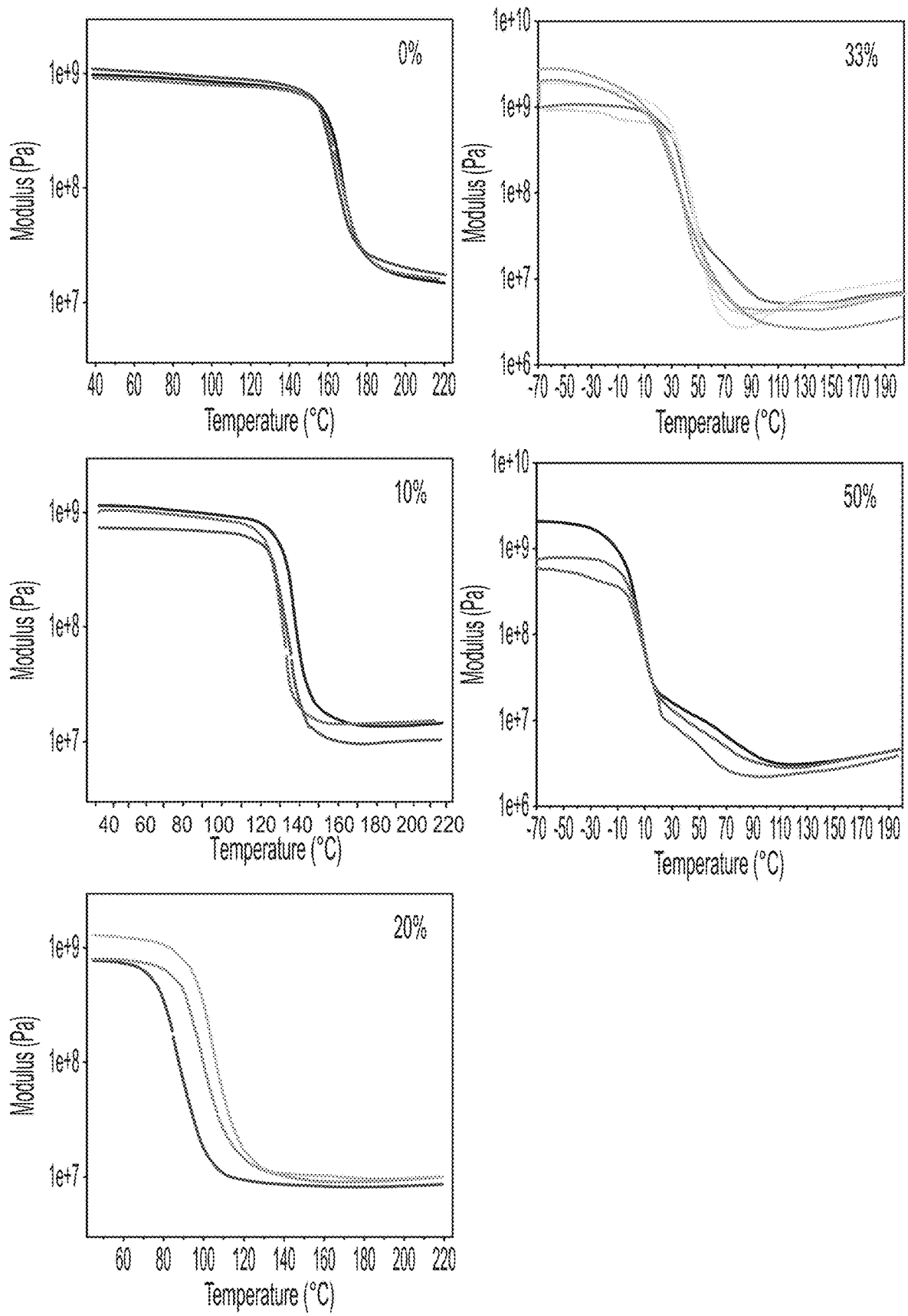
FIG. 4. Full DMA traces from pDCPD samples containing different levels of iPrSi.
Figure 5:
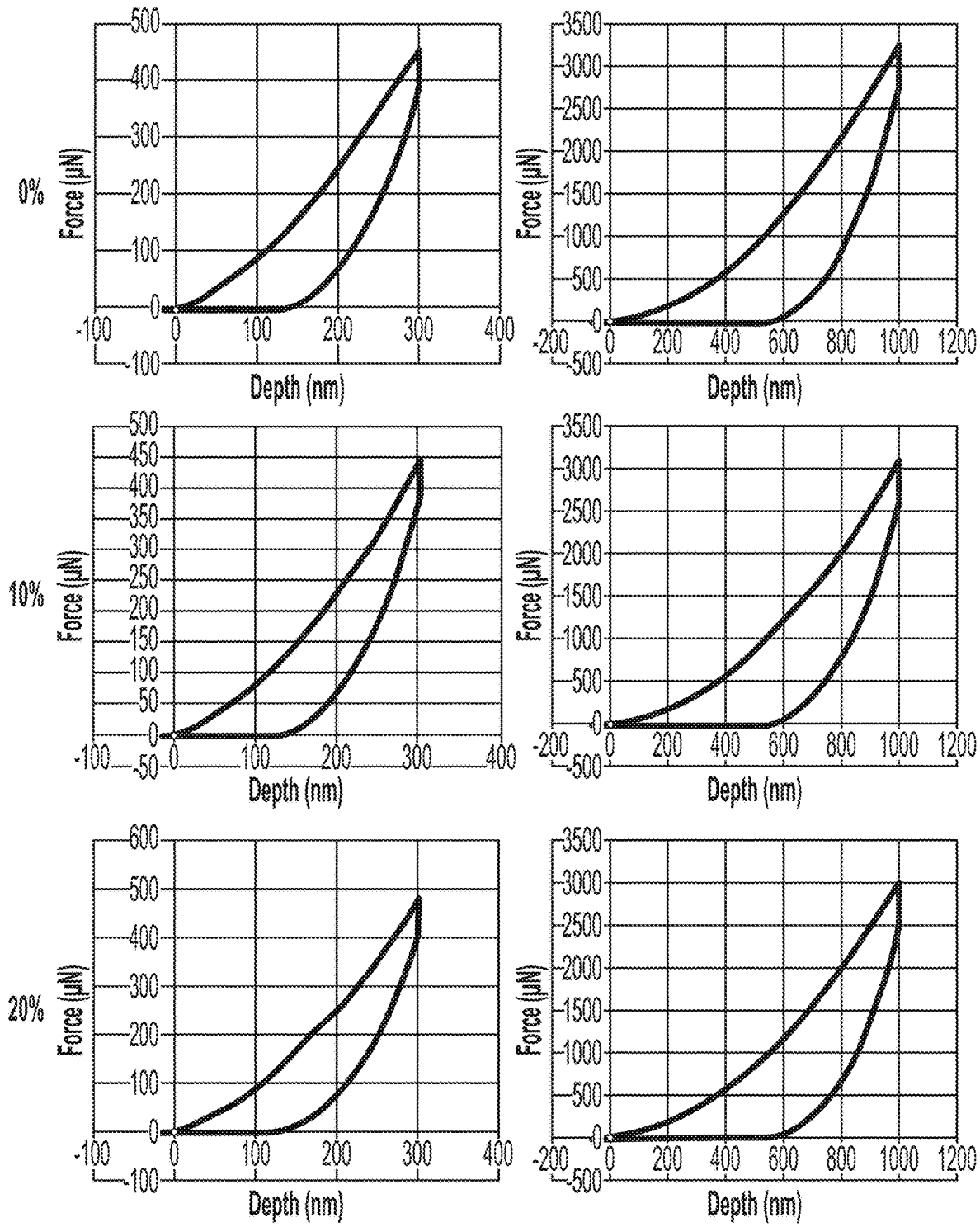
FIG. 5. Representative nanoindentation traces from pDCPD samples containing different levels of iPrSi.
Figure 5:
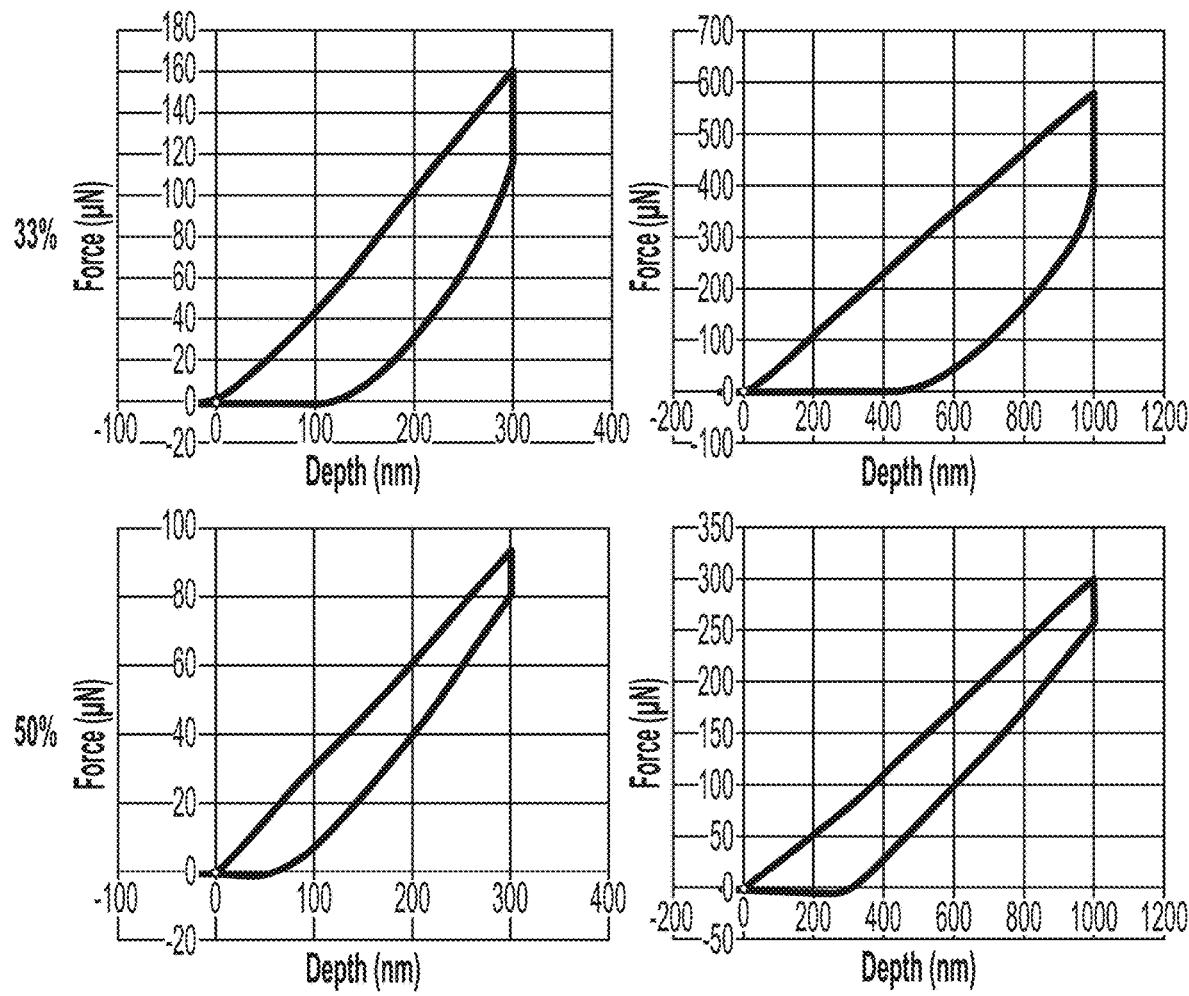
Figure 6:
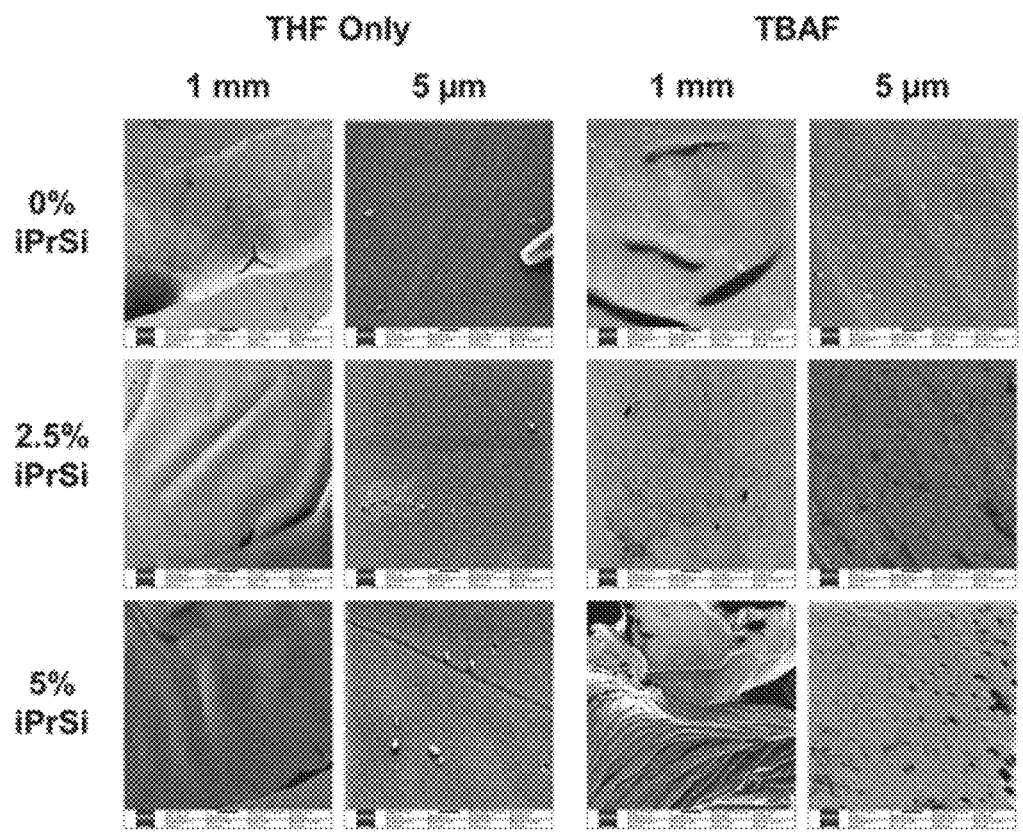
FIG. 6. Images of samples of pDCPD containing 0, 2.5, or 5% iPrSi, treated with TBAF for 12 hours or swollen in THF for 12 hours, then dried. Samples were sputter coated with AuPd alloy before He-ion imaging. Buckling of the THF-only samples is attributed to deformations induced by swelling and drying of the material. The 5% iPrSi sample, after TBAF treatment and drying, is significantly deformed (as evidenced in the 1 mm image). No microporosity was observed in any of TBAF-treated samples (no pores observed at 5 μm), consistent with full collapse of the partially degraded polymer networks upon solvent removal.
Figure 19E:
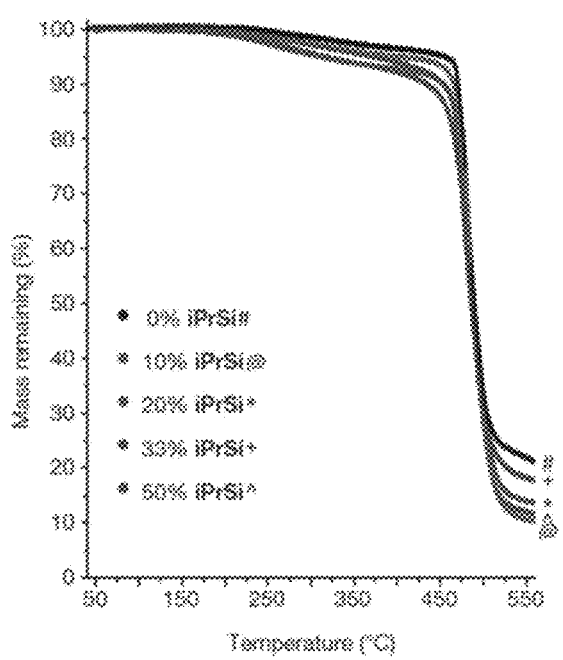
Figure 19F:
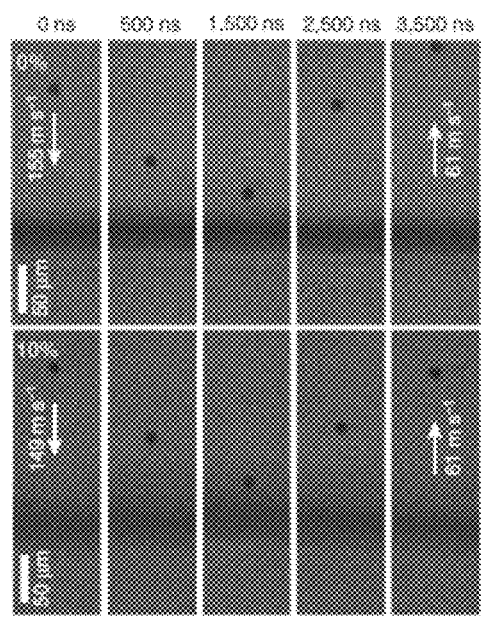
Figure 24A:
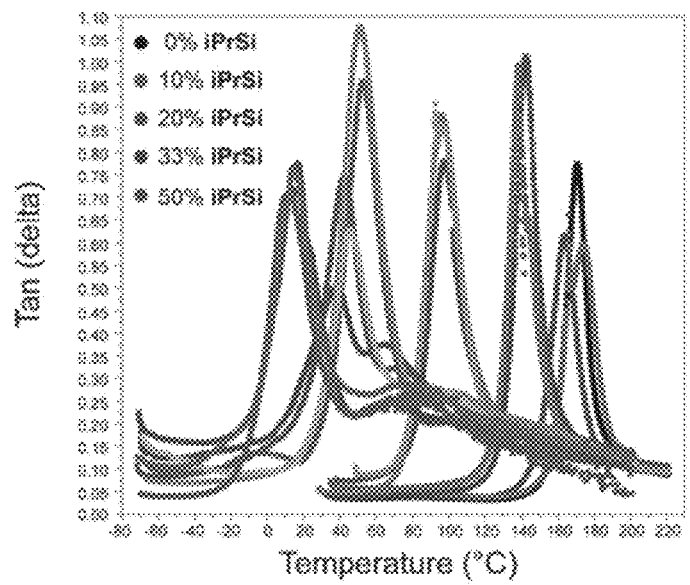
FIGS. 24A-24B. Characterization of mechanical and thermal properties of iPrSi-doped pDCPD by DMA.
Figure 24B:
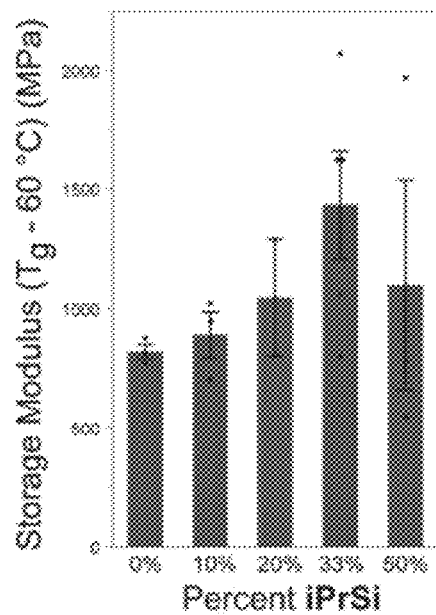
Figure 25A:
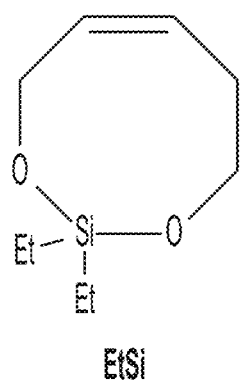
FIGS. 25A-25D. Synthesis and degradation of EtSi- and iPrSi-doped pDCPD.
Figure 25B:
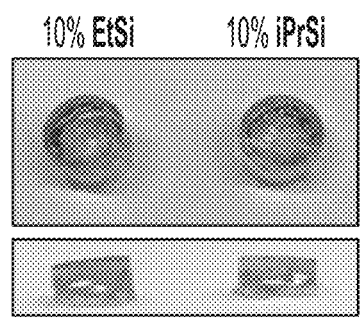
Figure 25C:
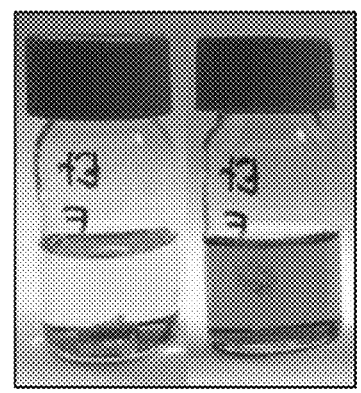
Figure 25D:
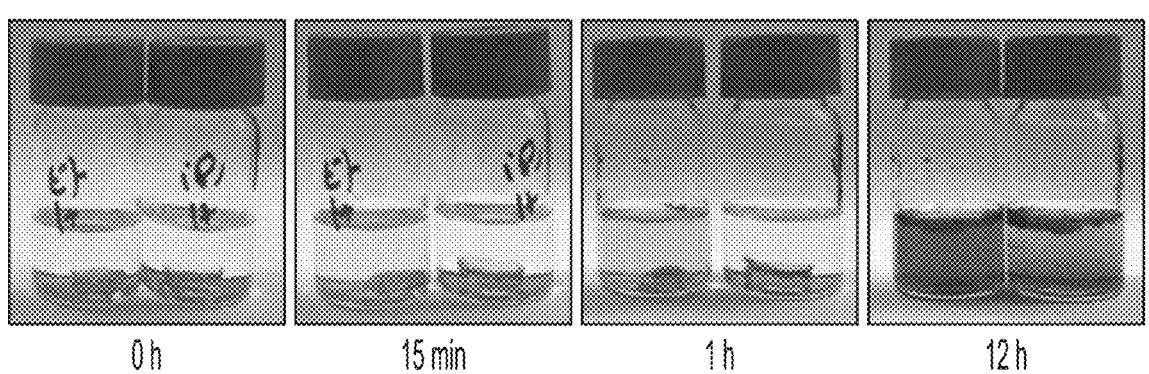

Thermal gravimetric analysis (TGA) showed similar decomposition temperatures for all samples (FIG. 19E). DMA showed a modest decline in $T_g$ from 166° C. for native pDCPD to 138° C. for the 10% iPrSi-doped sample and a further $T_g$ lowering for higher iPrSi loadings (FIG. 4, FIG. 24A). 33% and 50% iPrSi-doped samples exhibit Tg values closer to or below room temperature (46° C. and 14° C., respectively), which accounts for their lower moduli as measured by tensile testing at room temperature. In support of this notion, all of the samples displayed similar moduli at Tg—60° C. as measured by DMA (FIG. 24B).

Outstanding ballistic impact resistance is one of the most well-known properties of pDCPD.[28] To assess the ballistic impact response of our degradable analogues, laser induced projectile impact tests (LIPIT) were conducted on 10% iPrSi-doped and native pDCPD films (23.0±1.7 μm) using steel microparticles (12.8±0.4 μm diameter).[29] High-speed imaging revealed that films of 10% iPrSi-doped material stopped projectiles with the same efficiency as native pDCPD (FIG. 19F, FIGS. 61-63, Tables 3 and 4).

TABLE 3

LIPIT Data for 0% iPrSi–doped pDCPD.

| Impact Velocity m/s | Uncertainty | Post-Impact Velocity m/s | Uncertainty | Coefficient of Restitution | Uncertainty | Particle Diameter (μm) | Film Thickness (μm) |
|---|---|---|---|---|---|---|---|
| 718 | 14.36 | 0 | 0 | 0 | 0 | 13.2 | 21.75 |
| 820 | 16.4 | 154 | 3.08 | 0.187805 | 0.005312 | 12.5 | 22.5 |
| 675 | 13.5 | 0 | 0 | 0 | 0 | 12.5 | 23.25 |
| 895 | 17.9 | 310 | 6.2 | 0.346369 | 0.009797 | 12.2 | 23.25 |
| 851 | 17.02 | 342 | 6.84 | 0.40188 | 0.011367 | 12.7 | 22.75 |
| 949 | 18.98 | 512 | 10.24 | 0.539515 | 0.01526 | 12.2 | 22.75 |
| 841 | 16.82 | 291 | 5.82 | 0.346017 | 0.009787 | 12.9 | 22.5 |
| 606 | 12.12 | 0 | 0 | 0 | 0 | 12.3 | 21 |
| 910 | 18.2 | 530 | 10.6 | 0.582418 | 0.016473 | 12.7 | 22.5 |
| 855 | 17.1 | 322 | 6.44 | 0.376608 | 0.010652 | 11.8 | 24.75 |
| 691 | 13.82 | 0 | 0 | 0 | 0 | 12.7 | 24 |
| 593 | 11.88 | 0 | 0 | 0 | 0 | 12.9 | 24 |
| 155 | 3.1 | −61 | −1.22 | −0.39355 | −0.01113 | 12.8 | 25.5 |
| 488 | 9.76 | −38 | −0.76 | −0.07787 | −0.0022 | 13.2 | 27 |
| 572 | 11.44 | 0 | 0 | 0 | 0 | 13.2 | 24.75 |
| 567 | 11.34 | 0 | 0 | 0 | 0 | 13.1 | 24.75 |
| 376 | 7.52 | −51.7 | −1.034 | −0.1375 | −0.00389 | 13.2 | 24.75 |
| 328 | 6.56 | −63 | −1.26 | −0.19207 | −0.00543 | 13.6 | 24.75 |
| 430 | 8.6 | 0 | 0 | 0 | 0 | 13.9 | 21 |
| 255 | 5.1 | −79 | −1.58 | −0.3098 | −0.00876 | 13.4 | 23.25 |
| 261 | 5.22 | −67 | −1.34 | −0.2567 | −0.00726 | 13.2 | 24.75 |
| 300 | 6 | −81 | −1.62 | −0.27 | −0.00764 | 12.5 | 24.75 |
| 395 | 7.9 | −56 | −1.12 | −0.14177 | −0.00401 | 13.3 | 23.25 |
| 307 | 6.14 | −73 | −1.46 | −0.23779 | −0.00673 | 12.9 | 23.25 |
| 443 | 8.86 | −70 | −1.4 | −0.15801 | −0.00447 | 12.5 | 23.25 |
| 469 | 9.38 | −37 | −0.74 | −0.07889 | −0.00223 | 12.8 | 23.25 |

TABLE 4

LIPIT Data for 10% iPrSi-doped pDCPD.

| Impact Velocity m/s | Uncertainty | Post-Impact Velocity m/s | Uncertainty | Coefficient of Restitution | Uncertainty | Partticle Diameter (μm) | Film Thickness (μm) |
|---|---|---|---|---|---|---|---|
| 656 | 13.12 | 0 | 0 | 0 | 0 | 12.9 | 20.25 |
| 677 | 13.54 | 0 | 0 | 0 | 0 | 12.2 | 22.5 |
| 149 | 2.98 | −61 | −1.22 | 0.409396 | 0.011579 | 12.5 | 23.5 |
| 235 | 4.7 | −75 | −1.5 | 0.319149 | 0.009027 | 12.9 | 23.5 |
| 243 | 4.86 | −77 | −1.54 | 0.316872 | 0.008963 | 12.5 | 23.5 |
| 364 | 7.28 | −78 | −1.56 | 0.214286 | 0.006061 | 11.8 | 24.05 |
| 507 | 10.14 | 0 | 0 | 0 | 0 | 12.9 | 24.05 |
| 537 | 10.74 | 0 | 0 | 0 | 0 | 12.9 | 24.05 |
| 433 | 8.66 | 0 | 0 | 0 | 0 | 12.9 | 24 |

TABLE 4-continued

LIPIT Data for 10% iPrSi-doped pDCPD.

| Impact Velocity m/s | Uncertainty | Post-Impact Velocity m/s | Uncertainty | Coefficient of Restitution | Uncertainty | Particle Diameter (μm) | Film Thickness (μm) |
|---|---|---|---|---|---|---|---|
| 427 | 8.54 | −58 | −1.16 | 0.135831 | 0.003842 | 12.5 | 23.5 |
| 344 | 6.88 | −75 | −1.5 | 0.218023 | 0.006167 | 12.6 | 24.5 |
| 289 | 5.78 | −77 | −1.54 | 0.266436 | 0.007536 | 12.4 | 25.5 |
| 879 | 17.58 | 367 | 7.34 | −0.41752 | −0.01181 | 12.2 | 18 |
| 936 | 18.72 | 492 | 9.84 | −0.52564 | −0.01487 | 13.0 | 21 |
| 936 | 18.72 | 504 | 10.08 | −0.53846 | −0.01523 | 13.1 | 21 |
| 898 | 17.96 | 461 | 9.22 | −0.51336 | −0.01452 | 12.9 | 21 |
| 880 | 17.6 | 422 | 8.44 | −0.47955 | −0.01356 | 12.5 | 21 |
| 718 | 14.36 | 42 | 0.84 | −0.0585 | −0.00165 | 12.7 | 21 |
| 726 | 14.52 | 0 | 0 | 0 | 0 | 12.9 | 21 |
| 725 | 14.5 | 0 | 0 | 0 | 0 | 12.2 | 22 |
| 570 | 11.4 | 0 | 0 | 0 | 0 | 12.7 | 21 |
| 829 | 16.58 | 375 | 7.5 | −0.45235 | −0.01279 | 13.3 | 21 |
| 739 | 14.78 | 219 | 4.38 | −0.29635 | −0.00838 | 13.2 | 21 |
| 781 | 15.62 | 266 | 5.32 | −0.34059 | −0.00963 | 12.3 | 24 |
| 661 | 13.22 | 0 | 0 | 0 | 0 | 13.1 | 24 |
| 615 | 12.3 | 0 | 0 | 0 | 0 | 13.0 | 24 |

Figure 19G:
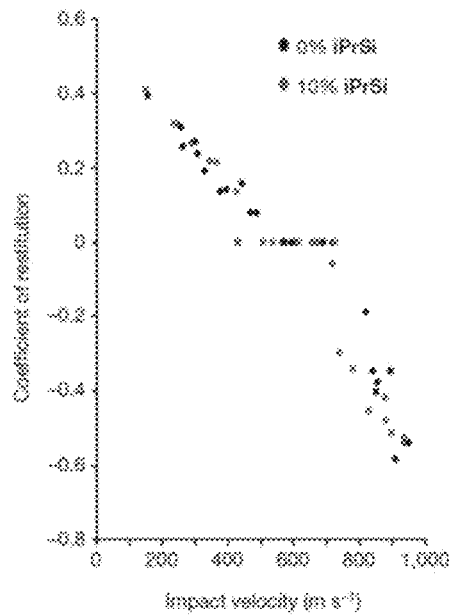

The coefficient of restitution (CoR), defined as the ratio of rebound velocity to impact velocity, was similar for these materials across impact velocity regimes of particle rebound, embedment, and film perforation (FIG. 19G), indicating indistinguishable high strain-rate responses.

Figure 41:
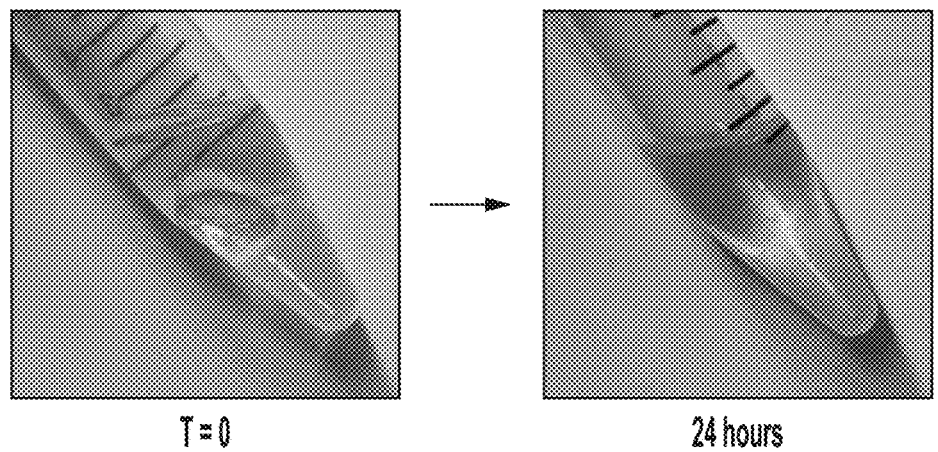

Next, the degradation of these materials was probed in more detail. In addition to TBAF, which is convenient for laboratory scale reactions, hydrofluoric acid, which is used to etch silicon on large scale in the semiconductor industry, readily dissolved our iPrSi doped pDCPD at room temperature (FIG. 41). Silyl ethers are also susceptible to cleavage under acidic or basic conditions[30]; however, due to their hydrophobic nature, iPrSi-doped pDCPD samples displayed sluggish hydrolysis in aqueous acidic (pH=0) or basic (pH=14) conditions, though they did show evidence of surface etching following exposure to aqueous sodium hydroxide for 30 minutes (FIG. 42). To demonstrate tuning the degradation of these materials, we prepared samples doped with 10% v/v of EtSi, a comonomer significantly more susceptible to hydrolysis.[17] These materials displayed enhanced degradation under mixed aqueous/organic acidic conditions (FIGS. 25A-25D). Through the use of a wider range of comonomers, it may be possible to generate thermosets with variable degradation rates and mechanisms (e.g., photochemical, enzymatic, etc.).[31]

Finally, given concerns over the accidental release of plastic waste into the natural environment,[32] degradation of iPrSi- and EtSi-doped pDCPD exposed to synthetic seawater and ultraviolet light for 16 days was studied (FIG. 2B, FIG. 7A, FIGS. 26A-26B). Significant increases (up to ~2-3 fold) in the extent of degradation relative to native pDCPD were observed. Transmission electron microscopy (TEM) revealed the presence of sub-5-nm particles following degradation (FIG. 43). While the generation of microplastics (typically micrometre-millimetre-range particles) may be a concern,[33] nanoscale plastics could be important intermediates that enhance the total degradation rate of bulk plastics. Notably, optimization of the size and composition of pDCPD degradation products can be achieved by tuning the silyl ether monomer substituents and loading, which is challenging for less selective degradation processes.

Characterization of iPrSi-Doped pDCIPD Degradation Products and Reprocessing

The degradation products of iPrSi-doped pDCPD are hydroxylated polymers bearing cyclopentene functionalities that could be used for recycling or repurposing (FIG. 3C). To demonstrate this concept, samples of 10, 20, 33, or 50% iPrSi-doped pDCPD were prepared and subjected to degradation using TBAF (FIG. 44). The resulting soluble products were characterized by 1-D and 2-D solution-state NMR, including $^1$H, $^{13}$C, COSY, HSQC, HMBC, and NOESY (FIGS. 45-50) with greatly improved resolution compared to solid-state NMR (FIG. 3B). To enable comparison of the NMR spectra, a sample of linear, non-crosslinked pDCPD was independently prepared (FIGS. 51-52).[34] From the combination of these studies, a 3:2 ratio of aliphatic to olefin carbons could be assigned in the $^{13}$C NMR spectrum of the iPrSi-doped pDCPD degradation products, indicating that ~15% of the cyclopentenes of the polynorbornene strands had reacted (FIG. 3B). Based on our model (FIG. 17B), a material with 15% effective crosslinks would require >15% cleavable bonds to degrade into soluble products; thus, it was estimated that a large fraction of the reacted cyclopentene groups in pDCPD are consumed through intramolecular reactions (loops). This insight into the structure of pDCPD, uniquely enabled by the cleavable comonomer approach, lends clear and quantitative support to the model of pDCPD as being crosslinked by secondary metathesis reactions of cyclopentene substituents.[35]

Figure 20A:
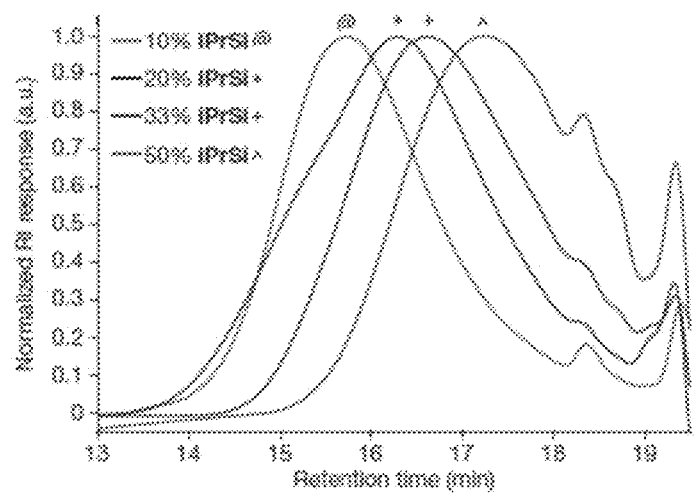
FIGS. 20A-20F. Soluble pDCPD fragments enable high-resolution characterization of pDCPD and can be recycled into new materials.

To examine the role of iPrSi loading on degradation product size, the soluble samples prepared above were analyzed by gel permeation chromatography (GPC) (FIG. 20A) and diffusion ordered spectroscopy (DOSY) (FIGS. 53-56), both of which showed an inverse relationship between iPrSi loading and degradation product size. From GPC, the weight-average molar masses of these samples ranged from 2-8 kDa (Table 5), while DOSY was used to estimate that the average diameter of the degradation products of the 10% iPrSi-doped material was ~4 nm, which is on the length scale of individual polymer strands. This result was further corroborated by TEM imaging (FIG. 3D).

TABLE 5

Calculated Fragment Molecular Weights from GPC-MALS

| Sample | $M_w$ | $M_n$ | $M_w/M_n$ |
|---|---|---|---|
| 10% iPrSi | $7.70 \times 10^3$ | $3.41 \times 10^3$ | 2.26 |
| 20% iPrSi | $5.72 \times 10^3$ | $2.13 \times 10^3$ | 2.69 |
| 33% iPrSi | $3.19 \times 10^3$ | $1.95 \times 10^3$ | 1.63 |
| 50% iPrSi | $1.91 \times 10^3$ | $1.38 \times 10^3$ | 1.38 |

Figure 20B:
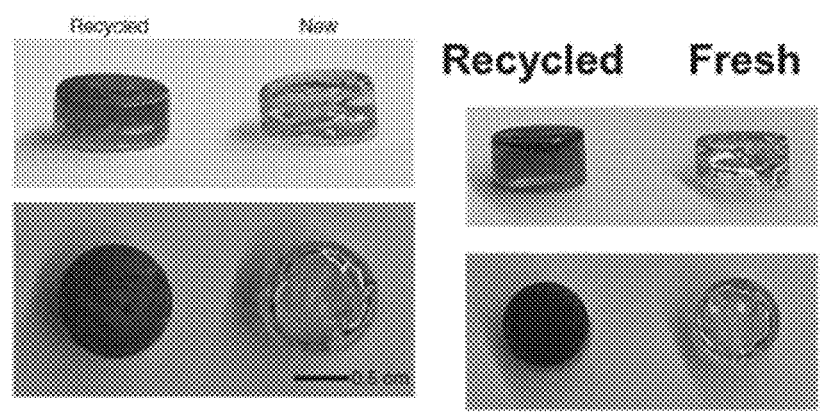
Figure 20C:
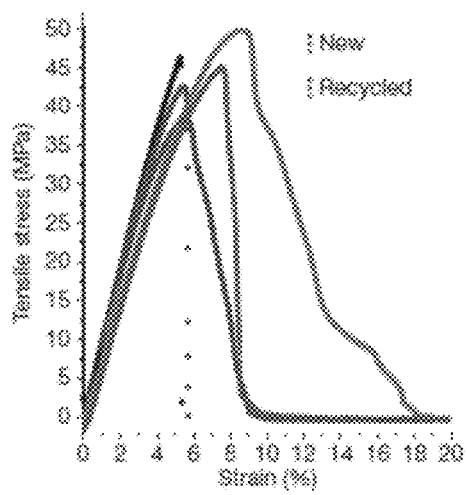
Figure 20D:
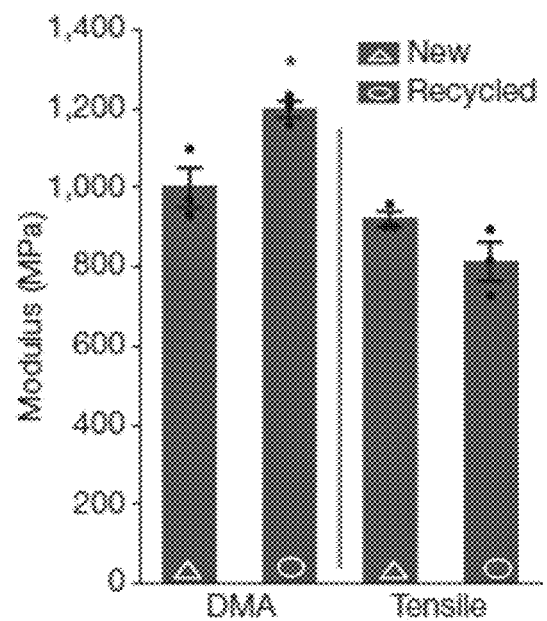
Figure 20E:
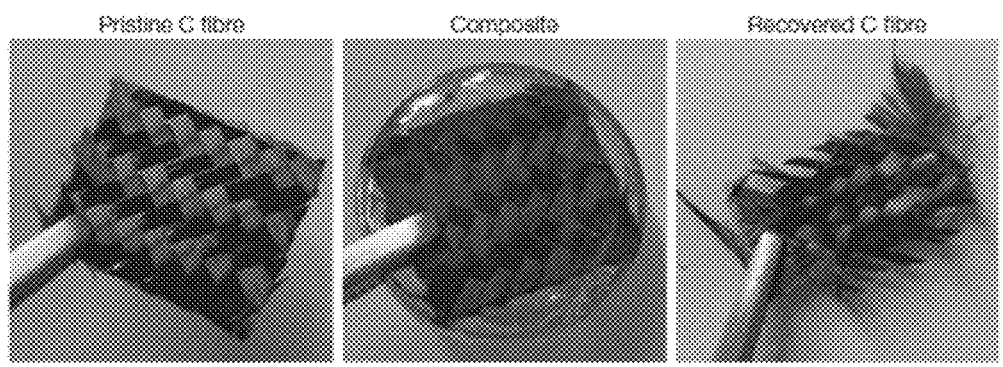
Figure 20F:
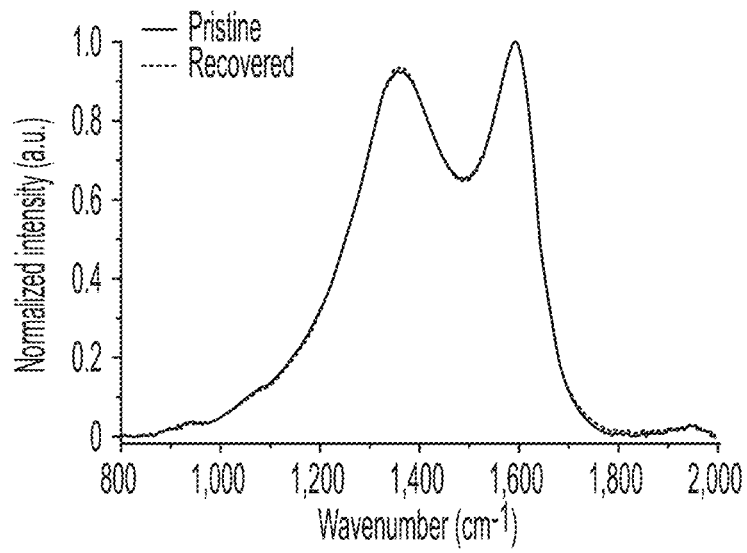

Given that these degradation products possess many unreacted cyclopentene substituents (FIGS. 3B-3C), it was reasoned that they could be reprocessed into new pDCPD materials. Indeed, mixing the degradation products of our 10% iPrSi-doped material (25 wt. %) with DCPD and curing following the same procedure used for native pDCPD produced recycled samples with comparable stress-strain behavior and elastic moduli (FIGS. 20B-20C, FIGS. 20B, 57). Moreover, the recycled samples displayed similar ballistic impact resistance to native pDCPD. Finally, carbon fiber composites of pDCPD have been explored for high-performance applications,[16] but the costly embedded carbon fiber typically cannot be recovered from such materials. When carbon fiber fabrics were embedded into 10% iPrSi-doped pDCPD, they could be quantitatively recovered (FIG. 20F). Raman spectra for pristine versus recovered carbon fiber were very similar, suggesting that the mild pDCPD degradation process has no impact on the fiber composition. These results hint at potential opportunities for thermoset composite recycling.

Methods

A General Theoretical Framework for Degradable Thermosets Via Copolymerization

The theoretical model for network degradation is described herein in further detail. The following variables were used, which are consistent with the terminology defined in FIGS. 17A-17D. Moreover, an additional variable was introduced for the dispersity of the degradation fragments. f=number-average degrees of polymerization of non-degradable, functional (crosslinkable) monomer (e.g, DCPD) c=number-average crosslinks per strand (i.e., the number off groups that have reacted to form crosslinks) x=number-average degrees of polymerization of degradable comonomer (e.g., iPrSi) D=dispersity of linear fragments obtained after strand degradation in reverse gel-point model.

Figure 21:
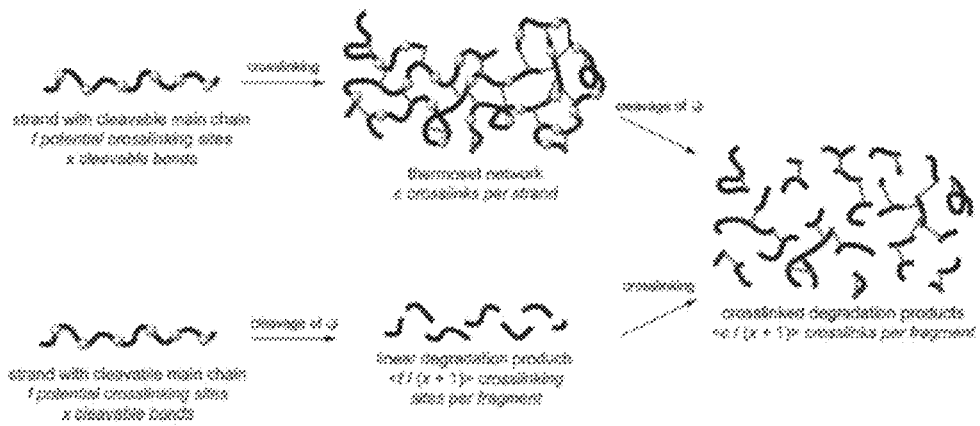
FIG. 21. The reverse gel-point concept used to derive the model of degradable thermosets shown in FIG. 17B. (Top) A thermoset network containing f potential crosslinks per strand, c actual crosslinks per strand and x cleavable bonds within each strand may or may not be degraded into soluble fragments after bond cleavage. A model that determines whether the material will dissolve can be described as a function of f, c and x (FIG. 17B). (Bottom) The reverse gel-point concept enables this model by assuming that the minimum x required to enable thermoset degradation for given c and f values corresponds to the value that will inhibit the gelation of degradation fragments derived from strands with f potential crosslinking sites and x cleavable bonds. Existing gelation theories (Miller-Macosko and Flory-Stockmayer) were used to solve for x, given f and c. Key to the reverse gel-point concept is the assumption that the network structure formed by the crosslinking of linear copolymer strands followed by cleavage of degradable bonds in those strands is identical to the network formed by first cleaving the linear copolymer strands and then crosslinking the resulting degradation products.
Figure 22A:
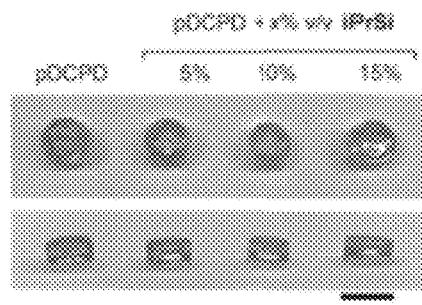
FIGS. 22A-22C. Characterization of pDCPD.
Figure 22B:
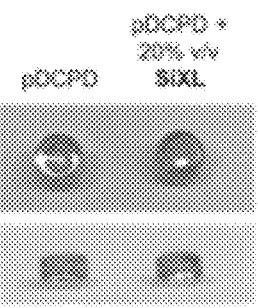
Figure 22C:
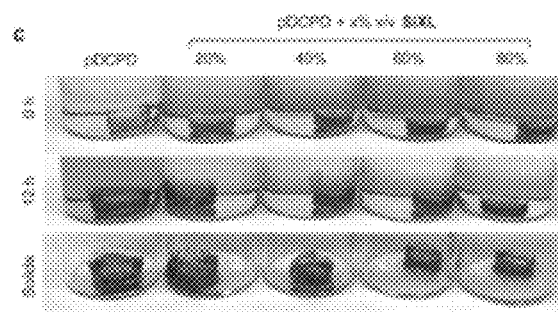
Figure 23A:
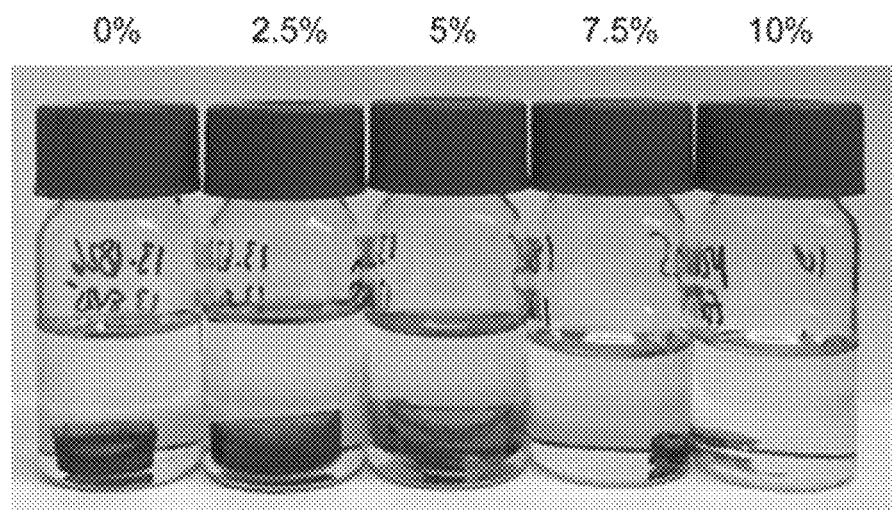
FIGS. 23A-23C. Further quantification of the impact of silyl ether incorporation into pDCPD strands.
Figure 23B:
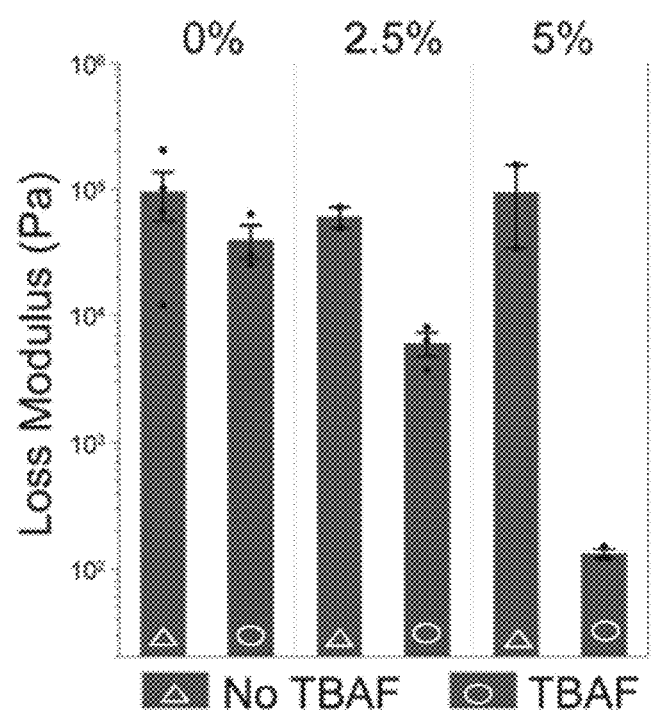
Figure 23C:
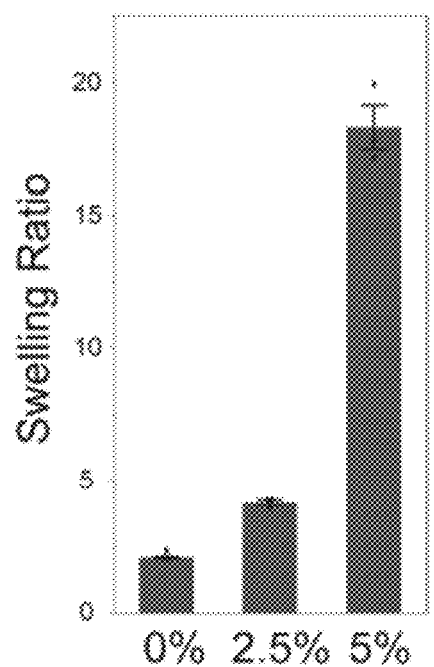

To begin, it was assumed that the network structure formed by the crosslinking of linear copolymer strands followed by cleavage of degradable bonds in those strands was identical to the network formed by first cleaving the linear copolymer strands and then cross-linking the resulting "fragments" as shown in FIGS. 21A-21B. Then, classical Flory-Stockmayer and Miller-Macosko theories were leveraged to determine what values of x would inhibit gelation for given values off and c. As is the case for these classical gelation theories, the model assumes that all functional groups of the same type have equal reactivity, that all functional groups react independently of each other, and that there are no intramolecular reactions. Moreover, it was assumed that degradable comonomers x are randomly distributed along the strand backbone.

The number-average degrees of polymerization (DP) of the linear fragments generated after degradable monomer cleavage was estimated as:

$$DP = \frac{f}{x+1} \quad (1)$$

To provide an estimate of D for these fragments, a Monte Carlo analysis was applied where x degradable co-monomers were randomly incorporated into a linear polymer of DP=f and calculated the fragment DP after degradation. This process was repeated $10^6$ times to arrive, as expected when $f \gg x \gg 1$,[36] a fragment dispersity of ~2.

Based on Miller-Macosko theory, the critical extent of reaction required for gelation during crosslinking a disperse mixture of polymer strands with a single cross-linking functionality was defined as $p_c$:

$$p_c = \frac{1}{f_w - 1} \quad (2)$$

where $f_w$ is the weight-average crosslink functionality of the fragments, which was defined as:

$$f_w = \frac{Đf}{x+1} \quad (3)$$

it was also noted that for crosslinked networks below the gel point:

$$\frac{c}{f} < p_c \quad (4)$$

Combining equations (2) and (4), the following was obtained:

$$\frac{c}{f} < \frac{1}{\left(\frac{Đf}{(x+1)}\right) - 1} \quad (5)$$

Solving for x provides the following relationship $$x > \frac{c(Đf - 1) - f}{c + f} \quad (6)$$

Assuming D=2 arrives at the expression provided in the main text and plotted in FIG. 17B for f=3000:

$$x > \frac{c(2f - 1) - f}{c + f} \quad (7)$$

While the model can account for any f or c value, in practice, many materials can be approximated by either of two limiting cases: $f \gg c$ or $f \sim c$. The limiting case of $f \gg c$ reflects materials where the number of crosslinks is low relative to the number of potential crosslinkable functionalities. Such is the case for vulcanized thermosets. In contrast, the limiting case of $f \sim c$ corresponds to materials where nearly every crosslinkable functionality is involved in a crosslink, as is found, for example, in many epoxy thermosets.

pDCPD Resin Precursor Preparation

Dicyclopentadiene (DCPD) and iPrSi were mixed in the desired ratio. Next, finely powdered Grubbs $2^{nd}$ generation ROMP initiator was dissolved into this mixture at a concentration of 2 mg/mL. The finely powdered initiator was generated by dissolving the commercially obtained Grubbs $2^{nd}$ generation complex in dichloromethane in a glass vial, evaporation of the solvent under vacuum, and scraping the residue from the side of the vial with a spatula. This process enabled the rapid and full dissolution of the catalyst in DCPD/iPrSi mixtures. The solutions remained liquid at room temperature at silyl ether concentrations of 10% or higher, while solidification occurred at 5% or lower concentrations. In these cases, the solidified monomer mixture was melted by gentle heating in a water bath (~40° C.). The homogenous pink solutions were used within 5 min to prepare resins of the desired geometry. pDCPD Resin Synthesis (Pellets) 200 µL of the solutions described above were added to 2 mL flat-bottom screw thread glass vials (VWR, Part No. 46610-772, 12×32 mm). The vials were heated to 120° C. for 15 min in an oven, during which time the pink solution turned into a yellow solid as it polymerized and crosslinked to form pDCPD. The vials were then removed from the oven, cooled to room temperature, and broken with a hammer to release the sample. The collected pDCPD samples were cured for another 30 minutes at 120° C. and then stored at room temperature until further use.

Laser-Induced Projectile Impact Testing of iPrSi-Doped pDCPD

Laser induced projectile impact testing (LIPIT) served as a platform for studying the high strain-rate impact response of materials[29]. LIPIT has been utilized previously to study the impact responses of gels, metals, ceramics, and a range of other materials[29,37-40]. In brief, a high-energy laser pulse (Nd:YAG, 532 nm, 10 ns) was focused onto a glass substrate (210 µm) coated with an ablative gold layer (60 nm), and a polyurea film (40 µm)—this glass-gold-polyurea configuration will hereafter be referred to as the "launch pad". The launch pad was coated with microparticles and after ablation of the gold layer by a high-energy laser pulse, a particle was propelled at high speeds ranging from tens of m/s up to 2 km/s, with the characteristic strain-rate defined as the impact velocity divided by particle diameter. The projectile speed was varied by adjusting the laser pulse energy. Particle trajectory and impact were captured via an ultra-high-speed camera (SIMX16, Specialized Imaging) with 16 independently triggered CCDs, illuminated by a second pulsed laser (640 nm, 30 µs). This provided 16 frames with a minimum exposure time of 5 ns and varied interframe time. The particle pre-impact velocity ($v_i$) and post-impact velocity ($v_r$) were extracted from the image sequences. All particle diameters were measured prior to impact, and film thicknesses were measured with confocal microscopy after impact.

In this experiment, steel microparticles (12.8±0.4 µm diameter) were launched with speeds ranging between 150±3 and 950±19 m/s at film samples with thicknesses of 23.0±1.7 µm. Three regimes of impact response were observed: particle rebound, particle embedment, and film perforation. The coefficient of restitution (CoR), the ratio of pre- and post-impact velocities ($-v_r/v_i$), was calculated and plotted to compare the impact responses of the two films. Positive, zero, and negative CoR correspond to particle rebound, embedment and film perforation respectively.

Weathering Experiments

To assess pDCPD degradability under the marine environment, the material was exposed to a synthetic seawater matrix both in the dark and under simulated solar irradiation. It was hypothesized that photooxidation of iPrSi-doped pDCPD would further enhance its aqueous wettability by introducing oxygen functional groups, assisting the hydrolysis of silyl ether groups. An approximately 100 mg polymer pellet was submerged in the bottom of 60 mL of synthetic seawater matrix in a clear vial sealed with PTFE-lined cap. The synthetic seawater recipe was: 420 mM NaCl, 0.8 mM NaBr, 29 mM $Na_2SO_4$, 54 mM $MgCl_2.6H_2O$, 11 mM $CaCl_2.2H_2O$, 10 mM KCl, 0.35 mM $H_3BO_3$, 1.8 mM $NaHCO_3$, and 0.26 mM $Na_2CO_3$, 5 nM $FeCl_3{}^{41}$.

Figure 7A:
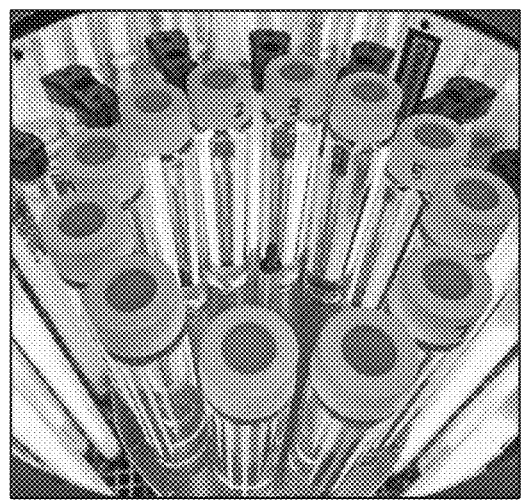
FIGS. 7A-7C.
Figure 7B:
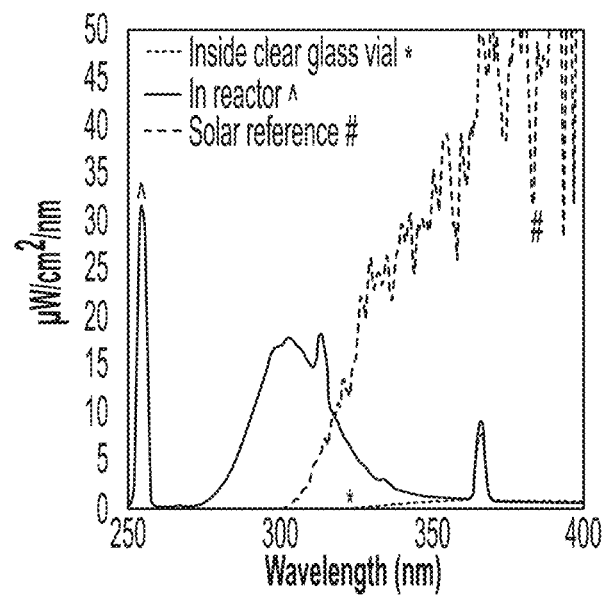
Figure 7C:
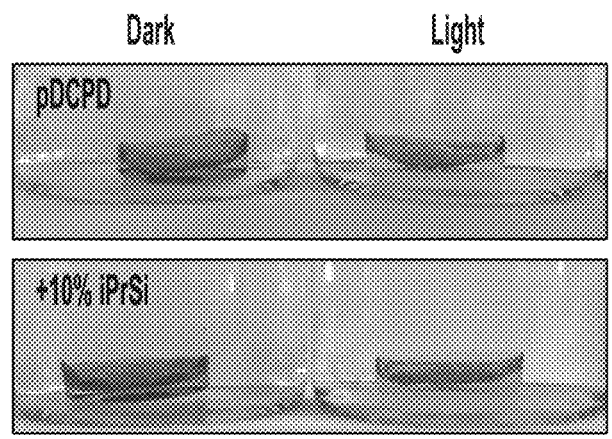
Figure 8:
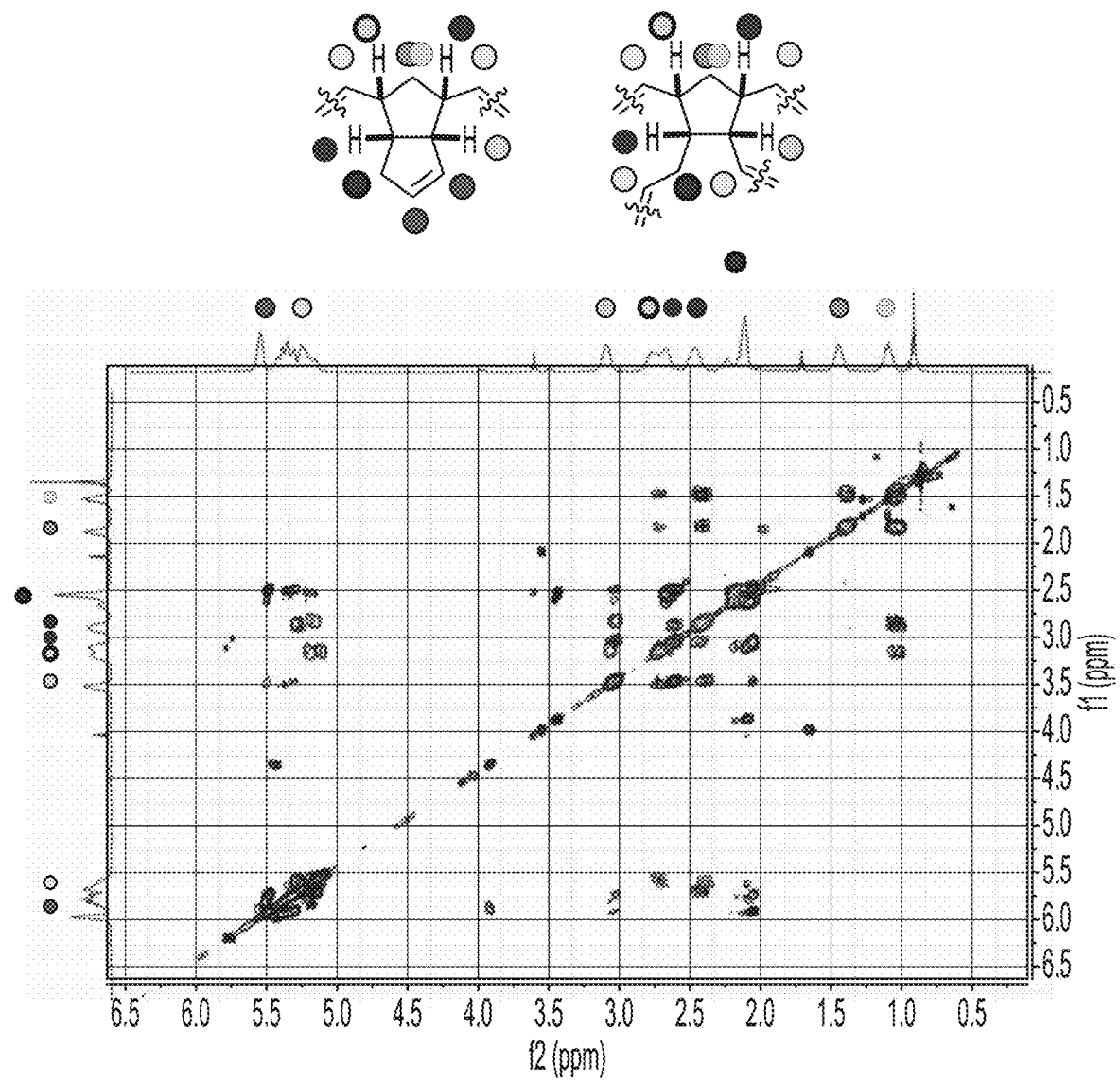
FIG. 8. Solution-phase COSY spectrum of the degradation solution derived from 10% iPrSi doped pDCPD.
Figure 9:
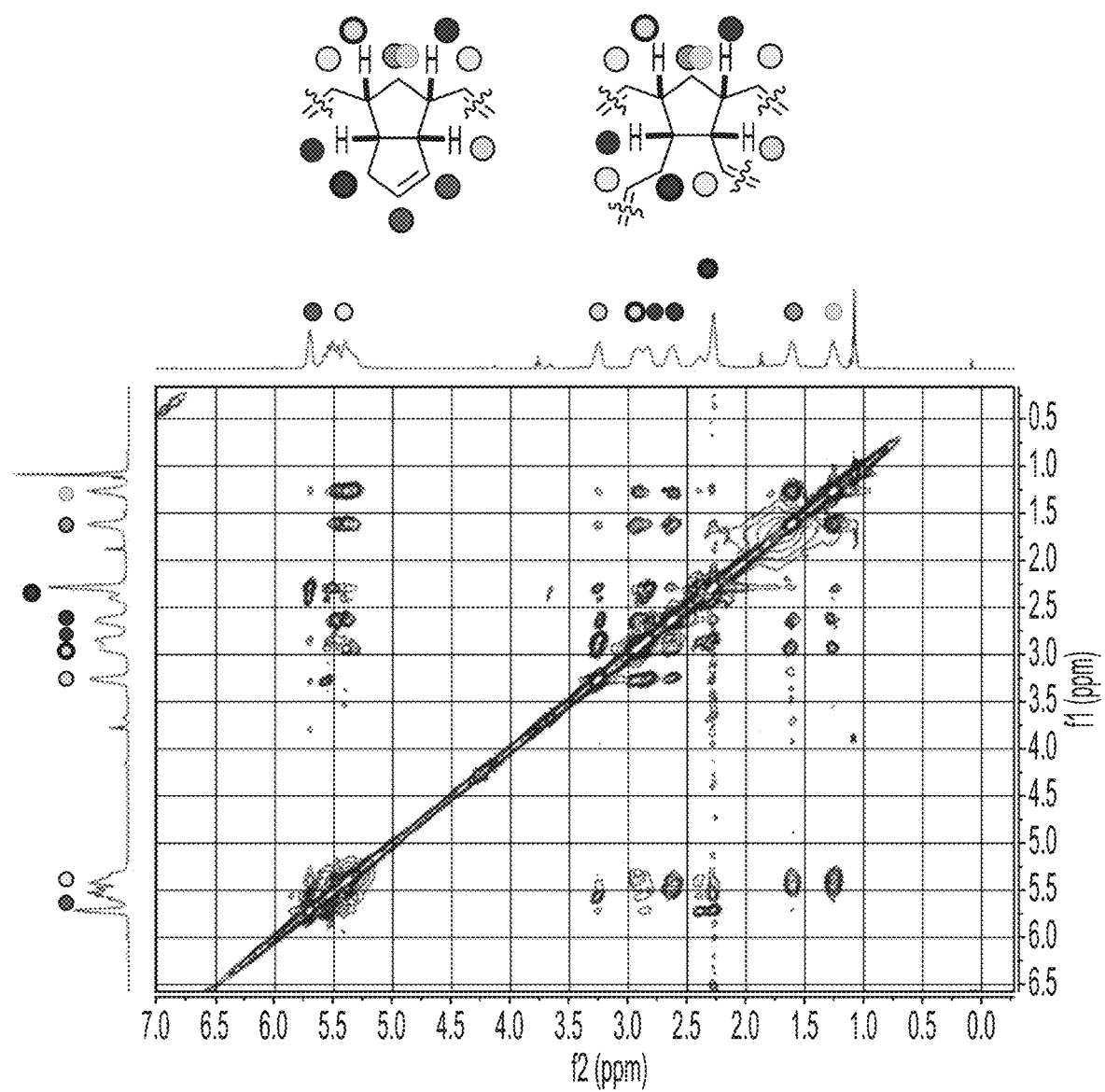
FIG. 9. Solution-phase NOESY spectrum of the degradation solution from 10% iPrSi-doped pDCPD.
Figure 26A:
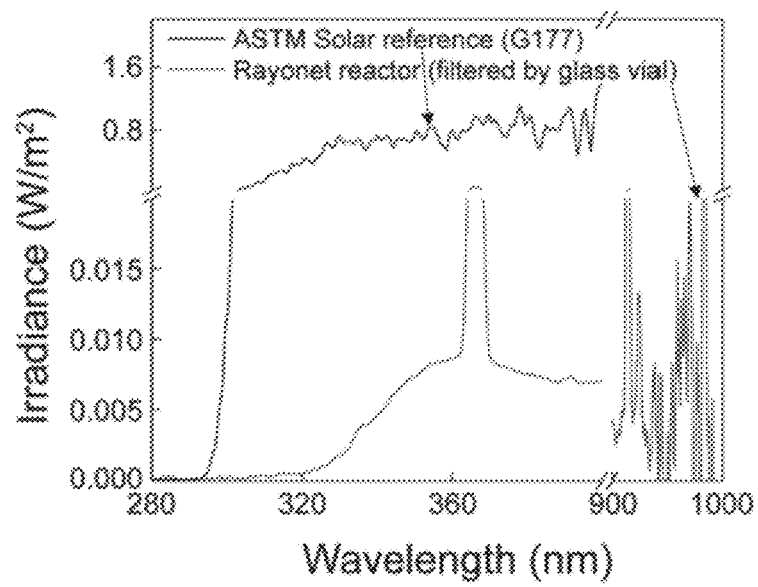
FIGS. 26A-26B Weathering studies.
Figure 26B:
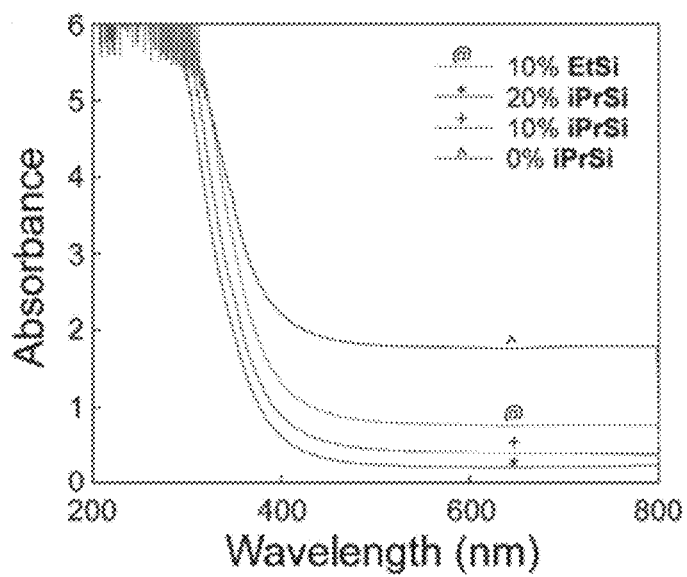
Figure 27:
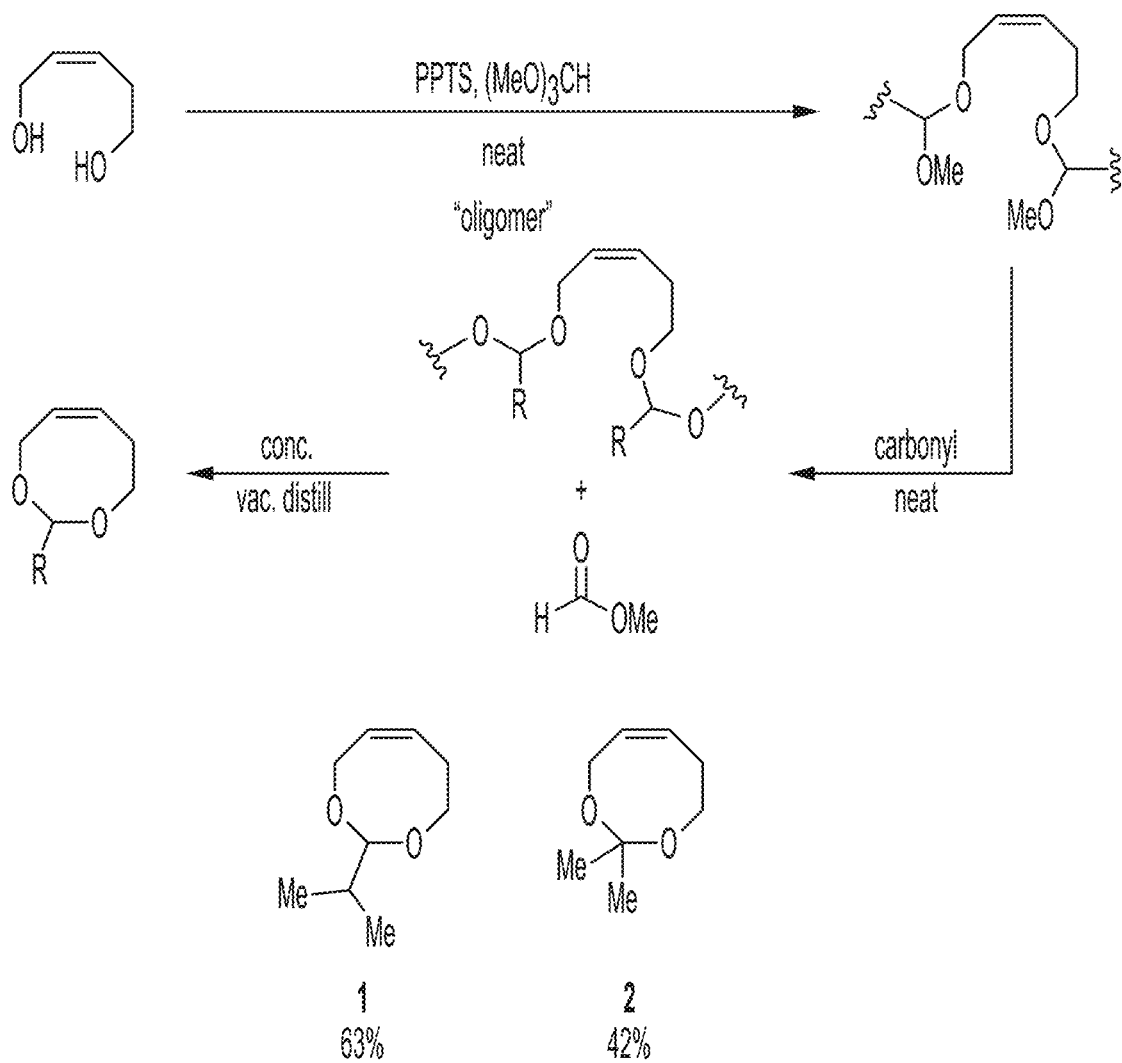
FIG. 27. Schematic showing synthesis of cyclic acetals. This is in principle generalizablel to any low molecular weight acetal derivative that can be purified by distillation.
Figure 28:
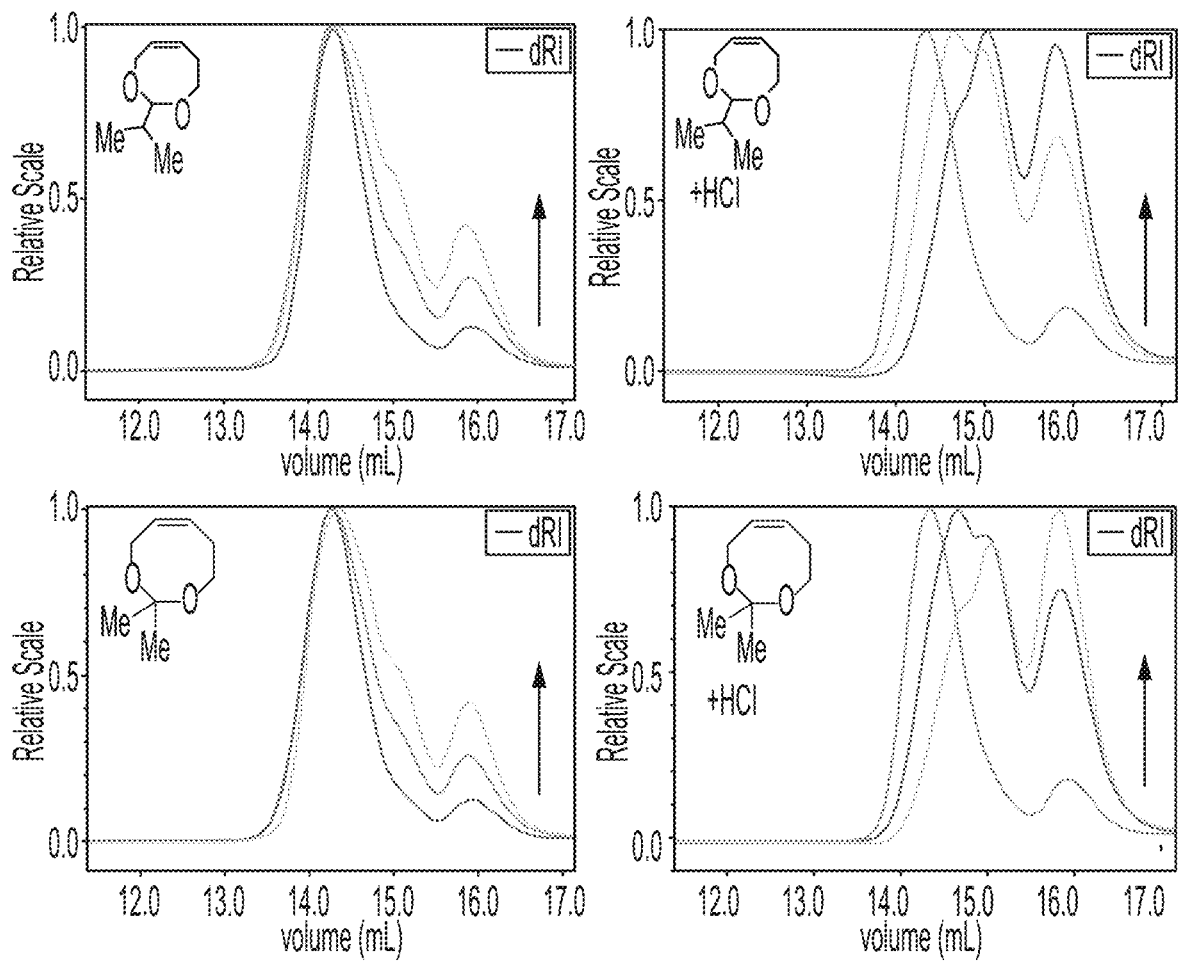
FIG. 28. Results of GPC analysis. PEG-MM (DP=8) was copolymerized with 0, 1, or 2 equivalents of acetal. After 30 minutes, the reaction was quenched with EVE and analyzed by GPC. The material was concentrated under vacuum for 30 minutes, then redissolved in THF containing 10% 2M HCl. The solution was stirred for 30 minutes, then dried over $Na_2SO_4$. The remaining material was then analyzed by GPC.
Figure 29:
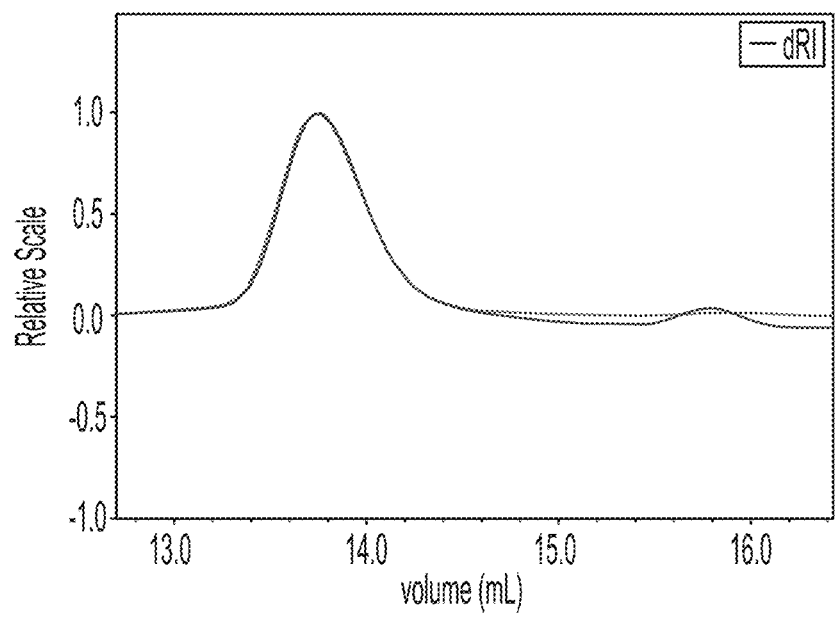
FIG. 29. GPC analysis of PEG Bottlebrush, DP=30, +/−HCl PEG Bottlebrush, DP=30, 1:1 PEG/iPrAc-7

The vial was then exposed placed within a Rayonet photoreactor with Hg lamps and an output spectrum shown in FIG. 7A and FIG. 26A (measured by OceanInsight FLAME-S-XR1-ES spectroradiometer) for 16 days. Glass containers were used to filter sub-300-nm light to more closely emulate the solar distribution (represented by ASTM 177 reference spectra). The temperature was controlled in both the light and dark experiments to 45-46° C., where the temperature inside the Rayonet reactor was monitored and the dark experiments were kept in an oven maintained at 45-46° C.

Degradation was calculated as the mass of carbon released in the seawater solution over the mass of carbon in the original material. Total organic carbon was measured as non-purgable organic carbon by a Shimazu TOC-5000. Prior to analysis, the sample was acidified with 50% HCl to pH<3 and sparged with $N_2$ for 8 min to remove inorganic carbon in seawater matrix. Total organic carbon in the virgin polymer was inferred from the chemical formulas and mass fractions of iPrSi or EtSi co-monomers. A paired t-Test was performed to determine whether content of iPrSi or light exposure has an impact on degradability.

Recycling of pDCPD Fragments pDCPD fragments derived from 10% iPrSi-doped pDCPD were prepared following the standard workflow described above. 500 mg of the fragments were then dissolved in 1.5 g of DCPD, forming a viscous brown liquid. To this liquid was added 8 mg of finely powdered Grubbs' $2^{nd}$generation ROMP initiator. The material was poured into vials (for forming discs) and silicone molds (for tensile and DMA measurements) and cured at 120° C. for 30 min.

Comparison of EtSi vs. iPrSi-Doped pDCPD

10% EtSi doped pDCPD was prepared in an analogous manner to that of iPrSi doped pDCPD to generate ~200 mg pellets. For dissolution experiments, the material was placed into a 20 mL vial and 10 mL of 15% conc. HCl in THF or 0.5 M TBAF were added. The resulting mixtures were then monitored over time.

Dissolution of iPrSi-Doped pDCPD with HF-Pyridine Complex

A ~200 mg pellet of 10% iPrSi-doped pDCPD was covered with 2 mL of THF in a 15 mL Falcon tube. Next, 20 µL of HF-pyridine complex was added. The material was allowed to incubate for 24 hours, upon which time the bulk of the material had entirely dissolved.

Techno-Economic Analysis

A systematic search of several synthetic pathways was performed to identify existing literature precedents for transformations performed on scale. Calculations used to calculate the prices for each reagent are shown below:

Calculations for Feedstock Contribution to Price of iPrSi
   Isopropylchloride (IPC)

$$\left[\left(\frac{\$1.00}{1 \text{ kg } Prop.}\right)\left(\frac{42.08 \text{ kg}}{1 \text{ kmol } Prop.}\right)\left(\frac{1 \text{ kmol } Prop.}{0.94 \text{ kmol } IPC}\right)+\right.$$

-continued $$\left(\frac{\$0.50}{1 \text{ kg HCl}}\right)\left(\frac{36.46 \text{ kg}}{1 \text{ kmol HCl}}\right)\left(\frac{1 \text{ kmol HCl}}{0.94 \text{ kmol IPC}}\right)\right] =$$

$$\frac{\$64.16}{1 \text{ kmol IPC}} \text{ or } \frac{\$0.82}{1 \text{ kg IPC}}$$

$iPr_2SiCl_2$ $$\left[\left(\frac{\$64.16}{1 \text{ kmol IPC}}\right)\left(\frac{2 \text{ kmol IPC}}{1 \text{ kmol iPr}_2\text{SiCl}_2}\right) + \right.$$
$$\left.\left(\frac{\$2.65}{1 \text{ kg Silicon}}\right)\left(\frac{28.09 \text{ kg}}{1 \text{ kmol Silicon}}\right)\left(\frac{1 \text{ kmol Silicon}}{1 \text{ kmol iPr}_2\text{SiCl}_2}\right)\right] =$$

$$\frac{\$202.76}{1 \text{ kmol iPr}_2\text{SiCl}_2} \text{ or } \frac{\$1.10}{1 \text{ kg iPr}_2\text{SiCl}_2}$$

3-Butene-1-ol (3B1O)

$$\left[\left(\frac{\$1.00}{1 \text{ kg Prop.}}\right)\left(\frac{42.08 \text{ kg}}{1 \text{ kmol Prop.}}\right)\left(\frac{1 \text{ kmol Prop.}}{0.88 \text{ kmol 3B1O}}\right) + \right.$$
$$\left.\left(\frac{\$1.08}{1 \text{ kg CH}_2\text{O}}\right)\left(\frac{30.03 \text{ kg}}{1 \text{ kmol CH}_2\text{O}}\right)\left(\frac{1 \text{ kmol CH}_2\text{O}}{0.88 \text{ kmol 3B1O}}\right)\right] =$$

$$\frac{\$84.67}{1 \text{ kmol 3B1O}} \text{ or } \frac{\$1.17}{1 \text{ kg 3B1O}}$$

2-pentene-1,5-diol (PDO)

$$\left[\left(\frac{\$84.67}{1 \text{ kmol 3B1O}}\right)\left(\frac{1 \text{ kmol 3B1O}}{0.45 \text{ kmol PDO}}\right) + \right.$$
$$\left.\left(\frac{\$1.08}{1 \text{ kg CH}_2\text{O}}\right)\left(\frac{30.03 \text{ kg}}{1 \text{ kmol CH}_2\text{O}}\right)\left(\frac{1 \text{ kmol CH}_2\text{O}}{0.45 \text{ kmol PDO}}\right)\right] =$$

$$\frac{\$260.23}{1 \text{ kmol PDO}} \text{ or } \frac{\$2.55}{1 \text{ kg PDO}}$$

iPrSi $$\left[\left(\frac{\$260.23}{1 \text{ kmol PDO}}\right)\left(\frac{1 \text{ kmol PDO}}{0.5 \text{ kmol iPrSi}}\right) + \right.$$
$$\left.\left(\frac{\$202.76}{1 \text{ kmol iPr}_2\text{SiCl}_2}\right)\left(\frac{1 \text{ kmol iPr}_2\text{SiCl}_2}{0.5 \text{ kmol iPrSi}}\right)\right] =$$

$$\frac{\$925.98}{1 \text{ kmol iPrSi}} \text{ or } \frac{\$4.32}{1 \text{ kg iPrSi}}$$

TEM Characterization of Organic Material Released During Weathering

To characterize the organic material released into solution during weathering, approximately 10 mL of post-irradiation sample was extracted with 5 mL DCM. 2 mL of the organic layer was then collected and the solvent removed. The remaining organic residue was dissolved in 200 µL of DCM. 5 µL of sample was cast onto a TEM grid. The samples were then stained with RuO4 vapor for 5 minutes and imaged by TEM on an FEI Tecnai transmission electron microscope (FIG. 43).

Crosslink Quanification from $^{13}$C NMR

We assigned the peak at 55 ppm to the allylic carbon of the ring-closed DCPD monomer (red circle, C4). Upon ring opening, the chemical shift of this peak moves upfield to resemble more closely the two bridgehead norbornene carbons (blue circles, C2/C5). HSQC allowed for the assignment of the peaks from 35-40 ppm to the norbornene methylene (yellow circle, C7) and the peaks at 35 ppm to the allylic cyclopentene carbon (green circle, C8). We found that the integral under the 55 ppm C4 peak was lower than expected (only 85%) when compared to the integrations for C7 or C8, suggesting 15% of the cyclopentenes were ring-opened. $^{13}$C measurements for integration were acquired on a Bruker Neo 500 in CDCl$_3$. A total of 2048 scans (300 ms delay time, 1 s overall recycle time, 30-45 degree acquisition pulse) were used for acquisition. Peak integration was performed using MestreNova. As none of the carbons are quaternary, we assume that these acquisition parameters are sufficient to provide accurate integration values in our analysis. To confirm the suitability of these parameters, we performed an additional measurement using a 10 s overall recycle time, which provided identical relative integrations for the peaks under analysis.

Recovery of Carbon Fiber from pDCPD Composites

Twill-weave carbon fiber (McMaster Carr) was mounted on a piece of tape and cut into a 15×15 mm square. The tape was placed into a 20 mL vial and covered with 1 mL of 10/iPrSi-doped DCPD precursor (with Grubbs' catalyst, 2 mg/mL). The material was then cured at 120° C. for 30 minutes and the sample removed from the vial. The sample was then placed into a glass chamber and covered with 5 mL of 0.2 M TBAF. After 8 hours, the carbon fiber was carefully removed from the chamber and allowed to dry overnight. Some fraying of the material was observed, which is attributed to loss of the tape used to mount the material over the course of composite synthesis and TBAF dissolution.

Raman Spectroscopy Characterization of Recovered Carbon Fiber

Raman spectra were collected using a Horiba Jobin-Yvon LabRam (Model HR 800) Raman confocal microscope with a 532 nm laser (1.2 µm spot size) excitation and an acquisition time of 3 seconds. Laser intensity was set to 25% for the 532 nm excitation wavelength. Raman spectra were normalized to the G-band (~1590 cm$^{-1}$) and averaged from three individual spectra recorded at different locations on the sample surface.

ADDITIONAL REFERENCES

1. Ma, S. & Webster, D. C. Degradable thermosets based on labile bonds or linkages: A review. *Prog. Polym. Sci.* 76, 65-110 (2018).
2. Post, W., Susa, A., Blaauw, R., Molenveld, K. & Knoop, R. J. I. A Review on the Potential and Limitations of Recyclable Thermosets for Structural Applications. *Polym. Rev.* 1-30 (2019). doi:10.1080/15583724.2019.1673406
3. Kloxin, C. J., Scott, T. F., Adzima, B. J. & Bowman, C. N. Covalent adaptable networks (CANs): A unique paradigm in cross-linked polymers. *Macromolecules* 43, 2643-2653 (2010).
4. Gu, Y., Zhao, J. & Johnson, J. A. Polymer Networks: From Plastics and Gels to Porous Frameworks. *Angew. Chemie—Int. Ed.* 59, 5022-5049 (2020).
5. Winne, J. M., Leibler, L. & Du Prez, F. E. Dynamic covalent chemistry in polymer networks: A mechanistic perspective. *Polym. Chem.* 10, 6091-6108 (2019).
6. Montarnal, D., Capelot, M., Tournilhac, F. & Leibler, L. Silica-like malleable materials from permanent organic networks. *Science* 334, 965-968 (2011).

7. Röttger, M. et al. High-performance vitrimers from commodity thermoplastics through dioxaborolane metathesis. *Science* 356, 62-65 (2017).
8. Li, L., Chen, X., Jin, K. & Torkelson, J. M. Vitrimers Designed Both to Strongly Suppress Creep and to Recover Original Cross-Link Density after Reprocessing: Quantitative Theory and Experiments. *Macromolecules* 51, 5537-5546 (2018).
9. Asaro, L., Gratton, M., Seghar, S. & Aft Hocine, N. Recycling of rubber wastes by devulcanization. *Resour. Conserv. Recycl.* 133, 250-262 (2018).
10. Yang, S. el al. Reworkable Epoxies: Thermosets with Thermally Cleavable Groups for Controlled Network Breakdown. *Chem. Mater.* 10, 1475-1482 (1998).
11. Christensen, P. R, Scheuermann, A. M., Loeffler, K. E. & Helms, B. A. Closed-loop recycling of plastics enabled by dynamic covalent diketoenamine bonds. *Nat. Chem.* 11, 442-448 (2019).
12. Li, L., Chen, X. & Torkelson, J. M. Reprocessable Polymer Networks via Thiourethane Dynamic Chemistry: Recovery of Cross-link Density after Recycling and Proof-of-Principle Solvolysis Leading to Monomer Recovery. *Macromolecules* 52, 8207-8216 (2019).
13. Fortman, D. J., Brutman, J. P., Cramer, C. J., Hillmyer, M. A. & Dichtel, W. R. Mechanically Activated, Catalyst-Free Polyhydroxyurethane Vitrimers. *J. Am. Chem. Soc.* 137, 14019-14022(2015).
14. Rule, J. D. & Moore, J. S. ROMP reactivity of endo- and exo-dicyclopentadiene.
Macromolecules 35, 7878-7882 (2002).
15. Kessler, M. R. & White, S. R. Cure kinetics of the ring-opening metathesis polymerization of dicyclopentadiene. *J. Polym. Sci. Part A Polym. Chem.* 40, 2373-2383 (2002).
16. Robertson, I. D. et al. Rapid energy-efficient manufacturing of polymers and composites via frontal polymerization. *Nature* 557, 223-227 (2018).
17. Shieh, P., Nguyen, H. V. T. & Johnson, J. A. Tailored silyl ether monomers enable backbone-degradable polynorbornene-based linear, bottlebrush and star copolymers through ROMP. *Nat. Chem.* 11, 1124-1132 (2019).
18. Wang, B., Ma, S., Yan, S. & Zhu, J. Readily recyclable carbon fiber reinforced composites based on degradable thermosets: A review. *Green Chem.* 21, 5781-5796 (2019).
19. Fortman, D. J. et al. Approaches to Sustainable and Continually Recyclable Cross-Linked Polymers. *ACS Sustain. Chem. Eng.* 6, 11145-11159 (2018).
20. Takahashi, A., Ohishi, T., Goseki, R. & Otsuka, H. Degradable epoxy resins prepared from diepoxide monomer with dynamic covalent disulfide linkage. *Polymer* 82, 319-326 (2016).
21. Wiles, D. M. & Scott, G. Polyolefins with controlled environmental degradability. *Polym. Degrad Stab.* 91, 1581-1592 (2006).
22. Sommazzi, A. & Garbassi, F. Olefin-carbon monoxide copolymers. *Progress in Polymer Science (Oxford)* 22, 1547-1605 (1997).
23. Macosko, C. W. & Miller, D. R. A New Derivation of Average Molecular Weights of Nonlinear Polymers *Macromolecules* 9, 199-206 (1976).
24. Flory, P. J. Molecular Size Distribution in Three Dimensional Polymers. I. Gelation. *J. Am. Chem. Soc.* 63, 3083-3090 (1941).
25. Stockmayer, W. H. Theory of molecular size distribution and gel formation in branched polymers: II. General cross linking. *J. Chem. Phys.* 12, 125-131 (1944).
26. Wang, J. et al. Counting loops in sidechain-crosslinked polymers from elastic solids to single-chain nanoparticles. *Chem. Sci.* 10, 5332-5337 (2019).
27. Takayama, S. et al. Topographical micropatterning of poly(dimethylsiloxane) using laminar flows of liquids in capillaries. *Ad. Mater.* 13, 570-574 (2001).
28. Long, T. R et al. Ballistic response of polydicyclopentadiene vs. epoxy resins and effects of crosslinking. in *Conference Proceedings of the Society for Experimental Mechanics Series* 1B, 285-290 (Springer New York LLC, 2017).
29. Veysset, D. el al. Dynamics of supersonic microparticle impact on elastomers revealed by real-time multi-frame imaging. *Sci. Rep.* 6, (2016).
30. Davies, J. S., Higginbotham, C. L., Tremeer, E. J., Brown, C. & Treadgold, R. C. Protection of hydroxy groups by silylation: use in peptide synthesis and as lipophilicity modifiers for peptides. *J. Chem. Soc. Perkin Trans.* 13043 (1992). doi:10.1039/p19920003043
31. Tournier, V. et al. An engineered PET depolymerase to break down and recycle plastic bottles. *Nature* 580, 216-219 (2020).
32. Cole, M., Lindeque, P., Halsband, C. & Galloway, T. S. Microplastics as contaminants in the marine environment: A review. *Marine Pollution Bulletin* 62, 2588-2597 (2011).
33. Hann, S., Ettlinger, S., Gibbs, A. & Hogg, D. *The Impact of the Use of 'Oro-degradable' Plastic on the Environment. European Commission* (2016). doi:10.2779/992559
34. Autenrieth, B. et al. Stereospecific ring-opening metathesis polymerization (ROMP) of endo-dicyclopentadiene by molybdenum and tungsten catalysts. *Macromolecules* 48, 2480-2492 (2015).
35. Chen, J., Burns, F. P., Moffitt, M. G. & Wulff, J. E. Thermally Crosslinked Functionalized Polydicyclopentadiene with a High Tg and Tunable Surface Energy. *ACS Omega* 1, 532-540(2016).

Cyclic Olefin Monomers for Backbone Degradable ROMP Copolymers

Described herein are a class of low molecular weight cyclic olefin monomers that copolymerize efficiently with norbornenes. When mixed with norbornene monomers before polymerization, the resulting polymers are shown to degrade under aqueous acidic conditions. The low molecular weight of these monomers and their ease of preparation opens the door to many opportunities for backbone degradable materials.

Silyl ether monomers that copolymerized efficiently with norbornenes to generate backbone degradable ROMP polymers were previously disclosed. These monomers, however, were prepared through expensive silyl chloride intermediates. In contrast, other types of cyclic olefin monomers that can be prepared readily from inexpensive reagents and on scale would overcome this limitation. Ultimately, this design feature—cyclic monomers that contain an endo-cyclic cleavable bonds—copolymerize with norbornenes, provide a general solution to endow degradability to all norbornene-based polymeric materials prepared by ROMP.

Synthetic Protocols 1.02 g (10 mmol) of diol and 1.09 mL of trimethyl orthoformate were added to a flask. Next, 0.126 g of PPTS was added and the mixture was stirred for 30 minutes. The solution was then concentrated to yield a waxy solid. Then, 0.741 mL (1 equivalent) of dry acetone was added and the reaction was stirred for 24 hours. The mixture was then distilled under vacuum to yield acetal 1 as a clear oil. (0.587 g).

1.02 g (10 mmol) of diol and 1.09 mL of trimethyl orthoformate were added to a flask. Next, 0.126 g of PPTS was added and the mixture was stirred for 30 minutes. The solution was then concentrated to yield a waxy solid. Then, 0.912 mL (1 equivalent) of isobutyraldehyde was added and the reaction was stirred for 24 hours. The mixture was then distilled under vacuum to yield acetal 2 as a clear oil. (0.99 g).

Synthesis of iPrAc-7 and iPrAc 2.64 g of (Z)-2-butene-1,4-diol, 3.18 g of trimethylorthoformate, and 376 mg of pyridinium para-toluene sulfonate were combined in a vial and stirred for 30 minutes. The material was then concentrated under gentle vacuum to yield a viscous oil. Next, 2.16 g of isobutyraldehyde was added and the material was stirred overnight. The residual liquid was concentrated under gentle vacuum and further distilled to yield crude iPrAc-7

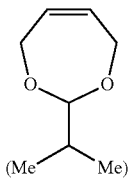

as a clear oil. The material was passed through a plug of silica with hexanes to yield 1.7 g of iPrAc-7 as a clear oil.

1.01 g of (Z)-pent-2-ene-1,5-diol, 1.06 g of trimethylorthoformate, and 126 mg of pyridinium para-toluene sulfonate were combined in a vial and stirred for 30 minutes. The material was then concentrated under gentle vacuum to yield a viscous oil. Next, 720 mg of isobutyraldehyde was added and the material was stirred overnight. The residual liquid was concentrated under gentle vacuum and further distilled to yield crude iPrAc

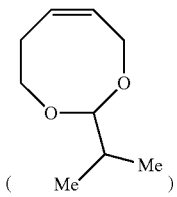 [SMILES: CC(C)C1OC/C=C\CCO1]

as a clear oil. The material was passed through a plug of silica with hexanes to yield 550 mg of iPrAc as a clear oil.

Copolymerization of iPrAc and iPrAc-7 with PEG-Macromonomers

Bottlebrush polymers were synthesized using 200 mg of PEG-macromonomers (PEG-MM) in 800 µL of dioxane. 200 µL of solution were added into each of four one-dram vials, followed by 30 µL of 0.5 M comonomer in dioxane or 30 µL of dioxane. Finally, 75 µL of 0.02 M Grubbs' 3rd generation catalyst in dioxane were added to target a DP of 10 for each monomer. The mixture was stirred for 30 min, quenched with a drop of EVE, and analyzed by GPC.

To force degradation of the material, the polymerization solution was concentrated in a vacuum chamber at room temperature to remove residual EVE and diluted in 100 µL of dioxane. To the solution were added 10 µL of 2M HCl. The mixture was stirred for 30 minutes. Excess sodium sulfate was added and the mixture was allowed to sit for 5 min. Finally, the mixture was extracted with DCM, filtered with a 0.2 µm nylon filter, concentrated, and analyzed by GPC.

Synthesis and Degradation of iPrAc/iPrAc-7 Doped pDCPD 25, 50, 75, and 100 µL of iPrAc/iPrAc-7 were combined with 975, 950, 925, or 900 µL of DCPD, respectively. The combined monomers were added to 2 mg of finely powdered Grubbs' $2^{nd}$ generation catalyst. 150 µL aliquots of material were added to glass vials and cured at 120° C. for 30 minutes.

The samples were removed from the vial, dissolved in 3 mL of THF with 10% v/v 2 M HCl in $Et_2O$ and incubated for 1-12 hours. After 1 hour, pDCPD containing 7.5% or 10% v/v iPrAc had dissolved (where as the corresponding iPrAc-7 samples did not). For a 10% iPrAc sample, the soluble material was collected, diluted with 10 mL fresh THF, and basicified by stirring with solid $CaCO_3$ for 30 minutes. The solvent was then removed under vacuum. The material was dissolved in choroform, concentrated, and analyzed by NMR.

Sample Preparation of pDCPD Containing DHF

135 µL of DCPD was added to 15 µL of DHF

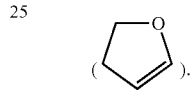

The mixture was added to a vial containing 2 mg/mL of finely powdered Grubbs' $2^{nd}$ generation catalyst. The resulting mixture was added in its entirety to a glass vial, left at room temperature for 2 hours to form a high boiling point pre-polymer, then heated at 120° C. for 30 minutes to cure. The vials were then broken to release the samples.

Samples were incubated in 1 mL of THF with 2 equivalents of HCl (2M in water) relative to DHF for 24 hours. The soluble fragments were carefully removed by pipette and the residual solids were resuspended in fresh THF. The fragments were redissolved in chloroform, concentrated, and characterized by NMR.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A functional oligomer or functional polymer comprising:
   i) one or more instances of linear units, wherein each instance of the linear units is of the formula:

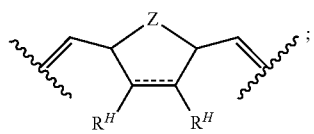

ii) one or more instances of functional units, wherein each instance of the functional units is independently of the formula:

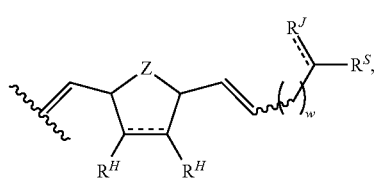

-continued

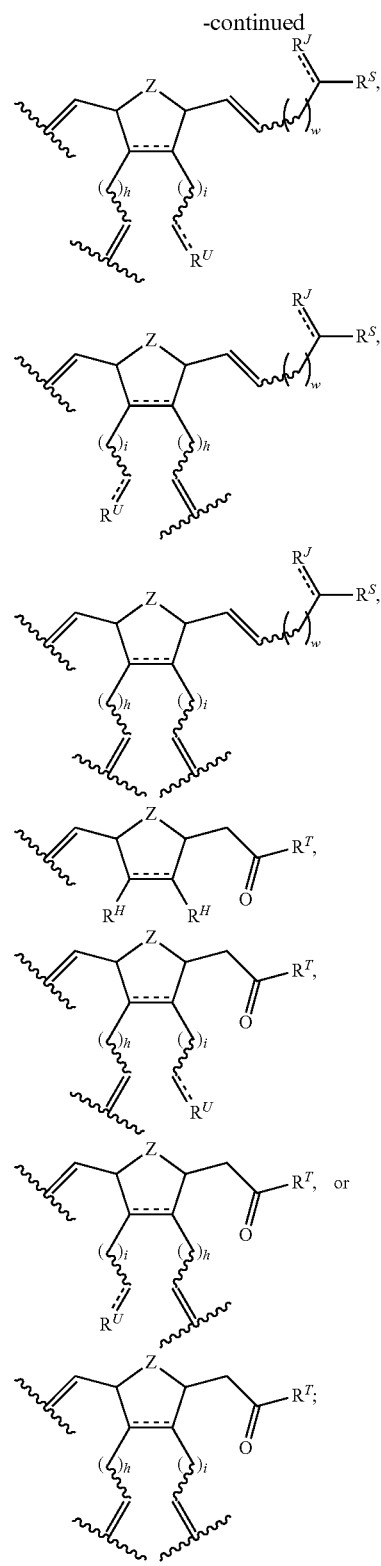

$C(=O)-O-$, $-C(=O)-O-C(=O)-$, $-S(=O)-OH$, $-S(=O)$-(a leaving group), $-S(=O)_2-OH$, $-S(=O)_2$-(a leaving group), $-OH$, or $-O$-(a leaving group).

iii) optionally one or more instances of crosslinking units, wherein each instance of the crosslinking units is of the formula:

[Structural formulas shown]

or

;

and
  iv) optionally one or more additional linear units, one or more additional terminal units, and/or one or more additional crosslinking units;
wherein:
  each instance of Z is independently a single bond, $C(R^P)_2$, or O;
  each instance of $R^P$ is independently hydrogen, halogen, or substituted or unsubstituted, C1-6 alkyl;
  each instance of ==== is independently a single or double bond;
  each instance of $R^H$ is independently hydrogen, halogen, unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —OCN, —$OC(=O)R^a$, —$OC(=S)R^a$, —$OC(=O)OR^a$, —$OC(=O)N(R^a)_2$, —$OS(=O)R^a$, —$OS(=O)OR^a$, —$OS(=O)N(R^a)_2$, —$OS(=O)_2R^a$, —$OS(=O)_2OR^a$, —$OS(=O)_2N(R^a)_2$, —$OSi(R^a)_3$, —$OSi(R^a)_2(OR^a)$, —$OSi(R^a)(OR^a)_2$, —$OSi(OR^a)_3$, oxo, —$N(R^a)_2$, —$N=C(R^a)_2$, =$NR^a$, —NC, —NCO, —$N_3$, —$NO_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$SR^a$, —SCN, —$S(=O)R^a$, —$S(=O)OR^a$, —$S(=O)N(R^a)_2$, —$S(=O)_2R^a$, —$S(=O)_2OR^a$, —$S(=O)_2N(R^a)_2$, —$SeR^a$, halogen, —CN, —$C(=NR^a)R^a$, —$C(=NR^a)OR^a$, —$C(=NR^a)N(R^a)_2$, —$C(=O)R^a$, —$C(=O)OR^a$, —$C(=O)SR^a$, —$C(=S)OR^a$, or —$C(=O)N(R^a)_2$;
  or the two instances of $R^H$ of one or more instances of

[Structural formula with $R^H$ $R^H$]

are joined with the intervening carbon atoms to independently form a substituted or unsubstituted, monocyclic carbocyclic ring, unsubstituted, monocyclic heterocyclic ring, unsubstituted, monocyclic aryl ring, or substituted or unsubstituted, monocyclic heteroaryl ring;

each instance of $R^a$ is independently hydrogen, substituted or unsubstituted alkyl, substituted or unsubstituted alkenyl, substituted or unsubstituted alkynyl, substituted or unsubstituted, monocyclic carbocyclyl, substituted or unsubstituted, monocyclic heterocyclyl, substituted or unsubstituted, monocyclic aryl, substituted or unsubstituted, monocyclic heteroaryl, a nitrogen protecting group when attached to a nitrogen atom, an oxygen protecting group when attached to an oxygen atom, or a sulfur protecting group when attached to a sulfur atom, or two instances of $R^a$ are joined to form substituted or unsubstituted heterocyclyl or substituted or unsubstituted heteroaryl;
  each instance of $R^J$ is independently —$OR^a$, —OCN, —$OC(=O)R^a$, —$OC(=S)R^a$, —$OC(=O)OR^a$, —$OC(=O)N(R^a)_2$, —$OS(=O)R^a$, —$OS(=O)OR^a$, —$OS(=O)N(R^a)_2$, —$OS(=O)_2R^a$, —$OS(=O)_2OR^a$, —$OS(=O)_2N(R^a)_2$, —$OSi(R^a)_3$, —$OSi(R^a)_2(OR^a)$, —$OSi(R^a)(OR^a)_2$, —$OSi(OR^a)_3$, oxo, —$N(R^a)_2$, —$N=C(R^a)_2$, =$NR^a$, —NC, —NCO, —$N_3$, —$NO_2$, —$NR^aC(=O)R^a$, —$NR^aC(=O)OR^a$, —$NRC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$SR^a$, —SCN, —$S(=O)R^a$, —$S(=O)OR^a$, —$S(=O)N(R^a)_2$, —$S(=O)_2R^a$, —$S(=O)_2OR^a$, —$S(=O)_2N(R^a)_2$, —$SeR^a$, halogen, —CN, $C(=NR^a)R^a$, —$C(=NR^a)OR^a$, —$C(=NR^a)N(R^a)_2$, —$C(=O)R^a$, —$C(=O)OR^a$, —$C(=O)SR^a$, —$C(=S)OR^a$, or —$C(=O)N(R^a)_2$;
  each instance of $R^S$ is independently hydrogen or —$OR^a$;
  each instance of w is independently 0, 1, 2, 3, or 4;
  each instance of h is independently 0, 1, 2, or 3;
  each instance of i is independently 0, 1, 2, or 3;
  each instance of $R^U$ is independently hydrogen, substituted or unsubstituted alkyl, substituted or unsubstituted alkenyl, substituted or unsubstituted alkynyl, substituted or unsubstitutedcarbocyclyl, substituted or unsubstitutedheterocyclyl, substituted or unsubstituted aryl, substituted or unsubstitutedheteroaryl, —$OR^a$, —OCN, —$OC(=O)R^a$, —$OC(=S)R^a$, —$OC(=O)OR^a$, —$OC(=O)N(R^a)_2$, —$OS(=O)R^a$, —$OS(=O)OR^a$, —$OS(=O)N(R^a)_2$, —$OS(=O)_2R^a$, —$OS(=O)_2OR^a$, —$OS(=O)_2N(R^a)_2$, —$OSi(R^a)_3$, —$OSi(R^a)_2(OR^a)$, —$OSi(R^a)(OR^a)_2$, —$OSi(OR^a)_3$, oxo, —$N(R^a)_2$, —$N=C(R^a)_2$, =$NR^a$, —NC, —NCO, —$N_3$, —$NO_2$, —$NRC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$SR^a$, —SCN, —$S(=O)R^a$, —$S(=O)OR^a$, —$S(=O)N(R^a)_2$, —$S(=O)_2R^a$, —$S(=O)_2OR^a$, —$S(=O)_2N(R^a)_2$, —$SeR^a$, halogen, —CN, —$C(=NR^a)R^a$, —$C(=NR^a)OR^a$, —$C(=NR^a)N(R^a)_2$, —$C(=O)R^a$, —$C(=O)OR^a$, —$C(=O)SR^a$, —$C(=S)OR^a$, or —$C(=O)N(R^a)_2$; and
  each instance of RT is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

2. A hydroxylated polymer prepared by hydrolyzing a copolymer prepared by a method comprising polymerizing in the presence of a metathesis catalyst:
  i) one or more instances of a first monomer, wherein each instance of the first monomer is independently of the formula:

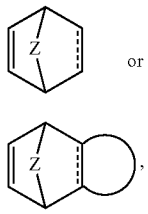

or salt thereof, wherein:
each instance of

is Ring B, wherein each instance of Ring B is independently a substituted or unsubstituted, monocyclic carbocyclic ring, unsubstituted, monocyclic heterocyclic ring, unsubstituted, monocyclic aryl ring, or substituted or unsubstituted, monocyclic heteroaryl ring;
  each instance of Z is independently $C(R^P)_2$ or O;
  each instance of $R^P$ is independently hydrogen, halogen, or substituted or unsubstituted, $C_{1-6}$ alkyl; and
  each instance of ==== is independently a single bond or double bond; and
ii) one or more instances of a second monomer, wherein each instance of the second monomer is of Formula (B):

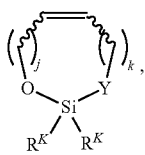

(B)

or a salt thereof; wherein:
  each instance of Y is independently O or $C(R^Q)_2$;
  each instance of $R^Q$ is independently hydrogen, halogen, or substituted or unsubstituted, C1-6 alkyl;
  each instance of $R^k$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;
  each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
  each instance of j is independently 1, 2, or 3; and
  each instance of k is independently 0, 1, 2, or 3;
wherein any two instances of the first monomer are the same as or different from each other, and any two instances of the second monomer are the same as or different from each other; and
wherein the step of hydrolyzing the copolymer comprises hydrolyzing one or more instances of the —O—Si bonds of the copolymer to form —OH.

3. The functional oligomer or functional polymer of claim 1, wherein the functional oligomer or functional is prepared by a method comprising hydrolyzing a copolymer prepared by a method comprising polymerizing in the presence of a metathesis catalyst:
  i) one or more instances of a first monomer, wherein each instance of the first monomer is of the formula:

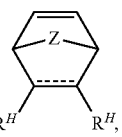

(A)

or salt thereof;
  ii) one or more instances of a second monomer, wherein each instance of the second monomer is of the formula:

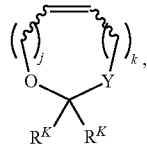

(B1)

or a salt thereof; wherein:
  Y is O or $C(R^Q)_2$;
  each instance of $R^Q$ is independently hydrogen, halogen, or substituted or unsubstituted, $C_{1-6}$ alkyl;
  each instance of $R^k$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;
  each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
  j is 1, 2, or 3; and
  k is 0, 1, 2, or 3; and
  iii) optionally one or more instances of a third monomer;
  wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other; and
wherein the step of hydrolyzing the copolymer comprises hydrolyzing one or more instances of the —O—Si bonds of the copolymer to form —OH.

4. The functional oligomer or functional polymer of claim 1, wherein the functional oligomer or functional polymer is prepared by a method comprising hydrolyzing a copolymer prepared by a method comprising polymerizing in the presence of a metathesis catalyst:
  i) one or more instances of a first monomer, wherein each instance of the first monomer is of the formula:

(A)

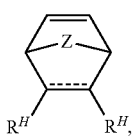

or salt thereof;
ii) one or more instances of a second monomer, wherein each instance of the second monomer is of the formula:

(B2)

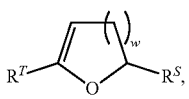

or a salt thereof; and
iii) optionally one or more instances of a third monomer;
wherein any two instances of the first monomer are the same as or different from each other, any two instances of the second monomer are the same as or different from each other, any two instances of the third monomer are the same as or different from each other, and each instance of the first monomer, the second monomer, and the third monomer if present, is different from each other; and
wherein the step of hydrolyzing the copolymer comprises hydrolyzing one or more instances of

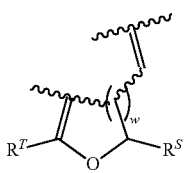

the copolymer to form

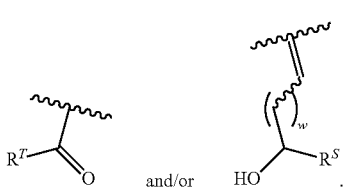

5. The functional oligomer or functional polymer of claim 1, wherein each instance of the linear units is of the formula:

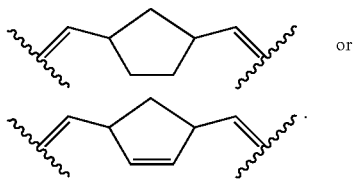

6. The functional oligomer or functional polymer of claim 1, wherein each instance of the linear units is independently of the formula:

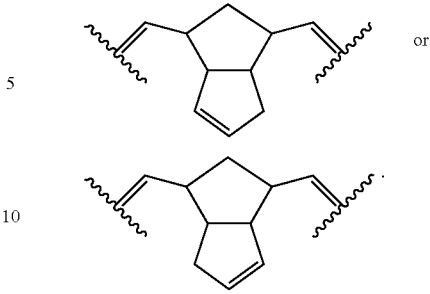

7. The functional oligomer or functional polymer of claim 1, wherein at least one instance of the functional units is independently of the formula:

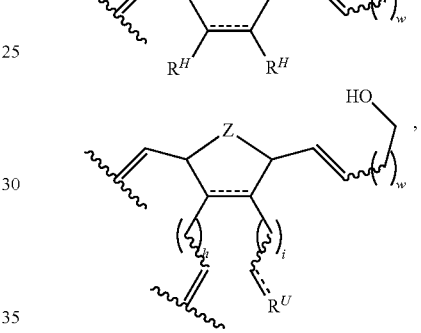

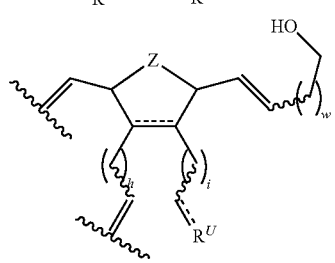

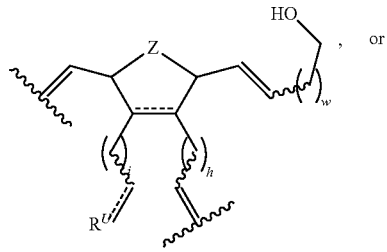

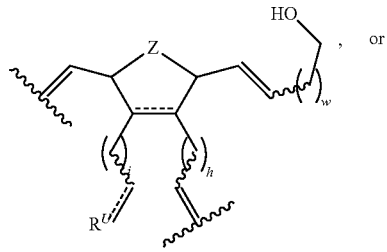

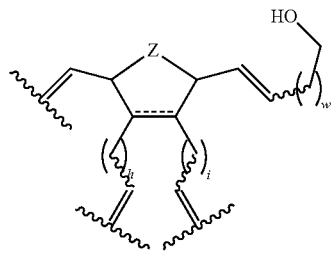

8. The functional oligomer or functional polymer of claim 1, wherein at least one instance of the functional units is independently of the formula:

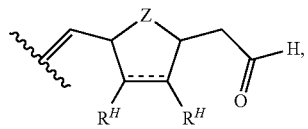

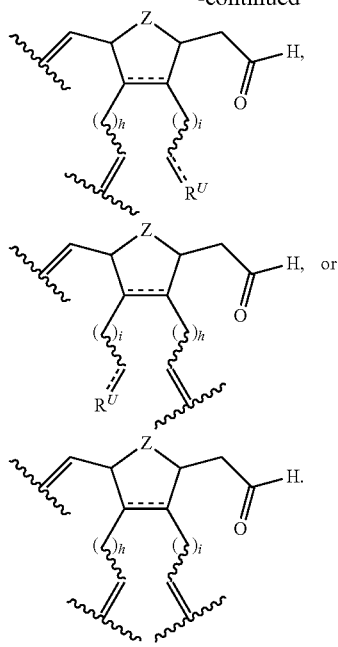

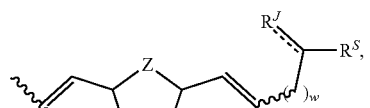

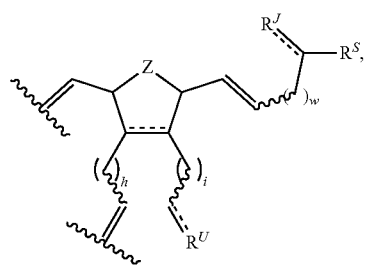

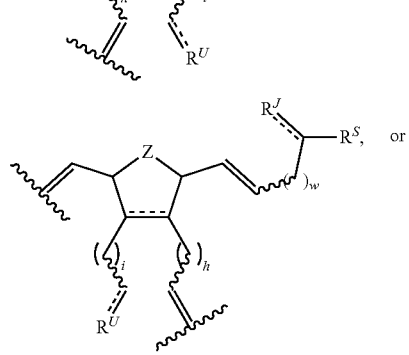

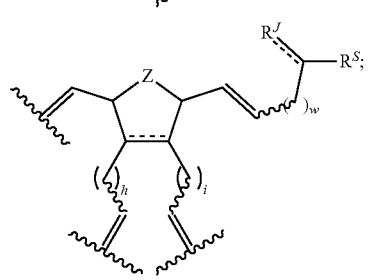

9. A composition comprising:
a hydroxylated polymer of claim 2; and
optionally an excipient.

10. A kit comprising:
a hydroxylated polymer of claim 2; and
instructions for using the hydroxylated polymer.

11. A conjugate prepared by reacting a hydroxy-reacting substance with a hydroxylated polymer of claim 2, wherein hydroxy-reacting substance comprises at least one instance of a hydroxy-reacting moiety.

12. A composition comprising:
a conjugate of claim 11; and
optionally an excipient.

13. A kit comprising:
a conjugate of claim 11; and
instructions for using the conjugate.

14. The functional oligomer or functional polymer of claim 1, wherein at least one instance of Z is $CH_2$.

15. The functional oligomer or functional polymer of claim 1, wherein the two instances of $R^H$ of one or more instances of

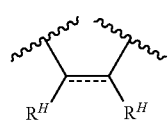

are joined with the intervening carbon atoms to independently form a substituted or unsubstituted, monocyclic carbocyclic ring.

16. The functional oligomer or functional polymer of claim 1, wherein:
at least one instance of the functional units is independently of the formula:

and
at least one instance of $R^J$ is —OH.

17. The functional oligomer or functional polymer of claim 16, wherein at least one instance of $R^S$ is hydrogen.

18. The functional oligomer or functional polymer of claim 1, wherein at least one instance of the functional units is independently of the formula:

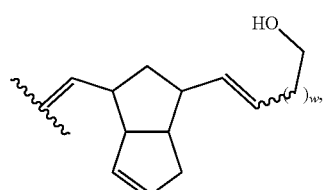

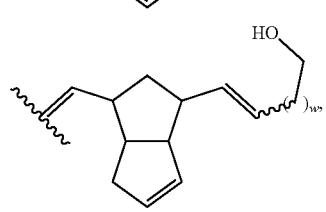

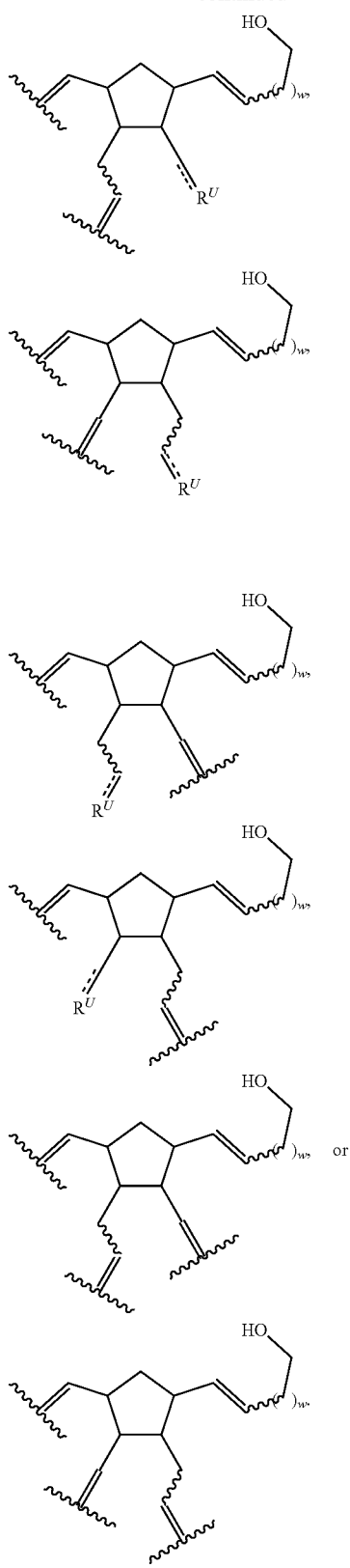
19. The functional oligomer or functional polymer of claim 1, wherein at least one instance of the functional units is independently of the formula:
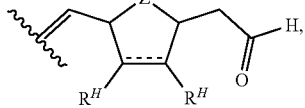
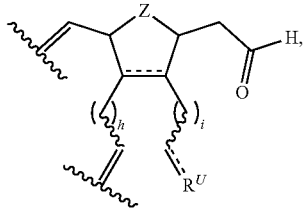
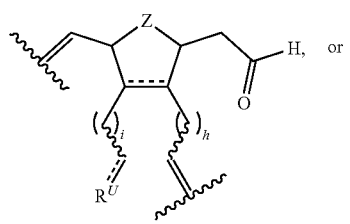
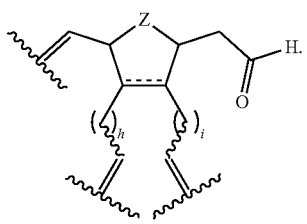
20. The functional oligomer or functional polymer of claim 1, wherein at least one instance of the functional units is independently of the formula:
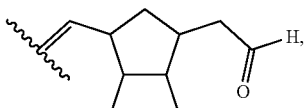
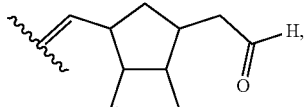
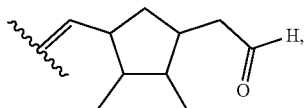
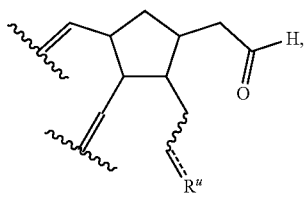

-continued

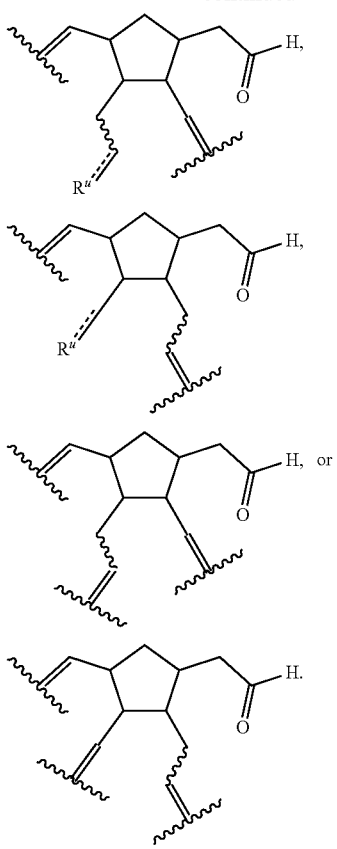

21. The functional oligomer or functional polymer of claim 1, wherein at least one instance of the crosslinking units is independently of the formula:

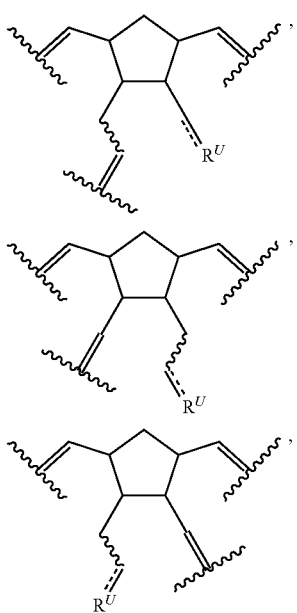

-continued

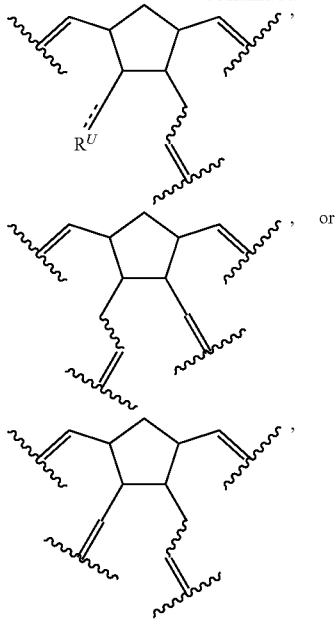

22. The functional oligomer or functional polymer of claim 1, wherein at least one instance of R is substituted or unsubstituted alkenyl, wherein the attachment point is a double bond.

23. The functional oligomer or functional polymer of claim 1, wherein the functional oligomer or functional polymer is crosslinked.

24. The functional oligomer or functional polymer of claim 1, wherein the average molecular weight of the functional oligomer or functional polymer as determined by gel permeation chromatography is between 1 kDa and 8 kDa, inclusive.

25. The functional oligomer or functional polymer of claim 4, wherein at least one instance of Z is $CH_2$.

26. The functional oligomer or functional polymer of claim 4, wherein two instances of $R^H$ of one or more instances of

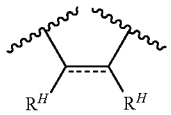

are joined with the intervening carbon atoms to independently form a substituted or unsubstituted, monocyclic carbocyclic ring.

27. The functional oligomer or functional polymer of claim 4, wherein at least one instance of the first monomer is of the formula:

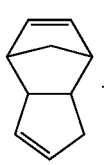

28. The functional oligomer or functional polymer of claim 4, wherein at least one instance of the second monomer is of the formula:

29. The hydroxylated polymer of claim 2, wherein each instance of the first monomer is independently of Formula (D1) or (D2):

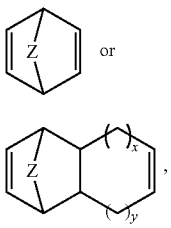

or a salt thereof, wherein:
each instance of x is independently 0, 1, or 2; and
each instance of y is independently 0, 1, or 2.

30. The hydroxylated polymer of claim 2, wherein at least one instance of Z is $CH_2$.

31. The hydroxylated polymer of claim 2, wherein at least one instance of Ring B is independently a substituted or unsubstituted, monocyclic carbocyclic ring.

32. The hydroxylated polymer of claim 2, wherein at least one instance of the first monomer is of the formula:

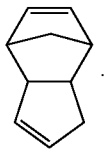

33. The hydroxylated polymer of claim 2, wherein each instance of Y is O.

34. The hydroxylated polymer of claim 2, wherein each instance of the second monomer is of the formula:

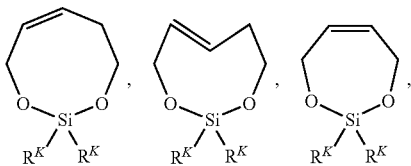

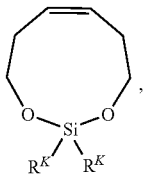

or a salt thereof.

35. The hydroxylated polymer of claim 2, wherein each instance of the second monomer is of the formula:

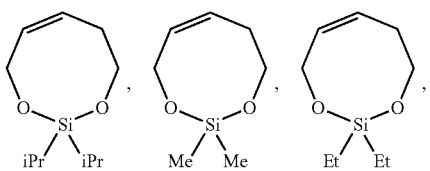

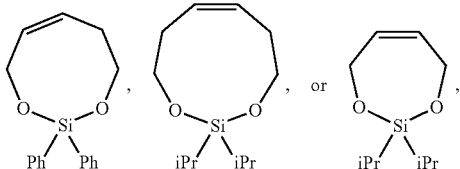

or a salt thereof.

36. The hydroxylated polymer of claim 2, wherein the molar ratio of the one or more instances of the first monomer to the second monomer is between 6:1 and 19:1, inclusive.

37. The hydroxylated polymer of claim 2, wherein the hydroxylated polymer is crosslinked.

38. The hydroxylated polymer of claim 2, wherein the average molecular weight of the hydroxylated polymer as determined by gel permeation chromatography is between 1 kDa and 8 kDa, inclusive.

39. The conjugate of claim 11, wherein the hydroxy-reacting substance is lactide, polyethylene glycol, or polysiloxane, wherein the polysiloxane comprises at least one instance of a hydroxy-reacting moiety, wherein at least one instance of the hydroxy-reacting moiety is Si(IV)—H, Si(IV)-(a leaving group), C(IV)-(a leaving group), —C(=O)—OH, —C(=O)-(a leaving group), —C(=O)-O-, -C(=O)-O-C(=O)-, -S(=O)-OH, -S(=O)-(a leaving group), -S(=O)2-OH, -S(=O)2-(a leaving group), -OH, or -O-(a leaving group).

* * * * *

UNITED STATES PATENT AND TRADEMARK OFFICE
CERTIFICATE OF CORRECTION

PATENT NO. : 12,054,570 B2
APPLICATION NO. : 17/022021
DATED : August 6, 2024
INVENTOR(S) : Jeremiah A. Johnson et al.

Page 1 of 4

It is certified that error appears in the above-identified patent and that said Letters Patent is hereby corrected as shown below:

In the Claims

In Claim 1, at Column 100, Lines 61-64, the text:
"C(=O)—O—, —C(=O)—O—C(=O)—, —S(=O)—OH, —S(=O)-(a leaving group), —S(=O)$_2$—OH, —S(=O)$_2$-(a leaving group), —OH, or —O-(a leaving group)." should be deleted.

In Claim 1, at Column 101, Line 28, the text:
"C1-6 alkyl"
Should be replaced with:
-- $C_{1-6}$ alkyl --.

In Claim 2, at Column 103, Line 47, the text:
"C1-6 alkyl"
Should be replaced with:
-- $C_{1-6}$ alkyl --.

In Claim 20, at Column 110, Lines 45-50, the formula:

"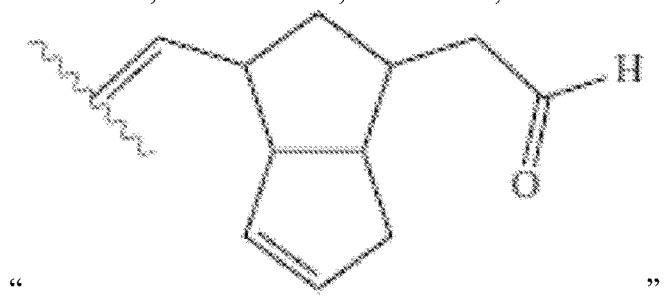"

Should be replaced with:

Signed and Sealed this
Twenty-eighth Day of January, 2025

Coke Morgan Stewart
*Acting Director of the United States Patent and Trademark Office*

CERTIFICATE OF CORRECTION (continued)
U.S. Pat. No. 12,054,570 B2

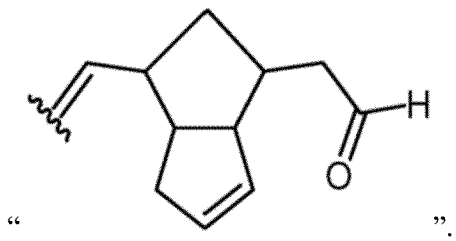

" ".

In Claim 20, at Column 110, Lines 51-57, the formula:

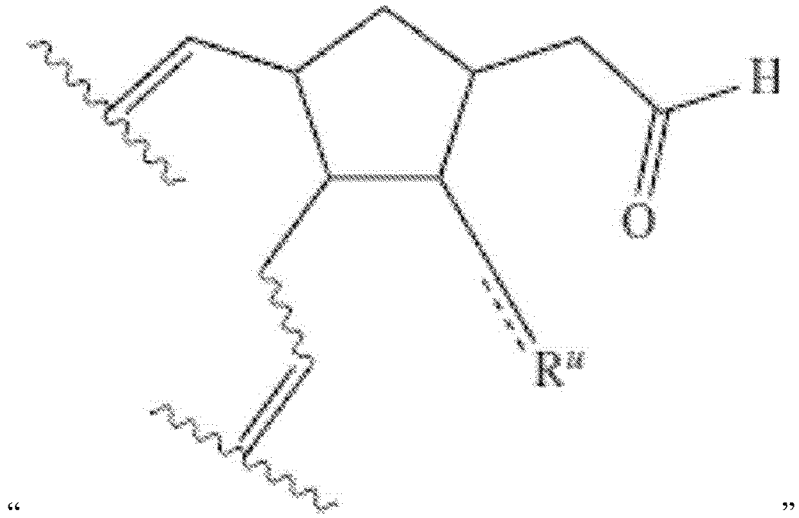

"  "

Should be replaced with:

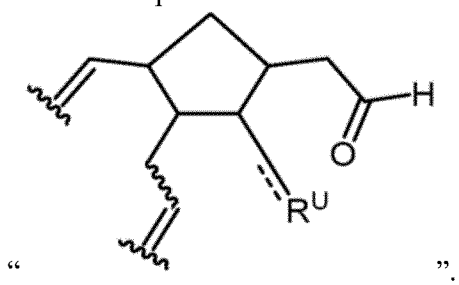

" ".

In Claim 20, at Column 110, Lines 58-65, the formula:

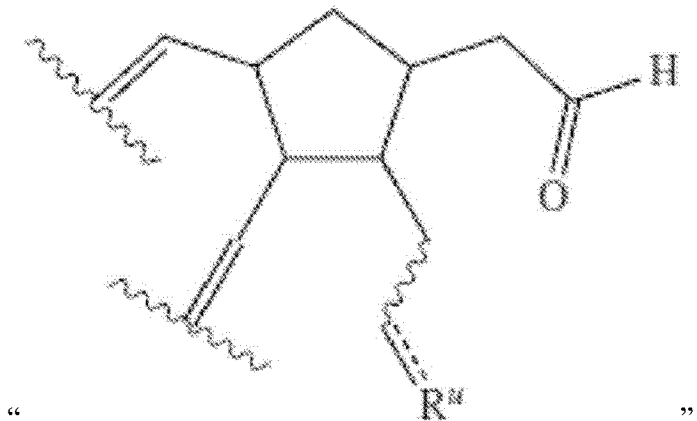

"  "

Should be replaced with:
" 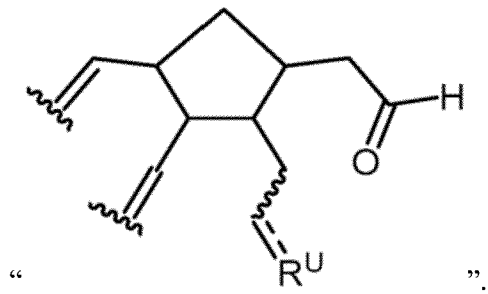 ".
In Claim 20, at Column 111, Lines 2-9, the formula:
" 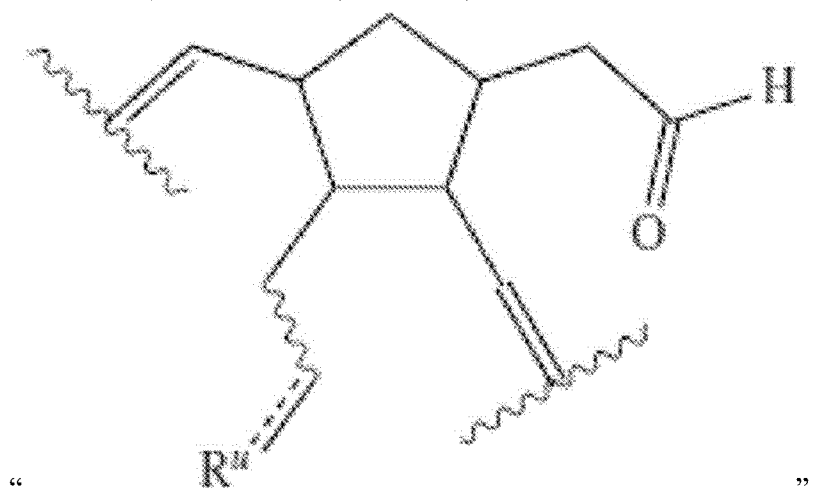 "
Should be replaced with:
" 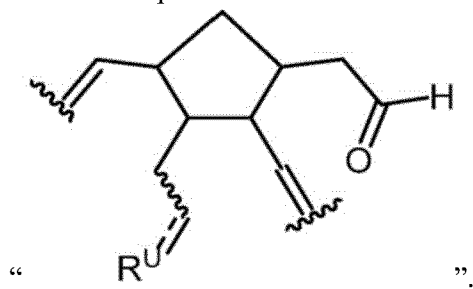 ".

In Claim 20, at Column 111, Lines 10-16, the formula:
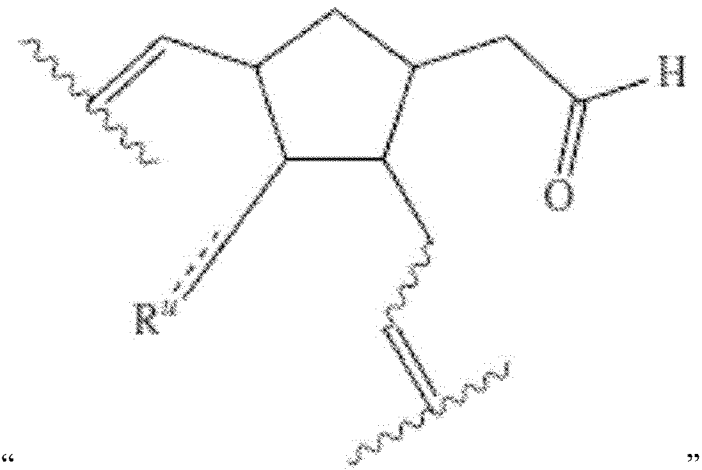
"                    "
Should be replaced with:
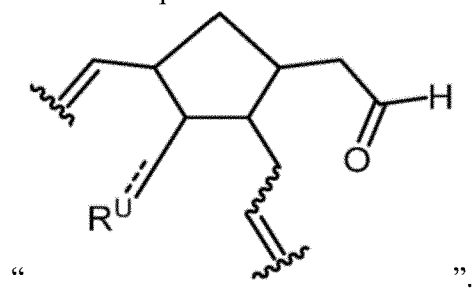
"                    ".
In Claim 39, at Column 114, Line 54, the text:
"-S(=O)2-OH, -S(=0)2-(a leaving group)"
Should be replaced with:
-- -S(=O)$_2$-OH, -S(=O)$_2$-(a leaving group) --.